(12) United States Patent
Li et al.

(10) Patent No.: US 11,634,467 B2
(45) Date of Patent: Apr. 25, 2023

(54) CYTOKINE-BASED BIOACTIVATABLE DRUGS AND METHODS OF USES THEREOF

(71) Applicant: Cugene Inc, Waltham, MA (US)

(72) Inventors: Yue-Sheng Li, Thousand Oaks, CA (US); Lingyun Rui, Weston, MA (US); Jing Xu, Waltham, MA (US)

(73) Assignee: Cugene Inc., Waltham, MA (US)

( * ) Notice: Subject to any disclaimer, the term of this patent is extended or adjusted under 35 U.S.C. 154(b) by 14 days.

(21) Appl. No.: 17/254,054

(22) PCT Filed: Jun. 20, 2019

(86) PCT No.: PCT/US2019/038229
§ 371 (c)(1),
(2) Date: Dec. 18, 2020

(87) PCT Pub. No.: WO2019/246392
PCT Pub. Date: Dec. 26, 2019

(65) Prior Publication Data
US 2021/0139553 A1    May 13, 2021

Related U.S. Application Data

(60) Provisional application No. 62/689,053, filed on Jun. 22, 2018.

(51) Int. Cl.
*C07K 14/54* (2006.01)
*C07K 14/55* (2006.01)
*A61K 38/00* (2006.01)

(52) U.S. Cl.
CPC .......... *C07K 14/5443* (2013.01); *C07K 14/55* (2013.01); *A61K 38/00* (2013.01); *C07K 2319/30* (2013.01)

(58) Field of Classification Search
CPC ................................................ C07K 14/5443
See application file for complete search history.

(56) References Cited

U.S. PATENT DOCUMENTS

| | | |
|---|---|---|
| 5,731,168 A | 3/1998 | Carter et al. |
| 6,955,807 B1 | 10/2005 | Shanafelt |
| 7,468,352 B1 | 12/2008 | Leppla et al. |
| 7,888,071 B2 | 2/2011 | Gillies et al. |
| 8,399,219 B2 | 3/2013 | Stagliano et al. |
| 8,734,774 B2 | 5/2014 | Frelinger et al. |
| 9,169,321 B2 | 10/2015 | Daugherty et al. |
| 9,328,159 B2 | 5/2016 | Wong et al. |
| 9,428,573 B2 | 8/2016 | Wong et al. |
| 9,493,533 B2 | 11/2016 | Bernard et al. |
| 9,580,486 B2 | 2/2017 | Gavin et al. |
| 10,206,980 B2 | 2/2019 | Qu et al. |
| 10,265,382 B2 | 4/2019 | Felber et al. |
| 10,335,460 B2 | 7/2019 | Felber et al. |
| 10,550,185 B2 | 2/2020 | Bernett et al. |
| 10,696,724 B2 | 6/2020 | Winston et al. |
| 11,053,294 B2 | 7/2021 | Karow et al. |
| 2019/0076524 A1 | 3/2019 | May et al. |
| 2019/0209653 A1 | 7/2019 | Felber et al. |
| 2021/0106655 A1 | 4/2021 | Qu et al. |

FOREIGN PATENT DOCUMENTS

| | | |
|---|---|---|
| WO | 2008096158 | 8/2008 |
| WO | 2016077505 | 5/2016 |
| WO | 2017156178 | 9/2017 |
| WO | 2017158436 | 9/2017 |
| WO | 2017162587 | 9/2017 |

OTHER PUBLICATIONS

Puskas et al. Development of an attenuated interleukin-2 fusion protein that can be activated by tumor-expressed proteases. Immunology 133(2): 206-220 (Mar. 23, 2011).
Skrombolas et al. Challenges and developing solutions for increasing the benefits of IL-2 treatment in tumr therapy. Expert Review of Clinical Immunology 10(2): 207-217 (Feb. 1, 2014).
Strohl Fusion Proteins for Half-Life Extension of Biologies as a Straegy to Make Biobetters. Biodrugs, 29(4): 215-239 (Jul. 16, 2015).
Arenas-Ramirez N et al. Interleukin-2: Biology, Design and Application. Trends Immunol, 36(12): 763-777 (2015).
Cathcart J et al. Targeting matrix metalloproteinases in cancer: Bringing new life to old ideas. Genes & Diseases 2, 26e34 (2015).
Chirifu M et al. Crystal structure of the IL-15-IL-15Ra complex, a cytokine-receptor unit presented in trans. Nature Immunol. 8(9): 1001-1007 (2007).
Choi KY et al. Protease-Activated Drug Development. Theranostics 2(2): 156-178 (2012).
Desnoyers LR et al. Tumor-Specific Activation of an EGFR-Targeting Probody Enhances Therapeutic Index. Sci Transl Med. 5(207):207ra144. (2013).

(Continued)

*Primary Examiner* — Prema M Mertz
(74) *Attorney, Agent, or Firm* — Craig A Crandall, APC; Craig A Crandall

(57) ABSTRACT

The present disclosure provides a cytokine-based bioactivatable drug construct ("VitoKine") platform that aims to reduce systemic mechanism-based toxicities and lead to broader therapeutic utility for proteins and cytokines such as IL-15 and IL-2 for the treatment of cancer, autoimmune diseases, inflammatory diseases, viral infection, transplantation and various other disorders. The novel VitoKine constructs of the present invention comprise: 1) a tissue or disease site targeting moiety D1 domain ("D1"), 2) a bioactivatable moiety D2 domain ("D2"), and a concealing moiety D3 domain ("D3"). Importantly, because the "active moiety" of the VitoKine construct will remain inert until activated locally by proteases that are upregulated in diseased tissues, this will limit binding of the active moiety to the receptors or to the targets in the peripheral or on the cell-surface of non-diseased cells and tissue to prevent over-activation of the pathway and reduce undesirable "on-target" "off tissue" toxicities. Additionally, the inertness of the VitoKine active moiety prior to protease activation will significantly decrease the potential antigen or target sink, and thus, prolong the in vivo half-life and result in improved biodistribution, bioavailability and therapeutic efficacy.

9 Claims, 35 Drawing Sheets
Specification includes a Sequence Listing.

(56) References Cited

OTHER PUBLICATIONS

Dudani JS et al. Harnessing Protease Activity to Improve Cancer Care. Annu. Rev. Cancer Biol. 2:353-76 (2018).
Geiger M et al. Protease-activation using anti-idiotypic masks enables tumor specificity of a folate receptor 1-T cell bispecific antibody. Nature Communications 11:3196 (2020).
Hezareh M et al. Effector Function Activities of a Panel of Mutants of a Broadly Neutralizing Antibody against Human Immunodeficiency Virus Type 1. J Virol 75: 12161-8 (2001).
Mortier E et al. Soluble Interleukin-15 Receptor α (IL-15Rα)-sushi as a Selective and Potent Agonist of IL-15 Action through IL-15Rβ/γ. J Biol Chem 281:1612-1619 (2006).
Poreba M et al. Highly sensitive and adaptable fluorescence-quenched pair discloses the substrate specificity profiles in diverse protease families. Scientific Reports 7: 43135 (2017).
Ring AM et al. Mechanistic and structural insight into the functional dichotomy between interleukin-2 and interleukin-15. Nat Immunol 13(12): 1187-1195 (2012).
Shields RL et al. High resolution mapping of the binding site on human IgG1 for Fc gamma RI, Fc gamma RII, Fc gamma RIII, and FcRn and design of IgG1 variants with improved binding to the Fc gamma R. J Biol Chem 276 (9):6591-604 (2001).
Spangler JB et al. Insights into Cytokine-Receptor Interactions from Cytokine Engineering. Annu Rev Immunol 33: 139-167 (2015).
Steel JC et al. Interleukin-15 biology and its therapeutic implications in cancer. Trends Pharmacol Sci 33(1): 35-41 (2012).
Weidle UH et al. Proteases as Activators for Cytotoxic Prodrugs in Antitumor Therapy. Cancer Genomics Proteomics 11: 67-80 (2014).
PCT International Search Report—Written Opinion, dated Sep. 18, 2019.

FIG. 3A
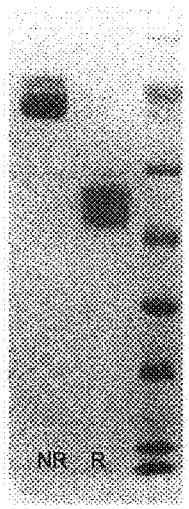
FIG. 3B
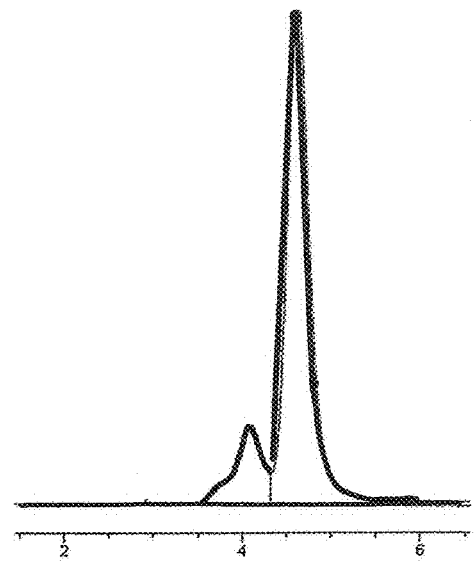
FIGS. 3A-3B

FIG. 6A
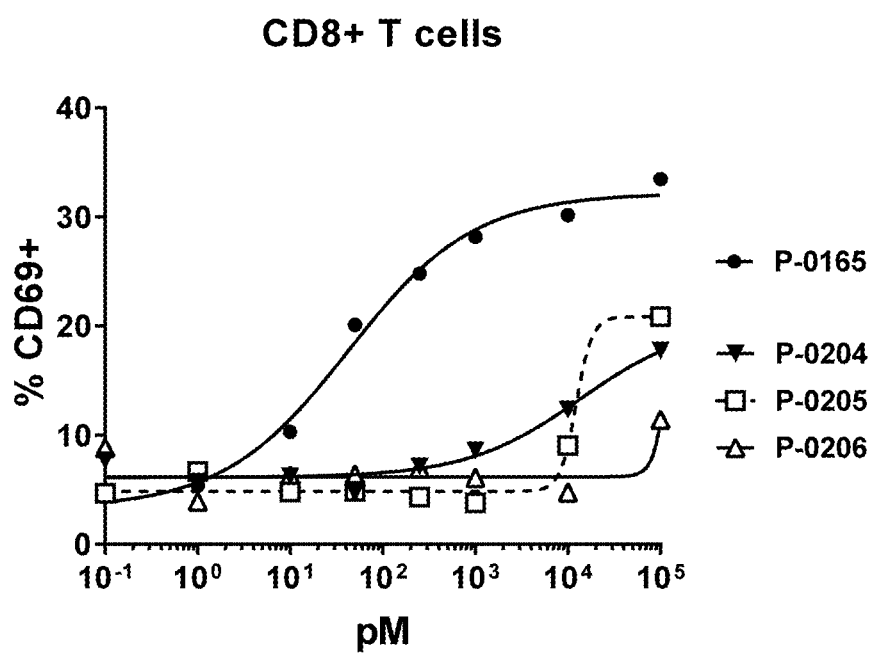
FIG. 6B
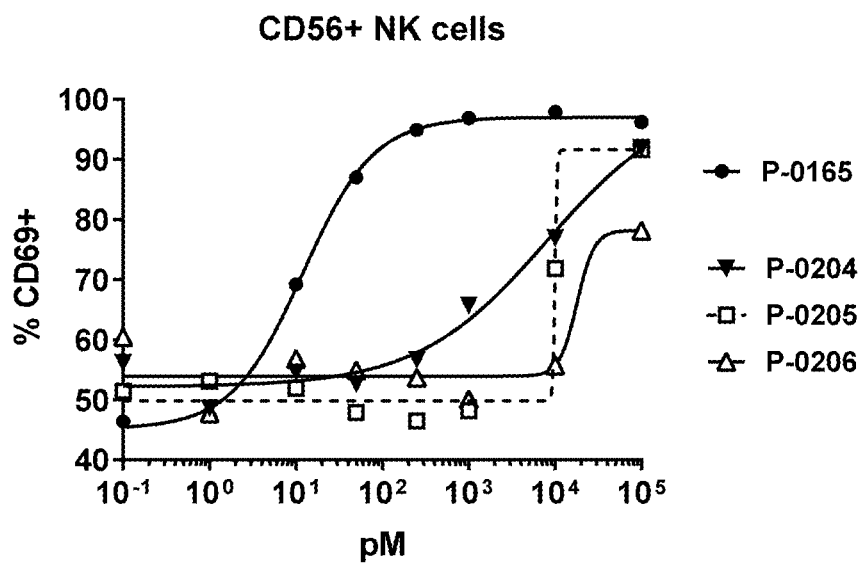
FIGS. 6A-6B

FIG. 8A
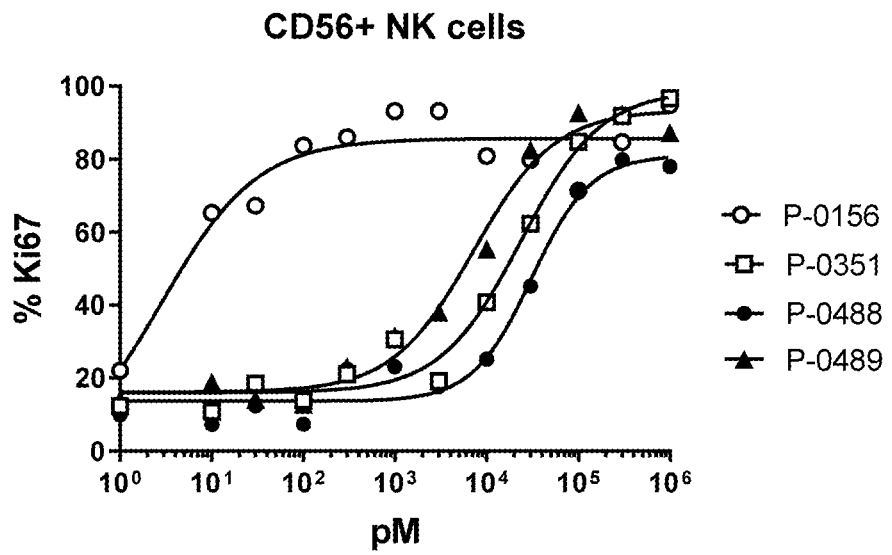
FIG. 8B
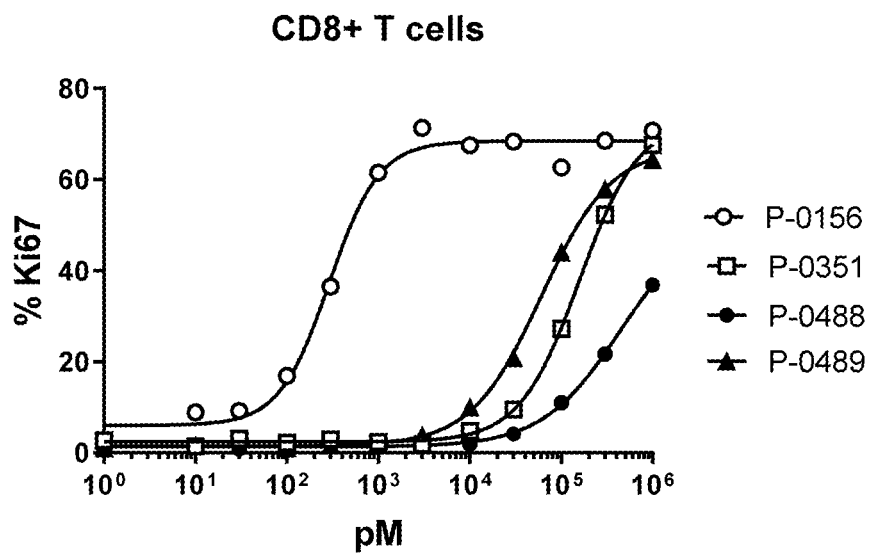
FIGS. 8A-8B

FIG. 10A
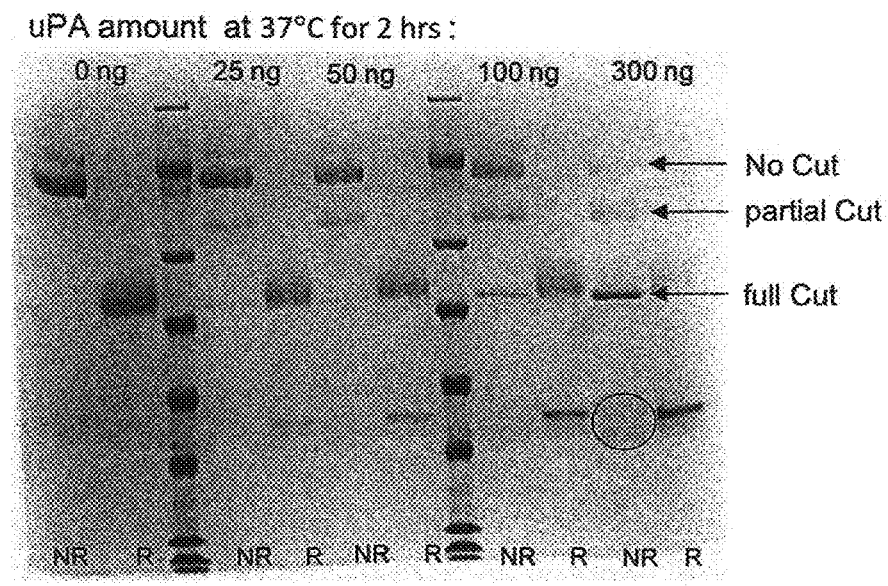
FIG. 10B
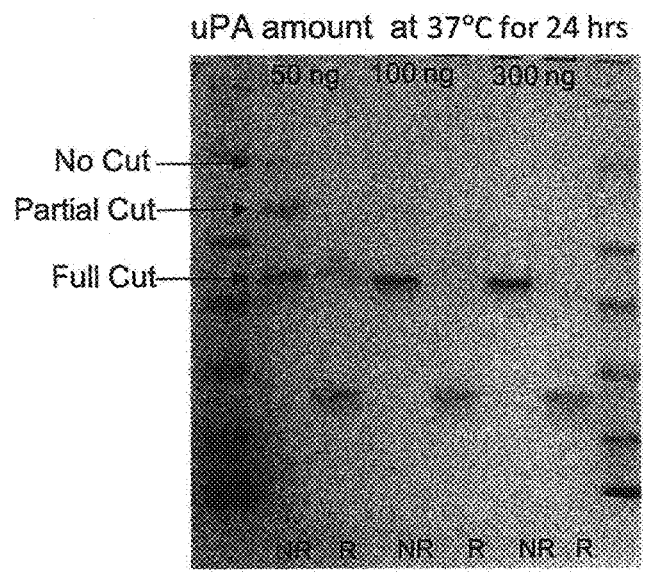
FIGS. 10A-10B

FIG. 12A
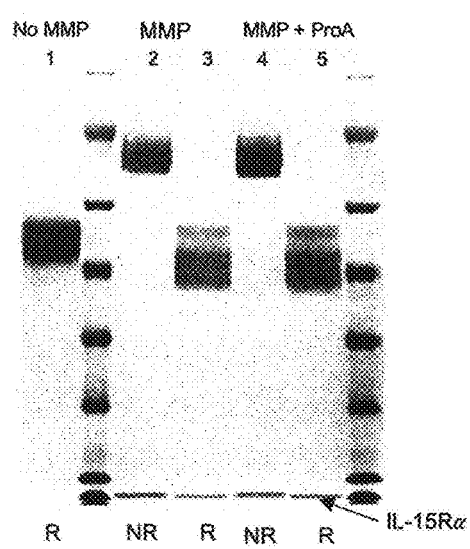
FIG. 12B
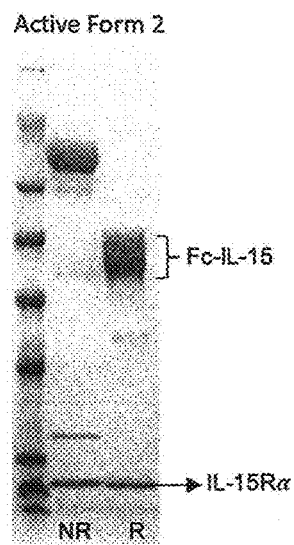
FIG. 12C
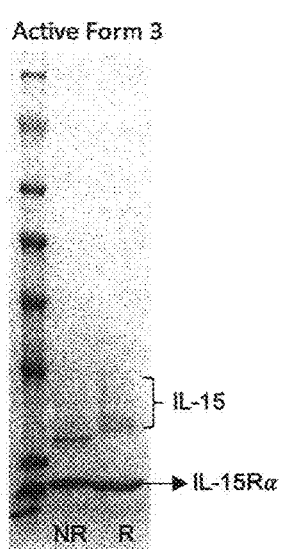
FIGS. 12A-12C

FIG. 13A
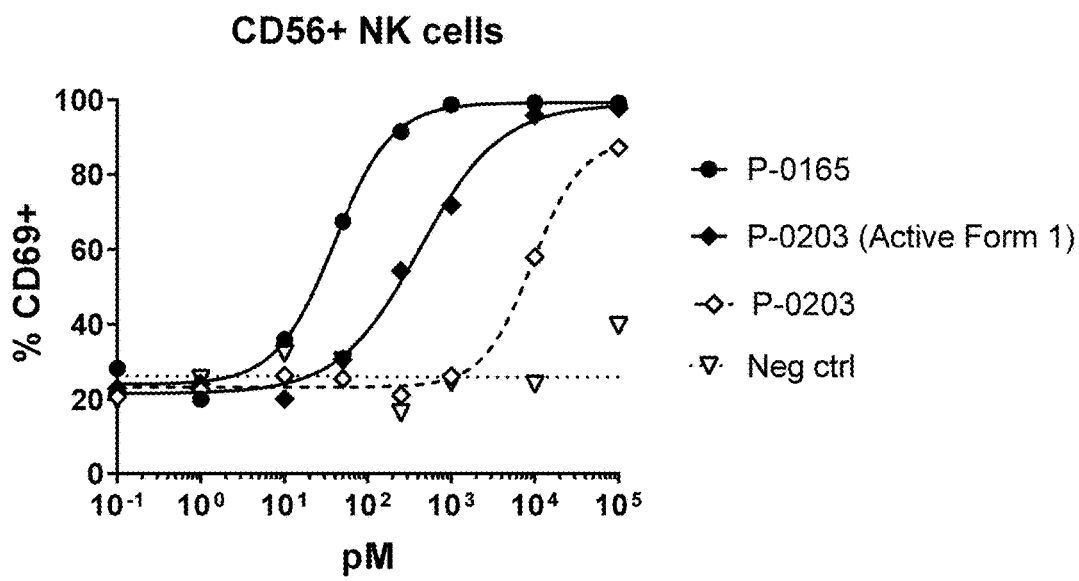
FIG. 13B
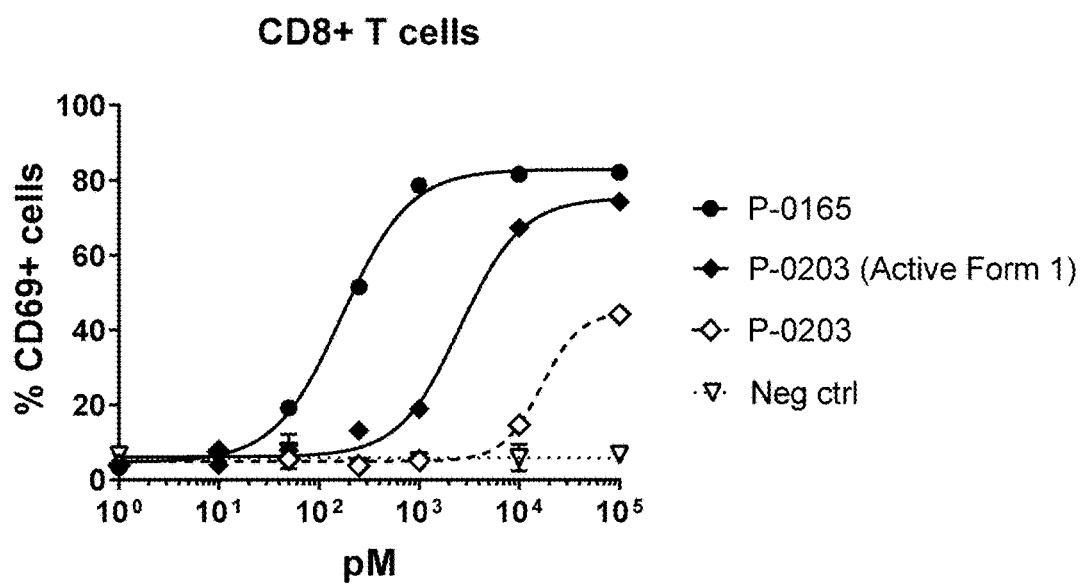
FIGS. 13A-13B

FIG. 14A
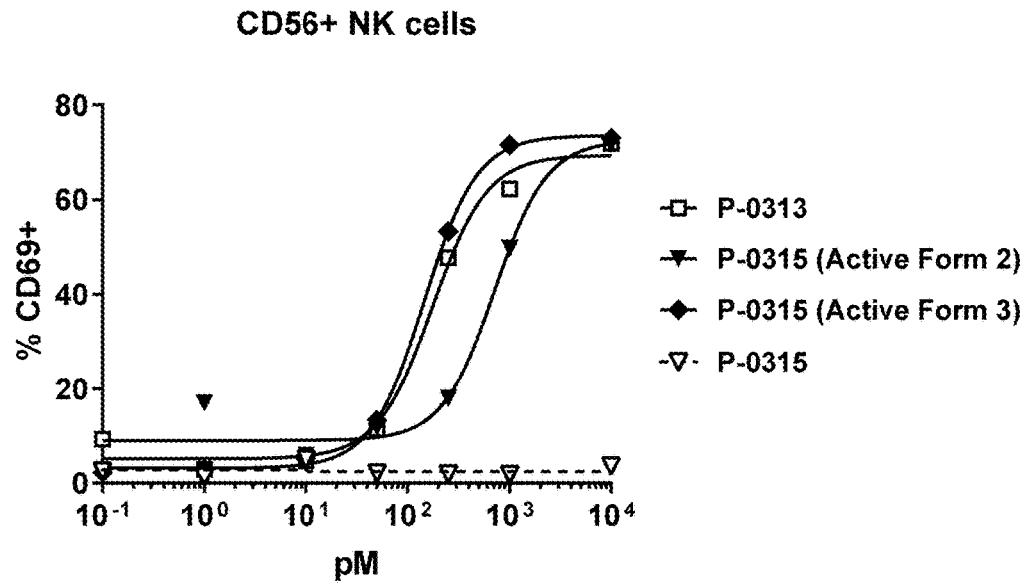
FIG. 14B
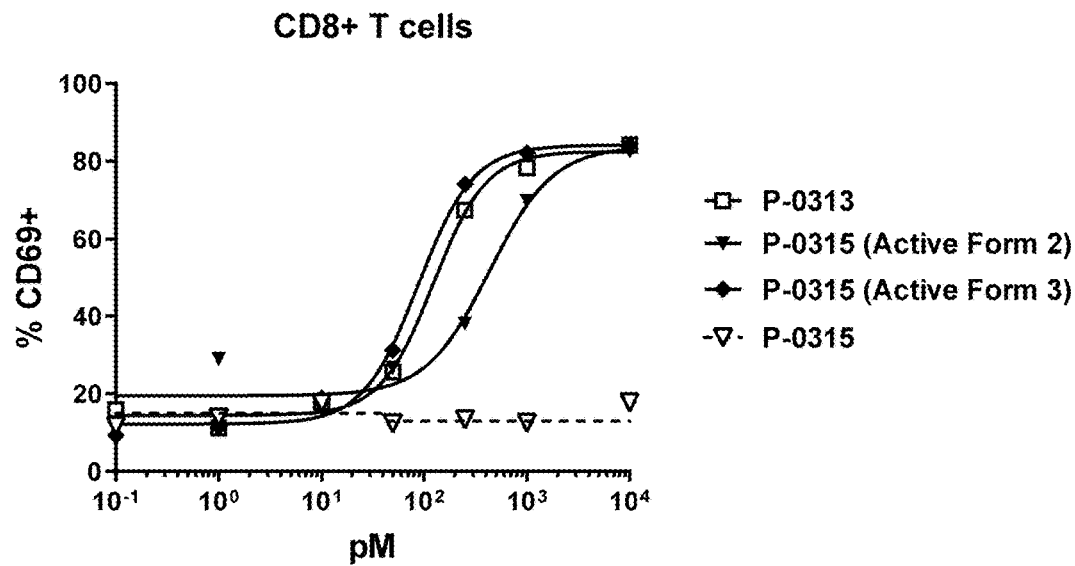
FIGS. 14A-14B

FIG. 15A
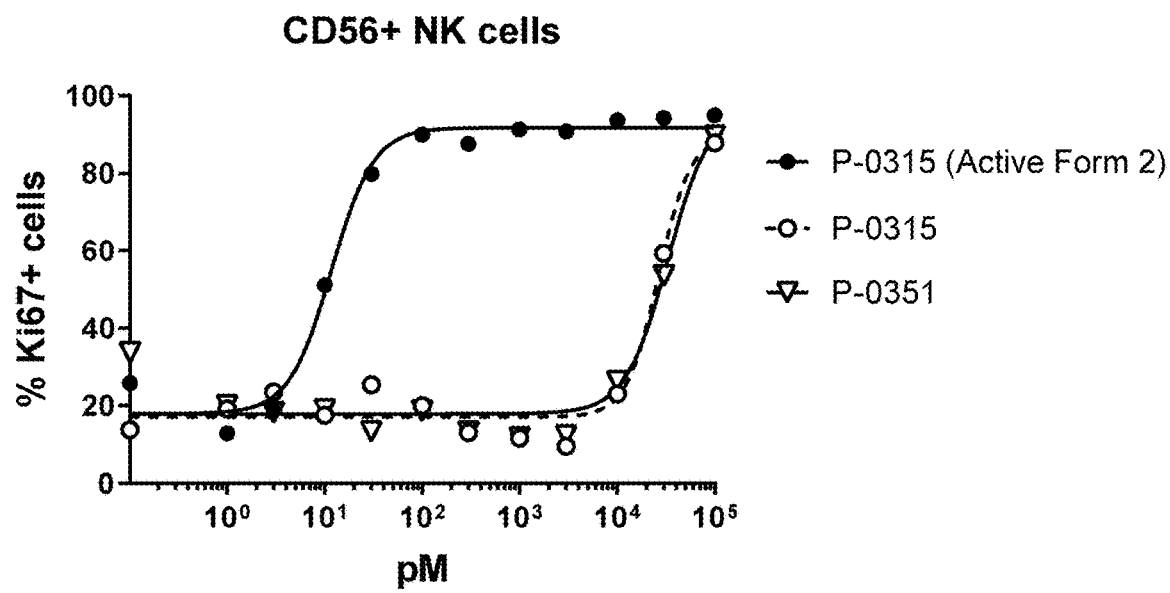
FIG. 15B
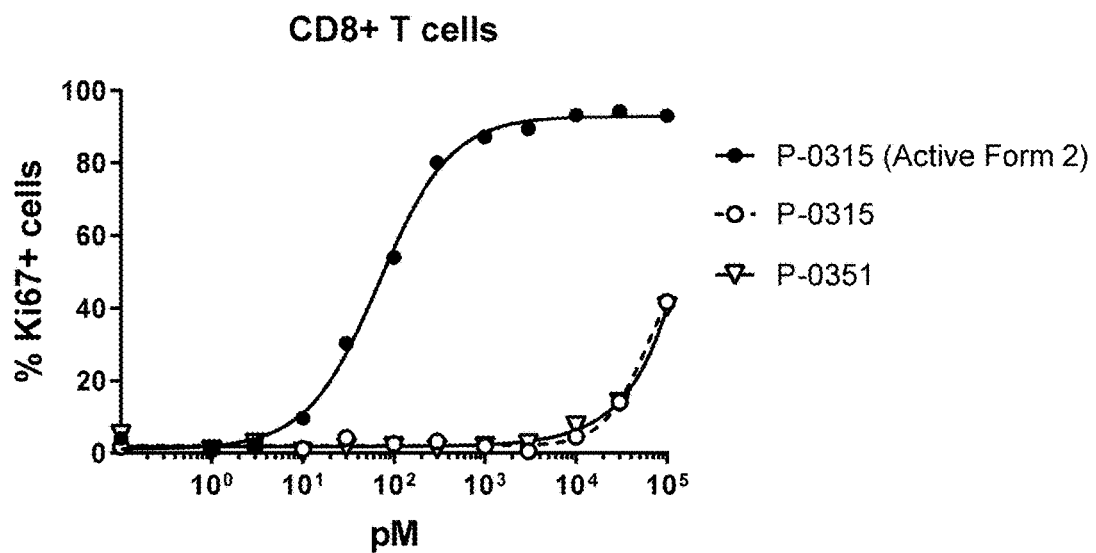
FIGS. 15A-15B

FIG. 16A
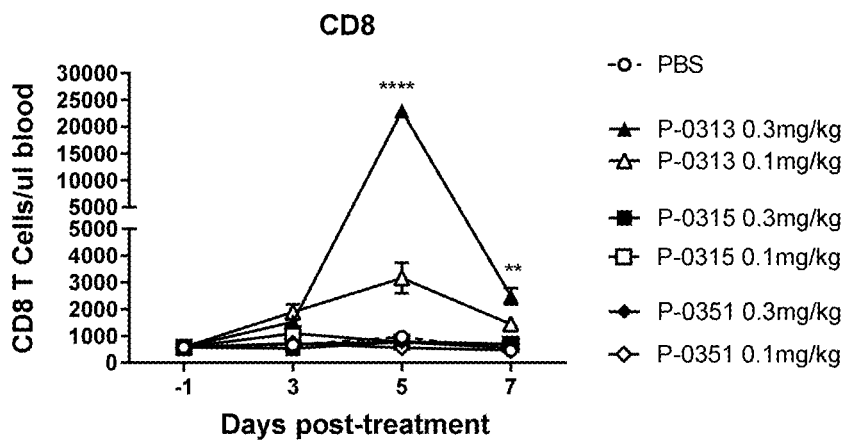
FIG. 16B
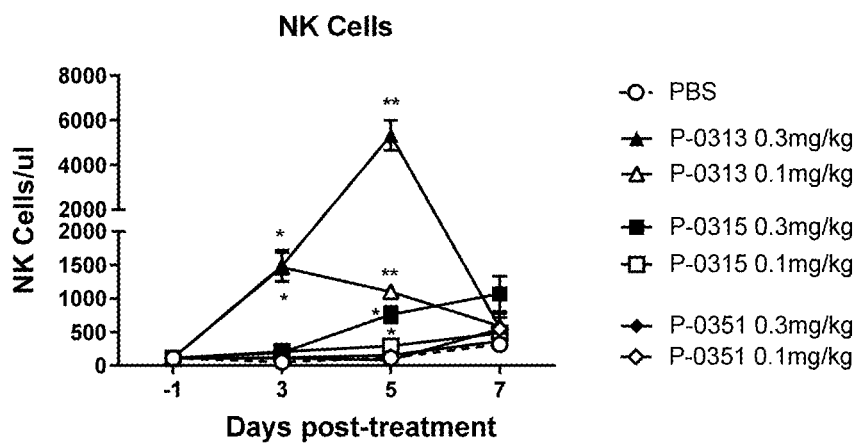
FIG. 16C
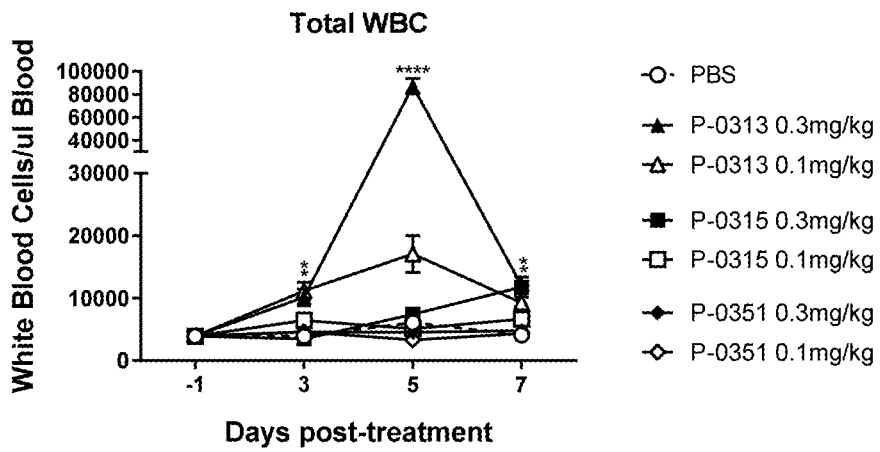
FIGS. 16A-16C

FIG. 18A
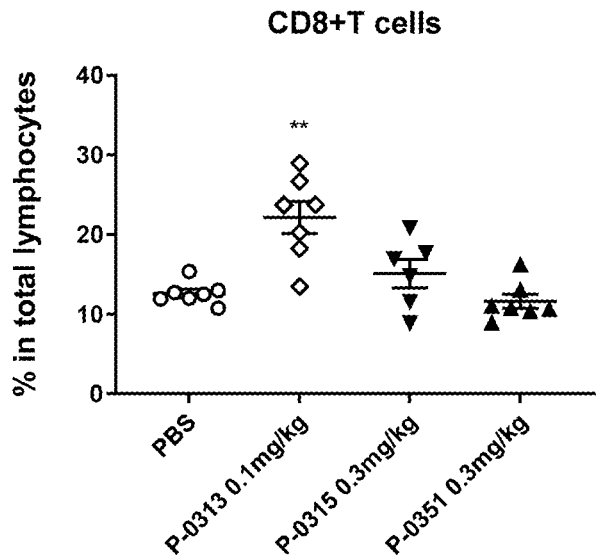
FIG. 18B
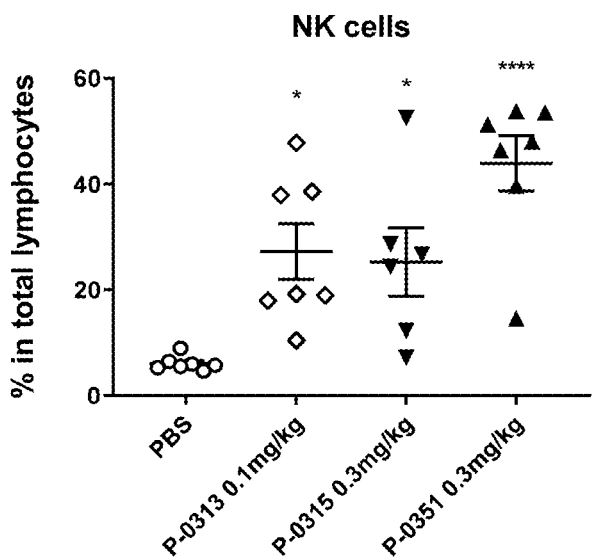
FIGS. 18A-18B

FIG. 21A
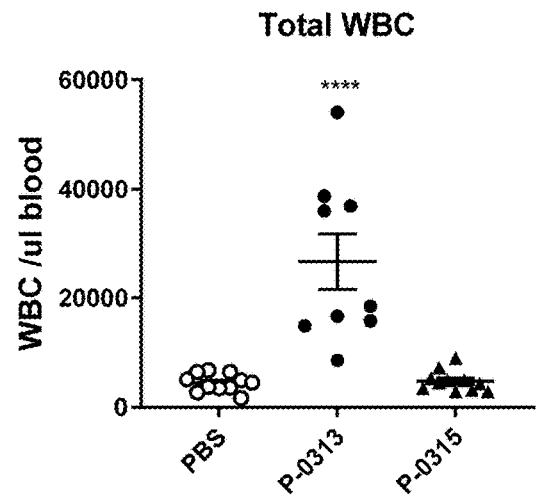
FIG. 21B
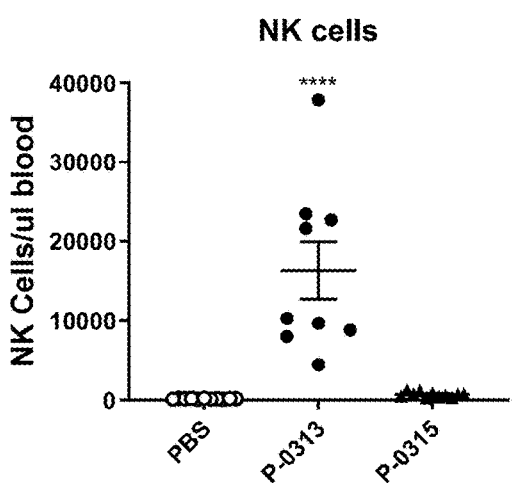
FIG. 21C
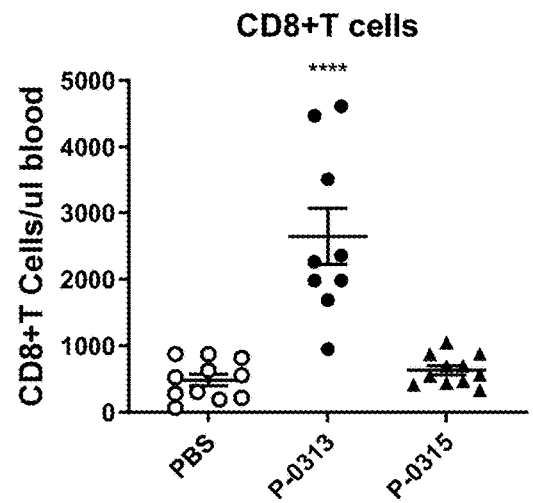
FIGS. 21A-21C

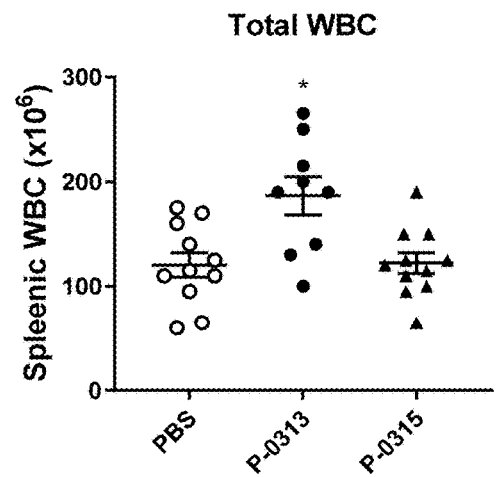
FIG. 22A
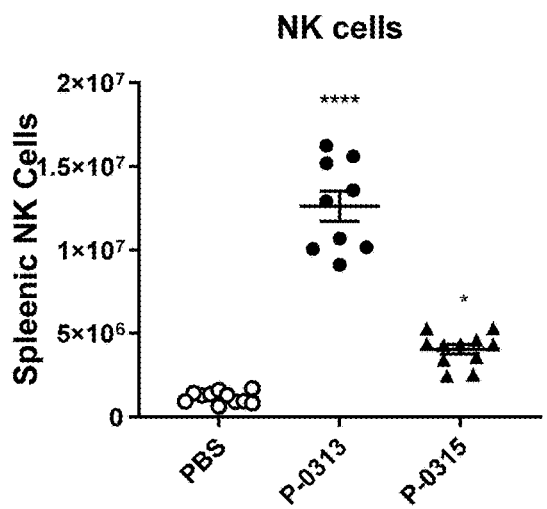
FIG. 22B
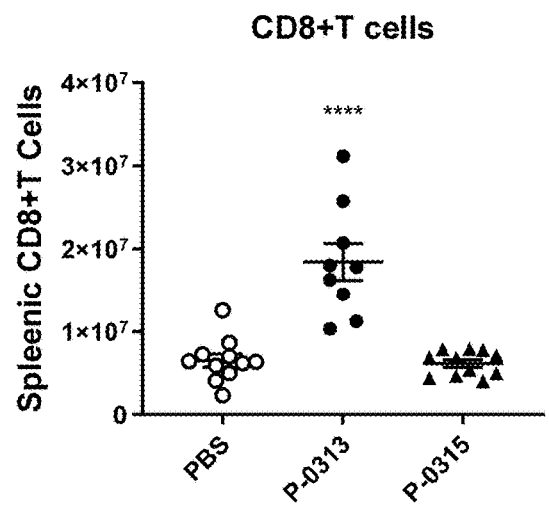
FIG. 22C
FIGS. 22A-22C

FIG. 23A
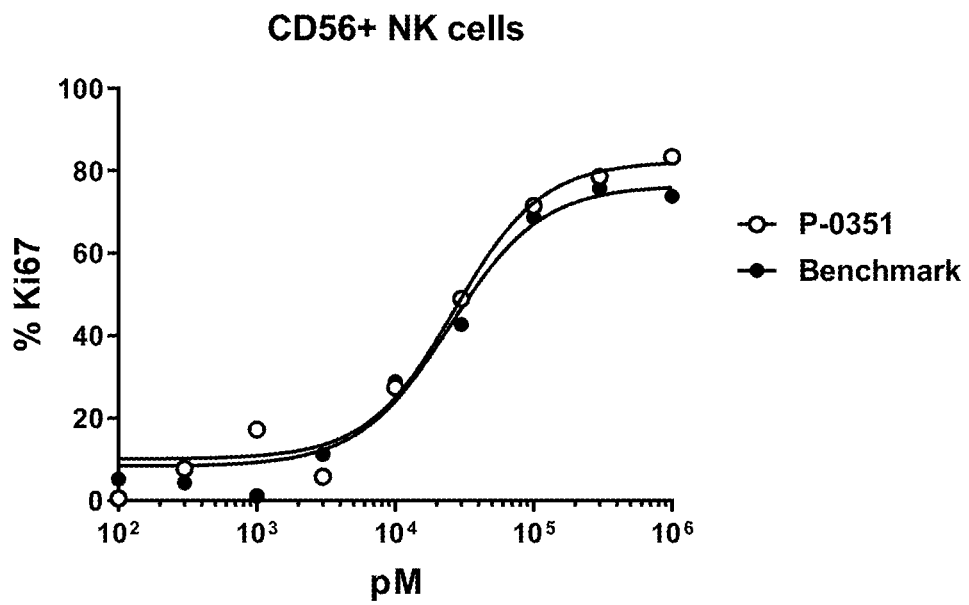
FIG. 23B
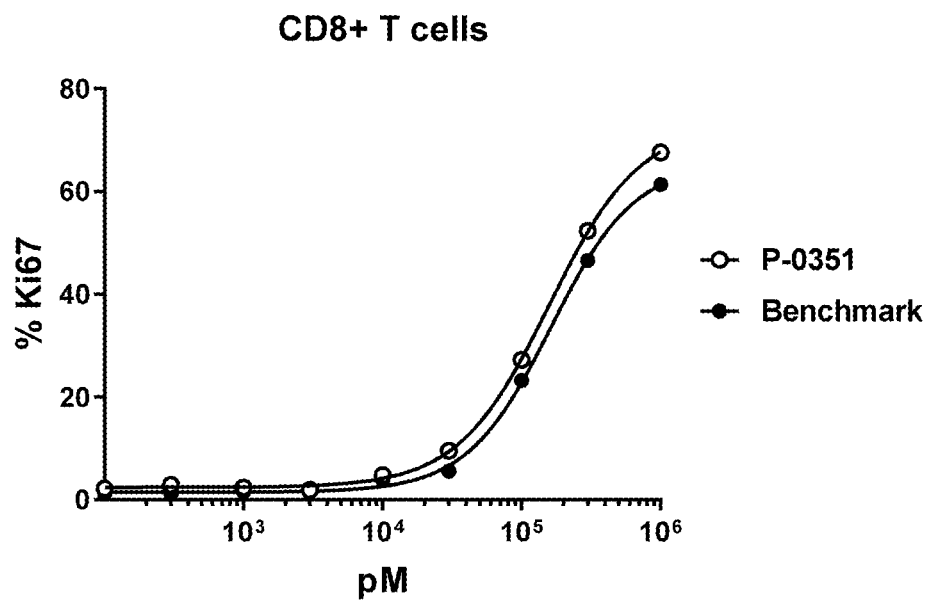
FIGS. 23A-23B

FIG. 24A
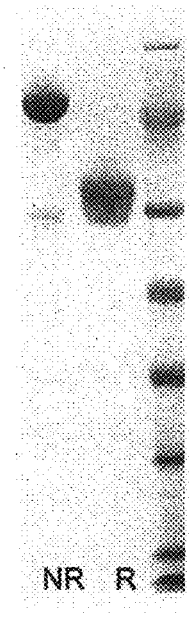
FIG. 24B
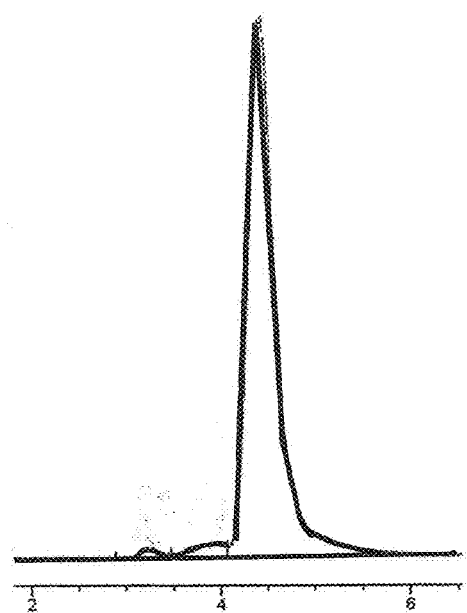
FIGS. 24A-24B

FIG. 25A
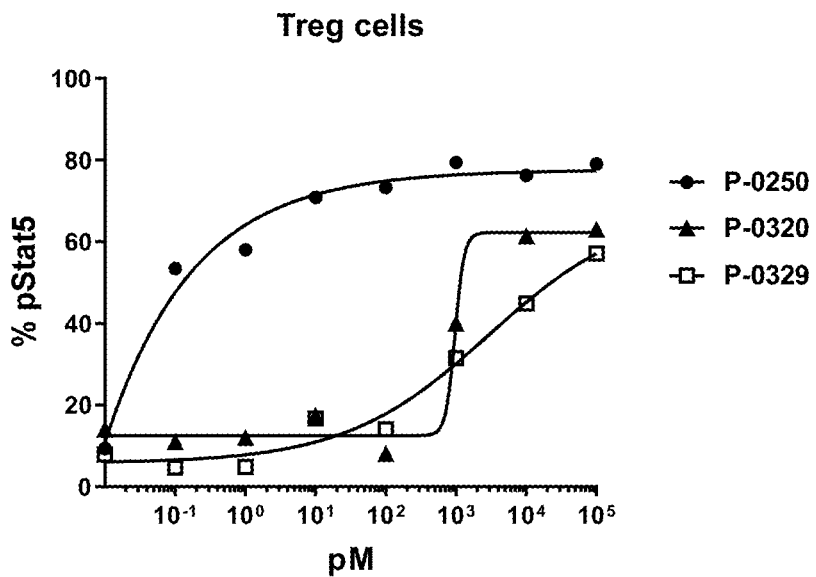
FIG. 25B
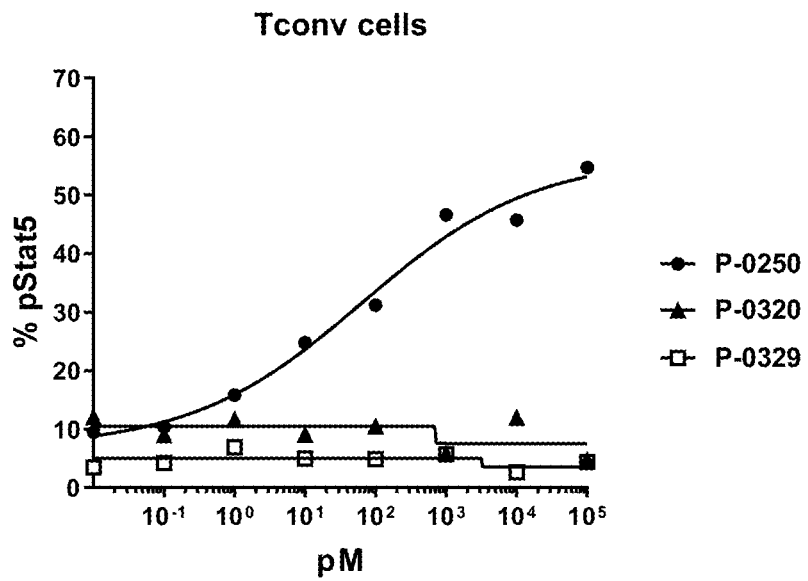
FIGS. 25A-25B

IL-2 VitoKine P-0382

FIG. 27A
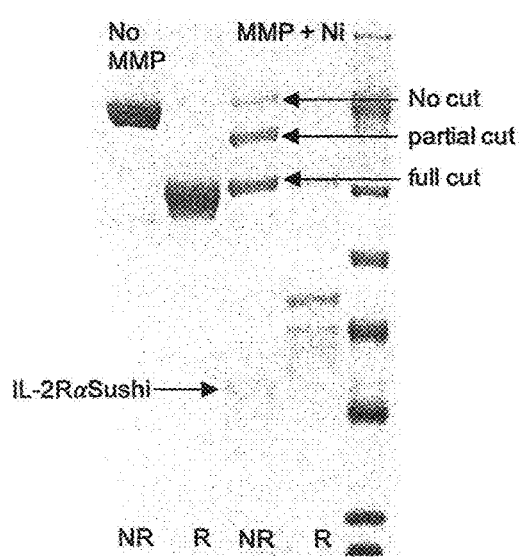
FIG. 27B
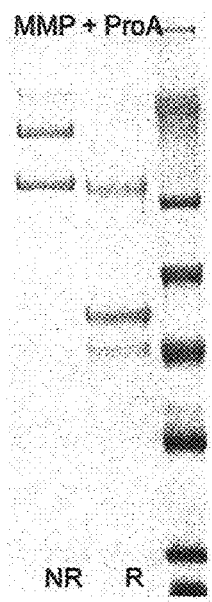
FIGS. 27A-27B

FIG. 28A
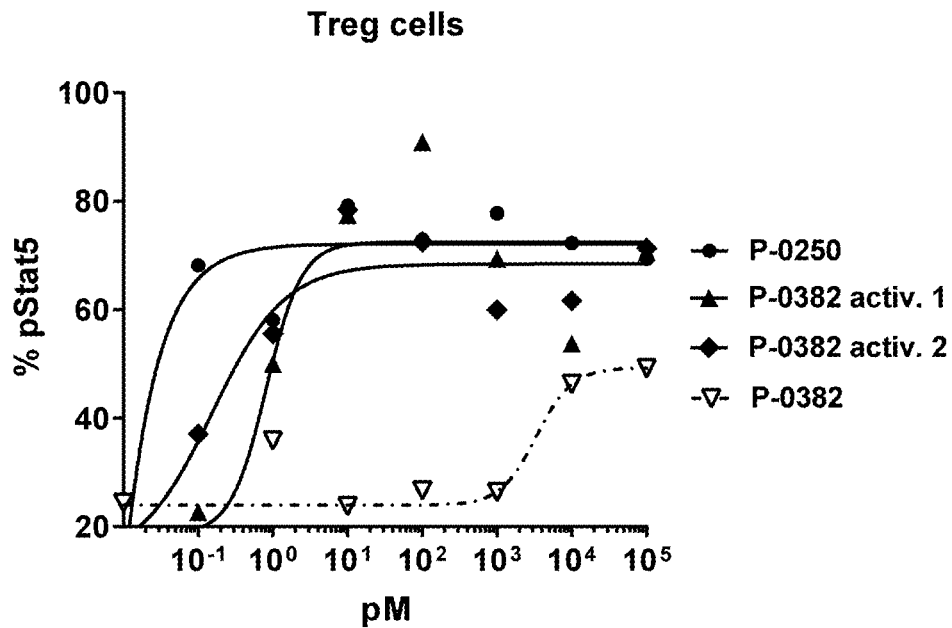
FIG. 28B
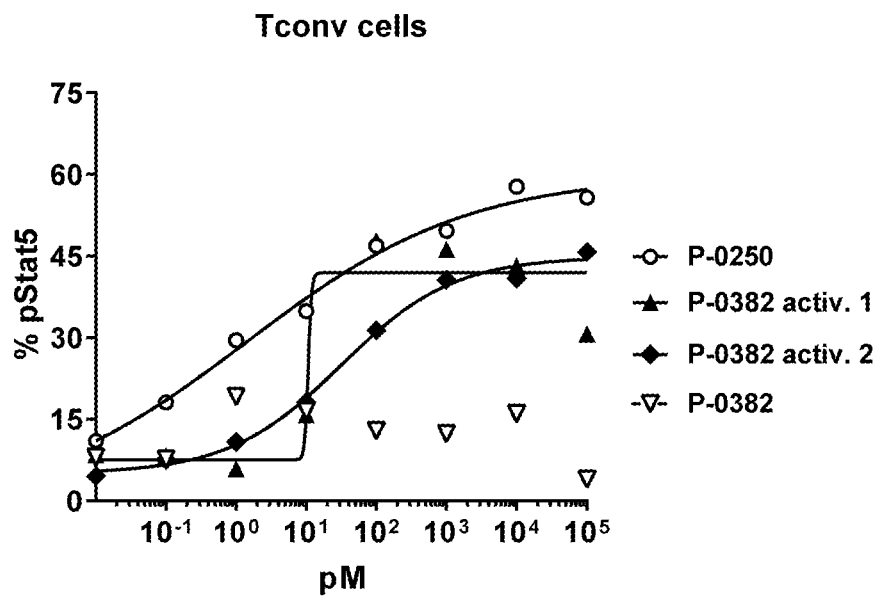
FIGS. 28A-28B

FIG. 29A
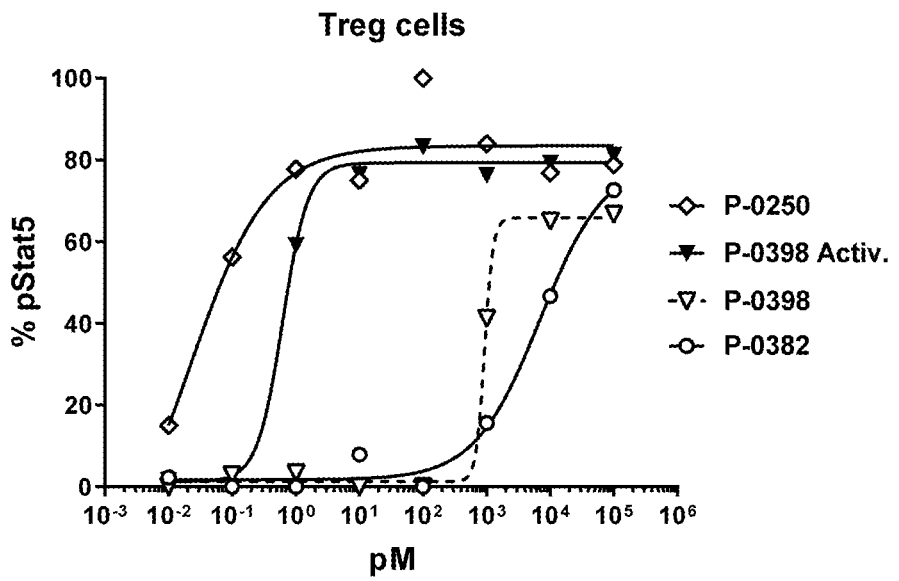
FIG. 29B
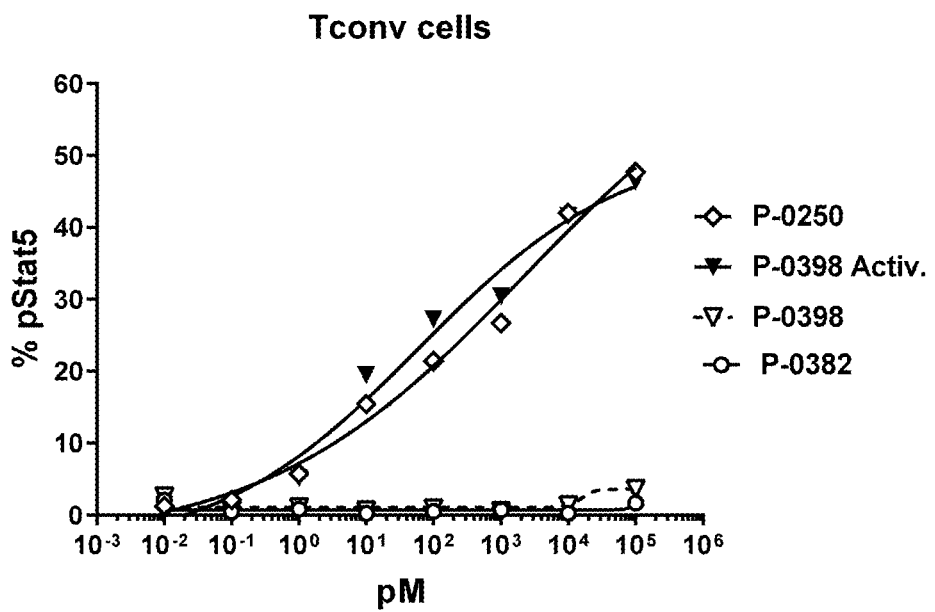
FIGS. 29A-29B

FIG. 30A
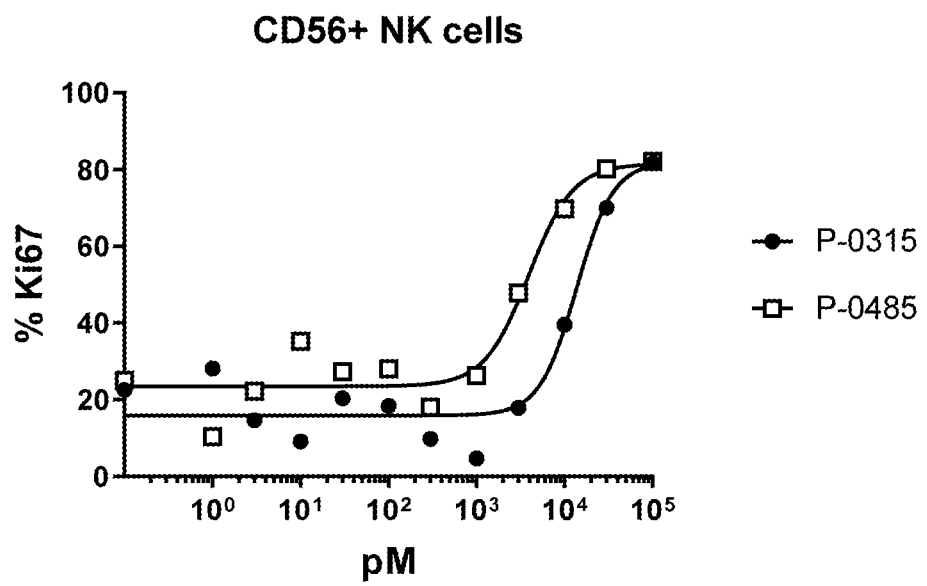
FIG. 30B
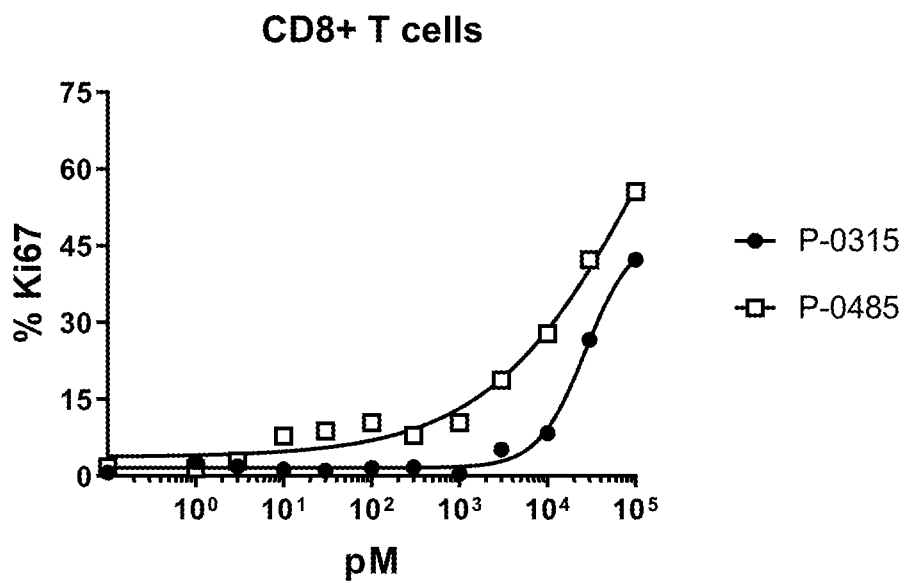
FIGS. 30A-30B

FIG. 33A
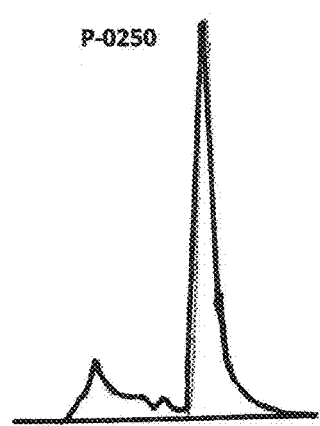
FIG. 33B
FIG. 33C
FIG. 33D
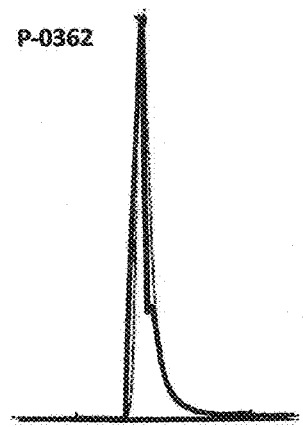
FIG. 33E
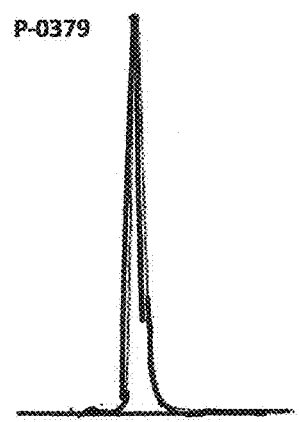
FIGS. 33A-33E

CYTOKINE-BASED BIOACTIVATABLE DRUGS AND METHODS OF USES THEREOF

RELATED PATENT APPLICATIONS

This application is a U.S. National Stage Application pursuant to 35 U.S.C. § 371 of PCT/US2019/038229, filed Jun. 20, 2019, which claims benefit of U.S. Provisional Application No. 62/689,053, filed on Jun. 22, 2018, each incorporated in its entirety by reference herein.

BACKGROUND

Many cytokines have been evaluated as potential therapeutic agents for treating diseases. However, their systemic overstimulation or over-suppression of body immune system has severely hindered their development and clinical utilities.

Interleukin-2 (IL-2) and Interleukin-15 (IL-15) share common receptor components ($\gamma_C$ and IL-2Rβ) and signaling pathways and have several similar functions. Both cytokines stimulate the proliferation of T cells; induce the generation of cytotoxic T lymphocytes (CTLs); facilitate the proliferation of, and the synthesis of immunoglobulin by, B cells; and induce the generation and persistence of natural killer (NK) cells. Based on numerous pre-clinical studies as well as multiple clinical assessments, both cytokines are considered as potentially valuable therapeutics in cancer, autoimmune disorders, inflammatory disorders, transplantation and various other disorders. Recombinant IL-2 has been approved for use in patients with metastatic renal-cell carcinoma and malignant melanoma. For IL-15, there are several on-going oncology clinical trials but no approved uses yet. Additionally, both IL-2 and IL-15 have a third, unique, non-signaling receptor α-subunit: IL-2Rα (also known as CD25) or IL-15Rα, respectively, which may contribute to their distinct receptor specificity and biological functions.

Recombinant human IL-2 is an effective immunotherapy being used for metastatic melanoma and renal cancer, with durable responses in approximately 10% of patients. However short half-life and severe toxicity limits the optimal dosing of IL-2. Further, IL-2 also binds to its heterotrimeric receptor IL-2Rαβγ with greater affinity, which preferentially expands immunosuppressive regulatory T cells (Tregs) expressing high constitutive levels of IL-2Rα. Expansion of Tregs may represent an undesirable effect of IL-2 for cancer immunotherapy. However, the capability of IL-2 to stimulate Treg cells even at low doses could be harnessed for the treatment of autoimmune and chronic inflammatory disorders. More recently, it was found that IL-2 could be modified to selectively stimulate either cytotoxic effector T cells or Treg cells. Various approaches have led to the generation of IL-2 variants with improved and selective immune modulating activities.

Both IL-2 and IL-15 are potent immune effector cell agonists, and it is crucial that cytotoxic immune cells are fully activated only when at or in close proximity to a disease site, e.g, cancer site, to only specifically destroy tumor cells; or inflammatory issue site to only act as anti-autoimmune and chronic inflammatory disorders. Improving specificity and selectivity for targets and leaving healthy cells and tissues intact and undamaged is of great interest for all cytokines, chemokines, and growth factors.

DISCLOSURE OF THE INVENTION

In one aspect, the present invention provides a cytokine-based bioactivatable drug ("VitoKine") platform that aims to reduce systemic mechanism-based toxicities and lead to broader therapeutic utility for cytokines, chemokines, hormones and growth factors, such as IL-15 and IL-2, for the treatment of cancer, autoimmune disorders, inflammatory disorders, and various other disorders. The VitoKine platform is defined by the constructs as depicted in FIG. 1 and the proposed methods of activation as depicted in FIG. 2. Referring to FIG. 1, the novel VitoKine constructs of the present invention comprise 3 domains: 1) a D1 domain ("D1") selected from the group consisting of: a tissue targeting domain; a half-life extension domain; or a dual functional moiety domain, 2) a D2 domain ("D2") which is an "active moiety domain", and 3) a D3 domain ("D3") which is a "concealing moiety domain". Importantly, the D2 domain of the VitoKine construct remains nearly inert or of minimal activity until activated locally by proteases that are upregulated in diseased tissues, or by hydrolysis at the disease sites, which will limit binding of the active moiety to the receptors in the peripheral or on the cell-surface of non-diseased cells or normal tissues to prevent over-activation of the pathway and reduce undesirable "on-target" "off tissue" toxicity, and unwanted target sink.

In various embodiments, the VitoKine constructs of the present invention comprise a D1 that is a targeting moiety such as an antibody or antibody fragment binding to a tumor associated antigen (TAA), or a tissue-specific antigen, a cell surface molecule or extracellular matrix protein or protease(s) or any post-translational modification residue(s). In various embodiments, the VitoKine constructs of the present invention comprise a D1 that is a targeting moiety such as a protein or peptide that exhibits binding affinity to a diseased cell or tissue. In various embodiments, the VitoKine constructs of the present invention comprise a D1 that is a modified protein or peptide, such as glycan-modified, that exhibits binding affinity to a specific receptor, such as c-type lectin receptor, expressed on a diseased cell or tissue. In various embodiments, the VitoKine constructs of the present invention comprise a D1 domain that is an antibody to an immune checkpoint modulator. In various embodiments, the VitoKine constructs of the present invention comprise a D1 that functions for retention of the cytokine at the tissue site. In various embodiments, the VitoKine constructs of the present invention comprise a D1 that is bifunctional, e.g., tissue targeting and retention. In various embodiments, the VitoKine constructs of the present invention comprise a D1 domain that is a polymer. In various embodiments, the VitoKine constructs of the present invention comprise a D1 domain that is a half-life extension moiety. In various embodiments, the VitoKine constructs of the present invention comprise a D1 domain that is an Fc domain (or functional fragment thereof).

"Fc domain" refers to a dimer of two Fc domain monomers that generally includes full or part of the hinge region. In various embodiments, the Fc domain is selected from the group consisting of human IgG1 Fc domain, human IgG2 Fc domain, human IgG3 Fc domain, human IgG4 Fc domain, IgA Fc domain, IgD Fc domain, IgE Fc domain, IgG Fc domain and IgM Fc domain; or any combination thereof. In various embodiments, the Fc domain includes an amino acid change that results in an Fc domain having altered complement or Fc receptor binding properties. Amino acid changes known to produce an Fc domain with altered complement or Fc receptor binding properties are known in the art. In various embodiments, the Fc domain sequence used to make VitoKine constructs is the human IgG1-Fc domain sequence set forth in SEQ ID NO: 13. In various embodiments, the Fc domain sequence used to make VitoKine constructs is the sequence set forth in SEQ ID NO: 14 which contains amino acid substitutions that ablate FcγR and C1q binding. In various embodiments, the Fc domain includes amino acid changes that result in further extension of in vivo half-life. Amino acid changes known to produce an Fc domain with further extended half-life are known in the art. In various embodiments, the Fc domain sequence used to make Vito-Kine constructs is the sequence set forth in SEQ ID NOS: 156 or 166, both of which contains amino acid substitutions that ablate FcγR and C1q binding and extend in vivo half-life. In various embodiments, the heterodimeric Fc domain sequence used to make VitoKine constructs is derived from the Knob-Fc domain sequence set forth in SEQ ID NO: 15. In various embodiments, the heterodimeric Fc domain sequence used to make VitoKine constructs is derived from the Hole-Fc domain sequence set forth in SEQ ID NO: 16. In various embodiments, the heterodimeric Fc domain sequence used to make VitoKine constructs is derived from the Knob-Fc domain with extended in vivo half-life sequence set forth in SEQ ID NO: 167. In various embodiments, the heterodimeric Fc domain sequence used to make VitoKine constructs is derived from the Hole-Fc domain with extended in vivo half sequence set forth in SEQ ID NO: 168.

In various embodiments, the VitoKine constructs of the present invention comprise a D2 domain that is a protein. In various embodiments, the VitoKine constructs of the present invention comprise a D2 domain that is a cytokine selected from the group including, but not limited to, IL-1, IL-2, IL-4, IL-5, IL-6, IL-7, IL-9, IL-10, IL-12, IL-15, IL-23 and Ligands of transforming growth factor β (TGFβ) superfamily, e.g, TGFβ (SEQ ID NO: 24). In various embodiments, the VitoKine constructs of the present invention comprise a D2 domain that is IL-15. In various embodiments, the VitoKine constructs of the present invention comprise a D2 domain that is an IL-15 variant (or mutant) comprising one or more amino acid substitution, deletion or insertion to IL-15 polypeptide. In various embodiments, the VitoKine constructs of the present invention comprise a D2 domain that is IL-2. In various embodiments, the VitoKine constructs of the present invention comprise a D2 domain that is an IL-2 variant (or mutant) comprising one or more amino acid substitution, deletion or insertion to IL-2 polypeptide.

In various embodiments, the D2 domain of the VitoKine construct is an IL-15 domain which comprises the sequence of the mature human IL-15 polypeptide (also referred to herein as huIL-15 or IL-15 wild type (wt)) as set forth in SEQ ID NO: 2. In various embodiments, the IL-15 domain will be an IL-15 variant (or mutant) comprising a sequence derived from the sequence of the mature human IL-15 polypeptide as set forth in SEQ ID NO: 2. In various embodiments, the IL-15 domain will be an IL-15 variant (or mutant) comprising a sequence having at least 80%, at least 85%, at least 90%, or at least 95% sequence homology with SEQ ID NO: 2. Variants (or mutants) of IL-15 are referred to herein using the native amino acid, its position in the mature sequence and the variant amino acid. For example, huIL-15 "S58D" refers to human IL-15 comprising a substitution of S to D at position 58 of SEQ ID NO: 2. In various embodiments, the IL-15 variant functions as an IL-15 agonist as demonstrated by, e.g., increased binding activity for the IL-15Rβγc receptors compared to the native IL-15 polypeptide. In various embodiments, the IL-15 variant functions as an IL-15 antagonist as demonstrated by e.g., decreased binding activity for the IL-15Rβγc receptors, or similar or increased binding activity for the IL-15Rβγc receptors but reduced or abolished signaling activity compared to the native IL-15 polypeptide. In various embodiments, the IL-15 variant has increased binding affinity or a decreased binding activity for the IL-15Rβγc receptors compared to the native IL-15 polypeptide. In various embodiments, the sequence of the IL-15 variant has at least one (i.e., 1, 2, 3, 4, 5, 6, 7, 8, 9, 10, or more) amino acid change compared to the native IL-15 sequence. The amino acid change can include one or more of an amino acid substitution, deletion, or insertion in the IL-15 polypeptide, such as in the domain of IL-15 that interacts with IL-151:16 and/or IL-15Rβc. In various embodiments, the amino acid change is one or more amino acid substitutions or deletions at position 30, 31, 32, 58, 62, 63, 67, 68, or 108 of SEQ ID NO:2. In various embodiments, the amino acid change is the substitution of D to T at position 30, V to Y at position 31, H to E at position 32, S to D at position 58, T to D at position 61, V to F at position 63, I to V at position 67, I to F or H or D or K at position 68, or Q to A or M or S at position 108 of the mature human IL-15 sequence, or any combination of these substitutions. In various embodiments, the amino acid change is the substitution of S to D at position 58 of the mature human IL-15 sequence. In various embodiments, the IL-15 polypeptide comprises the IL-15 variant of SEQ ID NO: 3. In various embodiments, the IL-15 domain has any combinations of amino acid substitutions, deletions and insertions.

In various embodiments, the D2 domain of the VitoKine constructs of the present invention comprise an IL-2 polypeptide. In various embodiments, the VitoKine constructs of the present invention comprise a D2 domain that is an IL-2 variant (or mutant) comprising one or more amino acid substitution, deletion, or insertion. In various embodiments, the VitoKine construct comprises a D2 domain wherein the IL-2 domain comprises the sequence of the mature human IL-2 polypeptide (also referred to herein as huIL-2 or IL-2 wild type (wt) as set forth in SEQ ID NO: 8. In various embodiments, the IL-2 domain will be an IL-2 variant (or mutant) comprising a sequence derived from the sequence of the mature human IL-2 polypeptide as set forth in SEQ ID NO: 8. In various embodiments, the IL-2 domain will be an IL-2 variant (or mutant) comprising a sequence having at least 80%, at least 85%, at least 90%, or at least 95% sequence homology with SEQ ID NO: 8. In various embodiments, the IL-2 variant functions as an IL-2 agonist. In various embodiments, the IL-2 variant functions as an IL-2 antagonist. In various embodiments, the amino acid change is one or more amino acid substitutions at position 19, 20, 38, 41, 42, 44, 88, 107, 125 or 126 of SEQ ID NO: 8. In various embodiments, the amino acid change is the substitution of L to D or H or N or P or Q or R or S or Y at position 19, D to E or I or N or Q or S or T or Y at position 20, R to E or A at position 38, T to A or G or V at position 41, F to A at position 42, F to G or V at position 44, N to D, E or G or I or M or Q or T or R at position 88, Y to G or H or L or V at position 107, S to E, H, K, I, or W at position 125, Q to D or E or K or L or M or N at position 126, of the mature human IL-2 sequence, or any combination of these substitutions.

In various embodiments, the VitoKine constructs of the present invention comprise a "concealing moiety domain" (D3) that is a cognate receptor/binding partner, or any binding partner identified for the D2 protein or cytokine. In various embodiments, the D3 domain is a variant of the cognate receptor/binding partner for the D2 domain. In various embodiments, the D3 domain has enhanced binding to the D2 domain compared to the wild-type cognate receptor/binding partner. In various embodiments, the D3 domain has reduced or abolished binding to the D2 domain compared to the wild-type cognate receptor/binding partner. In various embodiment, the D3 domain is a protein, or a peptide, or an antibody, or an antibody fragment that is able to conceal the activity of D2. In various embodiments, D3 domain is a DNA, RNA fragment or a polymer, such as PEG. In various embodiments, the VitoKine constructs of the present invention comprise a D3 domain that is an IL-15Rα extracellular domain or a functional fragment thereof. In various embodiments, the VitoKine constructs of the present invention comprise a D3 domain that is an IL-15RαSushi domain. In various embodiments, the VitoKine constructs of the present invention comprise a D3 domain that is IL-2Rα extracellular domain or a functional fragment thereof. In various embodiments, the VitoKine constructs of the present invention comprise a D3 domain that is IL-2RαSushi domain. In various embodiments, the D3 domain is capable of concealing the functional activity of D2 until activated at the intended site of therapy.

In various embodiments, the D1, D2 and D3 domains of the VitoKine construct are linked by a protease cleavable polypeptide linker sequence. In various embodiments, the D1, D2 and D3 domains of the VitoKine construct are linked by a non-cleavable polypeptide linker sequence. In various embodiments, L1 and L2 of the VitoKine constructs of the present invention are both a protease cleavable peptide linker. In various embodiments, L1 of the VitoKine constructs of the present invention is a protease cleavable peptide linker and L2 is a non-cleavable peptide linker. In various embodiments, L1 of the VitoKine constructs of the present invention is a non-cleavable peptide linker and L2 is a protease cleavable peptide linker. In various embodiments, L1 and L2 of the VitoKine constructs of the present invention are both non-cleavable linkers. In various embodiments, the linker is rich in G/S content (e.g., at least about 60%, 70%, 80%, 90%, or more of the amino acids in the linker are G or S. Each peptide linker sequence can be selected independently. In various embodiments, the protease cleavable linker is selected from the group of sequences set forth in SEQ ID NOs: 71-96 and 157-161. In various embodiments, the protease cleavable linker can have additional peptide spacer of variable length on the N-terminus of the cleavable linker or on the C-terminus of the cleavable linker or on both termini of the cleavable linker. In various embodiments, the non-cleavable linker is selected from the group of sequences set forth in SEQ ID NOs: 107-127. In various embodiments, the linker is either flexible or rigid and of a variety of lengths.

In various embodiments, the D2 and D3 domains of the VitoKine construct are placed at the N-terminus of the D1 domain as depicted in FIG. 1. In various embodiments, the D2 and D3 domains of the VitoKine construct are placed either at the C-terminus of the D1 domain as depicted in FIG. 1.

In various embodiments, the D1, D2 and D3 domains of the VitoKine construct can be monomer or dimer or a combination of dimer and monomer, such as D1 is dimer and D2 and D3 are monomer.

In another aspect, the present disclosure provides a method for treating cancer or cancer metastasis in a subject, comprising administering a therapeutically effective amount of the pharmaceutical compositions of the invention to a subject in need thereof. In one embodiment, the subject is a human subject. In various embodiments, the cancer is selected from pancreatic cancer, gastric cancer, liver cancer, breast cancer, ovarian cancer, colorectal cancer, melanoma, leukemia, myelodysplastic syndrome, lung cancer, prostate cancer, brain cancer, bladder cancer, head-neck cancer, or rhabdomyosarcoma or any cancer.

In another aspect, the present disclosure provides a method for treating cancer or cancer metastasis in a subject, comprising administering a therapeutically effective amount of the pharmaceutical compositions of the invention in combination with a second therapy selected from the group consisting of: cytotoxic chemotherapy, immunotherapy, small molecule kinase inhibitor targeted therapy, surgery, radiation therapy, stem cell transplantation, cell therapies including CAR-T, CAR-NK, iPS induced CAR-T or iPS induced CAR-NK and vaccine such as Bacille Calmette-Guerine (BCG). In various embodiments, the combination therapy may comprise administering to the subject a therapeutically effective amount of immunotherapy, including, but are not limited to, treatment using depleting antibodies to specific tumor antigens; treatment using antibody-drug conjugates; treatment using agonistic, antagonistic, or blocking antibodies to co-stimulatory or co-inhibitory molecules (immune checkpoints) such as CTLA-4, PD-1, PD-L1, CD40, OX-40, CD137, GITR, LAGS, TIM-3, Siglec 7, Siglec 8, Siglec 9, Siglec 15 and VISTA; treatment using bispecific T cell engaging antibodies (BiTE®) such as blinatumomab: treatment involving administration of biological response modifiers such as IL-12, IL-21, GM-CSF, IFN-α, IFN-β and IFN-γ; treatment using therapeutic vaccines such as sipuleucel-T; treatment using dendritic cell vaccines, or tumor antigen peptide vaccines; treatment using chimeric antigen receptor (CAR)-T cells; treatment using CAR-NK cells; treatment using tumor infiltrating lymphocytes (TILs); treatment using adoptively transferred anti-tumor T cells (ex vivo expanded and/or TCR transgenic); treatment using TALL-104 cells; and treatment using immunostimulatory agents such as Toll-like receptor (TLR) agonists CpG and imiquimod; and treatment using vaccine such as BCG; wherein the combination therapy provides increased effector cell killing of tumor cells, i.e., a synergy exists between the VitoKine constructs and the immunotherapy when co-administered.

In another aspect, the present disclosure provides a method for treating virus infection in a subject, comprising administering a therapeutically effective amount of the pharmaceutical compositions of the invention to a subject in need thereof. In one embodiment, the subject is a human subject. In various embodiments, the virus is HIV.

In another aspect, the present disclosure provides a method for treating virus infection in a subject, comprising administering a therapeutically effective amount of the pharmaceutical compositions of the invention in combination with a second therapy including but are not limited to acyclovir, Epclusa, Mavyret, Zidovudine, and Enfuvirtide.

In another aspect, the present disclosure provides a method for treating an autoimmune disease in a subject, comprising administering a therapeutically effective amount of the pharmaceutical compositions of the invention to a subject in need thereof. In one embodiment, the subject is a human subject. In various embodiments, the autoimmune disease is selected from the group consisting of systemic lupus erythematosus (SLE), pemphigus vulgaris, myasthenia gravis, hemolytic anemia, thrombocytopenia purpura, Grave's disease, Sjogren's disease, dermatomyositis, Hashimoto's disease, polymyositis, inflammatory bowel disease, multiple sclerosis (MS), diabetes mellitus, rheumatoid arthritis, and scleroderma.

In another aspect, the present disclosure provides a method for treating an inflammatory disease in a subject, comprising administering a therapeutically effective amount of the pharmaceutical compositions of the invention to a subject in need thereof. In one embodiment, the subject is a human subject. In various embodiments, the inflammatory disease is selected from the group consisting of Crohn's disease, ulcerative colitis, collagenous colitis, lymphocytic colitis, ischemic colitis, diversion colitis, Behcet's syndrome and indeterminate colitis.

In various embodiments, the inflammatory disease is selected from the group consisting of other autoimmune and inflammatory diseases such as: Achalasia, Adult Still's Disease, Agammaglobulinemia, Amyloidosis, Anti-GBM/Anti-TBM Nephritis, Antiphospholipid Syndrome, Autoimmune Angioedema, Autoimmune Dysautonomia, Autoimmune Encephalomyelitis, Autoimmune Inner Ear Disease, Autoimmune Oophoritis, Autoimmune Orchitis, Autoimmune Pancreatitis, Autoimmune Retinopathy, Autoimmune Urticaria, Axonal & Neuronal Neuropathy, Balo Disease, Behcet's Disease, Benign Mucosal Pemphigoid, Castleman Disease, Chagas Disease, Chronic Inflammatory Demyelinating Polyneuropathy, Chronic Recurrent Multifocal Osteomyelitis, Churg-Strauss Syndrome, Cicatricial Pemphigoid, Cogan's Syndrome, Coxsackie Myocarditis, CREST Syndrome, Dermatitis Herpetiformis, Devic's Disease/Neuromyelitis Optica, Discoid Lupus, Dressler's Syndrome, Eosinophilic Esophagitis, Eosinophilic Fascitis, Erythema Nodosum, Essential Mixed Cryoglobulinemia, Fibrosing Alveolitis, Giant Cell Arteritis, Giant Cell Myocarditis, Henoch-Schonlein Purpura, Herpes Gestationis or Pemphigoid Gestationis, IgA Nephropathy, IgG4-Related Sclerosing Disease, Immune-Related Adverse Events, Inclusion Body Myositis, Interstitial Cystitis, Juvenile Arthritis, Juvenie Myositis, Lambert-Eaton Syndrome, Leukocytoclastic Vasculitis, Lichen Planus, Lichen Sclerosis, Ligneous Conjunctivitis, Linear IgA Disease, Lyme Disease Chronic, Meniere's Disease, Microscopic Polyangitis, Mixed Connective Tissue Disease, Mooren's Ulcer, Mucha-Habermann Disease, Multifocal Motor Neuropathy, Optic Neuritis, Palindromic Rheumatism, PANDAS, Paraneoplastic Cerebellar Degeneration, Parry Romberg Syndrome, Pars Planitis, Parsonage-Turner Syndrome, Perivenous Encephalomyelitis, POEMS Syndrome, Polyarteritis *Nodosa*, Polyglandular Syndromes, Polymyalgia Rheumatica, Postmyocardial Infarction Syndrome, Post Pericardiotomy Syndrome, Primary Sclerosis Cholangitis, Progesterone Dematitis, Psoriatic Arthritis, Pure Red Cell Aplasia, Pyoderma Gangrenosum, Reynaud's Phenomenon, Reflex Sympathetic Dystrophy, Relapsing Polychondritis, Retroperitoneal Fibrosis, Scleritis, Sperm & Testicular Autoimmunity, Stiff Person Syndrome, Subacute Bacterial Endocarditis, Susac's Syndrome, Sympathetic Ophthalmia, Takayasu's Arteritis, Thrombocytopenic Purpura, Tolosa-Hunt Syndrome, Transverse Myeltitis, Undifferentiated Connective Tissue Disease, Vogt-Koyonagi-Harada Disease.

In another aspect, the disclosure provides uses of the VitoKine constructs for the preparation of a medicament for the treatment of cancer.

In another aspect, the disclosure provides uses of the VitoKine constructs for the preparation of a medicament for the treatment of virus infection.

In another aspect, the disclosure provides uses of the VitoKine constructs for the preparation of a medicament for the treatment of an autoimmune disease.

In another aspect, the disclosure provides uses of the VitoKine constructs for the preparation of a medicament for the treatment of inflammation.

In another aspect, the disclosure provides use of the VitoKine constructs of the invention in combination with a second therapeutic agent or cell therapy capable of treating cancer, virus infection, or an autoimmune disease, or inflammation.

In another aspect, the present disclosure provides isolated nucleic acid molecules comprising a polynucleotide encoding a VitoKine construct of the present disclosure. In another aspect, the present disclosure provides vectors comprising the nucleic acids described herein. In various embodiments, the vector is an expression vector. In another aspect, the present disclosure provides isolated cells comprising the nucleic acids of the disclosure. In various embodiments, the cell is a host cell comprising the expression vector of the disclosure. In another aspect, methods of making the VitoKine constructs are provided by culturing the host cells under conditions promoting expression of the proteins or polypeptides.

In another aspect, the present disclosure provides a pharmaceutical composition comprising the isolated VitoKine constructs in admixture with a pharmaceutically acceptable carrier.

BRIEF DESCRIPTION OF THE FIGURES

FIG. 3 depicts protein profile of A) SDS-PAGE, in the absence and presence of reducing agent, B) size exclusion chromatogram, of exemplary IL-15 VitoKine P-0315 after protein A purification.

FIG. 6 depicts the induction of CD69 expression on A) CD8+ T cells, and B) NK (CD56+) cells of human PBMC by illustrative VitoKine constructs (P-0204, P-0205, and P-0206) with different linker lengths in comparison with highly active IL-15/IL-15Rα Fc fusion protein P-0165.

FIG. 8 depicts the proliferation of A) NK (CD56+) cell, and B) CD8+ T cell in human PBMC by illustrative Fc IL-15 VitoKine constructs (P-0351, P-0488, and P-0489) with different L2 linker sequence compositions measured by FACS in comparison to IL-15/IL-15Rα Fc fusion protein P-0156.

FIG. 10 depicts SDS-PAGE analysis of Fc IL-15 VitoKine P-0203 proteolysis using uPA under different conditions to determine the appropriate reaction conditions for complete cleavage.

FIG. 12 depicts A) SDS-PAGE analysis of Fc IL-15 VitoKine P-0315 before and after proteolysis by MMP-2. The gel also shows the profile of MMP-2 digested and Protein A purified P-0315; B) protein profile of the Active Form 2 of VitoKine P-0315, which was resulted from MMP-2 digestion followed by Protein A purification; C) protein profile of Active Form 3 of VitoKine P-0315, which was resulted from dual proteolysis by both MMP-2 and uPA, followed by Protein A purification in flow-through mode.

FIG. 13 depicts activity assessment of the protease (uPA) activated Fc IL-15 VitoKine P-0203 by analyzing the induction of activation marker CD69 on A) CD56+ NK cells and B) CD8+ T cells. P-0165, a highly active IL-15 fusion protein was included as the positive control.

FIG. 14 depicts activity assessment of two forms of protease activated Fc IL-15 VitoKine P-0315 by analyzing the induction of activation marker CD69 on A) CD56+ NK cells and B) CD8+ T cells. P-0315 Active Form 2 was resulted from MMP-2 digestion and P-0315 Active Form 3 was resulted from dual proteolysis by both MMP-2 and uPA. P-0313, a highly active IL-15 fusion protein with structural resemblance to Active Form 2 of P-0315, was included as the positive control.

FIG. 15 depicts activity assessment of MMP-2 activated IL-15 VitoKine P-0315 (Active Form 2) by analyzing the induction of proliferation marker Ki67 on A) CD56+ NK cells and B) CD8+ T cells. P-0351, contains both non-cleavable L1 and L2 linkers and shares the same L2 linker length with P-0315, was included for comparison.

FIG. 16 depicts dose- and time-dependent effects of the cleavable Fc IL-15 VitoKine P-0315, the non-cleavable Fc IL-15 VitoKine P-0351 on the expansion of CD8+T (A), NK cells (B), and white blood cells (C) in peripheral blood following a single injection in Balb/C mice. The fully active IL-15 Fc fusion P-0313 was included for comparison. Blood was collected on days −1, 3, 5, and 7 for lymphocyte phenotyping by FACS analysis. Data are expressed as mean±SEM. Statistical analysis was performed by two-way anova followed by Tukey's post hoc test. ** p<0.0001, * p<0.001, * p<0.05 compared to PBS group at respective time point.

FIG. 18 depicts A) % CD8+ T cells and B) % NK cells in total blood lymphocytes in CT26 metastasis mice. Cell numbers were determined by flow cytometry 4 days after three Q5D i.p. injections of P-0315, P-0351, P-0313, or PBS control. All comparisons versus PBS group; ** p<0.0001;  p<0.01; *p<0.05.

FIG. 21 depicts the immuno-pharmacodynamic profiling of peripheral mice blood following P-0315 or P-0313 treatment in CT26 murine colorectal carcinoma tumor model. Following two Q5D treatments initiated 11 days after tumor implantation, increases in the number of circulating (per µl whole blood) A) total white blood cells, B) NK cells, and C) CD8+ T cells on day 19 were determined by flow cytometry. ** P<0.0001 vs PBS FIG. 22 depicts the immuno-pharmacodynamic profiling of the spleens following P-0315 or P-0313 treatment in CT26 murine colorectal carcinoma tumor model. Following two Q5D treatments initiated 11 days after tumor implantation, increases in the number of splenic A) total white blood cells, B) NK cells, and C) CD8+ T cells on day 19 were determined by flow cytometry. **, P<0.0001, * P<0.05, vs PBS.

FIG. 23 depicts activity comparison of the non-cleavable Fc IL-15 VitoKine P-0351 and Benchmark by analyzing the induction of proliferation marker Ki67 on A) CD56+ NK cells and B) CD8+ T cells.

FIG. 24 depicts protein profile of A) SDS-PAGE, in the absence and presence of reducing agent, and B) size exclusion chromatogram, of exemplary IL-2 VitoKine P-0320 after protein A purification.

FIG. 25 depicts activity assessment of two Fc IL-2 VitoKines, P-0320 (IL-2 fused at the C-terminal of Fc) and P-0329 (IL-2 fused at the N-terminal Fc) by analyzing the pStat5 levels in A) CD4+ Foxp3+/CD25$^{high}$ Treg and B) CD4+ Foxp3-/D25$^{low}$ CD4 conventional T cell subsets in fresh human PBMC. P-0250, an IL-2 Fc fusion protein with high activity, was included as the positive control.

FIG. 27 depicts A) SDS-PAGE analysis of IL-2 VitoKine P-0382 and its activation by MMP-2 digestion followed by Ni-Excel purification. B) protein profile of the MMP-2 activated P-0382 purified by Protein A in bind-and-elute mode.

FIG. 28 depicts activity assessment of the protease activated IL-2 VitoKines P-0382 by analyzing the pStat5 levels in A) CD4+ Foxp3+/CD25$^{high}$ Treg and B) CD4+ Foxp3-/D25$^{low}$CD4 conventional T (Tconv) cell subsets in fresh human PBMC. The two activated samples were either purified by Ni-Excel resin to remove the protease (activ. 1) or by Protein A to remove both the protease and IL-2RαSushi domain resulted from proteolysis (activ. 2). P-0250, an IL-2 Fc fusion protein with high activity, was included as the positive control.

FIG. 29 depicts activity assessment of Fc IL-2 VitoKine P-0398 before and after MMP-2 proteolysis by analyzing the pStat5 levels in A) CD4+ Foxp3+/CD25$^{high}$ Treg and B) CD4+ Foxp3-/D25$^{low}$ CD4 Tconv cell subsets in fresh human PBMC. P-0382, differs from P-0398 only in the L2 linker length, and P-0250, an IL-2 Fc fusion protein with high activity, were included for comparison.

FIG. 30 depicts activity assessment of Fc IL-15 VitoKine P-0315 versus antibody IL-15 VitoKine P-0485 by analyzing the induction of proliferation marker Ki67 on A) CD56+ NK cells and B) CD8+ T cells determined by flow cytometry.

Figure 31:
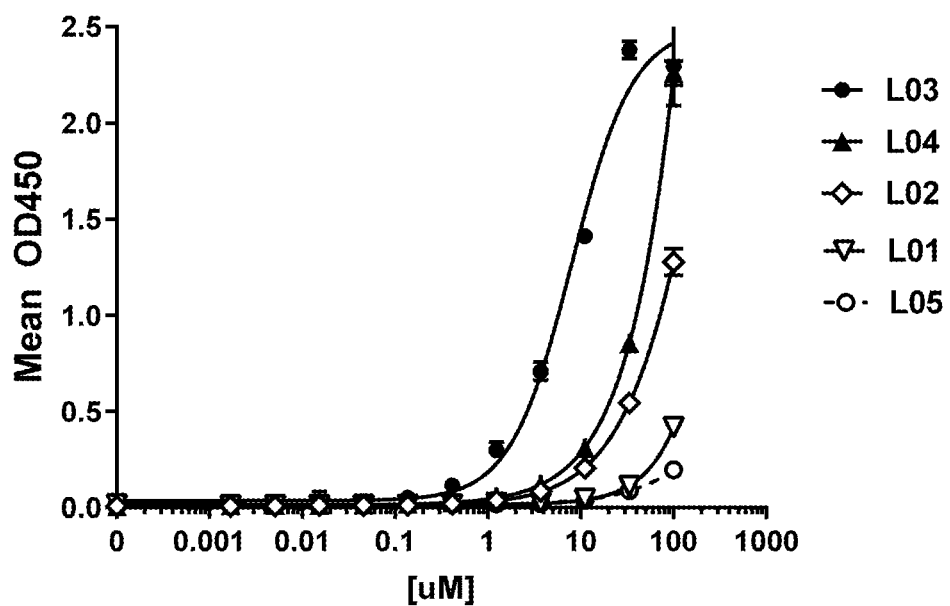

FIG. 31 depicts blocking peptides (L01, L02, L03, L04 and L05) binding to IL-15 in ELISA format.

Figure 32:
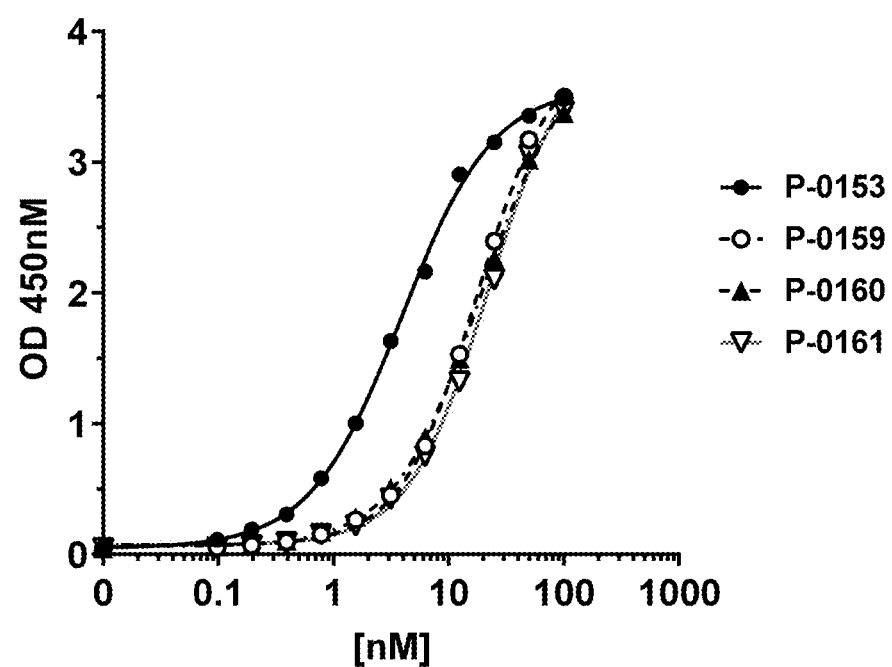

FIG. 32 depicts binding of IL-15 fusion proteins (P-0153, P-0159, P-0160 and P-0161) containing IL-2Rβ-based blocking peptide to IL-2Rβ coated on the plate.

FIG. 33 depicts size exclusion chromatogram of four IL-2 VitoKines (P-0320, P-0382, P-0362, and P-0379) (B-E) and one P-0250 counterpart Fc fusion protein harboring a single amino acid substitution S125I in IL-2 versus that of IL-2 Fc fusion protein P-0250 (A).

Figure 34A:
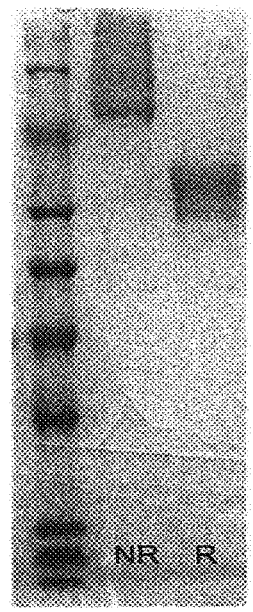
Figure 34B:
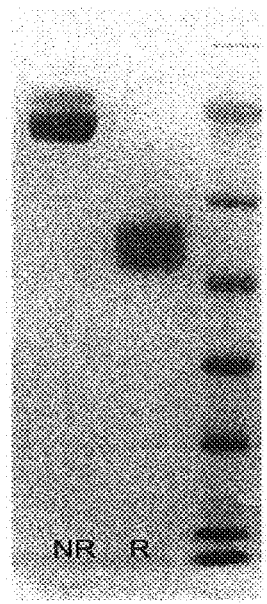

FIG. 34 depicts the SDS-PAGE gel of Fc IL-15 VitoKines P-0389 (A) in comparison with that of P-0315 (B).

MODE(S) FOR CARRYING OUT THE DISCLOSURE

Figure 1:
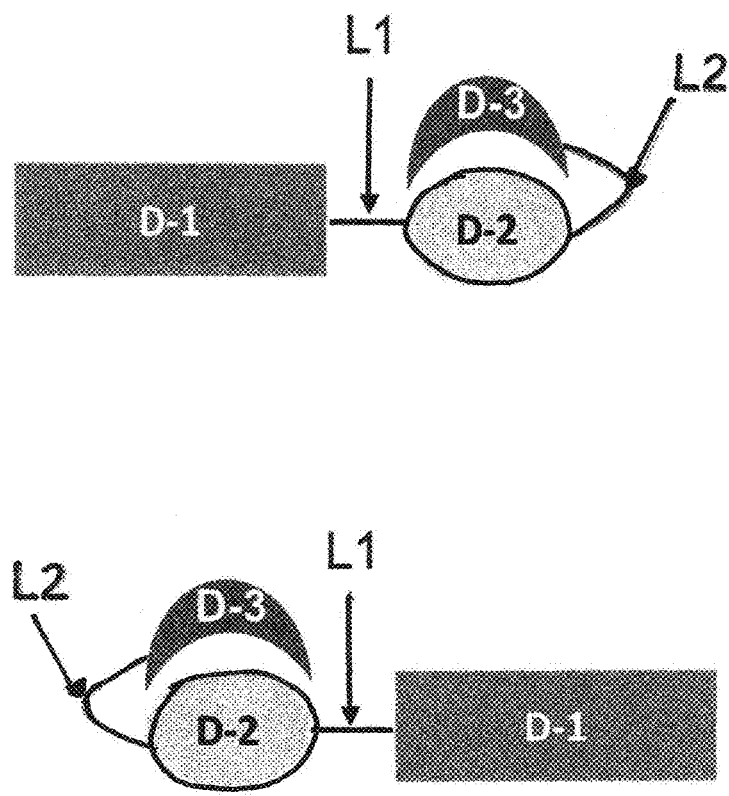
FIG. 1 depicts a representative VitoKine construct formats of the present invention.
Figure 2:
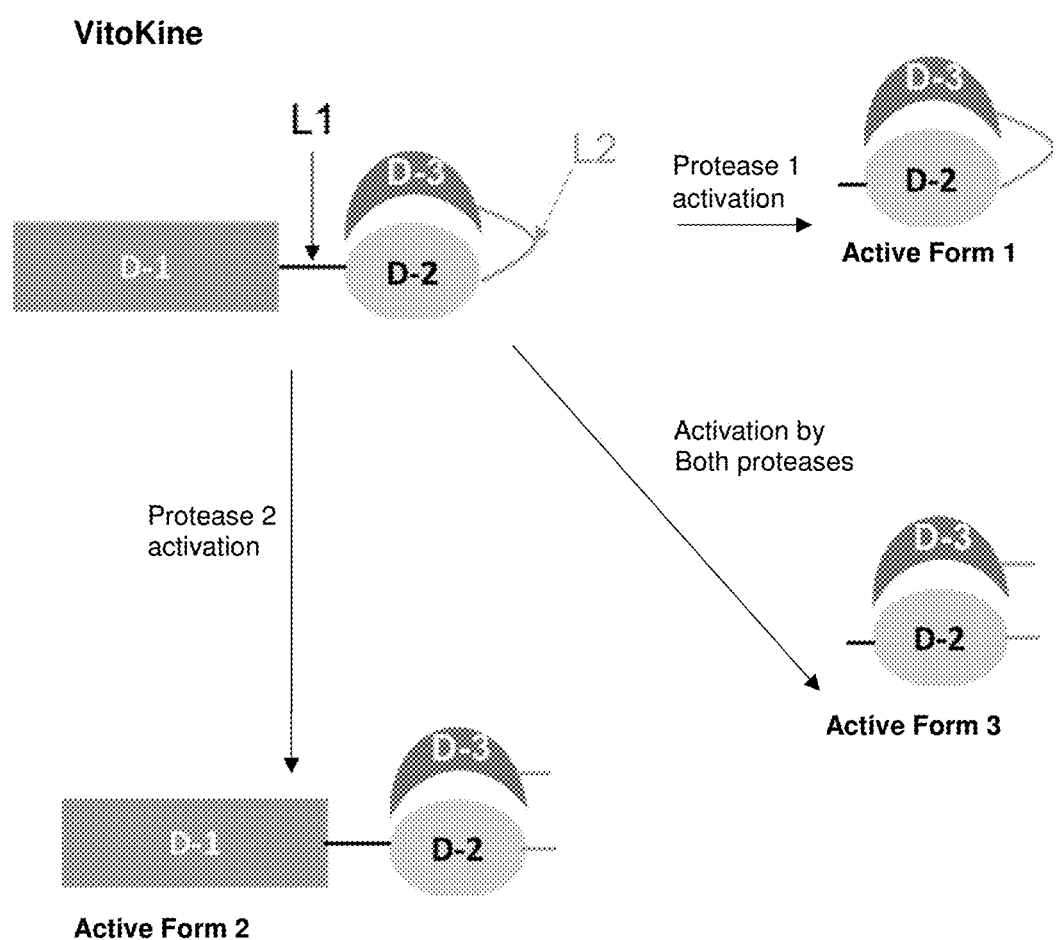
FIG. 2 depicts the proposed mechanism of activation for the VitoKine constructs. The exemplary VitoKine comprises two protease cleavable linkers; protease 1 activation resulted from cleavage of L1 linker yields Active Form 1; protease 2 activation resulted from cleavage of L2 linker yields Active Form 2; activation by both proteases resulted from cleavage of L1 and L2 linkers yields Active Form 3.

The present disclosure provides novel "VitoKine" constructs as a platform technology to reduce systemic on-target toxicity and enhance therapeutic index of cytokines intended for use in the treatment of cancer, virus infection, autoimmune diseases, or inflammatory diseases. Referring to FIG. 1, the VitoKine platform is defined by the constructs as depicted in FIG. 1 and the proposed methods of activation as depicted in FIG. 2. Referring to FIG. 1, the novel VitoKine constructs of the present invention comprise 3 domains: 1) a D1 domain ("D1") selected from the group consisting of: a tissue targeting domain; a half-life extension domain; or a dual functional moiety domain, 2) a D2 domain ("D2") which is an "active moiety domain", and 3) a D3 domain ("D3") which is a "concealing moiety domain". Importantly, the D3 domain is capable of concealing or attenuating the functional activity of D2 until activated at the intended site of therapy.

The three domains are linked using linkers having variable length and rigidity coupled with protease cleavable sequences, which are peptide substrates of specific protease subtypes with elevated or dysregulated expression in the disease sites, thus allowing for a functional D2 domain to be revealed or released at the site of disease. The linker length and composition were optimized to drive the best concealing of the accessibility of D2 domain to its receptors to reduce its systemic engagement, while maintaining the stability of the VitoKines in the blood circulation and allowing efficient cleavage after encountering specific proteases at intended site of disease. The design of the "VitoKine" was also steered rationally based on the knowledge of the molecular interaction of cytokines with their cognate receptors. Cytokine receptors typically function as an oligomeric complex consisting of two to four receptor subunits. The different subunits perform specialized functions such as ligand-binding or signal transduction. The alpha subunit of the cytokine receptors is the binding receptor that confers ligand specificity, enhances the ligand interaction with the signaling receptors and converts the signaling receptor from low affinity to high affinity. The D3 domain of the VitoKine is, therefore, preferably the cognate binding receptor of the D2 domain. After cleavage, the D3 domain may dissociate or re-associate with the D2 domain and fully restore the binding and signaling activity of the D2 domain locally. Therefore, the D3 domain may have a dual role in regulating the function of the D2 domain. It keeps the D2 domain inert when the VitoKine is inactivated and may participate the D2 function when the VitoKine is cleaved and activated. However, the D3 domain can be any protein, peptide, antibody, antibody fragment or polymer or nucleotides that are able to conceal the activity of D2.

In another aspect, addition of the D3 domain can also result in significantly improved developability profile of the VitoKine construct with enhanced expression yield and reduced aggregation propensity.

The D1 domain can be a half-life extension domain to prolong the circulating half-life of the VitoKine in addition to serve as an additional domain to conceal the functional activity of the D2 domain. The D1 domain can also be disease- or tissue-targeting motif that guides the VitoKine specifically to the site of interest and restrict the activation of the VitoKine locally to further improve the therapeutic index. Consequently, the "VitoKine" platform allows selective activation of the cytokines at the intended site and have the benefits of reducing systemic toxicity while increasing the therapeutic effect at sites of disease, thus improving its therapeutic index.

The D2 domain of the VitoKine construct is the active moiety but remains inert until activated locally by proteases that are upregulated in diseased tissues, this will limit binding of the active moiety to the receptors in the peripheral or on the cell-surface of non-diseased cells or tissue to prevent over-activation of the pathway and reduce undesirable "on-target" "off tissue" toxicity. Additionally, the inertness of the VitoKine active moiety prior to protease activation will significantly decrease the potential antigen sink, and thus, prolong the in vivo half-life and result in improved biodistribution, bioavailability and efficacy at intended sites of therapy.

Further, based on the current invention, the VitoKine platform can enhance protein developability profile, including but not limited to, improving expression level and reducing aggregation propensity, such as when using cognate receptor alpha as D3 domain.

Although the cleavable linkages are preferable for most VitoKines to limit the systemic activation and release the active domain at the intended site after administration, non-cleavable linkers may be desired to provide persistent systemic exposure of pharmacologically active VitoKine and to improve therapeutic efficacy.

In exemplary embodiments, the VitoKine constructs comprise an active moiety (D2) that is IL-15-based, IL-15 variant-based, IL-2-based, or an IL-2 variant-based. For these IL-15 and/or IL-2 based VitoKine constructs, the unique and non-signaling α-subunit of receptors for each cytokine is used as one of the concealing moiety domain (D3) via a protease-cleavable linker to reversibly conceal the cytokine activity. Depending on the contrastive properties of each receptor complex and distinct requirements for different disease indications indented to be treated by the VitoKine molecules, the concealing α-subunit may preferably be complexed with the activated cytokine through non-covalent association after protease cleavage of the linker (e.g., for IL-15), or preferred to dissociate away (e.g., for IL-2 in selectively expanding Treg cells). As a result, amino acid modifications of the α-receptor to modulate the binding affinity to its cognate cytokine may be needed.

This concept of coupling a cognate receptor, a protein, an antibody, an antibody fragment, a binding peptide to a cytokine via an activatable linker to conceal its functional activity until activated at the intended sites of therapy can be tailored to various cytokines, including, but not limited to, IL-4, IL-7, IL-9, IL-10, IL-12, IL-22, IL-23 and TGFβ, chemokines such as CXCR3, or various growth factors, such as TNF family, TGFα and TGFβ and hormones. The same concept can also be applied to other proteins to create proproteins to achieve enhanced targeting to the disease site and broaden therapeutic utility.

Definitions

The terms "polypeptide", "peptide" and "protein" are used interchangeably herein to refer to a polymer of amino acid residues. In various embodiments, "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (amino group when participating in a peptide bond) of an amino acid at any other location within the peptide. Similarly, the term "carboxy terminus" (abbreviated C-terminus) refers to the free carboxyl group on the carboxy terminus of a peptide or the carboxyl group of an amino acid at any other location within the peptide. Peptides also include essentially any polyamino acid including, but not limited to, peptide mimetics such as amino acids joined by an ether as opposed to an amide bond Polypeptides of the disclosure include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (5) confer or modify other physicochemical or functional properties.

An amino acid "substitution" as used herein refers to the replacement in a polypeptide of one amino acid at a particular position in a parent polypeptide sequence with a different amino acid. Amino acid substitutions can be generated using genetic or chemical methods well known in the art. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" refers to the substitution in a polypeptide of an amino acid with a functionally similar amino acid. The following six groups each contain amino acids that are conservative substitutions for one another:

1) Alanine (A), Serine (S), and Threonine (T)
2) Aspartic acid (D) and Glutamic acid (E)
3) Asparagine (N) and Glutamine (Q)
4) Arginine (R) and Lysine (K)
5) Isoleucine (I), Leucine (L), Methionine (M), and Valine (V)
6) Phenylalanine (F), Tyrosine (Y), and Tryptophan (W)

A "non-conservative amino acid substitution" refers to the substitution of a member of one of these classes for a member from another class. In making such changes, according to various embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, J. Mol. Biol. 157:105-131). It is known that certain amino acids may be substituted for other amino acids having a similar hydropathic index or score and still retain a similar biological activity. In making changes based upon the hydropathic index, in various embodiments, the substitution of amino acids whose hydropathic indices are within ±2 is included. In various embodiments, those that are within ±1 are included, and in various embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as disclosed herein. In various embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in various embodiments, the substitution of amino acids whose hydrophilicity values are within ±2 is included, in various embodiments, those that are within ±1 are included, and in various embodiments, those within ±0.5 are included.

Exemplary amino acid substitutions are set forth in Table 1.

TABLE 1

| Original Residues | Exemplary Substitutions | Preferred Substitutions |
|---|---|---|
| Ala | Val, Leu, Ile | Val |
| Arg | Lys, Gln, Asn | Lys |
| Asn | Gln | |
| Asp | Glu | |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of polypeptides as set forth herein using well-known techniques. In various embodiments, one skilled in the art may identify suitable areas of the molecule that may be changed without destroying activity by targeting regions not believed to be important for activity. In other embodiments, the skilled artisan can identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, the skilled artisan can predict the importance of amino acid residues in a polypeptide that correspond to amino acid residues important for activity or structure in similar polypeptides. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of a polypeptide with respect to its three-dimensional structure. In various embodiments, one skilled in the art may choose to not make radical changes to amino acid residues predicted to be on the surface of the polypeptide, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

The term "polypeptide fragment" and "truncated polypeptide" as used herein refers to a polypeptide that has an amino-terminal and/or carboxy-terminal deletion as compared to a corresponding full-length protein. In various embodiments, fragments can be, e.g., at least 5, at least 10, at least 25, at least 50, at least 100, at least 150, at least 200, at least 250, at least 300, at least 350, at least 400, at least 450, at least 500, at least 600, at least 700, at least 800, at least 900 or at least 1000 amino acids in length. In various embodiments, fragments can also be, e.g., at most 1000, at most 900, at most 800, at most 700, at most 600, at most 500, at most 450, at most 400, at most 350, at most 300, at most 250, at most 200, at most 150, at most 100, at most 50, at most 25, at most 10, or at most 5 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

The terms "polypeptide variant", "hybrid polypeptide" and "polypeptide mutant" as used herein refers to a polypeptide that comprises an amino acid sequence wherein one or more amino acid residues are inserted into, deleted from and/or substituted into the amino acid sequence relative to another polypeptide sequence. In various embodiments, the number of amino acid residues to be inserted, deleted, or substituted can be, e.g., at least 1, at least 2, at least 3, at least 4, at least 5, at least 10, at least 25, at least 50, at least 75, at least 100, at least 125, at least 150, at least 175, at least 200, at least 225, at least 250, at least 275, at least 300, at least 350, at least 400, at least 450 or at least 500 amino acids in length. Hybrids of the present disclosure include fusion proteins.

A "derivative" of a polypeptide is a polypeptide that has been chemically modified, e.g., conjugation to another chemical moiety such as, for example, polyethylene glycol, albumin (e.g., human serum albumin), phosphorylation, and glycosylation.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm and means that a given sequence is at least 80% identical to another length of another sequence. In various embodiments, the % identity is selected from, e.g., at least 60%, at least 65%, at least 70%, at least 75%, at least 80%, at least 85%, at least 90%, at least 95%, or at least 99% or more sequence identity to a given sequence. In various embodiments, the % identity is in the range of, e.g., about 60% to about 70%, about 70% to about 80%, about 80% to about 85%, about 85% to about 90%, about 90% to about 95%, or about 95% to about 99%.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. In various embodiments, the % homology is selected from, e.g., at least 60%, at least 65%, at least 70%, at least 75%, at least 80%, at least 85%, at least 90%, at least 95%, or at least 99% or more sequence homology to a given sequence. In various embodiments, the % homology is in the range of, e.g., about 60% to about 70%, about 70% to about 80%, about 80% to about 85%, about 85% to about 90%, about 90% to about 95%, or about 95% to about 99%.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., J. Mol. Biol. 215:403-10, 1990 (with special reference to the published default setting, i.e., parameters w=4, t=17) and Altschul et al., Nucleic Acids Res., 25:3389-3402, 1997. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix.

In addition to calculating percent sequence identity, the BLAST algorithm also performs a statistical analysis of the similarity between two sequences (see, e.g., Karlin & Altschul, Proc. Nat'l. Acad. Sci. USA, 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is, e.g., less than about 0.1, less than about 0.01, or less than about 0.001.

The term "modification" as used herein refers to any manipulation of the peptide backbone (e.g. amino acid sequence) or the post-translational modifications (e.g. glycosylation) of a polypeptide.

The term "knob-into-hole modification" as used herein refers to a modification within the interface between two immunoglobulin heavy chains in the CH3 domain. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001).

The term "bioactivatable drug" or "VitoKine" as used herein means a compound that is a drug precursor which, following administration to a subject, releases the drug in vivo via some chemical or physiological process such that the bioactivatable drug is converted into a product that is active to the target tissues. A bioactivatable drug is any compound that undergoes bioactivation before exhibiting its pharmacological effects. Bioactivatable drugs can thus be viewed as drugs containing specialized non-toxic protective groups used in a transient manner to alter or to eliminate undesirable properties in the parent molecule.

The term "fusion protein" as used herein refers to a fusion polypeptide molecule comprising two or more genes that originally coded for separate proteins, wherein the components of the fusion protein are linked to each other by peptide-bonds, either directly or through peptide linkers. The term "fused" as used herein refers to components that are linked by peptide bonds, either directly or via one or more peptide linkers.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences. A "cleavable linker" refers to a linker that can be degraded, digested, or otherwise severed to separate the two components connected by the cleavable linker. Cleavable linkers are generally cleaved by enzymes, typically peptidases, proteases, nucleases, lipases, and the like. Cleavable linkers may also be cleaved by environmental cues, such as, for example, changes in temperature, pH, salt concentration, etc.

The term "peptide linker" as used herein refers to a peptide comprising one or more amino acids, typically about 1-30 amino acids. Peptide linkers are known in the art or are described herein. Suitable, non-immunogenic linker peptides include, for example, $(G_4S)_n$, $(SG_4)_n$ or $G_4(SG_4)_n$ peptide linkers. "n" is generally a number between 1 and 10, typically between 2 and 4.

"Pharmaceutical composition" refers to a composition suitable for pharmaceutical use in an animal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, vehicles, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 21st Ed. 2005, Mack Publishing Co, Easton. A "pharmaceutically acceptable salt" is a salt that can be formulated into a compound for pharmaceutical use including, e.g., metal salts (sodium, potassium, magnesium, calcium, etc.) and salts of ammonia or organic amines.

As used herein, "treatment" (and grammatical variations thereof such as "treat" or "treating") refers to clinical intervention in an attempt to alter the natural course of a disease in the individual being treated and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

The term "effective amount" or "therapeutically effective amount" as used herein refers to an amount of a compound or composition sufficient to treat a specified disorder, condition or disease such as ameliorate, palliate, lessen, and/or delay one or more of its symptoms. In reference to cancers or other unwanted cell proliferation, an effective amount comprises an amount sufficient to: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. An effective amount can be administered in one or more administrations.

The phrase "administering" or "cause to be administered" refers to the actions taken by a medical professional (e.g., a physician), or a person controlling medical care of a patient, that control and/or permit the administration of the agent(s)/compound(s) at issue to the patient. Causing to be administered can involve diagnosis and/or determination of an appropriate therapeutic regimen, and/or prescribing particular agent(s)/compounds for a patient. Such prescribing can include, for example, drafting a prescription form, annotating a medical record, and the like. Where administration is described herein, "causing to be administered" is also contemplated.

The terms "patient," "individual," and "subject" may be used interchangeably and refer to a mammal, preferably a human or a non-human primate, but also domesticated mammals (e.g., canine or feline), laboratory mammals (e.g., mouse, rat, rabbit, hamster, guinea pig), and agricultural mammals (e.g., equine, bovine, porcine, ovine). In various embodiments, the patient can be a human (e.g., adult male, adult female, adolescent male, adolescent female, male child, female child) under the care of a physician or other health worker in a hospital, psychiatric care facility, as an outpatient, or other clinical context. In various embodiments, the patient may be an immunocompromised patient or a patient with a weakened immune system including, but not limited to patients having primary immune deficiency, AIDS; cancer and transplant patients who are taking certain immunosuppressive drugs; and those with inherited diseases that affect the immune system (e.g., congenital agammaglobulinemia, congenital IgA deficiency). In various embodiments, the patient has an immunogenic cancer, including, but not limited to bladder cancer, lung cancer, melanoma, and other cancers reported to have a high rate of mutations (Lawrence et al., Nature, 499(7457): 214-218, 2013).

The term "immunotherapy" refers to cancer treatments which include, but are not limited to, treatment using depleting antibodies to specific tumor antigens; treatment using antibody-drug conjugates; treatment using agonistic, antagonistic, or blocking antibodies to co-stimulatory or co-inhibitory molecules (immune checkpoints) such as CTLA-4, PD-1, PDL-1, CD40, OX-40, CD137, GITR, LAGS, TIM-3, SIRPa, CD47, GITR, ICOS, CD27, Siglec 7, Siglec 8, Siglec 9, Siglec 15 and VISTA, CD276, CD272, TIM-3, B7-H4; treatment using bispecific T cell engaging antibodies (BiTE®) such as blinatumomab: treatment involving administration of biological response modifiers such as IL-2, IL-4, IL-7, IL-10, IL-12, IL-15, IL-21, IL-22, GM-CSF, IFN-α, IFN-β and IFN-γ, TGF-β antagonist or TGF-β trap; treatment using therapeutic vaccines such as sipuleucel-T; treatment using therapeutic virus, including, but not limited to oncolytic virus such as T-vec; treatment using dendritic cell vaccines, or tumor antigen peptide or neoantigen vaccines; treatment using NK cells; treatment using chimeric antigen receptor (CAR)-T cells; treatment using CAR-NK cells; treatment using DC or T cells; treatment using treatment using iPS induced-NK cells; treatment using iPS induced-T cells, and treatment using vaccine such as Bacille Calmette-Guerine (BCG); treatment using tumor infiltrating lymphocytes (TILs); treatment using adoptively transferred anti-tumor T cells (ex vivo expanded and/or TOR-T cells); treatment using TALL-104 cells; and treatment using immunostimulatory agents such as Toll-like receptor (TLR) agonists CpG, TLR7, TLR8, TLR9, and imiquimod.

"Resistant or refractory cancer" refers to tumor cells or cancer that do not respond to previous anti-cancer therapy including, e.g., chemotherapy, surgery, radiation therapy, stem cell transplantation, and immunotherapy. Tumor cells can be resistant or refractory at the beginning of treatment, or they may become resistant or refractory during treatment. Refractory tumor cells include tumors that do not respond at the onset of treatment or respond initially for a short period but fail to respond to treatment. Refractory tumor cells also include tumors that respond to treatment with anticancer therapy but fail to respond to subsequent rounds of therapies. For purposes of this invention, refractory tumor cells also encompass tumors that appear to be inhibited by treatment with anticancer therapy but recur up to five years, sometimes up to ten years or longer after treatment is discontinued. The anticancer therapy can employ chemotherapeutic agents alone, radiation alone, targeted therapy alone, surgery alone, or combinations thereof. For ease of description and not limitation, it will be understood that the refractory tumor cells are interchangeable with resistant tumor.

The term "tumor associated antigen" (TAA) refers to, e.g., cell surface antigens that are selectively expressed by cancer cells or over-expressed in cancer cells relative to most normal cells. The terms "TAA variant" and "TAA mutant" as used herein refers to a TAA that comprises an amino acid sequence wherein one or more amino acid residues are inserted into, deleted from and/or substituted into the amino acid sequence relative to another TAA sequence. In various embodiments, the number of amino acid residues to be inserted, deleted, or substituted can be, e.g., at least 1, at least 2, at least 3, at least 4, at least 5, at least 10, at least 25, at least 50, at least 75, at least 100, at least 125, at least 150, at least 175, at least 200, at least 225, at least 250, at least 275, at least 300, at least 350, at least 400, at least 450 or at least 500 amino acids in length.

The term "neoantigen" refers to, e.g., cell surface antigens to which the immune system has not previously been exposed, especially one that arises by alteration of host antigens by radiation, chemotherapy, viral infection, neoplastictransformation/mutation, drug metabolism, etc., selectively expressed by cancer cells or over-expressed in cancer cells relative to most normal cells.

The term "antibody" as used herein is used in the broadest sense and encompasses various antibody structures (IgG1, 2, 3, or 4, IgM, IgA, IgE) including but not limited to monoclonal antibodies, polyclonal antibodies, multi-specific antibodies (e.g., bispecific or bifunctional antibodies), and antibody fragments so long as they exhibit the desired antigen-binding activity.

The term "antibody fragment" as used herein refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2, diabodies, linear antibodies, single-chain antibody molecules (e.g. scFv), and single-domain antibodies.

The term "Fab fragment" as used herein refers to an immunoglobulin fragment comprising a VL domain and a constant domain of a light chain (CL), and a VH domain and a first constant domain (CH1) of a heavy chain.

The terms "variable region" or "variable domain" as used herein refers to the domain of an immunoglobulin or antibody heavy or light chain that is generally involved in binding the immunoglobulin or antibody to antigen. The variable domains of the heavy chain and light chain (VH and VL, respectively) of an immunoglobulin or antibody generally have similar structures, with each domain comprising four conserved framework regions (FRs) and three Complementarity-determining regions (CDRs).

A "human immunoglobulin" as used herein is one which possesses an amino acid sequence which corresponds to that of an immunoglobulin produced by a human or a human cell or derived from a non-human source that utilizes human immunoglobulin repertoires or other human immunoglobulin-encoding sequences. This definition of a human immunoglobulin specifically excludes a humanized immunoglobulin comprising non-human antigen-binding residues.

The term "Fc domain" or "Fc region" as used herein is used to define a C-terminal region of an immunoglobulin heavy chain that contains at least a portion of the constant region. The term includes native sequence Fc regions and variant Fc regions. An IgG Fc region comprises an IgG CH2 and an IgG CH3 domain. The CH3 region herein may be a native sequence CH3 domain or a variant CH3 domain (e.g. a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical immunoglobulin heavy chains as herein described. Unless otherwise specified herein, numbering of amino acid residues in the Fc region or constant region is according to the EU numbering system.

The term "effector functions" as used herein refers to those biological activities attributable to the Fc region of an immunoglobulin, which vary with the immunoglobulin isotype. Examples of immunoglobulin effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

The term "regulatory T cell" or "Treg cell" as used herein is meant a specialized type of CD4+ T cell that can suppress the responses of other T cells (effector T cells). Treg cells are characterized by expression of CD4, the a-subunit of the IL-2 receptor (CD25), and the transcription factor forkhead box P3 (FOXP3) (Sakaguchi, Annu Rev Immunol 22, 531-62 (2004)) and play a critical role in the induction and maintenance of peripheral self-tolerance to antigens, including those expressed by tumors.

The term "conventional CD4+ T cells" as used herein is meant CD4+ T cells other than regulatory T cells.

The term "selective activation of Treg cells" as used herein is meant activation of Treg cells essentially without concomitant activation of other T cell subsets (such as CD4+T helper cells, CD8+ cytotoxic T cells, NK T cells) or natural killer (NK) cells. Methods for identifying and distinguishing these cell types are described in the Examples. Activation may include induction of IL-2 receptor signaling (as measured e.g. by detection of phosphorylated STAT5a), induction of proliferation (as measured e.g. by detection of Ki-67) and/or up-regulation of expression of activation markers (such as e.g. CD25).

As used herein, "specific binding" is meant that the binding is selective for the antigen and can be discriminated from unwanted or non-specific interactions. The ability of an immunoglobulin to bind to a specific antigen can be measured either through an enzyme-linked immunosorbent assay (ELISA) or other techniques familiar to one of skill in the art, e.g. Surface Plasmon Resonance (SPR) technique.

The terms "affinity" or "binding affinity" as used herein refers to the strength of the sum total of non-covalent interactions between a single binding site of a molecule (e.g. an antibody) and its binding partner (e.g. an antigen). The affinity of a molecule X for its partner Y can generally be represented by the dissociation constant (KD), which is the ratio of dissociation and association rate constants (koff and kon, respectively). A particular method for measuring affinity is Surface Plasmon Resonance (SPR).

The term "reduced binding", as used herein refers to a decrease in affinity for the respective interaction, as measured for example by SPR. Conversely, "increased binding" refers to an increase in binding affinity for the respective interaction.

The term "polymer" as used herein generally includes, but is not limited to, homopolymers; copolymers, such as, for example, block, graft, random and alternating copolymers; and terpolymers; and blends and modifications thereof. Furthermore, unless otherwise specifically limited, the term "polymer" shall include all possible geometrical configurations of the material. These configurations include, but are not limited to isotactic, syndiotactic, and random symmetries.

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is substantially identical to the nucleotide sequence of the polynucleotide binding partner of the second polynucleotide, or if the first polynucleotide can hybridize to the second polynucleotide under stringent hybridization conditions.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA. The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence-dependent and are different under different environmental parameters. An extensive guide to the hybridization of nucleic acids can be found in Tijssen, 1993, Laboratory Techniques in Biochemistry and Molecular Biology—Hybridization with Nucleic Acid Probes, part I, chapter 2, "Overview of principles of hybridization and the strategy of nucleic acid probe assays", Elsevier, N.Y.; Sambrook et al., 2001, Molecular Cloning: A Laboratory Manual, Cold Spring Harbor Laboratory, 3.sup.rd ed., NY; and Ausubel et al., eds., Current Edition, Current Protocols in Molecular Biology, Greene Publishing Associates and Wiley Interscience, NY.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than about 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes. See Sambrook et al. for a description of SSC buffer. A high stringency wash can be preceded by a low stringency wash to remove background probe signal. An exemplary medium stringency wash for a duplex of, e.g., more than about 100 nucleotides, is 1×SSC at 45° C. for 15 minutes. An exemplary low stringency wash for a duplex of, e.g., more than about 100 nucleotides, is 4-6×SSC at 40° C. for 15 minutes. In general, a signal to noise ratio of 2×(or higher) than that observed for an unrelated probe in the particular hybridization assay indicates detection of a specific hybridization.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe," when used in reference to a polynucleotide, refers to a polynucleotide that is capable of specifically hybridizing to a designated sequence of another polynucleotide. A probe specifically hybridizes to a target complementary polynucleotide but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties. In instances where a probe provides a point of initiation for synthesis of a complementary polynucleotide, a probe can also be a primer.

A "vector" is a polynucleotide that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06. A nucleotide sequence is "operably linked" to a regulatory sequence if the regulatory sequence affects the expression (e.g., the level, timing, or location of expression) of the nucleotide sequence.

A "host cell" is a cell that can be used to express a polynucleotide of the disclosure. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The term "isolated molecule" (where the molecule is, for example, a polypeptide or a polynucleotide) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

A protein or polypeptide is "substantially pure," "substantially homogeneous," or "substantially purified" when at least about 60% to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The terms "label" or "labeled" as used herein refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In various embodiments, labels are attached by spacer arms of various lengths to reduce potential steric hindrance.

The term "heterologous" as used herein refers to a composition or state that is not native or naturally found, for example, that may be achieved by replacing an existing natural composition or state with one that is derived from another source. Similarly, the expression of a protein in an organism other than the organism in which that protein is naturally expressed constitutes a heterologous expression system and a heterologous protein.

It is understood that aspect and embodiments of the disclosure described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the disclosure described herein include "consisting" and/or "consisting essentially of" aspects and variations.

Description of VitoKine Platform

The present invention provides a cytokine-based bioactivatable drug ("VitoKine") platform that aims to reduce systemic mechanism-based toxicities and lead to broader therapeutic utility for proteins, e.g., cytokines. Referring to FIG. 1, the novel VitoKine constructs of the present invention comprise a D1 domain that is a targeting domain, a half-life extension domain, or a dual or multi-functional moiety domain, an "active moiety domain" (D2) and a "concealing moiety domain" (D3). The proposed methods of activation of the VitoKine D2 domain is depicted in FIG. 2. Importantly, because D2 of the VitoKine construct will remain inert or of attenuated activity until activated locally by proteases that are upregulated in diseased tissues, this will limit binding of the active moiety to the receptors in the peripheral or on the cell-surface of non-diseased cells to prevent over-activation of the pathway and reduce undesirable "on-target" "off tissue" toxicity. Additionally, the inertness of the VitoKine active moiety prior to protease activation will significantly decrease the potential antigen or target sink, and thus, prolong the in vivo half-life and result in improved biodistribution and bioavailability at intended sites of therapy.

D1 Domain ("Targeting Domain, Half-Life Extension Domain or Dual or Multi-Functional Moiety Domain")

In various embodiments, the VitoKine constructs of the present invention comprise a D1 domain that is a targeting moiety in the form of an antibody or antibody fragment or protein or peptide to a tumor associated antigen. In various embodiments, the VitoKine constructs of the present invention comprise a D1 domain that is an antibody, an antibody fragment, a protein, or a peptide to an immune checkpoint modulator. In various embodiments, the VitoKine constructs of the present invention comprise a D1 domain that is an antibody or antibody fragment or protein or peptide as an autoimmune modulator. In various embodiments, the VitoKine constructs of the present invention comprise a D1 that functions for retention of the D2 domain at the tissue site, such as tumor microenvironment (TME) or inflammatory tissue sites. In various embodiments, the VitoKine constructs of the present invention comprise a D1 that is bifunctional, e.g., tissue targeting and retention. In various embodiments, the VitoKine constructs of the present invention comprise a D1 domain that is a polymer. In various embodiments, the VitoKine constructs of the present invention comprise a D1 domain that is a half-life extension moiety. In various embodiments, the VitoKine constructs of the present invention comprise a D1 domain that is an Fc domain.

Fc Domains

Immunoglobulins of IgG class are among the most abundant proteins in human blood. Their circulation half-lives can reach as long as 21 days. Fusion proteins have been reported to combine the Fc regions of IgG with the domains of another protein, such as various cytokines and receptors (see, for example, Capon et al., Nature, 337:525-531, 1989; Chamow et al., Trends Biotechnol., 14:52-60, 1996); U.S. Pat. Nos. 5,116,964 and 5,541,087). The prototype fusion protein is a homodimeric protein linked through cysteine residues in the hinge region of IgG Fc, resulting in a molecule similar to an IgG molecule without the heavy chain variable and CH1 domains and light chains. The dimer nature of fusion proteins comprising the Fc domain may be advantageous in providing higher order interactions (i.e. bivalent or bispecific binding) with other molecules. Due to the structural homology, Fc fusion proteins exhibit in vivo pharmacokinetic profile comparable to that of human IgG with a similar isotype.

The term "Fc" refers to molecule or sequence comprising the sequence of a non-antigen-binding fragment of whole antibody, whether in monomeric or multimeric form. The original immunoglobulin source of the native Fc is preferably of human origin and may be any of the immunoglobulins, although IgG1 and IgG2 are preferred. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgM, IgA, IgE) or subclass (e.g., IgG1, IgG2, IgG3, IgG4, IgA1, IgGA2). One example of a native Fc is a disulfide-bonded dimer resulting from papain digestion of an IgG (see Ellison et al. (1982), Nucleic Acids Res. 10: 4071-9). The term "native Fc" as used herein is generic to the monomeric, dimeric, and multimeric forms. Fc domains containing binding sites for Protein A, Protein G, various Fc receptors and complement proteins.

In various embodiments, the term "Fc variant" refers to a molecule or sequence that is modified from a native Fc but still comprises a binding site for the salvage receptor, FcRn. International applications WO 97/34631 (published Sep. 25, 1997) and WO 96/32478 describe exemplary Fc variants, as well as interaction with the salvage receptor, and are hereby incorporated by reference. Furthermore, a native Fc comprises sites that may be removed because they provide structural features or biological activity that are not required for the fusion molecules of the present invention. Thus, in various embodiments, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement such as CDC, (6) binding to an Fc receptor other than a salvage receptor, or (7) antibody-dependent cellular cytotoxicity (ADCC).

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by recombinant gene expression or by other means. In various embodiments, an "Fc domain" refers to a dimer of two Fc domain monomers (SEQ ID NO: 13) that generally includes full or part of the hinge region. In various embodiments, an Fc domain may be mutated to lack effector functions. In various embodiments, each of the Fc domain monomers in an Fc domain includes amino acid substitutions in the CH2 antibody constant domain to reduce the interaction or binding between the Fc domain and an Fcγ receptor. In various embodiments, each subunit of the Fc domain comprises two amino acid substitutions that reduce binding to an activating Fc receptor and/or effector function wherein said amino acid substitutions are L234A and L235A. In various embodiments, each subunit of the Fc domain comprises three amino acid substitutions that reduce binding to an activating Fc receptor and/or effector function wherein said amino acid substitutions are L234A, L235A and G237A (SEQ ID NO: 14).

In various embodiments, an Fc domain may be mutated to further extend in vivo half-life. In various embodiments, each subunit of the Fc domain comprises three amino acid substitutions that enhance binding to human FcRn wherein said amino acid substitutions are M252Y, S254T, and T256E, disclosed in U.S. Pat. No. 7,658,921 (SEQ ID NO: 156). In various embodiments, each subunit of the Fc domain comprises one amino acid substitution that enhanced binding to human FcRn wherein said amino acid substitution is N434A (SEQ ID NO: 166), disclosed in U.S. Pat. No. 7,371,826. In various embodiments, each subunit of the Fc domain comprises one amino acid substitution that enhanced binding to human FcRn wherein said amino acid substitutions are M428L and N434S, disclosed in U.S. Pat. No. 8,546,543. In various embodiments, half-life extension mutations can be combined with amino acid substitutions that reduce binding to an activating Fc receptor and/or effector function.

In various embodiments, each of the two Fc domain monomers in an Fc domain includes amino acid substitutions that promote the heterodimerization of the two monomers. In various other embodiments, heterodimerization of Fc domain monomers can be promoted by introducing different, but compatible, substitutions in the two Fc domain monomers, such as "knob-into-hole" residue pairs. The "knob-into-hole" technique is also disclosed in U.S. Pat. No. 8,216,805. In yet another embodiment, one Fc domain monomer includes the knob mutation T366W and the other Fc domain monomer includes hole mutations T366S, L358A, and Y407V. In various embodiments, two Cys residues were introduced (S354C on the "knob" and Y349C on the "hole" side) that form a stabilizing disulfide bridge (SEQ ID NOS: 15 and 16). The use of heterodimeric Fc may result in monovalent VitoKine construct.

In various embodiments, the Fc domain sequence used to make VitoKine constructs is the human IgG1-Fc domain sequence set forth in SEQ ID NO: 14:

```
                                          (SEQ ID NO: 14)
DKTHTCPPCPAPEAAGAPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPG
``` wherein SEQ ID NO: 14 contains amino acid substitutions (underlined) that ablate FcγR and C1q binding.

In various embodiments, the heterodimeric Fc domain sequence used to make VitoKine constructs is the Knob-Fc domain sequence set forth in SEQ ID NO: 15:

```
                                          (SEQ ID NO: 15)
DKTHTCPPCPAPEAAGAPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSREEMTKNQVSLWCLVK
```

```
                                                 -continued
GFYPSDIAVEWESNGQPENNYKTTPPVLDSDGSFFLYSKLTVDKSRWQQG

NVFSCSVMHEALHNHYTQKSLSLSPG
``` wherein SEQ ID NO: 15 contains amino acid substitutions (underlined) that ablate FcγR and C1q binding.

In various embodiments, the heterodimeric Fc domain sequence used to make VitoKine constructs is the Hole-Fc domain sequence set forth in SEQ ID NO: 16:

```
                                              (SEQ ID NO: 16)
DKTHTCPPCPAPEAAGAPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCREEMTKNQVSLSCAVK

GFYPSDIAVEWESNGQPENNYKTTPPVLDSDGSFFLVSKLTVDKSRWQQG

NVFSCSVMHEALHNHYTQKSLSLSPG
``` wherein SEQ ID NO: 16 contains amino acid substitutions (underlined) that ablate FcγR and C1q binding.

In various embodiments, the Fc domain sequence used to make VitoKine constructs is the IgG1-Fc domain with reduced/abolished effector function and extended half-life and having the amino acid sequence set forth in SEQ ID NO: 156

```
                                             (SEQ ID NO: 156)
DKTHTCPPCPAPEAAGGPSVFLFPPKPKDTLYITREPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPG
``` wherein SEQ ID NO: 156 contains amino acid substitutions (underlined) that ablate FcγR and C1q binding and amino acid substitutions (bold) to extend half-life.

In various embodiments, the Fc domain sequence used to make VitoKine constructs is the human IgG1-Fc domain sequence set forth in SEQ ID NO: 166:

```
                                             (SEQ ID NO: 166)
DKTHTCPPCPAPEAAGAPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHAHYTQKSLSLSPG
``` wherein SEQ ID NO: 166 contains amino acid substitutions (underlined) that ablate FcγR and C1q binding and amino acid substitution (bold) to extend half-life.

In various embodiments, the heterodimeric Fc domain sequence used to make VitoKine constructs is the Knob-Fc domain with extended in vivo half-life sequence set forth in SEQ ID NO: 167:

```
                                             (SEQ ID NO: 167)
DKTHTCPPCPAPEAAGAPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVCTLPPSREEMTKNQVSLWC

LVKGFYPSDIAVEWESNGQPENNYKTTPPVLDSDGSFFLYSKLTVDKSR

WQQGNVFSCSVMHEALHAHYTQKSLSLSPG
``` wherein SEQ ID NO: 167 contains amino acid substitutions (underlined) that ablate FcγR and C1q binding and amino acid substitution (bold) to extend half-life.

In various embodiments, the heterodimeric Fc domain sequence used to make VitoKine constructs is the Hole-Fc domain with extended in vivo half-life sequence set forth in SEQ ID NO: 168:

```
                                             (SEQ ID NO: 168)
DKTHTCPPCPAPEAAGAPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPCREEMTKNQVSLSC

AVKGFYPSDIAVEWESNGQPENNYKTTPPVLDSDGSFFLVSKLTVDKSR

WQQGNVFSCSVMHEALHAHYTQKSLSLSPG
``` wherein SEQ ID NO: 168 contains amino acid substitutions (underlined) that ablate FcγR and C1q binding and amino acid substitution (bold) to extend half-life.

Disease Associated Target or Tumor Associated Antigen Antibodies and Protein/Peptide Binders In various embodiments, D1 can be a targeting moiety in the form of an antibody to a tumor associated antigen (TAA) or another protein or peptide that exhibit binding affinity to a diseased cell or diseased tissue. The TAA can be any molecule, macromolecule, combination of molecules, etc. against which an immune response is desired. The TAA can be a protein that comprises more than one polypeptide subunit. For example, the protein can be a dimer, trimer, or higher order multimer. In various embodiments, two or more subunits of the protein can be connected with a covalent bond, such as, for example, a disulfide bond. In various embodiments, the subunits of the protein can be held together with non-covalent interactions. Thus, the TAA can be any peptide, polypeptide, protein, nucleic acid, lipid, carbohydrate, or small organic molecule, or any combination thereof, against which the skilled artisan wishes to induce an immune response. In various embodiments, the TAA is a peptide that comprises about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 55, about 60, about 65, about 70, about 75, about 80, about 85, about 90, about 95, about 100, about 150, about 200, about 250, about 300, about 400, about 500, about 600, about 700, about 800, about 900 or about 1000 amino acids. In various embodiments, the peptide, polypeptide, or protein is a molecule that is commonly administered to subjects by injection. In various embodiments, after administration, the tumor-specific antibody or binding protein serves as a targeting moiety to guide the VitoKine to the diseased site, such as a cancer site, where the active domain can be released and interact with its cognate receptors on diseased cells or diseased tissue.

Any of the foregoing markers can be used as disease associated targets or TAA targets for the VitoKine constructs of this invention. In various embodiments, the one or more disease associated targets or its variant, or TAA, TAA variant, or TAA mutant contemplated for use in the VitoKine constructs and methods of the present disclosure is selected from, or derived from, the list provided in Table 2.

TABLE 2

| Tumor Associated Antigen | RefSeq (protein) |
|---|---|
| Her2/neu | NP_001005862 |
| Her3 | NP_001005915 |
| Her4 | NP_001036064 |
| EGF | NP_001171601 |
| EGFR | NP_005219 |
| CD2 | NP_001758 |
| CD3 | NM_000732 |
| CD5 | NP_055022 |
| CD7 | NP_006128 |
| CD13 | NP_001141 |
| CD19 | NP_001171569 |
| CD20 | NP_068769 |
| CD21 | NP_001006659 |
| CD22 | NP_001762 |
| CD23 | NP_001193948 |
| CD30 | NP_001234 |
| CD33 | NP_001234.3 |
| CD34 | NP_001020280 |
| CD38 | NP_001766 |
| CD40 | NP_001241 |
| CD46 | NP_002380 |
| CD55 | NP_000565 |
| CD59 | NP_000602 |
| CD69 | NP_001772 |
| CD70 | NM_001252 |
| CD71 | NP_001121620 |
| CD80 | NP_005182 |
| CD97 | NP_001020331 |
| CD117 | NP_000213 |
| CD127 | NP_002176 |
| CD134 | NP_003318 |
| CD137 | NP_001552 |
| CD138 | NP_001006947 |
| CD146 | NP_006491 |
| CD147 | NP_001719 |
| CD152 | NP_001032720 |
| CD154 | NP_000065 |
| CD195 | NP_000570 |
| CD200 | NP_001004196 |
| CD212 | NP_001276952 |
| CD223 | NP_002277 |
| CD253 | NP_001177871 |
| CD272 | NP_001078826 |
| CD274 | NP_001254635 |
| CD276 | NP_001019907 |
| CD278 | NP_036224 |
| CD279 | NP_005009 |
| CD309 (VEGFR2) | NP_002244 |
| DR6 | NP_055267 |
| PD-L1 | NP_001254635 |
| Kv1.3 | NP_002223 |
| 5E10 | NP_006279 |
| MUC1 | NP_001018016 |
| uPA | NP_002649 |
| SLAMF7 (CD319) | NP_001269517 |
| MAGE 3 | NP_005353 |
| MUC 16 (CA-125) | NP_078966 |
| KLK3 | NP_001025218 |
| K-ras | NP_004976 |
| Mesothelin | NP_001170826 |
| p53 | NP_000537 |
| Survivin | NP_001012270 |
| G250 (Renal Cell Carcinoma Antigen) | GenBank CAB82444.1 |
| PSMA | NP_001014986 |
| HLA-DR | NP_001020330 |
| 1D10 | NP_114143 |
| Collagen Type I | NP_000079 |
| Collagen Type II | NP_000080 |
| Fibronectin | XP_005246463 |
| Tenascin | NP_002151 |

TABLE 2-continued

| Tumor Associated Antigen | RefSeq (protein) |
|---|---|
| Matrix Metalloproteinase-2 (MMP-2) | NP_001121363 |
| Matrix Metalloproteinase-9 (MMP-9) | NP_004985 |
| Matrix Metalloproteinase-14 (MMP-14) | NP_004986 |
| Fibroblast Activation Protein (FAP) | NM_004460.3 |
| Siglec 8 | NP_055257 |
| Siglec 9 | NP_001185487 |
| Siglec 15 | NP_998767 |
| Legumain | NP_001008530 |
| Tyrosinase | NP_000363 |
| Melan-A (MART I) | NP_055502 |
| SSX-2 | NP_003138 |
| MAGE-1 | NP_004979 |
| NY-ESO-1 (CTAG1) | NP_001318 |
| PRAME | NP_006106 |
| PSA | NP_001639 |
| C35 | NP_115715 |
| SSX-4 | NP_783856 |
| gp100 (Pmel17) | NP_008859 |
| TTF1 | NP_003308 |
| mammaglobin | NP_002402 |
| Brst2 | NP_002643 |
| Mesothelin, isoform 1 | NP_005814 |
| Mesothelin, isoform 2 | NP_037536 |
| PSCA | NP_005663 |
| SYCP-1 | NP_003167 |
| PLK1 | NP_005321 |
| VEGF-A | NP_001020537.2 |
| Alpha fetoprotein (AFP) | NP_001125 |

Further examples of tumor-associated antigens include TRP-1, TRP-2, MAG-1, MAGE-3, BAGE, GAGE-1, GAGE-2, p15(58), CEA, RAGE, NY-BSO(LAGE), SCP-1, Hom/Mel-40, H-Ras, BCR-ABL, E2A-PRL, H4-RET, IGH-IGK, MYL-RAR, human papillomavirus (HPV) antigens E6 and E7, TSP-180, MAGE-4, MAGE-5, MAGE-6, p185erbB2, p180erbB-3, c-met nm-23H1, PSA, TAG-72-4, CA 19-9, CA 72-4, CAM 17.1, Numa, K-ras, β-Catenin, CDK4, Muni-1, p16, TAGE, PSCA, CT7, telomerase, 43-9F, 5T4, 791Tgp72, β-HCG, BCA225, BTAA, CA 15-3 (CA 27.29\BCAA), CA 195, CA 242, CA-50, CAM43, CD68\KF1, CO-029, FGF-5, G250, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, and TPS.

Immune Checkpoint Modulators

A number of immune-checkpoint protein antigens have been reported to be expressed on various immune cells, including, e.g., CD152 (expressed by activated CD8+ T cells, CD4+ T cells and regulatory T cells), CD279 (expressed on tumor infiltrating lymphocytes, expressed by activated T cells (both CD4 and CD8), regulatory T cells, activated B cells, activated NK cells, anergic T cells, monocytes, dendritic cells), CD274 (expressed on T cells, B cells, dendritic cells, macrophages, vascular endothelial cells, pancreatic islet cells), and CD223 (expressed by activated T cells, regulatory T cells, angergic T cells, NK cells, NKT cells, and plasmacytoid dendritic cells)(see, e.g., Pardoll, D., Nature Reviews Cancer, 12:252-264, 2012). Antibodies that bind to an antigen which is determined to be an immune-checkpoint protein are known to those skilled in the art. For example, various anti-CD276 antibodies have been described in the art (see, e.g., U.S. Pat. Public. No. 20120294796 (Johnson et al) and references cited therein); various anti-CD272 antibodies have been described in the art (see, e.g., U.S. Pat. Public. No. 20140017255 (Mataraza et al) and references cited therein); various anti-CD152/CTLA-4 antibodies have been described in the art (see, e.g., U.S. Pat. Public. No. 20130136749 (Korman et al) and references cited therein); various anti-LAG-3/CD223 antibodies have been described in the art (see, e.g., U.S. Pat. Public. No. 20110150892 (Thudium et al) and references cited therein); various anti-CD279/PD-1 antibodies have been described in the art (see, e.g., U.S. Pat. No. 7,488,802 (Collins et al) and references cited therein); various anti-PD-L1 antibodies have been described in the art (see, e.g., U.S. Pat. Public. No. 20130122014 (Korman et al) and references cited therein); various anti-TIM-3 antibodies have been described in the art (see, e.g., U.S. Pat. Public. No. 20140044728 (Takayanagi et al) and references cited therein); and various anti-B7-H4 antibodies have been described in the art (see, e.g., U.S. Pat. Public. No. 20110085970 (Terrett et al) and references cited therein). Each of these references is hereby incorporated by reference in its entirety for the specific antibodies and sequences taught therein.

In various embodiments, D1 may comprise an antibody, antibody fragment, or protein or peptide that exhibit binding to an immune-checkpoint protein antigen that is present on the surface of an immune cell. In various embodiments, the immune-checkpoint protein antigen is selected from the group consisting of, but not limited to, CD276, CD272, CD152, CD223, CD279, CD274, CD40, SIRPa, CD47, OX-40, GITR, ICOS, CD27, 4-1BB, TIM-3, B7-H4, Siglec 7, Siglec 8, Siglec 9, Siglec 15, and VISTA.

In various embodiments, D1 may comprise an antibody to an immune-checkpoint protein antigen is present on the surface of a tumor cell selected from the group consisting of, but are not limited to, PD-L1, B7-H3 and B7-H4.

Modulators for Autoimmune and Inflammatory Disorders

Any of the foregoing proteins highly expressed on various inflammatory tissues or immune cells can be used as autoimmune/inflammatory disease targets for the VitoKine constructs of this invention. In various embodiments, the one or more autoimmune/inflammatory disease target, its variant or its mutant/isoform contemplated for use in the VitoKine constructs and methods of the present disclosure is selected from, or derived from, the list provided in Table 3. These targets can be applicable as cancer targeting as well.

TABLE 3

Targets for Autoimmune and inflammatory disorders or cancer

| | |
|---|---|
| IL-1 alpha | NP_000566 |
| IL-1 beta | NP_000567 |
| IL-2 | NP_000577 |
| IL-4 | NP_000580 |
| IL-4 induced 1 | NP_690863 |
| IL-5 | NP_000870 |
| IL-6 | NP_000591 |
| IL-6Rα | NP_000556 |
| IL-7 | NP_000871 |
| IL-10 | NP_000563 |
| IL-12 (alpha and beta) | NP_000873 and NP_002178 |
| IL-13 | NP_002179 |
| IL-17 | NP_002181 |
| IL-21 | NP_068575 |
| IL-22 | NP_065386 |
| IL-23 | NP_057668 |
| IL-33 | NP_254274 |
| TNF family (TNF-alpha) | NP_000585 |
| TNFR (TNFRSF1A) | NP_001056 |
| GMCSF | NP_000749 |
| IFN | NP_008831 |
| IFN alpha-beta receptor 1 | NP_000620 |

TABLE 3-continued

Targets for Autoimmune and inflammatory disorders or cancer

| | |
|---|---|
| APRIL | NP_003799 |
| Integrins (Integrin $A_4\beta_7$) | NP_000880 |
| BAFF | NP_006564 |
| BAFFR | NP_443177 |
| CTLA4 | NP_005205 |
| BCR | NP_004318 |
| BLyS | NP_006564 |
| B7RP1 | NP_056074 |
| B7H1 | NP_054862 |
| B7H2 | NP_056074 |
| CXCR3 | NP_001495 |
| MCP1 | NP_002973 |
| BCMA | NP_001183 |
| TACI | NP_036584 |
| CD20 | NP_068769 |
| CD22 | NP_001762 |
| CD80 | NP_005182 |
| CD40 | NP_001241 |
| CD40L | NP_000065 |
| TSLP | NP_149024 |
| ICOS | NP_036224 |
| TLRs (TLR2 and TLR4) | NP_003255 and NP_003257 |
| HMGB-1 | NP_002119 |
| HLA-DR | NP_001020330 |
| Collagen Type I | NP_000079 |
| Collagen Type II | NP_000080 |
| Fibronectin | XP_005246463 |
| Tenascin | NP_002151 |
| 1D10 | NP_114143 |

In various embodiments, D1 targeting moiety, can be an inflammatory tissue-specific antibody, antibody fragment, another protein or peptide that exhibit binding to a diseased cell or disease microenvironment, such as TNF, TNFR, integrin $A_4\beta_7$, IL-6Rα, BLYS, TSLP.

Polymers

In various embodiments, D1 can be a polymer, e.g., polyethylene glycol (PEG). In various embodiments, a polymer, e.g., PEG, may be covalently attached at the N- or C-terminus or at an internal location, using conventional chemical methods, e.g., chemical conjugation. In various embodiments, a polymer, e.g., PEG, may be covalently attached at the N-terminal of the D2 domain via site-specific conjugation or other amino acid or engineered specific amino acid substitutions of cytokine.

Half-Life Extension Moieties

In various embodiments, other half-life extension moieties that can be used as D1 domains in the present invention to increase the serum half-life of VitoKine. Half-life extension moieties include, but are not limited to, an Fc domain, an Fc variant, an antibody, an antibody fragment (Fab, ScFv), and EXTEN (Schellenberger et al., Nat. Biotechnol. 27:1 186-1 192, 2009) and human serum albumin protein.

D2 Domain ("Active Moiety Domain")

D2 is the active moiety of a VitoKine construct, whose activity is reversibly concealed in the construct and can be restored upon protease cleavage at a disease site. This activity moiety may be any protein, including, but not limited to any native or variant interleukin or cytokine polypeptide. Importantly, because the "active moiety" of the VitoKine construct will remain inert or of attenuated activity until activated locally by proteases that are upregulated in diseased tissues, this will limit binding of the active moiety to the receptors in the peripheral or on the cell-surface of non-diseased cells to prevent over-activation of the pathway and reduce undesirable "on-target" "off tissue" toxicity. Additionally, the inertness of the VitoKine active moiety prior to protease activation will significantly decrease the potential antigen or target sink, and thus, prolong the in vivo half-life and result in improved biodistribution and exposure at intended sites of therapy.

IL-15

Interleukin-15 (IL-15) is a cytokine identified by two independent groups based upon its ability to stimulate proliferation of the IL-2-dependent CTLL-2 T-cell line in the presence of neutralizing anti-IL-2 antibodies (Steel et al., Trends in Pharmacological Sciences, 33(1):35-41, 2012). IL-15 and Interleukin-2 (IL-2) have similar biologic properties in vitro, consistent with their shared receptor (R) signaling components (IL-2/15Rβγ$_c$). However, specificity for IL-15 versus IL-2 is provided by unique private α-chain receptors that complete the IL-15Rαβγ and IL-2Rαβγ heterotrimeric high-affinity receptor complexes and thereby allow differential responsiveness depending on the ligand and high-affinity receptor expressed. Intriguingly, both IL-15 and IL-15Rα transcripts have a much broader tissue distribution than IL-2/IL-2Rα. Further, multiple complex posttranscriptional regulatory mechanisms tightly control IL-15 expression. Thus, based upon complex regulation, as well as differential patterns of IL-15 and IL-15Rα expression, it is likely that the critical in vivo functions of this receptor/ligand pair differ from those of IL-2 and IL-2Rα. Studies to date examining the biology of IL-15 have identified several key nonredundant roles, such as IL-15's importance during natural killer (NK) cell, NK-T cell, and intestinal intraepithelial lymphocyte development and function. A role for IL-15 during autoimmune processes such as rheumatoid arthritis and malignancies such as adult T-cell leukemia suggest that dysregulation of IL-15 may result in deleterious effects for the host (Fehniger et al., Blood, 97:14-32, 2001).

As used herein, the terms "native IL-15" and "native interleukin-15" in the context of proteins or polypeptides refer to any naturally occurring mammalian interleukin-15 amino acid sequences, including immature or precursor and mature forms. Non-limiting examples of GenBank Accession Nos. for the amino acid sequence of various species of native mammalian interleukin-15 include NP_032383 (*Mus musculus*, immature form), AAB60398 (*Macaca mulatta*, immature form), NP_000576 (human, immature form), CAA62616 (human, immature form), AA100964 (human, immature form), and AAH18149 (human). In various embodiments of the present invention, native IL-15 is the immature or precursor form of a naturally occurring mammalian IL-15. In other embodiments, native IL-15 is the mature form of a naturally occurring mammalian IL-15. In various embodiments, native IL-15 is the precursor form of naturally occurring human IL-15. In various embodiments, native IL-15 is the mature form of naturally occurring human IL-15. In various embodiments, the native IL-15 protein/polypeptide is isolated or purified. In various embodiments, the IL-15-based domain D2 is derived from the amino acid sequence of the human IL-15 precursor sequence set forth in SEQ ID NO: 1:

```
                                              (SEQ ID NO: 1)
MRISKPHLRSISIQCYLCLLLNSHFLTEAGIHVFILGCFSAGLPKTEAN

WVNVISDLKKIEDLIQSMHIDATLYTESDVHPSCKVTAMKCFLLELQVI

SLESGDASIHDTVENLIILANNSLSSNGNVTESGCKECEELEEKNIKEF

LQSFVHIVQMFINTS
```

In various embodiments, the IL-15-based domain D2 comprises the amino acid sequence of the human IL-15 mature form sequence set forth in SEQ ID NO: 2:

```
                                              (SEQ ID NO: 2)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS
```

In various embodiments, the IL-15-based domain D2 will be an IL-15 variant (or mutant) comprising a sequence derived from the sequence of the mature human IL-15 polypeptide as set forth in SEQ ID NO: 2. Variants (or mutants) of IL-15 are referred to herein using the native amino acid, its position in the mature sequence and the variant amino acid. For example, "huIL-15 S58D" refers to human IL-15 comprising a substitution of S to D at position 58 of SEQ ID NO: 2. In various embodiments, the D2 domain of the present invention comprises an IL-15 domain that is an IL-15 variant (also referred to herein as IL-15 mutant domain). In various embodiments, the IL-15 variant comprises a different amino acid sequence than the native (or wild type) IL-15 protein. In various embodiments, the IL-15 variant binds the IL-15Rα polypeptide and functions as an IL-15 agonist or antagonist. In various embodiments, the IL-15 variants with agonist activity have super agonist activity. In various embodiments, the IL-15 variant can function as an IL-15 agonist or antagonist independent of its association with IL-15Rα. IL-15 agonists are exemplified by comparable or increased biological activity compared to wild type IL-15. IL-15 antagonists are exemplified by decreased biological activity compared to wild type IL-15 or by the ability to inhibit IL-15-mediated responses. In various embodiments, the IL-15 variant binds with increased or decreased activity to the IL-15Rβγc receptors. In various embodiments, the sequence of the IL-15 variant has at least one amino acid change, e.g. substitution or deletion, compared to the native IL-15 sequence, such changes resulting in IL-15 agonist or antagonist activity. In various embodiments, the amino acid substitutions/deletions are in the domains of IL-15 that interact with IL-15Rβ and/or γ$_C$. In various embodiments, the amino acid substitutions/deletions do not affect binding to the IL-15Rα polypeptide or the ability to produce the IL-15 variant. Suitable amino acid substitutions/deletions to generate IL-15 variants can be identified based on known IL-15 structures, comparisons of IL-15 with homologous molecules such as IL-2 with known structure, through rational or random mutagenesis and functional assays, as provided herein, or other empirical methods. Additionally, suitable amino acid substitutions can be conservative or non-conservative changes and insertions of additional amino acids. In various embodiments, the IL-15 variants of the invention contain one or more than one amino acid substitutions or deletions at position 30, 31, 32, 58, 62, 63, 67, 68, or 108 of the mature human IL-15 sequence set forth in SEQ ID NO: 2. In various embodiments, the D30T ("D30" refers to the amino acid and residue position in the native mature human IL-15 sequence and "T" refers to the substituted amino acid residue at that position in the IL-15 variant), V31Y, H32E, D62T, I68F or Q108M substitutions result in IL-15 variants with antagonist activity and S58D substitutions result in IL-15 variants with agonist activity. In various embodiments, the IL-15 variant comprises the amino acid sequence set forth in SEQ ID NO: 3:

(SEQ ID NO: 3)
NWVNVISDLKKIEDLIQSMHIDATLYTESDVHPSCKVTAMKCFLLELQV
ISLESGDADIHDTVENLIILANNSLSSNGNVTESGCKECEELEEKNIKE
FLQSFVHIVQMFINTS

Exemplary Fc IL-15 VitoKine constructs are provided in Table 4:

TABLE 4

| Protein ID | SEQ ID NO: |
|---|---|
| P-0351 | 25 |
| P-0170 | 26 and 15 |
| P-0172 | 27 |
| P-0202 | 28 |
| P-0203 | 29 |
| P-0204 | 30 |
| P-0205 | 31 |
| P-0206 | 32 |
| P-0315 | 33 |
| P-0316 | 34 |
| P-0350 | 35 |
| P-0354 | 36 |
| P-0355 | 37 |
| P-0385 | 38 |
| P-0386 | 39 |
| P-0387 | 40 |
| P-0388 | 41 |
| P-0389 | 42 |
| P-0397 | 43 |
| P-0660 | 162 |
| P-0488 | 163 |
| P-0489 | 164 |
| P-0661 | 165 |
| P-0650 | 169 |
| P-0651 | 170 |
| P-0662 | 171 + 15 |
| P-0663 | 172 + 167 |
| P-0664 | 173 + 167 |
| P-0665 | 174 + 167 |

In various embodiments, the antibody IL-15 VitoKine or IL-15 Fc fusion molecules will contain two or more heterodimeric chains as set forth in Table 5:

TABLE 5

| Type | Protein ID | Chain 1 SEQ ID NO | Chain 2 SEQ ID NO | Chain 3 SEQ ID NO |
|---|---|---|---|---|
| IL-15 Fc fusion | P-0197 | 44 | 15 | 5 |
| | P-0198 | 45 | 44 | 5 |
| | P-0165 | 2 | 46 | 16 |
| | P-0313 | 47 | 5 | x |
| | P-0153 | 44 | 46 | x |
| | P-0170 | 26 | 15 | x |
| | P-0207 | 148 | 15 | 5 |
| | P-0217 | 149 | 15 | 5 |
| | P-0156 | 175 | 176 | x |
| | Benchmark | 177 | 178 | x |
| Antibody IL-15 VitoKine | P-0406 | 128 | 129 | x |
| | P-0407 | 130 | 131 | x |
| | P-0652 | 132 | 133 | x |
| | P-0653 | 134 | 135 | x |
| | P-0485 | 180 | 181 | x |

In various embodiments, the IL-15-based D2 domain will comprise an IL-15 construct containing an IL-2Rβ based blocking peptide selected from the constructs having the amino acid sequences set forth in SEQ ID NOs: 66-70.

In various embodiments, the IL-15-based D2 domain will comprise an IL-15 construct containing an IL-2Rβ based blocking peptide and having two or more heterodimeric chains as set forth in Table 6:

TABLE 6

| Protein ID | Chain 1 SEQ ID NO | Chain 2 SEQ ID NO | Chain 3 SEQ ID NO |
|---|---|---|---|
| P-0159 | 46 | 66 | X |
| P-0160 | 46 | 67 | X |
| P-0161 | 46 | 68 | X |
| P-0212 | 15 | 66 | 5 |
| P-0213 | 69 | 5 | X |
| P-0215 | 70 | 5 | x |

IL-2

Interleukin-2 (IL-2), a classic Th1 cytokine, is produced by T cells after activation through the T-cell antigen receptor and the co-stimulatory molecule CD28. The regulation of IL-2 occurs through activation of signaling pathways and transcription factors that act on the IL-2 promoter to generate new gene transcription, but also involves modulation of the stability of IL-2 mRNA. IL-2 binds to a multichain receptor, including a highly regulated a chain and β and γ chains that mediate signaling through the Jak-STAT pathway. IL-2 delivers activation, growth, and differentiation signals to T cells, B cells, and NK cells. IL-2 is also important in mediating activation-induced cell death of T cells, a function that provides an essential mechanism for terminating immune responses. A commercially available unglycosylated human recombinant IL-2 product, aldesleukin (available as the PROLEUKIN® brand of desalanyl-1, serine-125 human interleukin-2 from Prometheus Laboratories Inc., San Diego Calif.), has been approved for administration to patients suffering from metastatic renal cell carcinoma and metastatic melanoma. IL-2 has also been suggested for administration in patients suffering from or infected with hepatitis C virus (HCV), human immunodeficiency virus (HIV), acute myeloid leukemia, non-Hodgkin's lymphoma, cutaneous T-cell lymphoma, juvenile rheumatoid arthritis, atopic dermatitis, breast cancer and bladder cancer. Unfortunately, short half-life and severe toxicity limits the optimal dosing of IL-2.

As used herein, the terms "native IL-2" and "native interleukin-2" in the context of proteins or polypeptides refer to any naturally occurring mammalian interleukin-2 amino acid sequences, including immature or precursor and mature forms. Non-limiting examples of GenBank Accession Nos. for the amino acid sequence of various species of native mammalian interleukin-2 include NP_032392.1 (*Mus musculus*, immature form), NP_001040595.1 (*Macaca mulatta*, immature form), NP_000577.2 (human, precursor form), CAA01199,1 (human, immature form), AAD48509.1 (human, immature form), and AAB20900.1 (human). In various embodiments of the present invention, native IL-2 is the immature or precursor form of a naturally occurring mammalian IL-2. In other embodiments, native IL-2 is the mature form of a naturally occurring mammalian IL-2. In various embodiments, native IL-2 is the precursor form of naturally occurring human IL-2. In various embodiments, native IL-2 is the mature form of naturally occurring human IL-2. In various embodiments, the IL-2-based domain D2 is derived from the amino acid sequence of the human IL-2 precursor sequence set forth in SEQ ID NO: 6:

(SEQ ID NO: 6)
MYRMQLLSCIALSLALVTNSAPTSSSTKKTQLQLEHLLLDLQMILNGIN
NYKNPKLTRMLTFKFYMPKKATELKHLQCLEEELKPLEEVLNLAQSKNF

-continued
HLRPRDLISNINVIVLELKGSETTFMCEYADETATIVEFLNRWITFCQS

IISTLT

In various embodiments, the IL-2-based domain D2 comprises the amino acid sequence of the human IL-2 mature form wildtype sequence set forth in SEQ ID NO: 8, which contains substitution of cysteine at position 125 to serine, but does not alter IL-2 receptor binding compared to the naturally occurring IL-2:

(SEQ ID NO: 8)
APTSSSTKKTQLQLEHLLLDLQMILNGINNYKNPKLTRMLTFKFYMPKK
ATELKHLQCLEEELKPLEEVLNLAQSKNFHLRPRDLISNINVIVLELKG
SETTFMCEYADETATIVEFLNRWITFSQSIISTLT

In various embodiments, the IL-2-based domain D2 will be an IL-2 variant (or mutant) comprising a sequence derived from the sequence of the mature human IL-2 polypeptide as set forth in SEQ ID NO: 8. In various embodiments, the IL-2 variant comprises a different amino acid sequence than the native (or wild type) IL-2 protein. In various embodiments, the IL-2 variant binds the IL-2Rα polypeptide and functions as an IL-2 agonist or antagonist. In various embodiments, the IL-2 variants with agonist activity have super agonist activity. In various embodiments, the IL-2 variant can function as an IL-2 agonist or antagonist independent of its association with IL-2Rα. IL-2 agonists are exemplified by comparable or increased biological activity compared to wild type IL-2. IL-2 antagonists are exemplified by decreased biological activity compared to wild type IL-2 or by the ability to inhibit IL-2-mediated responses. In various embodiments, the sequence of the IL-2 variant has at least one amino acid change, e.g. substitution or deletion, compared to the native IL-2 sequence, such changes resulting in IL-2 agonist or antagonist activity. In various embodiments, the IL-2 variant has the amino acid sequence derived from SEQ ID NO: 8 with reduced/abolished binding to IL-2Rα to selectively activate and proliferate effective T cells (Teff) for treating cancer; exemplary amino acid substitutions are listed in Table 7. In various embodiments, the IL-2 variant has the amino acid sequence derived from SEQ ID NO: 8 with reduced binding to IL-2Rβ and/or γc and enhanced selectivity in activating and proliferating regulatory T cells (Treg) for treating autoimmune diseases; exemplary amino acid substitutions are listed in Table 7. As will be appreciated by those in the art, all of the mutations can be optionally and independently combined in any way to achieve optimal affinity and activity modulation.

TABLE 7

| Amino acid substitutions | Proposed function of the mutation |
|---|---|
| R38E/A<br>T41A/G/V<br>F42A<br>F44G/V<br>Y107G/H/L/V | Reduce/abolish binding to IL-2Rα to enhance Teff selectivity |
| L19N/R/Y/H/Q/D/P/S<br>D20E/I/N/Q/S/T/Y<br>N88E/G/I/M/Q/T<br>S125E/K/H/W/I<br>Q126D/E/K/L/M/N | Reduce binding to IL-2Rβ or γ$_C$ to enhance Treg selectivity |

Exemplary IL-2-based VitoKine constructs are provided in Table 8:

TABLE 8

| type | Protein ID | SEQ ID NO: |
|---|---|---|
| Fc IL-2 VitoKine | P-0320 | 49 |
|  | P-0321 | 179 |
|  | P-0352 | 50 |
|  | P-0382 | 51 |
|  | P-0398 | 52 |
|  | P-0362 | 53 |
|  | P-0380 | 54 |
|  | P-0384 | 55 |
|  | P-0400 | 56 |
|  | P-0404 | 57 |
|  | P-0399 | 58 |
|  | P-0379 | 59 |
|  | P-0381 | 60 |
|  | P-0383 | 61 |
|  | P-0329 | 62 |
|  | P-0401 | 63 |
|  | P-0402 | 64 |
|  | P-0403 | 65 |
|  | P-0420 | 150 |
|  | P-0421 | 151 |
|  | P-0423 | 152 |
|  | P-0424 | 153 |
|  | P-0425 | 154 |
|  | P-0426 | 155 |
| Antibody IL-2 VitoKine | P-0654 | 136 + 137 |
|  | P-0655 | 138 + 139 |
|  | P-0656 | 140 + 141 |
|  | P-0657 | 142 + 129 |
|  | P-0658 | 143 + 144 |
|  | P-0659 | 145 + 146 |

In various embodiments, the active moiety is selected from the group of sequences consisting of, but not limited to, the amino acid sequences of interleukin-4 (IL-4) (SEQ ID NO: 17), interleukin-7 (IL-7) (SEQ ID NO: 18), interleukin-9 (IL-9) (SEQ ID NO: 19), interleukin-10 (IL-10) (SEQ ID NO: 20), interleukin-12 alpha (IL-12α) (SEQ ID NO: 21), interleukin-12 beta (IL-12β) (SEQ ID NO: 22), interleukin-23 alpha (IL-23α) (SEQ ID NO: 23), and TGFβ (SEQ ID NO: 24). In various embodiments, the active moiety is a heterodimeric human IL-12 cytokine comprising SEQ ID NO: 21 as chain 1 and SEQ ID NO: 22 as chain 2. In various embodiments, the active moiety is a heterodimeric human IL-23 cytokine comprising SEQ ID NO: 23 as chain 1 and SEQ ID NO: 22 as chain 2.

D3 Domain ("Concealing Moiety Domain")

D3 domain is the "concealing moiety domain" and is mainly used to reversibly conceal the activity of the D2 domain in the specific VitoKine construct. The D3 domain is capable of concealing the functional activity of D2 until activated at the intended site of therapy. In various embodiments, the VitoKine constructs of the present invention comprise a "concealing moiety domain" (D3) that is a cognate receptor/binding partner for the D2 protein or cytokine. In various embodiments, the D3 domain is a variant of the cognate receptor/binding partner or a specific binder such as peptide or antibody fragment for the D2 domain. In various embodiments, the D3 domain has enhanced binding to the D2 domain compared to the wild-type cognate receptor/binding partner. In various embodiments, the D3 domain has reduced or abolished binding to the D2 domain compared to the wild-type cognate receptor/binding partner. In various embodiment, the D3 domain is a protein, or a peptide, or an antibody, or an antibody fragment that is able to conceal the activity of D2. In various embodiments, D3 domain is a DNA, RNA fragment or a polymer, such as PEG by a cleavable linker. In various embodiments, the VitoKine constructs of the present invention comprise a D3 domain that is an IL-15Rα extracellular domain or a functional fragment or variant thereof. In various embodiments, the VitoKine constructs of the present invention comprise a D3 domain that is an IL-15RαSushi domain (amino acids 1-65 of SEQ ID NO: 5). In various preferred embodiments, the VitoKine constructs of the present invention comprise a D3 domain that is an IL-15RαSushi+ domain that contains 1-30 additional IL-15Rα residues at the C-terminus of the Sushi domain (e.g., SEQ ID NO: 5). In various embodiments, the VitoKine constructs of the present invention comprise a D3 domain that is an IL-2Rα extracellular domain or a functional fragment thereof. In various preferred embodiments, the VitoKine constructs of the present invention comprise a D3 domain that is an IL-2RαSushi domain. In various embodiments, the D3 domain is capable of concealing the functional activity of D2 until activated at the intended site of therapy.

IL-15 Receptor Alpha

IL-15 receptor is a type I cytokine receptor consisting of a beta (β) and gamma (γ) subunit that it shares with IL-2 receptor, and an alpha (a) subunit which binds IL-15 with a high affinity. The full-length human IL-15Rα is a type-1 transmembrane protein with a signal peptide of 32 AAs, an extracellular domain of 173 AAs, a transmembrane domain of 21 AAs, a 37-AA cytoplasmic tail, and multiple N- or O-linked glycosylation sites (Anderson et al., J. Biol Chem, 270:29862-29869, 1995). It has been previously demonstrated that a natural soluble form of IL-15R alpha chain corresponding to the entire extracellular domain of IL-15R alpha behaves as a high affinity IL-15 antagonist. However, in sharp contrast with that finding, it was demonstrated that a recombinant, soluble sushi domain of IL-15R alpha, which bears most of the binding affinity for IL-15, behaves as a potent IL-15 agonist by enhancing its binding and biological effects (proliferation and protection from apoptosis) through the IL-15R beta/gamma heterodimer, whereas it does not affect IL-15 binding and function of the tripartite IL-15R alpha/beta/gamma membrane receptor. These results suggested that, if naturally produced, such soluble sushi domains might be involved in the IL-15 transpresentation mechanism (Mortier et al., J. Biol Chem, 281(3):1612-1619, 2006).

As used herein, the terms "native IL-15Rα" and "native interleukin-15 receptor alpha" in the context of proteins or polypeptides refer to any naturally occurring mammalian interleukin-15 receptor alpha ("IL-15Rα") amino acid sequence, including immature or precursor and mature forms and naturally occurring isoforms. Non-limiting examples of GenBank Accession Nos. for the amino acid sequence of various native mammalian IL-15Rα include NP_002180 (human), ABK41438 (*Macaca mulatta*), NP_032384 (*Mus musculus*), Q60819 (*Mus musculus*), CA141082 (human). In various embodiments, native IL-15Rα is the immature form of a naturally occurring mammalian IL-15Rα polypeptide. In various embodiments, native IL-15Rα is the mature form of a naturally occurring mammalian IL-15Rα polypeptide. In various embodiments, native IL-15Rα is a form of a naturally occurring mammalian IL-15Rα polypeptide. In various embodiments, native IL-15Rα is the full-length form of a naturally occurring mammalian IL-15Rα polypeptide. In various embodiments, native IL-15Rα is the immature form of a naturally occurring human IL-15Rα polypeptide. In various embodiments, native IL-15Rα is the mature form of a naturally occurring human IL-15Rα polypeptide. In various embodiments, native IL-15Rα is the full-length form of a naturally occurring human IL-15Rα polypeptide. In various embodiments, a native IL-15Rα protein or polypeptide is isolated or purified. In various embodiments, the IL-15Rα domain is derived from the amino acid sequence of the human IL-15Rα sequence set forth in SEQ ID NO: 4:

```
                                        (SEQ ID NO: 4)
MAPRRARGCRTLGLPALLLLLLLRPPATRGITCPPPMSVEHADIWVKSY

SLYSRERYICNSGFKRKAGTSSLTECVLNKATNVAHWTTPSLKCIRDPA

LVHQRPAPPSTVTTAGVTPQPESLSPSGKEPAASSPSSNNTAATTAAIV

PGSQLMPSKSPSIGITEISSHESSHGTPSQTTAKNWELTASASHQPPGV

YPQGHSDTTVAISTSTVLLCGLSAVSLLACYLKSRQTPPLASVEMEAME

ALPVTWGTSSRDEDLENCSHHL
```

In various embodiments, the VitoKine constructs of the present invention contain a D3 domain that is an IL-15RαSushi+ domain comprising the amino acid sequence of the mature human IL-15Rα polypeptide as set forth in SEQ ID NO: 5:

```
                                        (SEQ ID NO: 5)
ITCPPPMSVEHADIWVKSYSLYSRERYICNSGFKRKAGTSSLTECVLNK
ATNVAHWTTPSLKCIRDPALVHQRPAPP
```

In various embodiments, IL-15RαSushi+(SEQ ID NO: 5), the truncated cognate co-receptor of IL-15 which recapitulate the majority of binding affinity of the full-length IL-15Rα (SEQ ID NO: 4), was used as D3 domain to conceal IL-15 activity by tuning the cleavable or non-cleavable linker connecting IL-15 and IL-15RαShushi+ to make IL-15 VitoKine. As can be appreciated by skilled artisan, the length of the D3 domain can vary from the sequence set forth in SEQ ID NO: 5 as far as it can recapitulate the majority of binding activity of the full-length IL-15Rα (SEQ ID NO: 4), namely being functional fragment. The distinctness of IL-15 VitoKine design lies in taking full use of the unique features of IL-15 pathway, including the exceptionally high affinity between IL-15 and IL-15a (30 pM), and that the complexation of IL-15a enhance the activity of IL-15 in vivo. After the cleavage of the linker connecting the IL-15 and IL-15αSushi+ by proteases that are upregulated at disease site, IL-15RαShushi+ or any function fragment derived from IL-15RαECD is expected to remain non-covalent association of IL-15 and augments IL-15 activity.

IL-2 Receptor

The IL-2 receptor (IL-2R) is a heterotrimeric protein expressed on the surface of certain immune cells, such as lymphocytes, that binds and responds to a cytokine called IL-2. IL-2R has three subunits: α (CD25), β (CD122), and $\gamma_c$ (CD132, a shared chain with five other cytokine receptors: IL-4R, IL-7R, IL-9R, IL-15R, and IL-21R). Alpha chain (alias: Tac antigen or p55) of human receptor is encoded on chromosome 10p14-15 by the gene IL-2RA. The gene for the human β chain (IL-2RB, CD122) of the receptor is located on chromosome 22q11.2-12, while the gene for the common IL-2R$\gamma_C$ chain (IL-2RG) is on chromosome Xq13. Assembly of all three subunits of the receptor is important for the signal transduction into the B and T cells. IL-2R was found on the cell surface (either temporary or permanent) in almost all hematopoietic cells including lymphoid linages T, B, and NK cells, as well as myeloid ones like macrophages, monocytes, and neutrophils. The signal is transferred into the cell via the Janus kinases—Jak1 and Jak3. The phosphorylation of the intracytosolic part of the receptor's β chain enables homodimer formation of STAT-3 and STAT-5 factors. Homodimers of STAT-3 and STAT-5 show increased affinity for the nucleus, where they bind to specific DNA elements enhancing the transcription of IL-2-dependent genes.

As used herein, the terms "native IL-2Rα" and "native interleukin-2 receptor alpha" in the context of proteins or polypeptides refer to any naturally occurring mammalian interleukin-2 receptor alpha ("IL-2Rα") amino acid sequence, including immature or precursor and mature forms and naturally occurring isoforms. Non-limiting examples of GenBank Accession Nos. for the amino acid sequence of various native mammalian IL-2Rα include NP_032393.3 (*Mus musculus*), CAK26553.1 (human) and NP_000408.1 (human). In various embodiments, native IL-2Rα is the immature form of a naturally occurring mammalian IL-2Rα polypeptide. In various embodiments, native IL-2Rα is the mature form of a naturally occurring mammalian IL-2Rα polypeptide. In various embodiments, native IL-2Rα is a form of a naturally occurring mammalian IL-2Rα polypeptide. In various embodiments, native IL-2Rα is the full-length form of a naturally occurring mammalian IL-2Rα polypeptide. In various embodiments, native IL-2Rα is the immature form of a naturally occurring human IL-2Rα polypeptide. In various embodiments, native IL-2Rα is the mature form of a naturally occurring human IL-2Rα polypeptide. In various embodiments, native IL-2Rα is the full-length form of a naturally occurring human IL-2Rα polypeptide. In various embodiments, a native IL-2Rα protein or polypeptide is isolated or purified. In various embodiments, the IL-2Rα domain is derived from the amino acid sequence of the human IL-2Rα sequence set forth in SEQ ID NO: 9:

```
                                        (SEQ ID NO: 9)
MDSYLLMWGLLTFIMVPGCQAELCDDDPPEIPHATFKAMAYKEGTMLNC

ECKRGFRRIKSGSLYMLCIGNSSHSSWDNQCQCTSSATRNTTKQVTPQP

EEQKERKTTEMQSPMQPVDQASLPGHCREPPPWENEATERIYHFVVGQM

VYYQCVQGYRALHRGPAESVCKMTHGKTRWTQPQLICTGEMETSQFPGE

EKPQASPEGRPESETSCLVITTDFQIQTEMAATMETSIFTTEYQVAVAG

CVFLLISVLLLSGLTWQRRQRKSRRTI
```

In various embodiments, the VitoKine constructs of the present invention contain a D3 domain that is an IL-2RαSushi domain comprising the amino acid sequence of the mature human IL-2Rα polypeptide as set forth in SEQ ID NO: 10:

```
                                        (SEQ ID NO: 10)
ELCDDDPPEIPHATFKAMAYKEGTMLNCECKRGFRRIKSGSLYMLCTGN

SSHSSWDNQCQCTSSATRNTTKQVTPQPEEQKERKTTEMQSPMQPVDQA

SLPGHCREPPPWENEATERIYHFVVGQMVYYQCVQGYRALHRGPAESVC

KMTHGKTRWTQPQLICTG
```

In various embodiments, IL-2RαSushi (SEQ ID NO: 10) was used to conceal IL-2 activity to make IL-2 VitoKine. In contrast to IL-15Rα which contains a single sushi domain, IL-2Rα comprises two sushi domains separated by a linker region. In various embodiments, IL-2 VitoKine comprises IL-2RαSushi variant containing amino acid substitutions to break specific non-covalent interactions between IL-2Rα and IL-2, thus, reducing the binding affinity of the IL-2Rα to IL-2. While native IL-2Rα binds to IL-2 with a moderate affinity of 30 nM, there is still a chance that after cleaving the linker, IL-2Rα may not dissociate. The association of IL-2Rα with IL-2 may reduce the activity of IL-2 and/or tilt the balance of the T cell subpopulations to an undesired direction. With affinity reducing mutation(s) introduced into IL-2RαSushi, e.g., K38E, or Y43A, or the combination of the two substitutions, the IL-2Rα sushi domains are likely to dissociate away from the IL-2 after protease cleavage of the linker.

L1 and L2 Linkers
Cleavable Linkers

A cleavable linker, or a linker sensitive to a disease-associated enzyme may contain a moiety, e.g., a protein substrate, capable of being specifically cleaved by a protease that is present at elevated levels at the disease site as compared to non-disease tissues. There are reports in the literature of increased levels of enzymes having known substrates in various types of cancers, e.g., solid tumors. See, e.g., La Rocca et al., *Brit. J. Cancer* 90:1414-1421 and Ducry et al., *Bioconjug. Chem.* 21:5-13, 2010, each of which is incorporated by reference herein in its entirety. In various embodiments, the protease capable of cleaving the protease-cleavable linker is selected from the group consisting of metalloproteinase, e.g., matrix metalloproteinase (MMP) 1-28 and, serine protease, e.g., urokinase-type plasminogen activator (uPA) and Matriptase, cysteine protease, e.g., legumain, aspartic protease, and cathepsin protease. Exemplary protease substrate peptide sequences are provided in Table 9:

TABLE 9

| Protease family | Protease | RefSeq (Protein) |
| --- | --- | --- |
| Matrix Metalloproteins (MMPs) | MMP-1 (Collagenase 1) | NP_002412 |
| | MMP-2 (Gelatinase A) | NP_001121363 |
| | MMP-3 (Stromelysin 1) | NP_002413 |
| | MMP-7 (Matrilysin 1) | NP_002414 |
| | MMP-8 (Collagenase 2) | NP_002415 |
| | MMP-9 (Gelatinase B) | NP_004985 |
| | MMP-10 (Stromelysin 2) | NP_002416 |
| | MMP-11 (Stromelysin 3) | NP_005931.2 |
| | MMP-12 (Macrophage Elastase) | NP_002417.2 |
| | MMP-13 (Collagenase 3) | NP_002418 |
| | MMP-14 (MT1-MMP) | NP_004986 |
| | MMP-15 (MT2-MMP) | NP_002419 |
| | MMP-19 | NP_002420 |
| | MMP-23 (CA-MMP) | NP_008914 |
| | MMP-24 (MT5-MMP) | NP_006681 |
| | MMP-26 (Matrilysin 2) | NP_068573.2 |
| | MMP-27 (CMMP) | NP_071405.2 |
| Cysteine Proteases | Legumain | NP_001008530 |
| | Cathepsin C | NP_001805.3 |
| | Cathepsin K | NP_000387 |
| | Cathepsin L1 | NP_001903 |
| | Cathepsin S | NP_004070 |
| | Cathepsin X (Cathepsin Z) | NP_001327.2 |
| Aspartase Proteases | Cathepsin D | NP_001900 |
| | Cathepsin E | NP_001901 |
| | Secretase (BACE1) | NP_001193978 |
| Serine Proteases | Urokinase plasminogen activator (uPA) | NM_002658 |
| | Tissue-type plasminogen activator (tPA) | NP_000921 |
| | Plasmin | NP_000292 |
| | Thrombin | NP_000497 |
| | Prostate-specific antigen (PSA, KLK3) | NP_001639 |

TABLE 9-continued

| Protease family | Protease | RefSeq (Protein) |
|---|---|---|
| | human neutrophil elastase (HNE) | NP_001963 |
| | Elastase (CELA1) | NP_001962.3 |
| | Tryptase | NP_003285.2 |
| | Matriptase (ST14) | NP_068813 |
| Disintegrin and metalloproteinase (ADAM) | ADAM-10 | NP_001101 |
| | ADAM 17 | NP_003174 |

Exemplary protease substrate peptide sequences, which can be used as protease cleavable linkers with or without peptide spacers of various lengths on the C-terminus, or on the N-terminus, or on both termini of D2 domain, are provided in Table 10:

TABLE 10

| Proteases | Substrate peptide | SEQ ID NO: |
|---|---|---|
| MMP-2, 7, 9, 14 | SPLGLAGS | 71 |
| MMP-2, 7, 9, 14, matriptase | EPLELRAG | 72 |
| matriptase, uPA, Legumain | LSGRSDNH | 73 |
| MMP-2 | GPLGIAGQ | 74 |
| MMP-2, 14 | GTAHLMGG | 75 |
| MMP-14 | RIGSLRTA | 76 |
| MMP-14 | SGRSENIRTA | 157 |
| MMP-2, 9 | GPLGMLSQ | 77 |
| MMP-9, uPA | RPSASRSA | 78 |
| MMP | PLGLAG | 79 |
| uPA | LGGSGRSANAILE | 80 |
| uPA | GGSGRSANAI | 81 |
| uPA | SGRSA | 82 |
| Legumain | AANL | 83 |
| Legumain | GPTNKVR | 158 |
| Cathepsin C | GFFY | 84 |
| Cathepsin D | GPICFRLG | 85 |
| Cathepsin E | RQAGFSL | 86 |
| Matriptase | RQARAVGG | 159 |
| Prostate Specific antigen | HSSKLQ | 87 |

In various embodiments, the protease is MMP-9 or MMP-2. In a further specific embodiment, the protease is uPA. In a further specific embodiment, the protease is MMP-14. In further specific embodiment, the protease is legumain. In various embodiments, one VitoKine molecule contains two different proteases. In various embodiments, the protease-cleavable linker comprises the protease recognition sequence 'GPLGMLSQ' (SEQ ID NO: 77). In various embodiments, the protease-cleavable linker comprises the protease recognition sequence 'LGGSGRSANAILE' (SEQ ID NO: 80). In various embodiments, the protease-cleavable linker comprises the protease recognition sequence 'SGRSENIRTA' (SEQ ID NO: 157). In various embodiments, the protease-cleavable linker comprises the protease recognition sequence 'GPTNKVR' (SEQ ID NO: 158). In various embodiments, the linker (e.g., a cleavable linker) may be cleaved by tumor-associated proteases. In various embodiments, the cleavable linker may be cleaved by other disease-specific proteases, in diseases other than cancer such as inflammatory diseases.

In various embodiments, peptide spacers maybe incorporated on either side of the protease cleavable sequence or to flank both sides of the protease cleavable sequence, or as a non-cleavable linker without a protease substrate site Peptide spacer serves to position the cleavable linker to be more accessible to the enzyme responsible for cleavage. The length of the spacers may be changed or optimized to balance the accessibility for enzymatic cleavage and the spatial constrain required to reversibly conceal the D2 domain from exerting its biological activity. A spacer may include 1-100 amino acids. Suitable peptide spacers are known in the art and include but not limited to peptide linkers containing flexible amino acid residues, such as glycine and serine. In various embodiments, a spacer can contain motifs of GS, GGS, GGGGS, GGSG, or SGGG. In various embodiments, a spacer can contain 1 to 12 amino acids including motifs of G, S, GS (SEQ ID NO: 116), GGS (SEQ ID NO: 117), GSGS (SEQ ID NO: 121), GSGSGS (SEQ ID NO: 122), GSGSGSGS (SEQ ID NO: 123), GSGSGSGSGS (SEQ ID NO: 124), or GSGSGSGSGSGS (SEQ ID NO: 125). In other embodiments, a spacer can contain motifs of (GGGGS)$_n$, wherein n is an integer from 1 to 10. In other embodiments, a spacer can also contain amino acids other than glycine and serine.

Exemplary protease cleavable linkers with spacer peptide flanking the protease substrate peptide (underscored) are provided in Table 11:

TABLE 11

| Protease cleavable linker | SEQ ID NO: |
|---|---|
| GGGSGGGGSGGGGS<u>LSGRSDNH</u>GGSGGGGS | 88 |
| GS<u>SSGRSENIRTA</u>GT | 89 |
| GGGGSGGGGSGGGS<u>LGGSGRSANAILE</u>GGSGGGGS | 90 |
| GGGGSGGGGS<u>LGGSGRSANAILE</u>GGGGS | 91 |
| GGGGS<u>LGGSGRSANAILE</u>GGGS | 92 |
| GGGS<u>GPTNKVR</u>GGS | 93 |
| GGS<u>GPLGMLSQ</u>GGGS | 94 |
| GG<u>PLGMLSQ</u>GS | 95 |
| GGG<u>PLGMLSQ</u>GGS | 96 |
| GG<u>PTNKVR</u>GS | 160 |
| G<u>RQARAVGG</u>S | 161 |

In various embodiment, a cleavable linker can be activated by mechanisms other than proteolysis, including but not limited to hydrolysis, such as releasable PEGylation polymer that may be shed via a controlled release mechanism under different pH.

Non-Cleavable Linkers

Non-cleavable linker provides covalent linkage and additional structural and/or spatial flexibility between protein domains. As known in the art, peptide linkers containing flexible amino acid residues, such as glycine and serine, can be used as non-cleavable linkers. In various embodiments, non-cleavable linker may include 1-100 amino acids. In various embodiments, a spacer can contain motifs of GS (SEQ ID NO: 116), GGS (SEQ ID NO: 117), GGGGS (SEQ ID NO: 118), GGSG (SEQ ID NO: 119), or SGGG (SEQ ID NO: 120). In other embodiments, a linker can contain motifs of (GGGGS)n, wherein n is an integer from 1 to 10. In other embodiments, a linker can also contain amino acids other than glycine and serine. In another embodiment, the non-cleavable linker can be a simple chemical bond, e.g., an amide bond (e.g., by chemical conjugation of PEG). A non-cleavable linker is stable under physiological conditions as well as at a diseased site, such as a cancer site or at site of inflammatory diseases.

Exemplary non-cleavable linkers are provided in Table 12:

TABLE 12

| Linker sequence | SEQ ID NO: |
|---|---|
| EPKSSDKTHTSPPS | 107 |
| GGGSGGGSGGGS | 108 |
| GGGS | 109 |
| GSSGSGGSGGSG | 110 |
| GSSGT | 111 |
| GGGGSGGGSGGGS | 112 |
| AEAAAKEAAAKEAAAKA | 113 |
| GGGGSGGGGSGGGGSGGGGS | 114 |
| GGGSGGGS | 115 |
| GS | 116 |
| GGS | 117 |
| GGGGS | 118 |
| GGSG | 119 |
| SGGG | 120 |
| GSGS | 121 |
| GSGSGS | 122 |
| GSGSGSGS | 123 |
| GSGSGSGSGS | 124 |
| GSGSGSGSGSGS | 125 |
| GGGGSGGGGS | 126 |
| GGGGSGGGGSGGGGS | 127 |

A Combination of Cleavable and Non-Cleavable Linkers

In various embodiments, the L1 and L2 linkers can be both cleavable or both non-cleavable or a combination of cleavable and non-cleavable linkers to yield different forms of active moiety of the D2 domain to fulfill different therapeutic intentions or balance the risk/benefit ratio or conform different properties of the cytokines. The exemplary active forms released by cleavage of the linkers are depicted in FIG. 2. The active forms 1 and 3 derived from cleavage of L1 and both L1 and L2, respectively, are short-acting cytokines with various degrees of functional activity depending on the D3 conformation. The cleavages and the release from the half-life extension or disease-tissue targeting moiety D1 would increase local concentrations of the activated D2 domain. After acting locally, the short-acting active forms can be eliminated from systemic circulation quickly to reduce toxicities. In contrast, the active form 2 derived from the cleavage of L2 is a functionally fully restored, long-acting and tissue-targeting conserved cytokine that remains in the disease site persistently for longer and enhanced efficacy.

Polynucleotides

In another aspect, the present disclosure provides isolated nucleic acid molecules comprising a polynucleotide encoding IL-15, an IL-15 variant, IL-15Rα, an IL-15Rα variant, an Fc, an Fc variant, an IL-15-Fc fusion protein, an IL-15RαSushi-Fc fusion protein, or an VitoKine construct of the present disclosure. The subject nucleic acids may be single-stranded or double stranded. Such nucleic acids may be DNA or RNA molecules. DNA includes, for example, cDNA, genomic DNA, synthetic DNA, DNA amplified by PCR, and combinations thereof. Genomic DNA encoding VitoKine constructs is obtained from genomic libraries which are available for a number of species. Synthetic DNA is available from chemical synthesis of overlapping oligonucleotide fragments followed by assembly of the fragments to reconstitute part or all of the coding regions and flanking sequences. RNA may be obtained from prokaryotic expression vectors which direct high-level synthesis of mRNA, such as vectors using T7 promoters and RNA polymerase. The DNA molecules of the disclosure include full-length genes as well as polynucleotides and fragments thereof. The full-length gene may also include sequences encoding the N-terminal signal sequence. Such nucleic acids may be used, for example, in methods for making the novel VitoKine constructs.

In various embodiments, the isolated nucleic acid molecules comprise the polynucleotides described herein, and further comprise a polynucleotide encoding at least one heterologous protein described herein. In various embodiments, the nucleic acid molecules further comprise polynucleotides encoding the linkers or hinge linkers described herein.

In various embodiments, the recombinant nucleic acids of the present disclosure may be operably linked to one or more regulatory nucleotide sequences in an expression construct. Regulatory sequences are art-recognized and are selected to direct expression of the VitoKine construct. Accordingly, the term regulatory sequence includes promoters, enhancers, and other expression control elements. Exemplary regulatory sequences are described in Goeddel; Gene Expression Technology: Methods in Enzymology, Academic Press, San Diego, Calif. (1990). Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the present disclosure. The promoters may be either naturally occurring promoters, or hybrid promoters that combine elements of more than one promoter. An expression construct may be present in a cell on an episome, such as a plasmid, or the expression construct may be inserted in a chromosome. In various embodiments, the expression vector contains a selectable marker gene to allow the selection of transformed host cells. Selectable marker genes are well known in the art and will vary with the host cell used.

In another aspect of the present disclosure, the subject nucleic acid is provided in an expression vector comprising a nucleotide sequence encoding a VitoKine construct and operably linked to at least one regulatory sequence. The term "expression vector" refers to a plasmid, phage, virus or vector for expressing a polypeptide from a polynucleotide sequence. Vectors suitable for expression in host cells are readily available and the nucleic acid molecules are inserted into the vectors using standard recombinant DNA techniques. Such vectors can include a wide variety of expression control sequences that control the expression of a DNA sequence when operatively linked to it may be used in these vectors to express DNA sequences encoding a VitoKine construct. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., PhoS, the promoters of the yeast a-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered. An exemplary expression vector suitable for expression of VitoKine is the pDSRa, and its derivatives, containing VitoKine polynucleotides, as well as any additional suitable vectors known in the art or described below.

A recombinant nucleic acid of the present disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant VitoKine construct include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press, 1989) Chapters 16 and 17. In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the B-gal containing pBlueBac III).

In various embodiments, a vector will be designed for production of the subject VitoKine constructs in CHO cells, such as a Pcmv-Script vector (Stratagene, La Jolla, Calif.), pcDNA4 vectors (Invitrogen, Carlsbad, Calif.) and pCl-neo vectors (Promega, Madison, Wis.). As will be apparent, the subject gene constructs can be used to cause expression of the subject VitoKine constructs in cells propagated in culture, e.g., to produce proteins, including fusion proteins or variant proteins, for purification.

This present disclosure also pertains to a host cell transfected with a recombinant gene including a nucleotide sequence coding an amino acid sequence for one or more of the subject VitoKine construct. The host cell may be any prokaryotic or eukaryotic cell. For example, a VitoKine construct of the present disclosure may be expressed in bacterial cells such as E. coli, insect cells (e.g., using a baculovirus expression system), yeast, or mammalian cells. Other suitable host cells are known to those skilled in the art, such as Chinese Hamster Ovary (CHO) cells, or Human Embryonic Kidney 293 (HEK293) cells.

Accordingly, the present disclosure further pertains to methods of producing the subject VitoKine constructs. For example, a host cell transfected with an expression vector encoding a VitoKine construct can be cultured under appropriate conditions to allow expression of the VitoKine construct to occur. The VitoKine construct may be secreted and isolated from a mixture of cells and medium containing the VitoKine construct. Alternatively, the VitoKine construct may be retained cytoplasmically or in a membrane fraction and the cells harvested, lysed and the protein isolated. A cell culture includes host cells, media and other byproducts. Suitable medias for cell culture are well known in the art.

The polypeptides and proteins of the present disclosure can be purified according to protein purification techniques are well known to those of skill in the art. These techniques involve, at one level, the crude fractionation of the proteinaceous and non-proteinaceous fractions. Having separated the peptide polypeptides from other proteins, the peptide or polypeptide of interest can be further purified using chromatographic and electrophoretic techniques to achieve partial or complete purification (or purification to homogeneity). The term "isolated polypeptide" or "purified polypeptide" as used herein, is intended to refer to a composition, isolatable from other components, wherein the polypeptide is purified to any degree relative to its naturally-obtainable state. A purified polypeptide therefore also refers to a polypeptide that is free from the environment in which it may naturally occur. Generally, "purified" will refer to a polypeptide composition that has been subjected to fractionation to remove various other components, and which composition substantially retains its expressed biological activity. Where the term "substantially purified" is used, this designation will refer to a peptide or polypeptide composition in which the polypeptide or peptide forms the major component of the composition, such as constituting about 50%, about 60%, about 70%, about 80%, about 85%, or about 90% or more of the proteins in the composition.

Various techniques suitable for use in purification will be well known to those of skill in the art. These include, for example, precipitation with ammonium sulphate, PEG, antibodies (immunoprecipitation) and the like or by heat denaturation, followed by centrifugation; chromatography such as affinity chromatography (Protein-A columns), ion exchange, gel filtration, reverse phase, hydroxylapatite, hydrophobic interaction chromatography; isoelectric focusing; gel electrophoresis; and combinations of these techniques. As is generally known in the art, it is believed that the order of conducting the various purification steps may be changed, or that certain steps may be omitted, and still result in a suitable method for the preparation of a substantially purified polypeptide.

Pharmaceutical Compositions

In another aspect, the present disclosure provides a pharmaceutical composition comprising the VitoKine constructs in admixture with a pharmaceutically acceptable carrier. Such pharmaceutically acceptable carriers are well known and understood by those of ordinary skill and have been extensively described (see, e.g., Remington's Pharmaceutical Sciences, 18th Edition, A. R. Gennaro, ed., Mack Publishing Company, 1990). The pharmaceutically acceptable carriers may be included for purposes of modifying, maintaining or preserving, for example, the pH, osmolarity, viscosity, clarity, color, isotonicity, odor, sterility, stability, rate of dissolution or release, adsorption or penetration of the composition. Such pharmaceutical compositions may influence the physical state, stability, rate of in vivo release, and rate of in vivo clearance of the polypeptide. Suitable pharmaceutically acceptable carriers include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute thereof. In one embodiment of the present disclosure, compositions may be prepared for storage by mixing the selected composition having the desired degree of purity with optional formulation agents (Remington's Pharmaceutical Sciences, supra) in the form of a lyophilized cake or an aqueous solution. Further, the therapeutic composition may be formulated as a lyophilizate using appropriate excipients such as sucrose. The optimal pharmaceutical composition will be determined by one of ordinary skill in the art depending upon, for example, the intended route of administration, delivery format, and desired dosage.

When parenteral administration is contemplated, the therapeutic pharmaceutical compositions may be in the form of a pyrogen-free, parenterally acceptable aqueous solution comprising the desired VitoKine construct in a pharmaceutically acceptable vehicle. A particularly suitable vehicle for parenteral injection is sterile distilled water in which a polypeptide is formulated as a sterile, isotonic solution, properly preserved. In various embodiments, pharmaceutical formulations suitable for injectable administration may be formulated in aqueous solutions, preferably in physiologically compatible buffers such as Hanks' solution, Ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Optionally, the suspension may also contain suitable stabilizers or agents to increase the solubility of the compounds and allow for the preparation of highly concentrated solutions.

In various embodiments, the therapeutic pharmaceutical compositions may be formulated for targeted delivery using a colloidal dispersion system. Colloidal dispersion systems include macromolecule complexes, nanocapsules, microspheres, beads, and lipid-based systems including oil-in-water emulsions, micelles, mixed micelles, and liposomes. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

In various embodiments, oral administration of the pharmaceutical compositions is contemplated. Pharmaceutical compositions that are administered in this fashion can be formulated with or without those carriers customarily used in the compounding of solid dosage forms such as tablets and capsules. In solid dosage forms for oral administration (capsules, tablets, pills, dragees, powders, granules, and the like), one or more therapeutic compounds of the present disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

In various embodiments, topical administration of the pharmaceutical compositions, either to skin or to mucosal membranes, is contemplated. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface-active agents. Keratolytic agents such as those known in the art may also be included. Examples are salicylic acid and sulfur. Dosage forms for the topical or transdermal administration include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required. The ointments, pastes, creams and gels may contain, in addition to a subject compound of the disclosure (e.g., a VitoKine construct), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Additional pharmaceutical compositions contemplated for use herein include formulations involving polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art.

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the polypeptide is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.0001 mg/kg to up to about 100 mg/kg or more, depending on the factors mentioned above. Polypeptide compositions may be preferably injected or administered intravenously. Long-acting pharmaceutical compositions may be administered every three to four days, every week, or biweekly depending on the half-life and clearance rate of the particular formulation. The frequency of dosing will depend upon the pharmacokinetic parameters of the polypeptide in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

The route of administration of the pharmaceutical composition is in accord with known methods, e.g. orally, through injection by intravenous, intraperitoneal, intratumoral, intracerebral (intra-parenchymal), intracerebroventricular, intramuscular, intra-ocular, intraarterial, intraportal, intralesional routes, intramedullary, intrathecal, intraventricular, intravesical, transdermal, subcutaneous, or intraperitoneal; as well as intranasal, enteral, topical, sublingual, urethral, vaginal, or rectal means, by sustained release systems or by implantation devices. Where desired, the compositions may be administered by bolus injection or continuously by infusion, or by implantation device. Alternatively, or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

Therapeutic Uses

The present disclosure provides for a method of treating cancer cells in a subject, comprising administering to said subject a therapeutically effective amount (either as monotherapy or in a combination therapy regimen) of a VitoKine construct of the present disclosure in pharmaceutically acceptable carrier, wherein such administration inhibits the growth and/or proliferation of a cancer cell. Specifically, a VitoKine construct of the present disclosure is useful in treating disorders characterized as cancer. Such disorders include, but are not limited to solid tumors, such as cancers of the breast, respiratory tract, brain, reproductive organs, digestive tract, urinary tract, eye, liver, skin, head and neck, thyroid, parathyroid and their distant metastases, lymphomas, sarcomas, multiple myeloma and leukemia. Examples of breast cancer include, but are not limited to invasive ductal carcinoma, invasive lobular carcinoma, ductal carcinoma in situ, and lobular carcinoma in situ. Examples of cancers of the respiratory tract include but are not limited to small-cell and non-small-cell lung carcinoma, as well as bronchial adenoma and pleuropulmonary blastoma. Examples of brain cancers include but are not limited to brain stem and hypothalamic glioma, cerebellar and cerebral astrocytoma, neuroblastoma, medulloblastoma, ependymoma, as well as neuroectodermal and pineal tumor. Tumors of the male reproductive organs include but are not limited to prostate and testicular cancer. Tumors of the female reproductive organs include, but are not limited to endometrial, cervical, ovarian, vaginal, and vulvar cancer, as well as sarcoma of the uterus. Tumors of the digestive tract include, but are not limited to anal, colon, colorectal, esophageal, gallbladder, gastric, liver, breast, pancreatic, rectal, small-intestine, and salivary gland cancers. Tumors of the urinary tract include, but are not limited to bladder, penile, kidney, renal pelvis, ureter, and urethral cancers. Eye cancers include but are not limited to intraocular melanoma and retinoblastoma. Examples of liver cancers include but are not limited to hepatocellular carcinoma (liver cell carcinomas with or without fibrolamellar variant), cholangiocarcinoma (intrahepatic bile duct carcinoma), and mixed hepatocellular cholangiocarcinoma. Skin cancers include, but are not limited to squamous cell carcinoma, Kaposi's sarcoma, malignant melanoma, Merkel cell skin cancer, and non-melanoma skin cancer. Head-and-neck cancers include, but are not limited to nasopharyngeal cancer, and lip and oral cavity cancer. Lymphomas include, but are not limited to AIDS-related lymphoma, non-Hodgkin's lymphoma, cutaneous T-cell lymphoma, Hodgkin's disease, and lymphoma of the central nervous system. Sarcomas include but are not limited to sarcoma of the soft tissue, osteosarcoma, malignant fibrous histiocytoma, lymphosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia. In various embodiments, the cancer will be a cancer with high expression of TGF-β family member, such as activin A, myostatin, TGF-β and GDF15, e.g., pancreatic cancer, gastric cancer, liver cancer, breast cancer, ovarian cancer, colorectal cancer, melanoma leukemia, lung cancer, prostate cancer, brain cancer, bladder cancer, and head-neck cancer.

In various embodiments, the VitoKine construct can be used as a single agent for treatment of all kind of cancers, including but not limited to Non-Small Cell Lung, Small Cell Lung, Melanoma, Renal Cell Carcinoma, Urothelial, Liver, Breast, Pancreatic, Colorectal, Gastric, Prostate, and Sarcoma.

In another aspect, the present disclosure provides for a method of treating an autoimmune disease in a subject, comprising administering to said subject a therapeutically effective amount (either as monotherapy or in a combination therapy regimen) of a VitoKine construct of the present disclosure in pharmaceutically acceptable carrier. "Autoimmune disease" refers to a non-malignant disease or disorder arising from and directed against an individual's own tissues. Examples of autoimmune diseases or disorders include, but are not limited to, inflammatory responses such as inflammatory skin diseases including psoriasis and dermatitis (e.g. atopic dermatitis); responses associated with inflammatory bowel disease (such as Crohn's disease and ulcerative colitis); dermatitis; allergic conditions such as eczema and asthma; rheumatoid arthritis; systemic lupus erythematosus (SLE) (including but not limited to lupus nephritis, cutaneous lupus); diabetes mellitus (e.g. type 1 diabetes mellitus or insulin dependent diabetes mellitus); multiple sclerosis and juvenile onset diabetes.

In another aspect, the present disclosure provides for a method of treating an inflammatory disease in a subject, comprising administering to said subject a therapeutically effective amount (either as monotherapy or in a combination therapy regimen) of a VitoKine construct of the present disclosure in pharmaceutically acceptable carrier. "Inflammatory diseases" include all diseases associated with acute or chronic inflammation. Acute inflammation is the initial response of the body to harmful stimuli and results from an increased movement of plasma and leukocytes (such as e.g. granulocytes) from the blood into the injured tissues. A number of biochemical events propagates and matures the inflammatory response, involving the local vascular system, the immune system, and various cells within the injured tissue. Prolonged inflammation is referred to as chronic inflammation, which leads to a progressive shift in the type of cells present at the site of inflammation and is characterized by simultaneous destruction and healing of the tissue from the inflammatory process. Examples of inflammatory diseases are well known in the art. In various embodiments, the inflammatory disease is selected from the group consisting of inflammatory bowel disease, psoriasis and bacterial sepsis. The term "inflammatory bowel disease", as used herein, refers to a group of inflammatory conditions of the colon and small intestine including, for example, Crohn's disease, ulcerative colitis, collagenous colitis, lymphocytic colitis, ischemic colitis, diversion colitis, Behcet's syndrome and indeterminate colitis.

In another aspect, the present disclosure provides for a method of treating a viral infection in a subject, comprising administering to said subject a therapeutically effective amount (either as monotherapy or in a combination therapy regimen) of a VitoKine construct of the present disclosure in pharmaceutically acceptable carrier. In various embodiments, the viral infection to be treated can be caused by infectious agents including but not limited to bacteria, fungi, protozae, and viruses. Viral diseases that can be prevented, treated and/or managed in accordance with the methods described herein include, but are not limited to, those caused by hepatitis type A, hepatitis type B, hepatitis type C, influenza, varicella, adenovirus, herpes simplex type I (HSY-I), herpes simplex type II (HSY-II), rinderpest, rhinovirus, echovirus, rotavirus, respiratory syncytial virus, papilloma virus, papova virus, cytomegalovirus, echinovirus, arbovirus, hantavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral meningitis, encephalitis, dengue or small pox.

Bacterial diseases caused by bacteria (e.g., *Escherichia coli, Klebsiella pneumoniae, Staphylococcus aureus, Enterococcus faecalis, Candida albicans, Proteus vulgaris, Staphylococcus viridians*, and *Pseudomonas aeruginosa*) that can be prevented, treated and/or managed in accordance with the methods described herein include, but are not limited to, mycobacteria *rickettsia, mycoplasma, Neisseria, S. pneumonia, Borrelia burgdorferi* (Lyme dis-ease), *Bacillus antracis* (anthrax), tetanus, *Streptococcus, Staphylococcus, Mycobacterium*, pertussis, cholera, plague, diphtheria, *Chlamydia, S. aureus* and *Legionella*.

Protozoa diseases caused by protozoa that can be prevented, treated and/or managed in accordance with the methods described herein include, but are not limited to, *Leishmania*, kokzidioa, *Trypanosoma* or malaria.

Parasitic diseases caused by parasites that can be prevented, treated and/or managed in accordance with the methods described herein include, but are not limited to, *chlamydia* and *rickettsia*.

Therapeutically effective amount" or "therapeutically effective dose" refers to that amount of the therapeutic agent being administered which will relieve to some extent one or more of the symptoms of the disorder being treated.

A therapeutically effective dose can be estimated initially from cell culture assays by determining an $IC_{50}$. A dose can then be formulated in animal models to achieve a circulating plasma concentration range that includes the $IC_{50}$ as determined in cell culture. Such information can be used to more accurately determine useful doses in humans. Levels in plasma may be measured, for example, by HPLC. The exact composition, route of administration and dosage can be chosen by the individual physician in view of the subject's condition.

Dosage regimens can be adjusted to provide the optimum desired response (e.g., a therapeutic or prophylactic response). For example, a single bolus can be administered, several divided doses (multiple or repeat or maintenance) can be administered over time and the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the present disclosure will be dictated primarily by the unique characteristics of the antibody and the particular therapeutic or prophylactic effect to be achieved.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a subject may also be determined, as can the temporal requirements for administering each agent to provide a detectable therapeutic benefit to the subject. Accordingly, while certain dose and administration regimens are exemplified herein, these examples in no way limit the dose and administration regimen that may be provided to a subject in practicing the present disclosure.

It is to be noted that dosage values may vary with the type and severity of the condition to be alleviated and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this disclosure may be based on a variety of factors, including the type of disease, the age, weight, sex, medical condition of the subject, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present disclosure encompasses intra-subject dose-escalation as determined by the skilled artisan. Determining appropriate dosages and regimens are well-known in the relevant art and would be understood to be encompassed by the skilled artisan once provided the teachings disclosed herein.

An exemplary, non-limiting daily dosing range for a therapeutically or prophylactically effective amount of an VitoKine, or VitoKine variant, of the disclosure can be 0.0001 to 100 mg/kg, 0.0001 to 90 mg/kg, 0.0001 to 80 mg/kg, 0.0001 to 70 mg/kg, 0.0001 to 60 mg/kg, 0.0001 to 50 mg/kg, 0.0001 to 40 mg/kg, 0.0001 to 30 mg/kg, 0.0001 to 20 mg/kg, 0.0001 to 10 mg/kg, 0.0001 to 5 mg/kg, 0.0001 to 4 mg/kg, 0.0001 to 3 mg/kg, 0.0001 to 2 mg/kg, 0.0001 to 1 mg/kg, 0.001 to 50 mg/kg, 0.001 to 40 mg/kg, 0.001 to 30 mg/kg, 0.001 to 20 mg/kg, 0.001 to 10 mg/kg, 0.001 to 5 mg/kg, 0.001 to 4 mg/kg, 0.001 to 3 mg/kg, 0.001 to 2 mg/kg, 0.001 to 1 mg/kg, 0.010 to 50 mg/kg, 0.010 to 40 mg/kg, 0.010 to 30 mg/kg, 0.010 to 20 mg/kg, 0.010 to 10 mg/kg, 0.010 to 5 mg/kg, 0.010 to 4 mg/kg, 0.010 to 3 mg/kg, 0.010 to 2 mg/kg, 0.010 to 1 mg/kg, 0.1 to 50 mg/kg, 0.1 to 40 mg/kg, 0.1 to 30 mg/kg, 0.1 to 20 mg/kg, 0.1 to 10 mg/kg, 0.1 to 5 mg/kg, 0.1 to 4 mg/kg, 0.1 to 3 mg/kg, 0.1 to 2 mg/kg, 0.1 to 1 mg/kg, 1 to 50 mg/kg, 1 to 40 mg/kg, 1 to 30 mg/kg, 1 to 20 mg/kg, 1 to 10 mg/kg, 1 to 5 mg/kg, 1 to 4 mg/kg, 1 to 3 mg/kg, 1 to 2 mg/kg, or 1 to 1 mg/kg body weight. It is to be noted that dosage values may vary with the type and severity of the conditions to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Toxicity and therapeutic index of the pharmaceutical compositions of the disclosure can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effective dose is the therapeutic index and it can be expressed as the ratio $LD_{50}/ED_{50}$. Compositions that exhibit large therapeutic indices are generally preferred.

The dosing frequency of the administration of the VitoKine construct pharmaceutical composition depends on the nature of the therapy and the particular disease being treated. The subject can be treated at regular intervals, such as weekly or monthly, until a desired therapeutic result is achieved. Exemplary dosing frequencies include, but are not limited to: once weekly without break; once weekly, every other week; once every 2 weeks; once every 3 weeks; weakly without break for 2 weeks, then monthly; weakly without break for 3 weeks, then monthly; monthly; once every other month; once every three months; once every four months; once every five months; or once every six months, or yearly.

Combination Therapy

As used herein, the terms "co-administration", "co-administered" and "in combination with", referring to the a VitoKine construct of the disclosure and one or more other therapeutic agents, is intended to mean, and does refer to and include the following: simultaneous administration of such combination of a VitoKine construct of the disclosure and therapeutic agent(s) to a subject in need of treatment, when such components are formulated together into a single dosage form which releases said components at substantially the same time to said subject; substantially simultaneous administration of such combination of a VitoKine construct of the disclosure and therapeutic agent(s) to a subject in need of treatment, when such components are formulated apart from each other into separate dosage forms which are taken at substantially the same time by said subject, whereupon said components are released at substantially the same time to said subject; sequential administration of such combination of a VitoKine construct of the disclosure and therapeutic agent(s) to a subject in need of treatment, when such components are formulated apart from each other into separate dosage forms which are taken at consecutive times by said subject with a significant time interval between each administration, whereupon said components are released at substantially different times to said subject; and sequential administration of such combination of a VitoKine construct of the disclosure and therapeutic agent(s) to a subject in need of treatment, when such components are formulated together into a single dosage form which releases said components in a controlled manner whereupon they are concurrently, consecutively, and/or overlappingly released at the same and/or different times to said subject, where each part may be administered by either the same or a different route.

In another aspect, the present disclosure provides a method for treating cancer or cancer metastasis in a subject, comprising administering a therapeutically effective amount of the pharmaceutical compositions of the invention in combination with a second therapy, including, but not limited to immunotherapy, cytotoxic chemotherapy, small molecule kinase inhibitor targeted therapy, surgery, radiation therapy, and stem cell transplantation. For example, such methods can be used in prophylactic cancer prevention, prevention of cancer recurrence and metastases after surgery, and as an adjuvant of other conventional cancer therapy. The present disclosure recognizes that the effectiveness of conventional cancer therapies (e.g., chemotherapy, radiation therapy, phototherapy, immunotherapy, and surgery) can be enhanced through the use of the combination methods described herein.

A wide array of conventional compounds has been shown to have anti-neoplastic activities. These compounds have been used as pharmaceutical agents in chemotherapy to shrink solid tumors, prevent metastases and further growth, or decrease the number of malignant T-cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

In various embodiments, a second anti-cancer agent, such as a chemotherapeutic agent, will be administered to the patient. The list of exemplary chemotherapeutic agent includes, but is not limited to, daunorubicin, dactinomycin, doxorubicin, bleomycin, mitomycin, nitrogen mustard, chlorambucil, melphalan, cyclophosphamide, 6-mercaptopurine, 6-thioguanine, bendamustine, cytarabine (CA), 5-fluorouracil (5-FU), floxuridine (5-FUdR), methotrexate (MTX), colchicine, vincristine, vinblastine, etoposide, teniposide, cisplatin, carboplatin, oxaliplatin, pentostatin, cladribine, cytarabine, gemcitabine, pralatrexate, mitoxantrone, diethylstilbestrol (DES), fluradabine, ifosfamide, hydroxyureataxanes (such as paclitaxel and doxetaxel) and/or anthracycline antibiotics, as well as combinations of agents such as, but not limited to, DA-EPOCH, CHOP, CVP or FOLFOX. In various embodiments, the dosages of such chemotherapeutic agents include, but is not limited to, about any of 10 mg/m$^2$, 20 mg/m$^2$, 30 mg/m$^2$, 40 mg/m$^2$, 50 mg/m$^2$, 60 mg/m$^2$, 75 mg/m$^2$, 80 mg/m$^2$, 90 mg/m$^2$, 100 mg/m$^2$, 120 mg/m$^2$, 150 mg/m$^2$, 175 mg/m$^2$, 200 mg/m$^2$, 210 mg/m$^2$, 220 mg/m$^2$, 230 mg/m$^2$, 240 mg/m$^2$, 250 mg/m$^2$, 260 mg/m$^2$, and 300 mg/m$^2$.

In various embodiments, the combination therapy methods of the present disclosure may further comprise administering to the subject a therapeutically effective amount of immunotherapy, including, but are not limited to, treatment using depleting antibodies to specific tumor antigens; treatment using antibody-drug conjugates; treatment using agonistic, antagonistic, or blocking antibodies to co-stimulatory or co-inhibitory molecules (immune checkpoints), such as including, but not limited to antibody to, CTLA-4, PD-1, PDL-1, CD40, OX-40, CD137, GITR, LAGS, TIM-3, SIRPa, CD47, GITR, ICOS, CD27, Siglec 7, Siglec 8, Siglec 9, Siglec 15 and VISTA, CD276, CD272, TIM-3, B7-H4; treatment using bispecific T cell engaging antibodies (BiTE®) such as blinatumomab: treatment involving administration of biological response modifiers such as IL-2, IL-7, IL-10, IL-12, IL-15, IL-21, IL-22, GM-CSF, IFN-α, IFN-β, IFN-γ, TGF-β antagonist or TGF-β trap, treatment using therapeutic vaccines, including, but not limited to oncolytic virus, such as T-vec, or therapeutic vaccine, such as sipuleucel-T; treatment using dendritic cell vaccines, or tumor antigen peptide or neoantigen vaccines; treatment using chimeric antigen receptor (CAR)-T cells; treatment using CAR-NK cells; treatment using NK cell; treatment using iPS induced-NK cells; treatment using iPS induced-T cells; treatment using iPS induced CAR-T or iPS induced CAR-NK cells treatment using tumor infiltrating lymphocytes (TILs); treatment using adoptively transferred anti-tumor T cells (ex vivo expanded and/or TCR-T cells); treatment using TALL-104 cells; and treatment using immunostimulatory agents such as Toll-like receptor (TLR) agonists CpG, TLR7, TLR8, TLR9, and vaccine such as Bacille Calmette-Guerine (BCG), and imiquimod; wherein the combination therapy provides increased effector cell killing of tumor cells, i.e., a synergy exists between the VitoKine constructs and the immunotherapy when co-administered.

In various embodiments, the combination therapy methods of the present disclosure may further comprise administering to the subject a therapeutically effective amount of anti-inflammatory agents for autoimmune diseases, inflammatory diseases and other immune disorders, including, but not limited to, treatment using depleting antibodies to specific immune cells; treatment using modulating antibodies (agonist, antagonist or blocking) as immune response target modifiers towards targets (ligand or its receptor), including but not limited to IL-1α, IL-1β or IL-1R, IL-4 or IL-4R, IL-5 or IL-5R, IL-6 or IL-6R, IL-8 or IL-8R, IL-7 or IL-7R, IL-10 or IL-10R, IL-11 or IL-11R, IL-12 or IL-12R, IL-17 or IL-17R, IL-18 or IL-18R, IL-21 or IL-18R, IL-22 or IL-22R, IL-23 or IL-23R, MCSF or MCSF-R, GM-CSF or GM-CSFR, IFN-α, IFN-β, IFN-γ, TGF-α, TGF-β or TGF-β, TNF family or it's relevant receptors, integrin family (e.g. α4β7), TSLP, Complement 5 (C5) or C5a, IgE, APRIL, TACI, BCMA, CD20, CD22, CD40/CD40L, B7H1, B7H2, ICOS, BAFF, BCR, BLys, B7RP1, TLR7, TLR8, TLR9; treatment using modulating small molecule (agonist or antagonist) as immune response target modifiers towards targets, including but not limited to, NFkB, Jak1, Jak2, Jak3, Tyk2, Syk, BTK, PIK3, Cycloxygenase 2 and NMDA receptor; wherein the combination therapy provides increased efficacy of modulating immune responses, i.e., a synergy exists between the VitoKine constructs and the anti-inflammation therapy when co-administered.

In various embodiments, the combination therapy comprises administering a VitoKine construct and the second agent composition simultaneously, either in the same pharmaceutical composition or in separate pharmaceutical composition. In various embodiments, a VitoKine construct composition and the second agent composition are administered sequentially, i.e., a VitoKine construct composition is administered either prior to or after the administration of the second agent composition. In various embodiments, the administrations of a VitoKine construct composition and the second agent composition are concurrent, i.e., the administration period of a VitoKine construct composition and the second agent composition overlap with each other. In various embodiments, the administrations of a VitoKine construct composition and the second agent composition are non-concurrent. For example, in various embodiments, the administration of a VitoKine construct composition is terminated before the second agent composition is administered. In various embodiments, the administration second agent composition is terminated before a VitoKine construct composition is administered.

The following examples are offered to more fully illustrate the disclosure but are not construed as limiting the scope thereof.

Example 1

Construction and Production of IL-15 VitoKine Constructs

The goal was to design IL-15 VitoKine constructs that will remain inert until activated locally by proteases that are upregulated in cancer or diseased tissue. Described herein are VitoKines with wild-type IL-15 (SEQ ID NO: 2) or IL-15 mutein (e.g., SEQ ID NO: 3) as the active moiety that is reversibly concealed between an Fc domain and IL-15RαSushi+(SEQ ID NO: 5). These constructs include one or two cleavable linkers which are recognized by tumor specific proteases. In the presence of protease-expressing tumor cells, the linker connecting the Fc and IL-15 mutein and/or the linker connecting the IL-15 and IL-15αSushi+ will be cleaved and, thereby, IL-15 activity is recovered. Notably, the released IL-15αSushi+ after proteolysis is expected to remain non-covalently associated with IL-15 due to the exceptionally high affinity between IL-15 and IL-15Rα (30 pM). Fc IL-15 VitoKine constructs with various combinations of linkers and peptide spacers were produced and are schematically depicted in FIG. 1 with their respective sequences listed as SEQ ID NOS: 25-43, 162-165, and 169-174.

All genes were codon optimized for expression in mammalian cells, which were synthesized and subcloned into the recipient mammalian expression vector (GenScript). Protein expression is driven by an CMV promoter and a synthetic SV40 polyA signal sequence is present at the 3' end of the CDS. A leader sequence has been engineered at the N-terminus of the constructs to ensure appropriate signaling and processing for secretion.

The constructs were produced by co-transfecting HEK293-F cells growing in suspension with the mammalian expression vectors using polyethylenimine (PEI, 25,000 MW linear, Polysciences). If there were two or more expression vectors, the vectors will be transfected in a 1:1 ratio. For transfection, HEK293 cells were cultivated in serum free FreeStyle™ 293 Expression Medium (ThermoFisher). For production in 1000 ml shaking flasks (working volume 330 mL), HEK293 cells at density of $0.8 \times 10^6$ cells/ml were seeded 24 hours before transfection. Expression vectors to a total amount of 330 µg DNA were mixed with 16.7 ml Opti-mem Medium (ThermoFisher). After addition of 0.33 mg PEI diluted in 16.7 ml Opti-mem Medium, the mixture was vortexed for 15 sec and subsequently incubated for 10 min at room temperature. The DNA/PEI solution was then added to the cells and incubated at 37° C. in an incubator with 8% $CO_2$ atmosphere. Sodium butyrate (Millipore Sigma) at the final concentration of 2 mg/L was added to the cell culture on day 4 to help sustain protein expression. After 6 days cultivation, supernatant was collected for purification by centrifugation for 20 min at 2200 rpm. The solution was sterile filtered (0.22 µm filter, Corning). The secreted protein was purified from cell culture supernatants using Protein A affinity chromatography.

For affinity chromatography supernatant was loaded on a HiTrap MabSelectSure Protein A FF column (CV=5 mL, GE Healthcare) equilibrated with 25 ml phosphate buffered saline, pH 7.2 (ThermoFisher). Unbound protein was removed by washing with 5 column volumes PBS, pH 7.2 and target protein was eluted with 25 mM sodium citrate, 25 mM sodium chloride, pH 3.2. Protein solution was neutralized by adding 3% of 1 M Tris pH 10.2. Target protein was concentrated with Amicon® Ultra-15 concentrator 10 KDa NMWC (Merck Millipore Ltd.)

The purity and molecular weight of the purified constructs were analyzed by SDS-PAGE with or in the absence of a reducing agent and staining with Coomassie (Imperial® Stain). The NuPAGE® Pre-Cast gel system (4-12% or 8-16% Bis-Tris, ThermoFisher) was used according to the manufacturer's instruction. The protein concentration of purified protein samples was determined by measuring the UV absorbance at 280 nm (Nanodrop Spectrophotometer, ThermoFisher) divided by the molar extinction coefficient calculated on the basis of the amino acid sequence. The aggregate content of the constructs was analyzed on an Agilent 1200 high-performance liquid chromatography (HPLC) system. Samples were injected onto an AdvanceBio size-exclusion column (300 Å, 4.6×150 mm, 2.7 µm, LC column, Agilent) using 150 mM sodium phosphate, pH 7.0 as the mobile phase at 25° C.

P-0315 is a dimeric C-terminal Fc fusion IL-15 VitoKine containing uPA and MMP cleavage sequence in the L1 and L2 linker, respectively. The IL-15 is the S58D variant protein. As an example to demonstrate the protein profile of Fc IL-15 VitoKines, SDS-PAGE analyses of P-0315 (SEQ ID NO: 33) are shown in FIG. 3A. Size exclusion chromatogram in FIG. 3B.

Example 2

IL-15 In Vitro Activity was Effectively Concealed in the VitoKine Format

IL-15 VitoKine P-0172 (SEQ ID NO: 27) contains an IL-15/IL-15RαSushi+ fusion polypeptide connected by a short GS (SEQ ID NO: 116) peptide linker, which joins to the C-terminal of homodimeric Fc domain via an uPA-cleavable linker in homodimeric fusion format. P-0198 is a dimeric C-terminal Fc-IL-15 fusion protein with IL-15RαSushi non-covalently complexed. The two molecules have a similar configuration between Fc and IL-15 fusion with a major difference in the IL-15RαSushi incorporation. One is fused by a short GS linker (P-0172) and the other is free by non-covalency (P-0198). The binding activity of P-0172 to IL-2Rβ was determined by enzyme-linked immunosorbent assay (ELISA) in comparison to P-0198 (comprising SEQ ID NOS: 45, 44, and 5), an IL-15/IL-15Rα-Fc fusion protein of high activity.

Figure 4A:
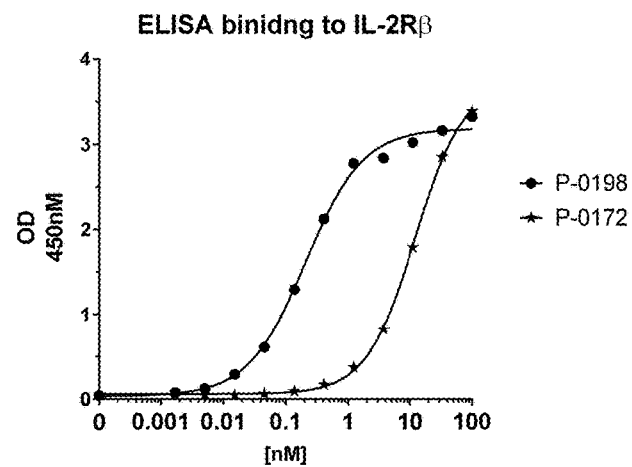
FIG. 4 depicts the binding and functional activity of IL-15 VitoKine P-0172 in comparison with a highly active IL-15 fusion protein P-0198. (A) The binding activity to IL-2Rβ measured by ELISA assay; (B-C) Induction of CD69 expression on human CD8+ T cells (B) and NK cells (C) of fresh human PBMC by FACS analysis.

Briefly, IL-2Rβ-ECD (SEQ ID NO: 12) was coated onto the wells of Nunc Maxisorp 96-well microplates at 1 µg/well. After overnight incubation at 4° C. and blocking with superblock (ThermoFisher), 3-fold serial dilutions of IL-15 compounds starting at 100 nM were added to each well at 100 µl/well. Following a one-hour incubation at room temperature, 100 µl/well of goat anti-human IgG Fc-HRP (1:5000 diluted in diluent) were added to each well and incubated at room temperature for 1 hour. Wells were thoroughly aspirated and washed three times with PBS/0.05% Tween-20 following each step. Finally, 100 µl TMB substrate was added to each well, the plate was developed at room temperature in the dark for 10 minutes, and 100 µl/well of stop solution (2N Sulfuric acid, Ricca Chemical) was added. Absorbance was determined at 450 nm and curves were fit using Prism software (GraphPad). As illustrated in FIG. 4A, the VitoKine P-0172 binds to IL-2Rβ with a significantly reduced potency as compared to P-0198 (12.2 nM vs 0.21 nM), which is likely due to the spatial constrain resulted from the short covalent linkage between IL-15 and IL-15RαSushi, suggesting the IL-15RαSushi in the VitoKine platform effectively concealed the IL-15 domain to bind to its receptor.

The functional activity of IL-15 VitoKine P-0172 in comparison with P-0198 was further assessed by examining IL-15 mediated induction of CD69 expression on human NK and CD8+ T cells from fresh human peripheral blood mononuclear cell (PBMC) by FACS analysis. CD69 is a cell surface glycoprotein that is early induced during lymphoid activation, including NK and T cells.

Briefly, human PBMCs were isolated by Ficoll-Hypaque centrifugation from buffy coat purchased from Oklahoma Blood Institute. Purified human PBMCs were treated with serial dilutions of each IL-15 test compound and incubated at 37° C. for 48 hours. Cells were collected by centrifugation at 300×g and resuspended in FACS buffer. After blocking Fc receptor by adding human TruStain FcX (1:50 dilution), cells were stained with anti-human CD56-FITC, anti-human CD69-PE and anti-human CD8-APC antibodies (1:50 dilution). After a 30-minute incubation with the antibodies at room temperature, cells were collected and washed, resuspended in FACS buffer and analyzed by flow cytometry. CD69 expression was determined by gating on CD56+ NK and CD8+ T cells and data are expressed as % of CD69 positive cells in the gated population.

Figure 4B:
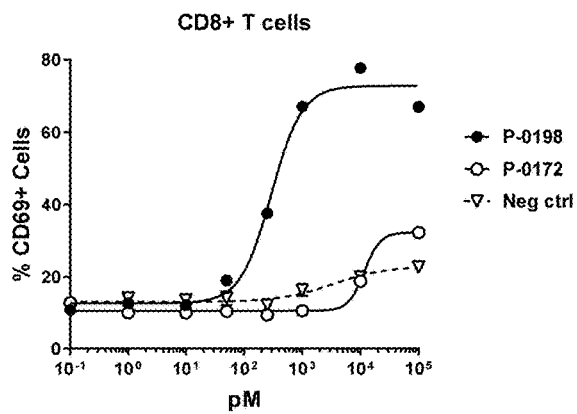
Figure 4C:
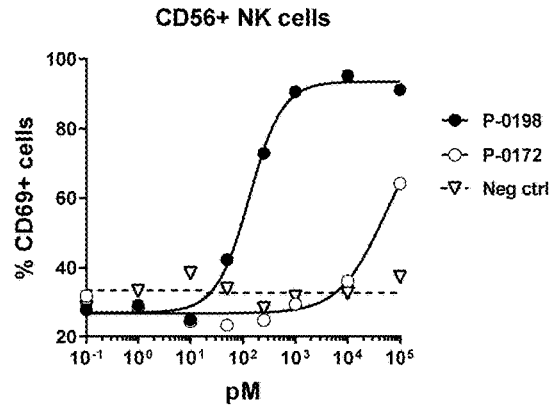

As demonstrated in FIGS. 4B and 4C, the CD69 activation on CD8+T and NK cells by the VitoKine P-0172 was drastically reduced and only measurable at the highest concentration tested, with potency at least 2-3 logs lower than that of P-0198. This indicates efficient concealing of IL-15 activity in the VitoKine format. The concealing effect was more pronounced in the PBMC CD69 activation assay than in the IL-2Rβ ELISA binding assay, suggesting a severe impairment of IL-15 activity is more evident in the physiologically condition than in vitro reconstituted condition on ELISA. Due to the presence of spatial constraints, VitoKine severely impairs the engagement of IL-15 to IL-2Rβ and $\gamma_C$ complex expressed on the lymphocytes, and consequently resulted in inefficient pathway activation and the severely impaired activity.

Figure 5:
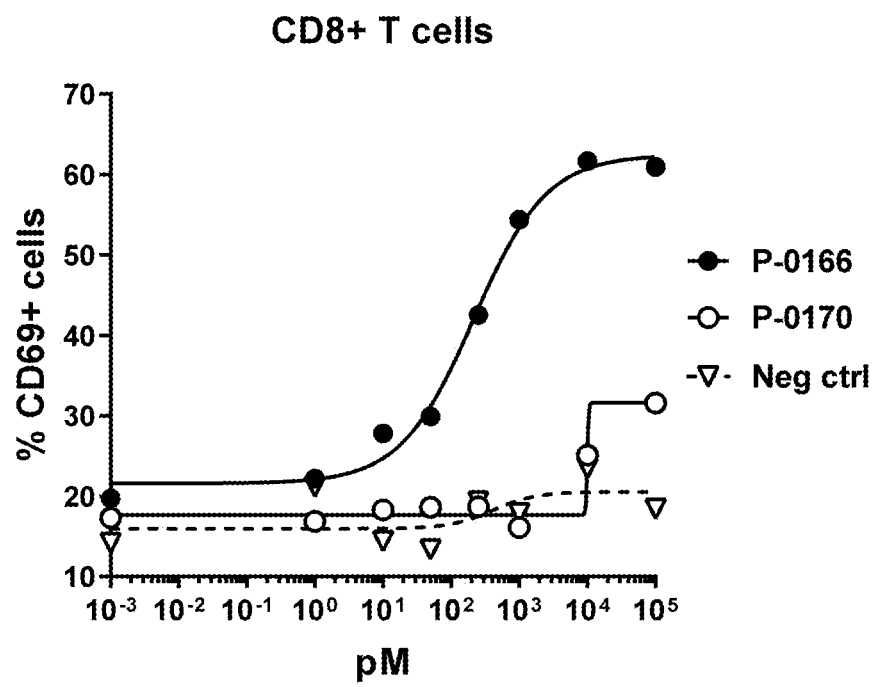
FIG. 5 depicts the functional activity of monomeric Fc IL-15 VitoKine P-0170 in comparison with a highly active IL-15 fusion protein P-0166. The induction of CD69 expression on human CD8+ T cells of fresh human PBMC was measured and analyzed by FACS.

The biological activity of the monomeric IL-15 VitoKine was also examined. P-0170 (SEQ ID NOS: 26 and 15) is the monomeric counterpart of P-0172 having the same linkers and the fusion configuration. Compared to the highly active IL-15 Fc fusion protein P-0166, P-0172 showed drastically reduced ability to activate CD69 on CD8+ T cells (FIG. 5), suggesting monomeric VitoKine platform effectively concealed the biological activity of IL-15 in the D2 domain.

Example 3

Comparison of Fc IL-15 VitoKine Concealing Efficiency of Varied Linker Lengths and Compositions Between IL-15 and IL-15RαSushi+ and Between Fc and IL15

The IL-15 VitoKine is constructed by fusing human IL-15 between two distinct domains, such as a half-life extension Fc domain and its cognate high-affinity co-receptor alpha domain, via peptide linkers L1 and L2 as depicted in FIG. 1. The differential effect of the two linkers joining the Fc and IL-15 verse connecting IL-15 and the 15RαSushi domain, as well as the length and composition of the linkers on the biological activity of IL-15 was examined for the desired impairment of the activity.

FACS analysis of the activation marker CD69 of immune cell subpopulations of fresh human PBMC was performed to assess IL-15 VitoKines of varied non-cleavable linker lengths between IL-15 and IL-15RαSushi+(L2). The same protocol as in Example 2 was followed.

P-0204 (SEQ ID NO: 30), P-0205 (SEQ ID NO: 31), and P-0206 (SEQ ID NO: 32) are Fc IL-15 VitoKines sharing the same uPA cleavable linker sequence between Fc and IL-15 (L1), but the linker connecting the IL-15 and IL-15RαSushi+ domains (L2) in the three VitoKines varies in length and are (GGGGS)$_3$ (SEQ ID NO: 127), (GGGGS)$_2$ (SEQ ID NO: 126), and GGGGS (SEQ ID NO: 118), respectively.

As demonstrated in FIG. 6, Fc IL-15 VitoKines of varied linker lengths from 5 to 15 amino acids between IL-15 and IL-15RαSushi+ all resulted in dramatic decreases in the potency of activating CD8+ T cells (FIG. 6A) or NK cells (FIG. 6B). Comparing the potency of P-0206, P-0205, and P-0204, it was evident that the shorter the linker length connecting the IL-15 and IL-15RαSushi+ domains, the more inactive the VitoKine becomes; suggesting that the extent of reduced activity can be further tuned by the L2 linker length; In summary, we have demonstrated a nearly complete loss of IL-15 activity by concealing it between an Fc domain and its cognate high-affinity co-receptor alpha by tuning the linker length between IL-15 and IL-15Rα (L2) to create appropriate level of spatial constraint.

Figure 7:
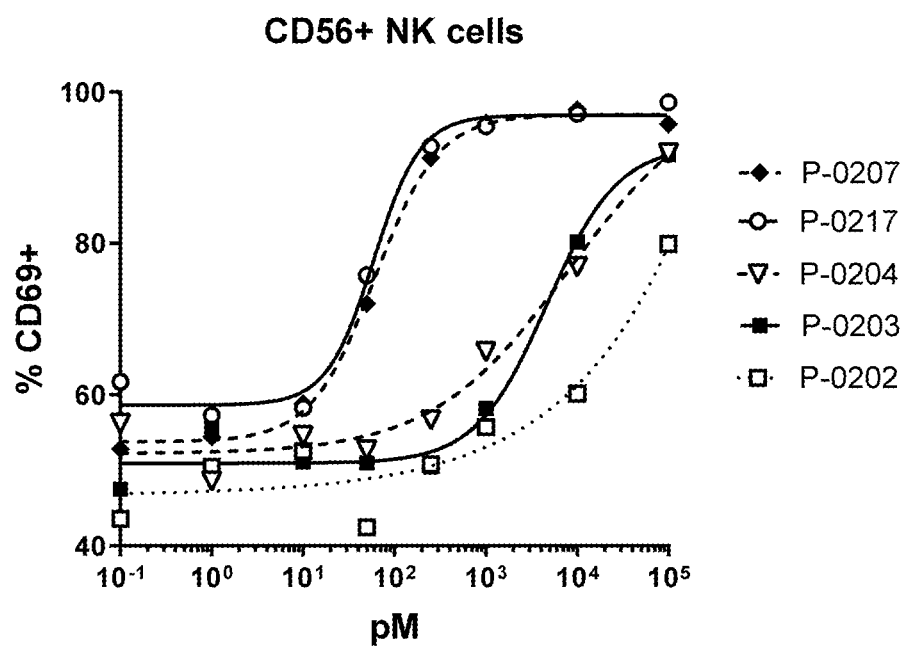
FIG. 7 depicts the proliferation of NK (CD56+) cells in human PBMC by illustrative VitoKine constructs with different L1 and L2 linkers (P-0202, P-0203, and P-0204) in comparison with fully active IL-15/IL-15Rα Fc fusion proteins P-0207 and P-0217.

The effect of the linker joining Fc and IL-15 (L1) on the biological activity of the VitoKines was also examined is illustrated in FIG. 7. P-0204 and P-0203 (SEQ ID NO: 29) share the same 15-amino acid flexible (G$_4$S)$_3$ linker between IL-15 and IL-15Rα (L2) but differ in the length of L1 linker, while P-0203 contains a longer peptide spacer by 7 GS residues flanking the uPA substrate peptide connecting Fc and IL-15 than P-0204. Despite the difference in the L1 linker length joining Fc and IL-15, the biological activities of P-0204 and P-0203 were similar (FIG. 7), suggesting the L1 linker joining Fc and IL-15 made minimal impact on the impairment of IL-15 activity when spanning from 13 to 35 amino acid residues. However, the L1 linker length less than or more than 13 to 35 amino acid residues or in different context of cytokine may impact concealing activity to the D2 domain. In the same study, P-0202 was included, which shares the same L1 linker joining the Fc and IL-15 but a 13 amino acid shorter L2 linker connecting IL-15 and IL-15RαSushi domain compared to P-0203. P-0202 showed lower biological activity than P-0203, confirming that the linker L2 is more important than linker L1 in masking activity of the VitoKine.

The effect of the linker composition or linker peptide sequence on VitoKine activity was investigated by measuring Ki67 expression in the nucleus of NK and CD8 T cells following IL-15 VitoKine treatment. Ki67 is a marker for cell proliferation and an ex vivo human PBMC assay was established. Briefly, purified human PBMCs were treated with serial dilutions of IL-15 VitoKine compounds and incubated at 37° C. for 5 days. On day 5, cells were washed once with FACS buffer (1% FBS/PBS) and first stained with Fc-blocker and surface marker antibodies, including anti-human CD56-FITC and anti-human CD8-APC (1:50 dilution). After 30-minutes incubation and wash, cell pellets were fully resuspended by 200 μl/well of 1X Foxp3 fixation & permeabilization working solution and incubated for 30-minutes at room temperature in dark. After centrifugation, 200 μl of 1X permeabilization buffer were added to each well for another wash. Cell pellets were resuspended in permeabilization buffer with anti-human Ki67-PE (1:25 dilution). After 30-minutes incubation at room temperature, cells were collected and washed, resuspended in FACS buffer, and analyzed by flow cytometry. Data are expressed as % of Ki67 positive cells in gated population.

Since the L2 linker exerts significant impact on the IL-15 VitoKine activity compared to the L1 linker, we examined the effect of different sequence compositions of the L2 linker on the biological activity of the IL-15 VitoKine. P-0351 (SEQ ID NO: 25), P-0488 (SEQ ID NO: 163), and P-0489 (SEQ ID NO: 164) all share the same $(G_4S)_3$ linker joining Fc and IL-15 (L1). The linkers joining IL-15 and IL-15Rα are all 10-amino acid long but are of different sequences. The linker is either $(G_4S)_2$ in P-0351, MMP-14 substrate peptide (SEQ ID NO: 157) in P-0488 or legumain substrate peptide (SEQ ID NO: 160) in P-0489.

As demonstrated in FIG. 8, all three IL-15 VitoKines had severely impaired potency in proliferating NK cells (FIG. 8A) or CD8+ T cells (FIG. 8B) in comparison to the highly active IL-15/IL-15Rα Fc fusion protein P-0156 (SEQ ID NOS: 175+176). Different peptide linker sequences had subtle impacts on the biological activity of the respective VitoKines (FIGS. 8A & 8B), likely due to the structural flexibility of each linker peptide. The more rigid the L2 linker peptide is, the more structural constraint it exerts on the VitoKine molecules, which could result in more profound activity impairment. However, the impact of L2 linker sequence composition on the VitoKine activity was minimal and the data support that different cleavable linkers can be incorporated as the L2 linker to efficiently conceal the activity of D2 domain, thereby expanding the broadness of VitoKine design and utility.

In summary, the data collectively demonstrated that the L2 linker connecting IL-15 (D2) and IL-15RαSushi+(D3) domains played a fundamental role in concealing D2 activity to yield inert VitoKine. The level of activity inertness could be further tuned by adjusting L2 linker length and varying linker sequence/flexibility. The choice of cleavable L2 linker length and sequence should be balanced between the presence of specific proteases at the site of intended disease indication, accessibility of the substrate peptide to the proteases, and the desired rate of proteolysis.

Example 4

Determination of the Appropriate Reaction Conditions for Complete Protease Cleavage Th initial in vitro protease cleavage experiments were performed using IL-15 VitoKine constructs P-0315 and P-0203 to determine protease cleavability and optimal cleavage conditions for MMP-2 and uPA, respectively. P-0315 (SEQ ID NO: 33) comprises an uPA cleavable linker connecting the Fc and IL-15 domains and MMP-2/9 cleavable linker connecting IL-15 and IL-15RαSushi+ domains. P-0203 (SEQ ID NO: 29) contains a single protease cleavable linker (uPA) connecting the Fc and IL-15 domains. The linker between IL-15 and IL-15RαSushi+ domains in P-0203 is a flexible $(G_4S)_3$ linker. Recombinant human uPA and MMP-2 were purchased from BioLegend. MMP-2 was supplied in the latent form and was activated by p-aminophenylmercuric acetate (APMA, Millipore Sigma) according to the manufacturer's instruction.

Figure 9:
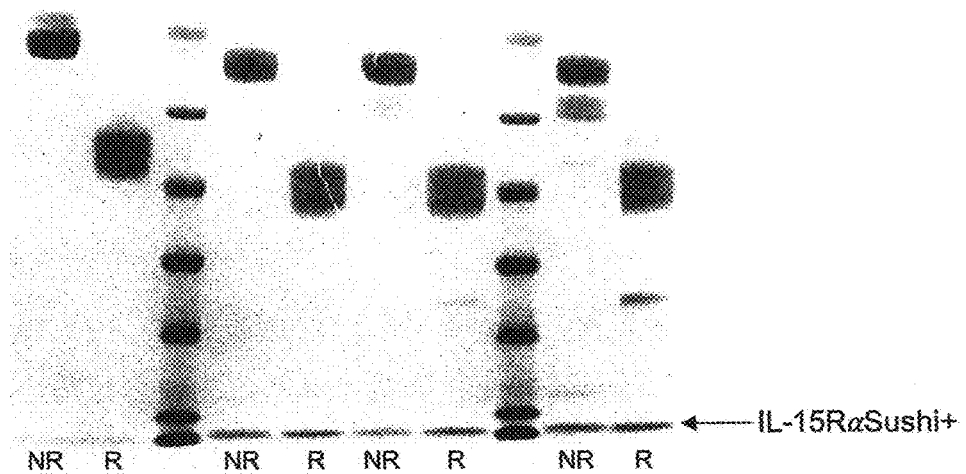
FIG. 9 depicts SDS-PAGE analysis of Fc IL-15 VitoKine P-0315 proteolysis using different amount of MMP-2.

For proteolytic cleavage by MMP-2, 4 μg P-0315 was incubated with 30 ng, 100 ng, or 300 ng of APMA-activated MMP-2 in the manufacturer's recommended assay buffer (100 mM Tris, 20 mM $CaCl_2$), 300 mM NaCl, 0.1% (w/v) Brij 35, pH 7.5) at 37° C. for 3 hours. To stop the reaction, SDS-PAGE loading dye was added to the reaction and the mixture was heated at 95° C. for 5 minutes. To assess cleavage, the digested samples were separated on a 4-12% Tris-Bis SDS-PAGE gel. Comparison of untreated and treated samples showed that the IL-15 VitoKine was completely cleaved off after treatment with MMP-2 at all tested concentrations. This was indicated by the size shift and the appearance of a sharp band of ~9 KDa in the SDS page gel (FIG. 9), which was the IL-15RαSushi+ domain cleaved off from P-0315.

Cleavability of uPA was assessed by using P-0203. First, different amounts of uPA were added to 2 μg of P-0203 in 20 μl PBS, pH 7.2 buffer and the reaction mixture was incubated at 37° C. for 2 hours. Cleavages performed with 0, 25 ng, 50 ng, 100 ng, and 300 ng of uPA are illustrated in FIG. 10A. The three arrows in FIG. 10A are for the non-reducing (NR) samples and indicate the change of the Fc chain with the uPA proteolysis. In "Partial cut", the IL-15/IL-15RαSushi+ fusion polypeptide was cleaved off from only one of the two Fc chains, while in "Full cut", the IL-15/IL-15RαSushi+ fusion polypeptide was cleaved off from both Fc chains. The smeary band circled in FIG. 10A was the IL-15/IL-15RαSushi+ fusion polypeptide cleaved off from the Fc, and the smeary appearance was most likely due to glycosylation. In reduced (R) samples, the upper band was the Fc chain linked to the IL-15/IL-15RαSushi+ fusion polypeptide, and the lower sharp band was the Fc chain with the IL-15/IL-15RαSushi+ fusion polypeptide cleaved off.

The SDS-PAGE gel clearly shows that with an increasing amount of uPA, there was an incremental increase in the amount of fully cut protein in the non-reducing samples. Likewise, there was an increased amount of cleaved Fc chain in the reduced sample, indicating an increased level of cleavage. However, no conditions resulted in complete cleavage. To achieve complete digestion, similar uPA digestion reactions were incubated for a longer time. FIG. 10B shows cleavage of 2 μg P-0203 with 50 ng, 100 ng, and 300 ng of uPA for at 37° C. for 24 hours. The data indicate that 100 ng uPA with a 24-hour incubation resulted in nearly complete cleavage.

Example 5

Figure 11A:
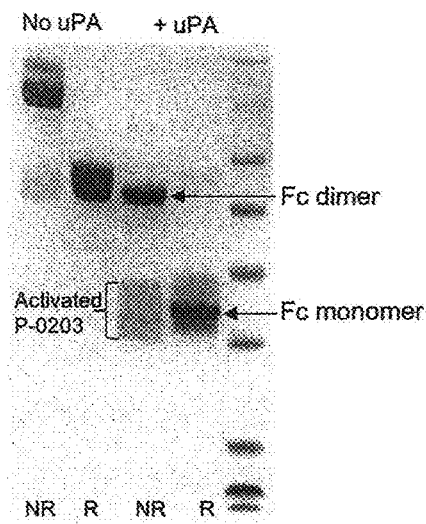
FIG. 11 depicts A) SDS-PAGE analysis of Fc IL-15 VitoKine P-0203 before and after proteolysis by uPA. B) Protein profile of the activated VitoKine P-0203 after uPA digestion and Protein A purification to remove cleaved Fc fragment.
Figure 11B:
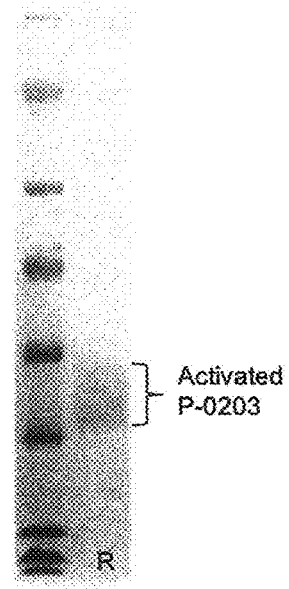

Protease Cleavage of Fc IL-15 VitoKine P-0203 to Derive Activated IL-15 Products VitoKine P-0203 (SEQ ID NO: 29) contains a uPA substrate peptide linker with spacer peptides flanking both ends (SEQ ID NO: 90) connecting Fc and IL-15, and a second 15-amino acid flexible linker (GGGGS)$_3$ (SEQ ID NO: 127) connects the IL-15 and IL-15RαSushi+ domains. In vitro protease cleavage was achieved by incubating 100 µg of VitoKine P-0203 with 5 µg recombinant human uPA (BioLegend) in 500 µl PBS, pH 7.2 buffer for 24 hours at 37° C. To stop the reaction, 25 µl of Ni-Excel resin (50% slurry equilibrated in PBS, GE Healthcare) was added to remove 6-His-tagged uPA from the solution. Meanwhile, 50 µl MabSelectSure Protein A resin (50% slurry equilibrated in PBS, GE Healthcare) was also added to the reaction to remove the cleaved Fc fraction and uncut or incompletely digested P-0203. After a room temperature incubation with both affinity resins for 15 min, the resins were removed by centrifugation and the flow-through containing protease-activated P-0203, namely IL-15/IL-15αSushi+ fusion polypeptide (schematically illustrated as Active Form 1 in FIG. 2) was recovered. As can be seen in FIGS. 11A and 11B, the activated P-0203 fragment migrates with smeary banding, most likely due to glycosylation.

Example 6

Protease Cleavage of Fc IL-15 VitoKine P-0315 to Derive Activated IL-15 Products VitoKine P-0315 (SEQ ID NO: 33) contains a uPA substrate peptide linker (SEQ ID NO: 92) connecting Fc and IL-15, and a second 10-amino acid MMP-2/9 cleavable linker (SEQ ID NO: 95) between the IL-15 and IL-15RαSushi+ domains. The IL-15 domain in P-0315 contains an S58D substitution to enhance binding to the receptor β subunit. Two activated forms of P-0315 were generated by protease digestion.

One activated form of P-0315 (schematically illustrated as Active Form 2 in FIG. 2) was obtained by in vitro protease cleavage using MMP-2. Briefly, 660 ng of latent MMP-2 (BioLegend) was activated by APMA (Millipore Sigma) according to the manufacturer's instructions, buffer exchanged, and added to P-0315 (80 µg) in 0.4 ml of the manufacturer's recommended assay buffer (100 mM Tris, 20 mM CaCl$_2$), 300 mM NaCl, 0.1% (w/v) Brij 35, pH 7.5). After incubation at 37° C. for 3 hours, 50 µl MabSelectSure Protein A resin (50% slurry equilibrated in PBS, GE Healthcare) was added to the reaction. The desired activated form 1 was eluted with 25 mM sodium citrate, 25 mM sodium chloride, pH 3.2. Protein was neutralized by adding 3% of 1M Tris pH 10.2. To assess cleavage, samples were separated on a 4-12% Tris-Bis SDS-PAGE gel (FIG. 12A). P-0315 prior to MMP-2 digestion in the presence of reducing agent was shown in Lane 1, and Lane 2 and 3 are non-reduced and reduced P-0315 after MMP-2 proteolysis but prior to Protein A purification. The appearance of IL-15Rα-sushi+ domain as a sharp band at 9 KDa on the gel confirmed the efficient MMP-2 cleavage at the MMP-2/9 substrate peptide linker. After protein A purification, the samples (Lane 4 and 5) show an identical migration pattern. This data suggests that the IL-15RαSushi+ domain released from the covalent linkage remain non-covalently associated with IL-15 that is fused with Fc as depicted as the Active Form 2 in FIG. 2; such an association was strong enough to withstand low-pH conditions during Protein A elution. FIG. 12B further illustrates the two non-covalently associated components of this activated form.

The other activated form of P-0315 (schematically illustrated as Active Form 3 in FIG. 2) was obtained by protease cleavage of P-0315 with both uPA and MMP-2. Briefly, 100 µg P-0315 was incubated with 5 µg in 400 µl PBS, pH 7.2 buffer for 20 hours. Then an equal volume of the buffer containing 200 mM Tris, 40 mM CaCl$_2$), 450 mM NaCl, 0.2% (w/v) Brij 35, pH 7.5 was added to the reaction to adjust the buffer close to the manufacturer's recommended MMP-2 assay buffer (100 mM Tris, 20 mM CaCl$_2$), 300 mM NaCl, 0.1% (w/v) Brij 35, pH 7.5). Latent MMP-2 (660 ng) was activated by APMA, buffer exchanged to the assay buffer, added to the reaction, and incubated at 37° C. for 3 hours. Ni-Excel resin (50 µl of 50% slurry equilibrated in PBS, GE Healthcare) was added to remove His-tagged MMP-2 and uPA from the solution. Meanwhile, 100 µl MabSelectSure Protein A resin (50% slurry equilibrated in PBS, GE Healthcare) was added to the reaction to remove the cleaved Fc fraction and remaining uncut or incompletely digested P-0315. After room temperature incubation with both affinity resins for 15 min, the resins were removed by centrifugation and the flow-through containing the Active Form 3 of P-0315 with schematic illustration in FIG. 2 was recovered. As illustrated in FIG. 12C, Active Form 3 of P-0315 contains IL-15/IL-15αSushi+ non-covalent complex as expected from dual proteolysis reactions; IL-15 migrates as a smear banding while IL-15RαSushi+ is a sharp band at ~9 KDa, as seen in Active Form 2 (FIG. 12B).

Example 7

Activity Assessment of the Protease Activated Fc IL-15 VitoKines by Human PBMC Assay FACS analysis of the activation marker CD69 of immune cell subpopulations from fresh human PBMC, as detailed in Example 2, was performed to assess the activity of protease activated IL-15 VitoKines. A comparison of P-0203 and its corresponding activated form (P-0203 Activ.; schematically illustrated as Active Form 1 in FIG. 2) resulting from uPA digestion is illustrated in FIG. 13. Activity of the VitoKine prior to protease activation was about 3 logs lower than the highly active IL-15/IL-15Rα Fc fusion protein P-0165, which agreed with the VitoKine activity described in Example 3. Potency in activating both CD56+ NK (FIG. 13A) cells and CD8+ T cells (FIG. 13B) was recovered significantly with uPA digestion but was still notably lower than that of P-0165, possibly due to the covalent linkage of IL-15 and IL-15Rα domain. Extending the length of the flexible linker connecting IL-15 and IL-15Rα is expected to enhance the potency of activated form. Paradoxically, linker length extension will also likely lower the activity concealing efficiency of D3 domain, and consequently results in VitoKine constructs of higher basal activity.

The biological activity of another IL-15 Fc VitoKine P-0315 and its two activated forms were assessed by measuring CD69 activation in activating immune cell subpopulations of fresh human PBMC. As seen in FIG. 14, the activity of un-cleaved P-0315 was barely measurable, confirming effective concealing of the active moiety in the VitoKine format. The Active Form 2 of P-0315 contains Fc-fused IL-15 that non-covalently complexes with IL-15RαSushi+ domain released from MMP-2 cleavage as illustrated in FIG. 2; it structurally resembles the positive control P-0313, a highly potent IL-15 IL-15Rα Fc fusion protein. The Active Form 3 of P-0315 contains free IL-15 domain cleaved off of the Fc domain by uPA, and IL-15RαSushi+ domain released from MMP-2 cleavage, two of which form non-covalent complexes as depicted in FIG. 2. Both activated forms of P-0315 showed complete or near-complete recovery of potency in activating both CD56+ NK cells (FIG. 14A) and CD8+ T cells (FIG. 14B); the Active Form 3 being moderately more active than the Active Form 2. The lack of Fc domain in the Active Form 3 may be beneficial when transient activation of the intended pathway in the tumor microenvironment is desirable.

The activity of P-0315 before and after MMP-2 proteolysis was also investigated by measuring Ki67 expression in the nucleus of NK cells (FIG. 15A) and CD8+ T cells (FIG. 15B) following treatment. P-0351, comprising two non-cleavable flexible linkers, was included for comparison. The data further demonstrated the activity inertness of the Vito-Kine and approximately 3 logs of potency restoration in both NK cells and CD8+ T cells after in vitro proteolytic activation. The observation that P-0351 and P-0315 had identical activity suggests that the two cleavable linkers in P-0315 remained intact during production, expression, and storage, and were specific to the respective proteases.

In summary, cleavage of IL-15 VitoKine P-0315 by MMP-2/9 and/or uPA leads to activation of the molecule and the cytokine activity was restored to similar levels as the highly active IL-15 compound P-0313 with $EC_{50}$ in the sub-nanomolar range.

Example 8

Minimal Systemic Cytokine Effect with Fc IL-15 VitoKines in Healthy Mice

The goal of the VitoKine platform technology is to reduce systemic on-target toxicity and enhance therapeutic window. The VitoKine conceals the active cytokine in an inert state and prevents its engagement to the receptors in the peripheral or on the cell-surface of non-diseased cells. As a consequence, the VitoKine platform limits over-activation of the cytokine pathway and reduces undesirable "on-target" "off tissue" toxicity. The VitoKine is intended to be activated locally by proteases that are upregulated in the diseased tissues. To evaluate this hypothesis, the protease cleavable and non-cleavable VitoKines were administered into healthy mice and their systemic cytokine effects were evaluated in comparison with highly active IL-15 Fc fusion protein.

P-0313 (SEQ ID NOS: 47 and 5) is a fully active IL-15/IL-15Rα Fc fusion molecule as a positive control. P-0315 (SEQ ID NO: 33) is an Fc IL-15 VitoKine containing two protease cleavable linkers. P-0351 (SEQ ID NO: 25) is a Fc IL-15 VitoKine comprising two non-cleavable linkers. Vehicle (PBS) was included as the negative control. Compounds were given one single i.p. injection into healthy BALB/c mice (8-10 weeks old, n=6/group) at 0.1 and 0.3 mg/kg doses. Blood samples were collected prior dosing (day −1) or on days 3, 5, and 7 post dosing for immunophenotyping.

After red blood cells were lysed by BD pharm lysis buffer, total viable mononuclear blood cells were counted by trypan blue dead cell exclusion method. After blocking Fc-receptors with purified anti-mouse CD16/CD32 (1:50 dilution), cells were stained with anti-mouse CD3-FITC, anti-mouse CD49b-APC and anti-mouse CD8-Percpcy5.5 (1:50 dilution). After a 30-minute incubation, cells were collected and washed, resuspended in FACS buffer and analyzed by flow cytometry.

As shown in FIG. 16, P-0313, the fully active IL-15 Fc fusion protein, dramatically expanded peripheral blood cytotoxic CD8+ T cells (FIG. 16A), NK cells (FIG. 16B) and total white blood cells (FIG. 16C) at two tested doses in a dose-dependent fashion. The cell expansions were observed on day 3, peaked on Day 5 and returned to near baseline on Day 7. In contrast, both cleavable (P-0315) and non-cleavable (P-0351) VitoKines showed no increases in CD8 T cells over the entire 7 days study. A minor and delayed increase in NK cell expansion was observed in mice treated with the high dose of the cleavable VitoKine P-0315. P-0351 and the low dose of P-0315 showed no sign of increase in any targeted cell population tested. Overall, compared to the active molecule P-0313, the two tested VitoKines showed minimal systemic activation and expansion of the targeted lymphocyte populations and demonstrated a successful masking and delaying the activity of IL-15 in the periphery.

Example 9

Inhibition of Colon Cancer Cell Lung Metastasis with Fc IL-15 VitoKines in Mice

Anti-metastatic efficacy and immunological responses of IL-15 Fc VitoKine molecules was investigated in a mouse CT26 pulmonary metastasis model. Briefly, $1 \times 10^5$ mouse colon carcinoma cells, CT26-WT (ATCC CRL-2638), were intravenously injected into female Balb/C mice (9-11 weeks old). Four Q5D treatments were initiated on the next day (day 1) via intraperitoneal injection. Treatment groups (total 6, n=7/group) includes 0.3 mg/kg P-0315, 0.3 mg/kg P-0351 and 0.1 mg/kg P-0313. P-0315 (SEQ ID NO: 33) is an Fc IL-15 VitoKine containing two protease cleavable linkers. P-0351 (SEQ ID NO: 25) is a non-cleavable Fc IL-15 VitoKine. P-0313 (SEQ ID NOS: 47 and 5) is a fully active IL-15/IL-15Rα Fc fusion molecule. Vehicle (PBS) was included as the negative control. On day 17, all mice were sacrificed for tissue harvesting. Lungs were inflated by 15% india ink and de-stained in Fekete's solution (10% formaldehyde, 5% glacial acetic acid and 60% ethanol). Lung tumor nodules were counted, and anti-metastatic effect were represented by different numbers of tumor nodules between treatment groups and vehicle control.

Figure 17:
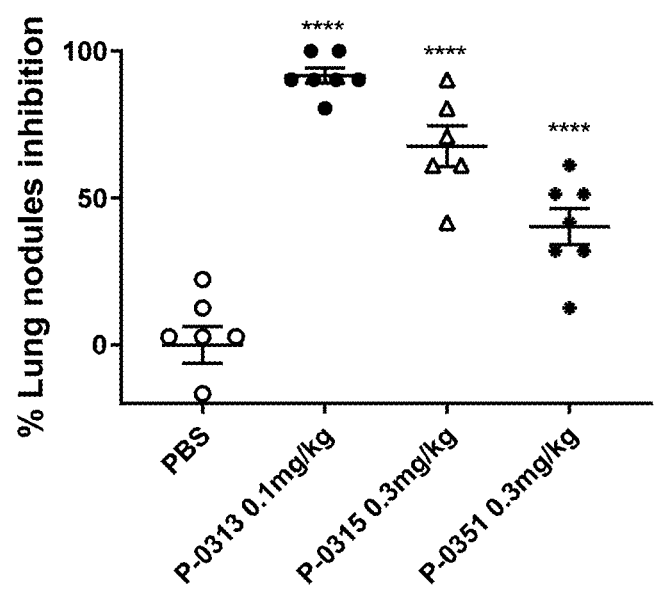
FIG. 17 depicts the inhibition of lung metastatic nodules in mouse CT26 pulmonary metastasis model one days after 4×Q5D doses of P-0315, P-0351, P-0313, or PBS control. The first dosing was initiated one day after the injection of CT26 cells. All comparisons versus PBS group unless otherwise specified; ** p<0.0001;  p<0.01; *p<0.05.

As illustrated in FIG. 17, P-0313 had a marked effect in suppressing the formation and growth of lung metastasis. At 0.1 mg/kg, P-0313 treatment resulted in close to complete inhibition of lung metastasis. The cleavable VitoKine P-0315 demonstrated 70% inhibition of the development of lung nodules; the anti-metastatic efficacy was comparable for all three doses (0.3, 1, or 3 mg/kg). The non-cleavable VitoKine P-0351 demonstrated relatively weaker but significant effect in reducing the metastatic development, suggesting some intrinsic basal activity at the high dose. Nevertheless, P-0315 demonstrated notably better anti-metastatic efficacy than P-0351 ($p<0.05$; FIG. 17), suggesting proteolytic cleavage of one or both linkers in P-0315 and subsequent release of the active form of IL-15 likely contributed to the in vivo efficacy superiority of P-0315 over P-0351. Tumor metastases development may lead to increased proteolytic activities in the vicinity of tumor microenvironment.

Immunological response following IL-15 compounds treatment was investigated by flow cytometric analysis of mouse peripheral blood on day 15 (4 days post the third treatment). Compared with control, expansion of CD8+ T cells were seen in mice treated with the active IL-15 Fc fusion P-0313 but not the cleavable VitoKines P-0315 or the non-cleavable VitoKine P-0351, suggesting the anti-colon cancer metastasis efficacy was observed at the absence of systemic elevation of CD8+ T cells by the VitoKines (FIGS. 17 & 18A). Peripheral blood NK cells, however, were elevated in all three IL-15 compound treated groups with the most pronounced increase in the non-cleavable VitoKine group after the repeated dosing (FIG. 18B). The increases in systemic expansion of NK cells but not CD8+ T cells in the VitoKine treated groups suggest that the NK cells are more responsive than CD8+ T cells to IL-15 treatment and the intrinsic basal activity of the VitoKine may lead to NK cell expansion. It is thus critical to adjust the dosing concentration of IL-15 VitoKines to reduce the residual systemic effect. The pronounced increase in NK cells in P-0351 group also suggest that the low potency non-cleavable VitoKine may weakly but persistently activate the pathway and lead to prolonged immune responses.

Example 10

Fc IL-15 VitoKine P-0315 Inhibited Established CT26 Tumor Growth in Mice with Minimal Systemic Cytokine Activation The anti-tumor efficacy and immunological responses of Fc IL-15 VitoKine P-0315 was investigated in CT26 murine colorectal carcinoma tumor model in comparison with the fully active IL-15/IL-15Rα-Fc fusion protein P-0313. Briefly, female Balb/C Mice (10-12 weeks old) were injected with $1\times10^5$ CT26 cells subcutaneously in the right flank. On day 11, when the average tumor volume was ~70 mm$^3$, mice were randomized into three groups (n=11/group) and received intraperitoneal injection of vehicle (PBS), or P-0315, or P-0313 at 0.1 mg/kg on the same day of randomization. One additional intraperitoneal injections of the respective testing agents were performed on day 16 (2×Q5D). Tumors were measured three times weekly using calipers, and the tumor volume was calculated as: volume=$0.5\times(\text{width})^2\times(\text{length})$. To study immunological response, non-terminal peripheral blood was collected in heparin-treated tubes on day 19. On day 21, all mice were sacrificed for tissue harvesting.

Figure 19A:
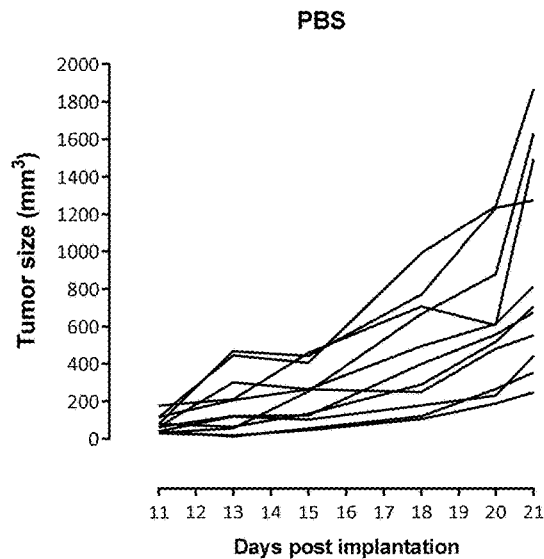
FIG. 19 depicts the antitumor efficacy of Fc IL-15 VitoKine P-0315 in comparison with the fully active IL-15 Fc fusion P-0313 in established CT26 murine colorectal carcinoma tumor model. Growth curve of CT26 s. c. tumors in individual mouse following two Q5D treatments was illustrated for A) vehicle PBS group, B) 0.1 mg/kg P-0315 group, or C) 0.1 mg/kg P-0313 group. (D) The mean tumor volume ±SEM over time for each treatment group. All comparisons versus vehicle treatment; n=11/group; **** P<0.0001.
Figure 19B:
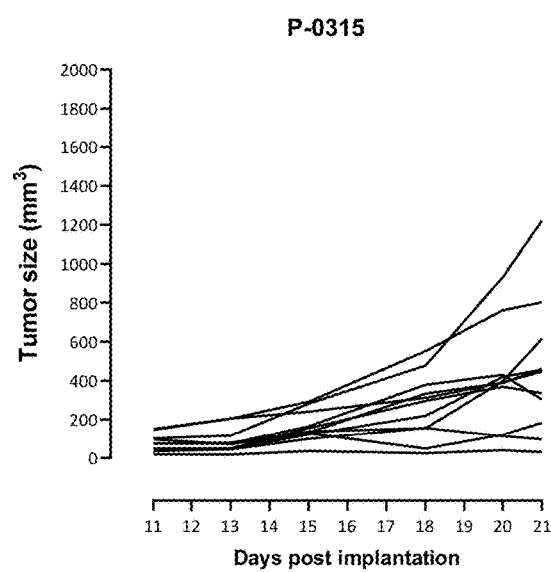
Figure 19C:
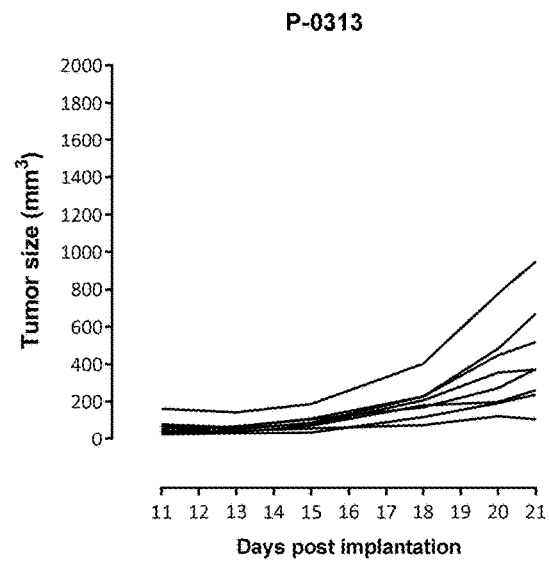
Figure 19D:
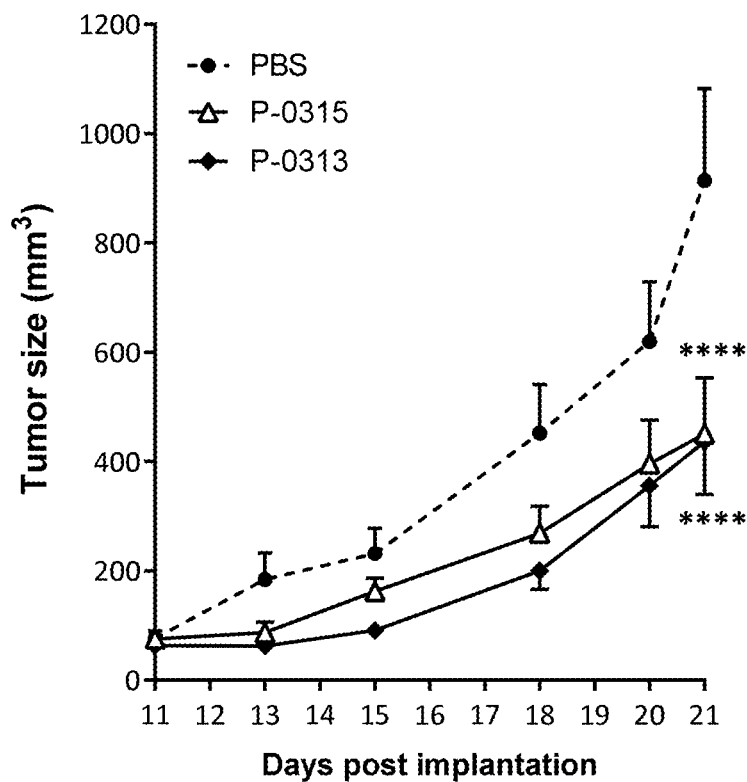

As shown in FIG. 19A, the PBS-treated mice rapidly developed large subcutaneous tumors, and treatment of mice with either P-0315 or P-0313 were approximately equipotent in delaying tumor growth (FIGS. 19B and 19C). On day 21 post-tumor inoculation, the mean tumor volume in the control-treated mice was 1000 mm$^3$ versus ~450 mm$^3$ in mice treated with P-0315 or P-0313 (****, $P<0.0001$; 1-way ANOVA with Tukey's post-test) (FIG. 19D). It was notable that P-0313 showed a greater decrease of tumor load than P-0315 initially, but the difference tapered off as the treatment proceeded. The delayed anti-tumor effect of P-0315 was likely due to the time it took to develop appropriate amount of protease(s) to access and cleave the substrate peptide linkers and activate the VitoKine.

Next, effect of P-0315 on CD8+ T cell and NK cell proliferation in the peripheral blood was investigated in comparison to P-0313 and vehicle by flow cytometry. The effect of P-0315 on peripheral and splenic populations of total WBC and lymphocyte subsets (CD8+T and NK cells) was also similarly assessed.

Figure 20A:
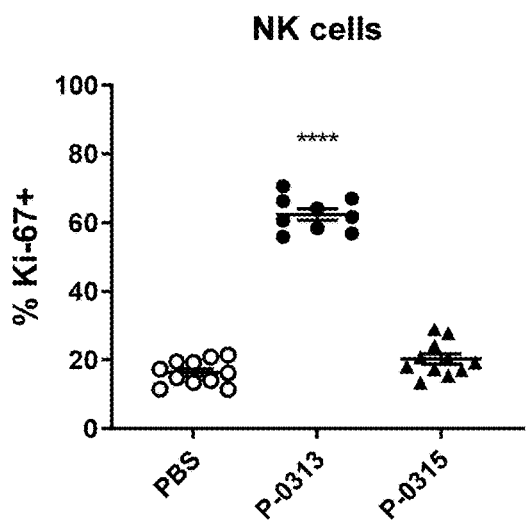
FIG. 20 depicts the immuno-pharmacodynamic profiling of peripheral mice blood following VitoKine P-0315 or the highly active IL-15 Fc fusion P-0313 treatment in CT26 murine colorectal carcinoma tumor model. Following two Q5D treatments initiated 11 days after tumor implantation, percentage increases in the proliferation marker Ki67 in A) NK cells and B) CD8+ T cells on day 19 were determined by flow cytometry. **** P<0.0001 vs PBS.
Figure 20B:
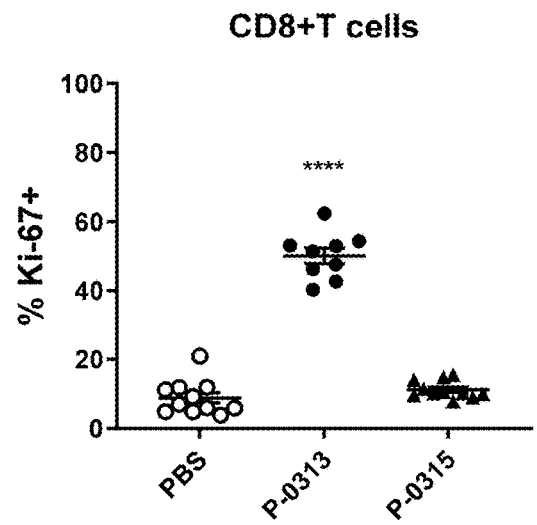

Injection of fully active IL-15/IL-15Rα Fc fusion P-0313 to tumor-bearing mice induced profound lymphocyte proliferation and expansion in both peripheral blood and spleens (FIGS. 20-22). Compared to the PBS group, Ki67 proliferation increased by 4-fold in peripheral NK cells (61% vs. 15%; FIG. 20A) and 5.3-fold in CD8+ cells (46% vs. 8.6%; FIG. 20B) following P-0313 treatment. Likewise, P-0313 treatment resulted in marked cell expansion of total white blood cells, NK cells, and CD8+ T cells in both peripheral blood (FIGS. 21A-21C) and spleens (FIGS. 22A-22C). For example, the peripheral total WCB cell number expanded 6-fold and CD8+ T cell number amplified 5-fold; a dramatic 85-fold increases of NK cell numbers were observed. In spleens, the most pronounced cell expansion was observed also for NK cells (10 fold), followed by CD8+ T cells, which expanded 2.9-fold. Total splenic WBC modestly expanded 1.7-fold. Robust activation of cytotoxic CD8+ T cells and NK cells are consistent with the overall immunomodulatory property of IL-15, and the potent immune responses were likely the major contributor for the anti-tumor activity of P-0313 in vivo. However, dramatically altered lymphocyte subsets in blood may cause toxicity and reduce therapeutic index.

In striking contrast to P-0313, treatment with Fc IL-15 VitoKine P-0315 resulted in minimal alteration in homeostasis of lymphocyte subsets in blood. The observations were demonstrated in FIG. 20 for Ki67 proliferation of peripheral NK and CD8+ T cells, FIG. 21 for cell expansion of total white blood cells, NK cells, and CD8+ T cells in peripheral blood. The only notable immuno-pharmacodynamic effect following P-0315 treatment was a 4-fold increases of NK cell numbers in spleens (FIG. 22B). As P-0315 was approximately equipotent as P-0313 in delaying established CT26 tumor growth (FIGS. 19A-19D), the in vivo anti-tumor activity of P-0315 was likely resulted from proteolysis of the cleavable linker(s) and subsequent activation of the VitoKine in proximity of tumor microenvironment. As activated VitoKine only presented close to tumor, response of peripheral lymphocytes to the administration of inert VitoKine molecule were much less marked than the fully active P-0313.

Taken together, IL-15 Fc VitoKine, exemplified with P-0315, was able to efficiently delay tumor growth without marked alteration in proliferation and expansion of lymphocyte subsets in blood and spleens. Consequently, over-activation of the pathway, undesirable "on-target" "off tissue" toxicity, and unwanted target sink generally associated with fully active cytokine could be prevented or reduced by VitoKine format without compromising the anti-tumor effect.

Example 11

Non-Cleavable VitoKine as a Potency-Attenuated Version of Cytokine

It is known in the field that the potent cytokine in vitro may not provoke the strongest lymphocyte response in vivo. Cytokines of high potency are often associated with stronger receptor stimulation, internalization and desensitization, attenuation of signaling, proliferation, and function, and increased cell death, or clonal exhaustion. Therefore, potency-attenuated cytokine may be highly desired to prevent excessively strong lymphocyte activation and to achieve persistent and enhanced in vivo pharmacodynamic effect and anti-tumor efficacy.

Non-cleavable Fc IL-15 VitoKine P-0351 exhibited marked potency reduction compared to fully active IL-15 compounds in vitro, yet it showed anti-metastatic efficacy and pronounced NK cell responses in a mouse CT26 pulmonary metastasis model (Example 8). Therefore, non-cleavable VitoKine constructs may be utilized to function as a potency-attenuated cytokine with sustained activity to optimize in vivo pharmacodynamics.

P-0351 exhibited identical potency in inducing Ki67 proliferation in both NK Cells and CD8+ T cells (FIGS. 23A and 23B) as the Benchmark molecule (SEQ ID NOs: 177 and 178), which is equivalent to XENP024306 in patent application WO2018071919A1. XENP024306 is an IL-15/IL-15Rα Fc fusion molecule containing amino acid substitutions (D30N/E64Q/N65D) in IL-15 and half-life extension mutations in Fc. The triple mutations in IL-15 chain of XENP024306 were reported to result in 200-fold potency reduction in vitro, but XENP024306 was demonstrated to be more active in vivo likely due to optimized in vivo pharmacodynamics.

Likewise, potency attenuation in P-0351 is expected to result in more sustained exposure for improved pharmacodynamics (PD) by avoiding or reducing over-activation and unwanted target sink generally associated with fully active cytokine. Thus, P-0351's half-life extended counterpart, P-0651 (SEQ ID NO: 170), will promote longer half-life and further extend PD in vivo.

Example 12

Construction and Production of Fc IL-2 VitoKines for Selective Expansion of Regulatory T Cells (Treg IL-2 VitoKine) to Treat Autoimmune Diseases, Inflammatory Disorders, Transplantation, and Other Disorders The goal is to design IL-2 VitoKine constructs that will remain inert until activated locally by proteases that are upregulated at inflammatory sites. Low-dose wild-type IL-2 preferentially stimulates Treg over effector T cells and IL-2 muteins with decreased binding affinity to IL-2Rβ are reported to widen the selectivity window. These molecules can be developed as therapeutics for prophylaxis of autoimmune diseases. Other mutations that interfere with IL-2Rβ and/or $\gamma_C$ binding and do not affect the interaction with IL-2Rα can also enlarge the selectivity window on Treg activation over Teff.

IL-2 Fc VitoKine comprising wild-type IL-2 or IL-2 mutein with increased selectivity to stimulate Treg over effector T cells was used as the active moiety, which is reversibly concealed between an Fc domain and IL-2RαSushi (SEQ ID NO: 10). IL-2Rα (SEQ ID NO: 9) contains two sushi domains separated by a natural peptide linker region. IL-2 VitoKine constructs include one or two cleavable linkers which are recognized by proteases reported to be upregulated at the sites of inflammatory disorders. While the linker connecting the Fc and IL-2/mutein can be both cleavable and non-cleavable, it is preferable that the linker connecting IL-2 and IL-2αSushi is capable of being specifically cleaved by a protease.

IL-2 mutein activity to selectively stimulate Treg is expected to recover after release and diffusion away of IL-2Rα from IL-2 following protease cleavage. Due to the nM binding affinity between IL-2Rα and IL-2, there is a chance that IL-2RαSushi remains non-covalently associated with IL-2 after cleavage of the linker; consequently, IL-2 remains blocked from interacting with IL-2Rα on Treg cells. To solve this potential issue, IL-2Rα muteins with amino acid substitutions at the interface with IL-2 were designed to weaken its binding to IL-2. Thus, after protease cleavage of the linker, the IL-2RαSushi mutant will dissociate and then diffuse away from IL-2, a mechanism of activation (schematically illustrated in FIG. 26) that is slightly different from that illustrated in FIG. 2.

Representative amino acid substitutions were made at positions 38 (i.e., K38E), and 43 (i.e. Y43A) of the IL-2Rα domain. Other IL-2Rα variants with substitutions on the IL-2-interacting residues are expected to disrupt IL-2 and IL-2Rα interactions and can be incorporated as well. As will be appreciated by those in the art, all of the mutations can be optionally and independently combined in any way to achieve optimal affinity modulation. IL-2 VitoKine molecules that contains different linker combinations, wild-type or variant IL-2, and wild-type or variant IL-2RαSushi were produced, and their respective sequences are listed as SEQ ID NO: 49-65.

Gene synthesis, expression vector construction, and protein production, purification, & characterization were conducted following the same procedures detailed in Example 1. As an example to demonstrate the protein profile of IL-2 VitoKines, SDS-PAGE analyses of P-0320 are shown in FIG. 24A. Size exclusion chromatogram in FIG. 24B indicated that <5% aggregation was present after initial protein A capture step without polishing step. The low aggregation propensity suggested favorable developability profile of IL-2 VitoKines.

Example 13

Construction and Production of Fc IL-2 VitoKines for Selective Expansion of Effector T Cells (Teff IL-2 VitoKine) for Treating Cancer and Other Disorders The goal is to design IL-2 VitoKine constructs that will remain inert until activated locally by proteases that are only present or upregulated at tumor sites. Preferential expansion of Tregs by IL-2 represents an undesirable effect of IL-2 for cancer immunotherapy as Treg can dampen effector T cell responses. To overcome these limitations, amino acid substitutions at the binding interface with IL-2Rα, including F42A and R38E (PNAS, 1991. 88: 4636-4640), were designed to IL-2 to reduce/abolish binding to IL-2Rα. Other mutations that only interfere with IL-2Rα binding, and do not affect the interaction with IL-2Rβγ, e.g., R38A, T41A, T41G, T41V, Y107G, Y107H, Y107L, or Y107V can also be incorporated. As will be appreciated by those in the art, all of the mutations can be optionally and independently combined in any way to achieve optimal affinity modulation.

Fc IL-2 VitoKine constructs comprise wild type IL-2 or IL-2 variant with reduced/abolished binding to IL-2Rα as the active moiety, which is reversibly concealed between an Fc domain and IL-2RαSushi (SEQ ID NO: 10). These constructs include one or two cleavable linkers which are recognized by proteases reported to be upregulated in various types of cancers, e.g., solid tumors. While the linker connecting the Fc and IL-2 mutein can be both cleavable and non-cleavable, the linker connecting IL-2 and IL-2αSushi is preferably capable of being specifically cleaved by a protease. The Il-2Rα may be preferably associated with IL-2 after cleavage to increase selectivity towards Teff function. IL-2 mutein activity is recovered after release and diffusion away of IL-2Rα from IL-2 following protease cleavage. IL-2 VitoKine molecules that incorporated different IL-2 muteins as the active moiety are schematically depicted in FIG. 1. Exemplary Fc IL-2 VitoKine molecules for selective expansion of Teff cells were constructed and produced, and their respective sequences are listed as SEQ ID NO: 59-61.

Gene synthesis, expression vector construction, and protein production, purification, & characterization were conducted following the same procedures as detailed in Example 1.

Example 14

Fc IL-2 VitoKine In Vitro Activity Assessment

The bioactivity of IL-2 VitoKines on T cells was determined by measuring phosphorylated STAT5 (pStat5) levels in specific T cell subsets in fresh human PBMC. Stat5 is known to be involved in the downstream intracellular signaling induced by IL-2 binding to the transmembrane IL-12Rβγ$_C$ complex. Levels of pStat5 were measured by flow cytometry in fixed and permeabilized cells using an antibody to a pStat5 peptide. Briefly, human PBMC were isolated by Ficoll-Hypaque centrifugation from the buffy coat of a healthy donor purchased from Oklahoma Blood Institute. PBMC at 2×10$^5$ were treated with serial dilutions of test compounds for 30 minutes at 37° C. Cells were then treated with Foxp3/Transcription Factor Staining Buffer Set (EBIO) according to the manufacturer's instructions. Cells were then fixed with Cytofix buffer and permeabilized with Perm Buffer III (BD Biosciences) and then washed. After blocking Fc receptor by adding human TruStain FcX (1:50 dilution), cells were stained with a mixture of anti-CD25-PE, anti-FOXP3-APC, anti-pSTAT5-FITC, and anti-CD4-PerCP-Cy5.5 antibodies at concentrations recommended by the manufacturer for 60 minutes at room temperature. Cells were then collected and washed, resuspended in FACS buffer and analyzed by flow cytometry. The flow cytometry data was gated into Foxp3+/CD25$^{high}$ and Foxp3-/D25$^{low}$ groups for the Treg and CD4 effector T cell subsets, respectively. Data are expressed as a percent of pStat5 positive cells in the gated population.

IL-2 VitoKines P-0320 (SEQ ID NO: 49) and P-0329 (SEQ ID NO: 62) were assessed for pStat5 activation in comparison to P-0250 (SEQ ID NO: 48). P-0320 contains a wild-type IL-2 domain with its N-terminal fused to an Fc domain via a uPA-cleavable linker, and its C-terminal linked to IL-2RαSushi domain with a flexible (GGGGS)$_3$ (SEQ ID NO: 127) linker. P-0329 contains a wild-type IL-2 domain with its C-terminus fused to an Fc domain via a uPA-cleavable linker, and its N-terminus linked to IL-2RαSushi domain with a flexible (GGGGS)$_3$ linker. P-0250 is a highly active IL-2 Fc fusion protein. The percentage of pStat5 positive cells in Treg and CD4+ conventional T cell (Tconv) subsets for the test compounds are illustrated in FIG. 25. It is clearly seen that the pStat5 activation for both IL-2 VitoKines are dramatically decreased in Treg compared to the fully active IL-2 fusion protein, and pStat5 activation was barely measurable for CD4+ Tconv cells. The data clearly demonstrates efficient concealing of IL-2 activity in the VitoKine format.

Example 15

Protease Activation of IL-2 VitoKine and In Vitro Activity Assessment

IL-2 VitoKine P-0382 (SEQ ID NO: 51) contains a flexible GGGSGGGS linker (SEQ ID NO: 115) connecting Fc and IL-2 and a 10-amino acid MMP-2/9 cleavable linker (SEQ ID NO: 77) between the IL-2 and IL-2RαSushi domains. The IL-2RαSushi domain in P-0382 contains an amino acid substitution (K38E) designed to reduce its binding affinity for the IL-2 to ensure dissociate and subsequent diffuse away from IL-2 after protease cleavage of the linker.

Figure 26:
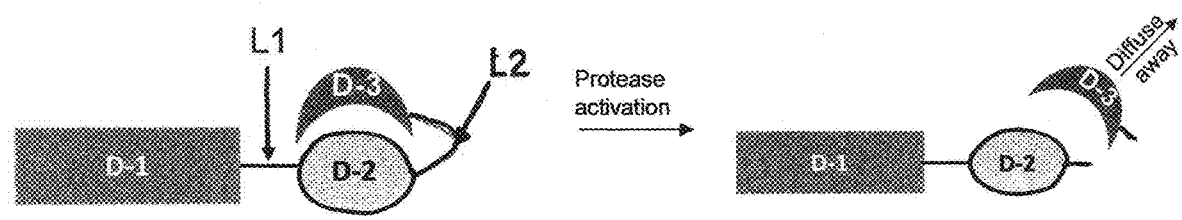
FIG. 26 depicts a variation of VitoKine activation mechanism from the illustration in FIG. 2, when releasing and diffusing away of D3 from D2 following protease cleavage are desirable.

P-0382 was activated by in vitro protease cleavage using MMP-2. Briefly, 3.3 μg of latent MMP-2 (BioLegend) was first activated by APMA (Millipore Sigma) according to the manufacturer's instruction, which was then buffer exchanged and added to the 120 μg P-0382 in 0.4 ml of the manufacture recommended assay buffer (100 mM Tris, 20 mM CaCl$_2$), 300 mM NaCl, 0.1% (w/v) Brij 35, pH 7.5). After incubation at 37° C. for 20 hrs, half of the reaction was purified with MabSelectSure Protein A resin and the activated VitoKine was eluted with 25 mM sodium citrate, 25 mM sodium chloride, pH 3.2. Protein was neutralized by adding 3% of 1 M Tris pH 10.2. Another half of the sample was incubated with Ni-Excel resin to stop the reaction by removing His-tagged MMP-2 protein, and the activated VitoKine was collected by removing Ni resin via centrifugation. Protein A purification was to confirm that IL-2RαSushi domain does not associate with IL-2 non-covalently after cleaving off of the polypeptide chain as schematically illustrated in FIG. 26. Samples were assessed on a 4-12% Tris-Bis SDS-PAGE shown in FIG. 27. Despite an increased amount of protease and prolonged reaction time compared to the structurally similar IL-15 VitoKines (e.g. P-0315), the reaction did not result in complete cleavage Comparison of the MMP-2 treated samples with and without protein A purification (FIGS. 27A and 27B) did confirm the IL-2RαSushi domain released from the covalent linkage and did not co-purify with the Fc-IL-2 fusion polypeptide.

Despite incomplete cleavage, the two MMP-2 activated samples, one as Ni-Excel flow-through (Activ. 1) and the other as Protein A eluant (Activ. 2), were assessed in pStat5 activation assay described in Example 13, and the data was illustrated in FIG. 28. Activity of P-0382 was very low in Treg and barely measurable for CD4+ Tconv cells, confirming again effective concealing of the active moiety in the IL-2 VitoKine format. Both activated samples showed near-complete recovery of activity. The modestly lower potency compared to P-0250 was likely due to the incomplete proteolysis.

The presence of MMP-2 cleaved IL-2RαSushi domain in Activ. 1 sample seemed not alter the activity of the activated IL-2 VitoKine as Activ.1 and Activ.2 had comparable potency in inducing pStat5 phosphorylation of both Treg and Tconv cells (FIGS. 28A and 28B). The data suggested that the IL-2RαSushi domain resulted from MMP-2 cleavage did not associate with IL-2 and should not interfere with the engagement of IL-2 with the receptor complexes expressed on the lymphocytes.

MMP-2 proteolysis of P-0382 did not yield complete cleavage, and it was reasoned that elongation of the cleavable linker may make the substrate peptide more accessible to the protease responsible for cleavage. The 10-amino acid linker (SEQ ID NO: 95) in P-0382 was replaced with a 15-amino acid MMP-2/9-cleavable linker (SEQ ID NO: 94) containing extra flanking residues and resulted in a new VitoKine construct P-0398 (SEQ ID NO: 52). P-0398 was activated by in vitro protease cleavage using MMP-2 following the same protocol detailed above. Three-fold lower amount of MMP-2 (1.5 μg MMP-2 for 180 μg P-0398 versus 3.3 μg MMP-2 for 120 μg P-0382) resulted in complete digestion of P-0398, evidenced by presence of only "full cut" band on SDS-PAGE gel (data not shown).

The bioactivity of the activated P-0398 with the removal of IL-2RαSushi domain by Protein A purification was determined in pStat5 assay (FIGS. 29A and 29B). Activated P-0398 resembles IL-2 Fc fusion molecule P-0250 in sequence and structure, and they had almost identical potency in inducing phosphorylation of Stat5 in both Treg and Tconv cells. While both VitoKines, P-0382 and P-0398, had significantly impaired bioactivity (4 logs) due to the covalent connection to the IL-2RαSushi domain, there seemed to be a trend that P-0398, comprising a longer L2 linker, was more active. Similar to the observation of IL-15 Fc VitoKine, the level of activity inertness of IL-2 VitoKines could be further tuned by adjusting L2 linker length. Likewise, the choice of cleavable L2 linker length and sequence should be balanced between the presence of specific proteases at the site of intended disease indication, accessibility of the substrate peptide to the proteases, and the desired rate of proteolysis.

In summary, compared to IL-15 VitoKine, IL-2 VitoKine necessitated a longer L2 linker for optimal enzyme accessibility to achieve complete proteolysis. Cleavage of exemplary IL-2 VitoKine constructs P-0382 and P-0398 by MMP-2 led to full activation of the molecules. The activated IL-2 VitoKines achieved similar bioactivity as the highly active IL-2 Fc fusion compound P-0250.

Example 16

Construction of Antibody VitoKine

The use of recombinant antibody-cytokine fusion proteins (immunocytokines) promises to enhance the therapeutic index of cytokines by targeting them to the site of disease. However, fusing a fully active cytokine to an antibody may result in peripheral activation and lack of tumor targeting. The activity inertness of VitoKine prior to activation at the intended site of therapy makes antibody VitoKine a novel and innovative form of immunocytokine. In addition to tumor-targeting antibodies, immune checkpoint blocking antibodies that bypass the immunosuppressive effects in the tumor microenvironment or immune-stimulatory antibodies to potentiate existing responses can also be used to construct antibody VitoKines, which can result in further enhancement of the immune system's activity against tumors. Further, antibody VitoKines targeting inflammatory issue site can be utilized to treat anti-autoimmune and chronic inflammatory disorders.

Following this concept, antibody VitoKine proteins comprising either IL-15 or IL-2 as the D2 domain were constructed. Exemplary antibodies include PD-1 blocking antibody JS-001, PD-L1 blocking antibody Tecentriq, anti-CTLA4 antibody ipilimumab, agonistic CD40 antibody R07009789, tumor-antigen-targeting antibodies, including L19 directed against the extra-domain of fibronectin, rituximab directed against CD20, Herceptin directed against Her-2, Cetuximab directed against EGFR, and anti-inflammatory antibodies Vedolizumab against integrin $\alpha_4\beta_7$ and Humira against TNFα. Sequences of exemplary antibody VitoKines are listed as SEQ ID NO: 128-143.

Gene synthesis, expression vector construction, and protein production, purification, & characterization were conducted following the same procedures detailed in Example 1. The bioactivity of an exemplary anti-PDL1 antibody IL-15 VitoKine P-0485 (SEQ ID NOS: 180 and 181) was tested by measuring Ki67 expression in NK cells (FIG. 30A) and CD8+ T cells (FIG. 30B) following treatment of human PBMC with IL-15 VitoKine compounds. P-0485 shares the same L1 & L2 linkers and D2 & D3 domains as its Fc VitoKine counterpart P-0315. Data in FIG. 29 suggested that both VitoKines had comparable and severely impaired bioactivity compared to the activated P-0315 illustrated in FIG. 15. P-0485 appeared to have slightly higher potency, which may be contributed from lymphocyte activation by PD-L1 blockade.

Example 17

IL-15Rβ-Based Blocking Peptides to Generated Protease-Activatable Inert IL-15 or IL-2 Fusion Proteins A different approach to generate protease-activatable inert IL-15 or IL-2 fusion proteins is to genetically fuse blocking peptides (e.g., an IL-2Rβ-based blocking peptide) to IL-15 or IL-2 by way of a cleavable linker. The blocking peptides explored are based on the two IL-2Rβ loops (SEQ ID NO: 97 and 98) that contain key residues in direct contact with IL-15. The peptides set forth in Table 13 are based on the sequences of these two loops.

TABLE 13

| Peptide ID | Peptide sequence | SEQ ID NO: |
|---|---|---|
| L01 | LGAPDSQKLTTVDIV | 97 |
| L02 | EISQASHYFERHL | 98 |
| L03 | CEISQASHYFERHLC | 99 |
| L04 | LGAPDSQKLTTVDIVGGGGGGGGEISQASHYFERHL | 100 |
| L05 | KPFENLRLMAPIS | 101 |
| P1 | GGGSLGGSGRSANAILEGGGSGGGSGGGSIYNCEISQASHY FERHLCYSI | 102 |
| P2 | GGGSLGGSGRSANAILEGGGSGGGSGGGSIYNCELHREFYH SAQSIEWCYSI | 103 |
| P3 | GGGSLGGSGRSANAILEGGGSGGGSGGGSETHRCNISWEIS QASHYFERHLEFEARTLCPGH | 104 |

TABLE 13-continued

| Peptide ID | Peptide sequence | SEQ ID NO: |
|---|---|---|
| P1' | QGQSGQCEISQASHYFERHLCYSIGSSGGSGGSGGSGLSG RSDNHGSSGT | 105 |
| P3' | QGQSGQCNISWEISQASHYFERHLEFEARTLCPGHGSSGGS GGSGGSGLSGRSDNHGSSGT | 106 |

The five peptides, L01 to L05 (SEQ ID NO: 97-101) in Table 13 were synthesized and assessed for their binding to IL-15 in ELISA format. Briefly, P-0153 (SEQ ID NO: 44 and 46), an IL-15/IL-15RαSushi+Fc fusion protein, was coated on the wells of Nunc Maxisorp 96-well microplates at 1 μg/well and 3-fold serial dilutions of biotinylated peptides starting at 100 μM were added to each well. Streptavidin-HRP complex at the manufacturer's recommended concentration was added and signal was developed by TMB substrate. As depicted in FIG. 30, specific binding was observed for L03 (SEQ ID NO: 99), which was a cyclized loop 2 (SEQ ID NO: 98).

Loop 2-based sequence was adopted as blocking peptides and incorporated into the IL-15 fusion protein. Exemplary sequences of fusion proteins containing an IL-2Rβ-based blocking peptide fused to IL-15 by way of a cleavable linker and peptide spacers (SEQ NO ID: 102-106) are shown in Table 13, in which bold indicates the IL-15Rβ-based blocking peptide, wavy-underline indicates the cleavable linker, and straight-underline indicates spacer peptide. IL-15RαSushi+(SEQ ID NO: 5) were co-expressed and form non-covalent complexation with the blocking peptide-containing IL-15 fusion protein.

Gene synthesis, expression vector construction, and protein production, purification, & characterization were conducted following the same procedures detailed in Example 1. These blocking peptide-containing IL-15 fusion proteins were first tested in ELISA assay to assess their capability to bind to IL-2Rβ. As illustrated in FIG. 32, there was moderate reduction in binding affinity due to the linkage of different blocking peptides compared to P-0153. However, PBMC assay assessing expression of activation of immune cells, including CD56+ NK cells or CD8+ T cells, by these blocking peptide-containing IL-15 fusion proteins did not demonstrate notable activity reduction (Data not shown), suggesting insufficient concealing efficiency of tested blocking peptides. Blocking peptides of different length, including the entire extracellular domain of IL-2Rβ, may be explored to see the efficiency of activity concealing. The same approach could be applied to IL-2 in a similar manner.

Example 18

VitoKine Format Improves Fusion Protein Developability

It is known in the field that naturally occurring IL-2 protein tends not to be very stable and is prone to aggregate. This was demonstrated in our experiments that the wild-type IL-2 Fc fusion protein (P-0250) expressed at a low level (around 3 mg/L transiently in HEK-293F cells) with high aggregation propensity, exemplified by SEC chromatogram depicted in FIG. 33A. Four IL-2 VitoKine molecules, P-0320, P-0382, P-0362, and P-0379, were compared to P-0250. P-0320 (SEQ ID NO: 49) contains a wild-type IL-2 domain with its N-terminal fused to an Fc domain, and its C-terminal linked to IL-2RαSushi domain. The L1 linker connecting Fc and IL-2 is a cleavable linker containing uPA substrate peptide and flanking spacer peptides (SEQ ID NO: 92), and the L2 linker between IL-2 and IL-22RαSushi is a flexible (GGGGS)$_3$ linker (SEQ ID NO: 127). P-0382 (SEQ ID NO: 51) differs from P-0320 only in the linker sequences; L1 linker of P-0382 is a flexible $(G_3S)_2$ liner (SEQ ID NO: 115) and L2 linker is an MMP-2/9 cleavable linker (SEQ ID NO: 95). P-0362 (SEQ ID NO:) and P-0379 (SEQ ID NO: 59) differ from P-382 with a single point mutation. P-0362 contains K38E mutation in IL-2RαSushi domain, while P-0379 contains F42A substitution in IL-2 domain. P-0250 (SEQ ID NO: 48) is an IL-2 Fc fusion protein with IL-2 fused to the C-terminal of Fc using a flexible $(G_3S)_2$ (SEQ ID NO: 115) linker.

The size exclusion diagrams of the 5 molecules are illustrated in FIGS. 33A-33E. It is very evident from the chromatograms that all the four IL-2 VitoKine constructs have significantly improved purity profiles over the IL-2 Fc fusion protein. P-0250 contains over 25% undesirable high-molecular-weight species. In contrast, all the four VitoKine molecules exhibit sharp monomer peaks with over 96% monomer content. Linker variations, mutations in either IL-2 or IL-2RαSushi did not notably impact the quality. Such significantly enhancement in protein quality was apparently attributed from the fusion of the IL-2αSushi domain in the VitoKine.

In addition to protein quality, the expression level of IL-2 VitoKines was also enhanced, especially for the VitoKine format with GS linker between Fc and IL-2 and a 10 amino acid MMP-2/9 activatable linker between IL-2 and IL-2RαSushi. While protein expression levels may vary between different batches due to the growth conditions of the cells, it is evident that the expression level of the VitoKines are consistently multiple-fold higher than the IL-2 Fc fusion protein. Table 14 lists protein expression titers in mg/L along with protein monomer percentage.

TABLE 14

| Protein ID | Expression titer (mg/L) | Monomer by SEC |
|---|---|---|
| P-0250 | 3.1 | 74.3% |
| P-0320 | 9.3 | 96.2% |
| P-0382 | 23.3 | 97.8% |
| P-0362 | 18.1 | 100% |
| P-0379 | 16.6 | 99.1% |

Further, the engineering efforts of the present inventors on IL-2 also identified a single amino acid substitution of serine with isoleucine at position 125 that resulted in universal improvement in developability of the IL-2 Fc fusion constructs with full retaining of biological activity. Ile substitution at position 125 of wild type IL-2 and IL-2 variants with different mutational context in Fc fusion format all resulted in 4 to 11-fold enhanced expression level and uniformly low aggregation propensity. The expression level in mg/L and purity of protein A purified material assessed by SEC chromatography in aggregation percentage of exemplary molecules are summarized in Table 15. The two molecules in the same row of Table 15 share the same other amino acid substitution(s) and differ only at residue 125 with either serine or isoleucine. As an example, the SEC chromatogram of P-250's IL-2-S125I counterpart molecule is further illustrated in FIG. 33A.

TABLE 15

S125I substitution improved developability profile of various IL-2 Fc fusion proteins

| mutation(s) in IL-2 | Serine-125 | | Isoleucine-125 | | expression |
| --- | --- | --- | --- | --- | --- |
| | Aggregation % (SEC) | Expression (mg/L) | Aggregation % (SEC) | Expression (mg/L) | fold↑ by S125I substitution |
| Wild type | 25.7 | 3.1 | 0.7 | 29.5 | 9.6 |
| L19H | 21.4 | 7.7 | 0.6 | 36.7 | 4.8 |
| L19D | 32.6 | 2.6 | 0 | 13.6 | 5.2 |
| L19Y | 21.7 | 4.0 | 1.0 | 19.3 | 4.8 |
| D20T | 29.4 | 1.4 | 0.5 | 11.7 | 8.4 |
| D20E | 21.1 | 0.7 | 1.7 | 7.9 | 11.3 |
| L19H/Q126E | 23.7 | 7.3 | 0.7 | 26.6 | 3.6 |
| L19Y/Q126E | 33.8 | 6.7 | 0.8 | 23.5 | 3.5 |

In conclusion, VitoKine platform significantly improved protein developability profile, which was demonstrated by the protein expression increase and substantial reduction of aggregation propensity of Fc IL-2 VitoKine constructs. Additionally, IL-2 (wild type or variant) VitoKine constructs incorporating the beneficial IL-2 S125I amino acid will have further enhanced developability profile.

Example 19

Choice of VitoKine D3 Domain can Dramatically Impact Protein Expression

The VitoKine platform was also explored with D3 domains that are a variant of the cognate receptor of D2 domain or an irrelevant protein domain. Based upon crystal structure analysis (Wang et al., Science 310: 1159-1163, 2005), IL-2Rα sushi domains 1 and 2 engage in a strand exchange event and the result was that residues 1-19 of IL-2Rα are a part of sushi domain 2 and residues 102-122 are a part of sushi domain 1. Such structural arrangement was reflected in an IL-2RαSushi variant (SEQ ID NO: 147) which contains IL-2Rα (SEQ ID NO: 10) residues 102-122 at the N-terminus and IL-2Rα residues 20-68 at the C-terminus. Such an IL-2RαSushi variant contains most of the interacting residues with IL-2 and is supposed to recapitulate the majority of the activity with the assumed structural integrity. Replacing the IL-2RαSushi domain in P-0320 (SEQ ID NO: 49) with the IL-2RαSushi variant resulted in IL-2 VitoKine P-0321 (SEQ ID NO: 179). Unexpectedly, P-0321 comprised of IL-2RαSushi variant as the D3 domain did not express at all or expressed at such a low level that no material could be captured and purified.

Similarly, the IL-15αSushi+ domain in VitoKine P-0315 (SEQ ID NO: 33) was replaced with IL-2RαSushi (SEQ ID NO: 10) and the resulting protein is P-0389 (SEQ ID NO: 42). P-0389 expressed at a significantly lower level compared to P-0315. Even more remarkably, purified P-0389 was mainly high molecular weight aggregates as demonstrated in the SDS-PAGE gel picture depicted in FIG. 34A. For comparison purposes, a SDS-PAGE gel picture of the counterpart molecule P-0315 is shown as FIG. 34B. Additionally, purified P-0389 was resistant to MMP-2 digestion despite of the presence of MMP-2/9 substrate peptide in the sequence, suggesting that the molecule was not correctly folded, or the aggregation limited the protease access.

In summary, D3 is a critical component of the VitoKine constructs. In addition to functioning as the concealing moiety, it can dramatically impact the protein developability profile, both positively and negatively.

All of the articles and methods disclosed and claimed herein can be made and executed without undue experimentation in light of the present disclosure. While the articles and methods of this disclosure have been described in terms of preferred embodiments, it will be apparent to those of skill in the art that variations may be applied to the articles and methods without departing from the spirit and scope of the disclosure. All such variations and equivalents apparent to those skilled in the art, whether now existing or later developed, are deemed to be within the spirit and scope of the disclosure as defined by the appended claims. All patents, patent applications, and publications mentioned in the specification are indicative of the levels of those of ordinary skill in the art to which the disclosure pertains. All patents, patent applications, and publications are herein incorporated by reference in their entirety for all purposes and to the same extent as if each individual publication was specifically and individually indicated to be incorporated by reference in its entirety for any and all purposes. The disclosure illustratively described herein suitably may be practiced in the absence of any element(s) not specifically disclosed herein. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

Sequence Listings

The nucleic and amino acid sequences listed in the accompanying sequence listing are shown using standard letter abbreviations for nucleotide bases and three letter codes for amino acids, as defined in 37 C.F.R. 1.822.

SEQ ID NO: 1 is a human IL-15 precursor amino acid sequence.

SEQ ID NO: 2 is a human IL-15 mature form amino acid sequence.

SEQ ID NO: 3 is the amino acid sequence of an IL-15 variant polypeptide.

SEQ ID NO: 4 is a human IL-15Rα amino acid sequence.

SEQ ID NO: 5 is a human IL-15Rα, sushi domain+ amino acid sequence.

SEQ ID NO: 6 is a human IL-2 precursor amino acid sequence.

SEQ ID NO: 7 is a human IL-2 mature form naturally occurring amino acid sequence.

SEQ ID NO: 8 is a human IL-2 mature form wild type amino acid sequence.

SEQ ID NO: 9 is a human IL-2Rα (CD25) precursor amino acid sequence.

SEQ ID NO: 10 is a human IL-2Rα, sushi domain amino acid sequence.

SEQ ID NO: 11 is a human IL-2Rβ precursor amino acid sequence.

SEQ ID NO: 12 is a human IL-2Rβ extracellular domain amino acid sequence.

SEQ ID NO: 13 is a human IgG1-Fc amino acid sequence.

SEQ ID NO: 14 is a human IgG1-Fc with reduced/abolished effector function sequence.

SEQ ID NO: 15 is a Knob-Fc amino acid sequence.

SEQ ID NO: 16 is a Hole-Fc amino acid sequence.

SEQ ID NO: 17 is a human IL-4 mature form amino acid sequence.

SEQ ID NO: 18 is a human IL-7 mature form amino acid sequence.

SEQ ID NO: 19 is a human IL-9 mature form amino acid sequence.

SEQ ID NO: 20 is a human IL-10 mature form amino acid sequence.

SEQ ID NO: 21 is a human IL-12 subunit alpha mature form sequence.

SEQ ID NO: 22 is a human IL-12 subunit beta mature form sequence.

SEQ ID NO: 23 is a human IL-23 subunit alpha mature form sequence.

SEQ ID NO: 24 is a human IL-27 subunit beta mature form sequence.

SEQ ID NOS: 25-43 are the amino acid sequences of various Fc IL-15 VitoKine constructs.

SEQ ID NO: 44 is the amino acid sequence of a Hole-Fc-IL-15 fusion protein.

SEQ ID NO: 45 is the amino acid sequence of a Knob-Fc-IL-15 fusion protein.

SEQ ID NO: 46 is the amino acid sequence of a Knob-Fc-IL-15Rα-Sushi+ fusion protein.

SEQ ID NO: 47 is the amino acid sequence of a Fc-IL-15 S58D fusion protein.

SEQ ID NO: 48 is the amino acid sequence of an IL-2 fusion protein.

SEQ ID NOS: 49-65 are the amino acid sequences of various Fc IL-2 VitoKine constructs.

SEQ ID NOS: 66-70 are the amino acid sequences of various IL-15 constructs comprising blocking peptide.

SEQ ID NOS: 71-87 and 157-159 are the amino acid sequences of various protease substrate peptides.

SEQ ID NOS: 88-96 and 160-161 are the amino acid sequences of various protease cleavable linkers comprising various spacer peptides flanking protease substrate peptides.

SEQ ID NOS: 97-106 are the amino acid sequences of various blocking peptide sequences.

SEQ ID NOS: 107-127 are the amino acid sequences of various non-cleavable linker sequences.

SEQ ID NOS: 128-146 are the amino acid sequences of various antibody VitoKine constructs.

SEQ ID NO: 147 is a human IL-2Rα variant sequence.

SEQ ID NO: 148-149 are the amino acid sequences of Hole-Fc-IL-15 fusion constructs.

SEQ ID NOS: 150-155 are the amino acid sequences of various Fc IL-2 VitoKine constructs.

SEQ ID NO: 156 is a human IgG1-Fc with reduced/abolished effector function and extended half-life sequence.

SEQ ID NOS: 162-165 are the amino acid sequences of various Fc IL-15 VitoKine constructs.

SEQ ID NO: 166 is a human IgG1-Fc with reduced/abolished effector function and extended half-life sequence.

SEQ ID NO: 167 is a Knob-Fc with extended half-life amino acid sequence.

SEQ ID NO: 168 is a Hole-Fc with extended half-life amino acid sequence.

SEQ ID NOS: 169-174 are the amino acid sequences of various Fc IL-15 VitoKine constructs.

SEQ ID NOS: 175-178 are the amino acid sequences of various IL-15 Fc fusion constructs.

SEQ ID NO: 179 is the amino acid sequence of an Fc IL-2 VitoKine construct.

SEQ ID NOS: 180-181 are the amino acid sequences of an antibody IL-15 VitoKine constructs.

SEQ ID NOS: 182-192 are the nucleotide sequences of various Fc IL-15 VitoKine constructs.

---

SEQUENCE LISTINGS

```
Human IL-15 precursor sequence
MRISKPHLRSISIQCYLCLLLNSHFLTEAGIHVFILGCFSAGLPKTEANWVNVISDLKKIEDLIQSM
HIDATLYTESDVHPSCKVTAMKCFLLELQVISLESGDASIHDTVENLIILANNSLSSNGNVTESGC
KECEELEEKNIKEFLQSFVHIVQMFINTS (SEQ ID NO: 1)

Human IL-15 mature form sequence
NWVNVISDLKKIEDLIQSMHIDATLYTESDVHPSCKVTAMKCFLLELQVISLESGDASIHDTVENLI
ILANNSLSSNGNVTESGCKECEELEEKNIKEFLQSFVHIVQMFINTS (SEQ ID NO: 2)

Human IL-15 S58D mutein
NWVNVISDLKKIEDLIQSMHIDATLYTESDVHPSCKVTAMKCFLLELQVISLESGDADIHDTVENL
IILANNSLSSNGNVTESGCKECEELEEKNIKEFLQSFVHIVQMFINTS (SEQ ID NO: 3)

Human IL-15Rα precursor sequence
MAPRRARGCRTLGLPALLLLLLRPPATRGITCPPPMSVEHADIWVKSYSLYSRERYICNSGFK
RKAGTSSLTECVLNKATNVAHWTTPSLKCIRDPALVHQRPAPPSTVTTAGVTPQPESLSPSGK
EPAASSPSSNNTAATTAAIVPGSQLMPSKSPSTGTTEISSHESSHGTPSQTTAKNWELTASASH
QPPGVYPQGHSDTTVAISTSTVLLCGLSAVSLLACYLKSRQTPPLASVEMEAMEALPVTWGTS
SRDEDLENCSHHL (SEQ ID NO: 4)

Human IL-15Rα, sushi domain+
ITCPPPMSVEHADIWVKSYSLYSRERYICNSGFKRKAGTSSLTECVLNKATNVAHWTTPSLKCI
RDPALVHQRPAPP (SEQ ID NO: 5)

Human IL-2 precursor sequence
MYRMQLLSCIALSLALVTNSAPTSSSTKKTQLQLEHLLLDLQMILNGINNYKNPKLTRMLTFKFY
MPKKATELKHLQCLEEELKPLEEVLNLAQSKNFHLRPRDLISNINVIVLELKGSETTFMCEYADE
TATIVEFLNRWITFCQSIISTLT (SEQ ID NO: 6)
```

SEQUENCE LISTINGS

Human IL-2 mature form naturally occurring sequence
APTSSSTKKTQLQLEHLLLDLQMILNGINNYKNPKLTRMLTFKFYMPKKATELKHLQCLEEELKP
LEEVLNLAQSKNFHLRPRDLISNINVIVLELKGSETTFMCEYADETATIVEFLNRWITFCQSIISTLT
(SEQ ID NO: 7)

Human IL-2 mature form wild-type sequence
APTSSSTKKTQLQLEHLLLDLQMILNGINNYKNPKLTRMLTFKFYMPKKATELKHLQCLEEELKP
LEEVLNLAQSKNFHLRPRDLISNINVIVLELKGSETTFMCEYADETATIVEFLNRWITFSQSIISTLT
(SEQ ID NO: 8)

Human IL-2Rα (CD25) precursor sequence
MDSYLLMWGLLTFIMVPGCQAELCDDDPPEIPHATFKAMAYKEGTMLNCECKRGFRRIKSGSL
YMLCTGNSSHSSWDNQCQCTSSATRNTTKQVTPQPEEQKERKTTEMQSPMQPVDQASLPG
HCREPPPWENEATERIYHFVVGQMVYYQCVQGYRALHRGPAESVCKMTHGKTRWTQPQLIC
TGEMETSQFPGEEKPQASPEGRPESETSCLVITTDFQIQTEMAATMETSIFTTEYQVAVAGCV
FLLISVLLLSGLTWQRRQRKSRRTI (SEQ ID NO: 9)

Human IL-2Rα Sushi
ELCDDDPPEIPHATFKAMAYKEGTMLNCECKRGFRRIKSGSLYMLCTGNSSHSSWDNQCQCT
SSATRNTTKQVTPQPEEQKERKTTEMQSPMQPVDQASLPGHCREPPPWENEATERIYHFVVG
QMVYYQCVQGYRALHRGPAESVCKMTHGKTRWTQPQLICTG (SEQ ID NO: 10)

Human IL-2Rβ precursor sequence
MAAPALSWRLPLLILLLPLATSWASAAVNGTSQFTCFYNSRANISCVWSQDGALQDTSCQVHA
WPDRRRWNQTCELLPVSQASWACNLILGAPDSQKLTTVDIVTLRVLCREGVRWRVMAIQDFK
PFENLRLMAPISLQVVHVETHRCNISWEISQASHYFERHLEFEARTLSPGHTWEEAPLLTLKQK
QEWICLETLTPDTQYEFQVRVKPLQGEFTTWSPWSQPLAFRTKPAALGKDTIPWLGHLLVGLS
GAFGFIILVYLLINCRNTGPWLKKVLKCNTPDPSKFFSQLSSEHGGDVQKWLSSPFPSSSFSPG
GLAPEISPLEVLERDKVTQLLLQQDKVPEPASLSSNHSLTSCFTNQGYFFFHLPDALEIEACQVY
FTYDPYSEEDPDEGVAGAPTGSSPQPLQPLSGEDDAYCTFPSRDDLLLFSPSLLGGPSPPSTA
PGGSGAGEERMPPSLQERVPRDWDPQPLGPPTPGVPDLVDFQPPPELVLREAGEEVPDAGP
REGVSFPWSRPPGQGEFRALNARLPLNTDAYLSLQELQGQDPTHLV (SEQ ID NO: 11)

Human IL-2Rβ extracellular domain sequence
AVNGTSQFTCFYNSRANISCVWSQDGALQDTSCQVHAWPDRRRWNQTCELLPVSQASWAC
NLILGAPDSQKLTTVDIVTLRVLCREGVRWRVMAIQDFKPFENLRLMAPISLQVVHVETHRCNIS
WEISQASHYFERHLEFEARTLSPGHTWEEAPLLTLKQKQEWICLETLTPDTQYEFQVRVKPLQ
GEFTTWSPWSQPLAFRTKPAALGKDT (SEQ ID NO: 12)

Human IgG1-Fc
DKTHTCPPCPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPG (SEQ ID NO: 13)

Human IgG1-Fc with reduced/abolished effector function
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPG (SEQ ID NO: 14)

Knob-Fc
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVCTLPPSREEMTKNQVSLWCLVKGFYPSDIAVEWESNGQPENNYKTTPPVLDSDGSFFLYS
KLTVDKSRWQQGNVFSCSVMHEALHNHYTQKSLSLSPG (SEQ ID NO: 15)

Hole-Fc
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPCREEMTKNQVSLSCAVKGFYPSDIAVEWESNGQPENNYKTTPPVLDSDGSFFLVSK
LTVDKSRWQQGNVFSCSVMHEALHNHYTQKSLSLSPG (SEQ ID NO: 16)

Human IL-4 mature form sequence
HKCDITLQEIIKTLNSLTEQKTLCTELTVTDIFAASKNTTEKETFCRAATVLRQFYSHHEKDTRCL
GATAQQFHRHKQLRFLKRLDRNLWGLAGLNSCPVKEANQSTLENFLERLKTIMREKYSKCSS
(SEQ ID NO: 17)

Human IL-7 mature form sequence
DCDIEGKDGKQYESVLMVSIDQLLDSMKEIGSNCLNNEFNFFKRHICDANKEGMFLFRAARKLR
QFLKMNSTGDFDLHLLKVSEGTTILLNCTGQVKGRKPAALGEAQPTKSLEENKSLKEQKKLNDL
CFLKRLLQEIKTCWNKILMGTKEH (SEQ ID NO: 18)

Human IL-9 mature form sequence
QGCPTLAGILDINFLINKMQEDPASKCHCSANVTSCLCLGIPSDNCTRPCFSERLSQMTNTTMQ
TRYPLIFSRVKKSVEVLKNNKCPYFSCEQPCNQTTAGNALTFLKSLLEIFQKEKMRGMRGKI
(SEQ ID NO: 19)

SEQUENCE LISTINGS

Human IL-10 mature form sequence
SPGQGTQSENSCTHFPGNLPNMLRDLRDAFSRVKTFFQMKDQLDNLLLKESLLEDFKGYLGC
QALSEMIQFYLEEVMPQAENQDPDIKAHVNSLGENLKTLRLRLRRCHRFLPCENKSKAVEQVK
NAFNKLQEKGIYKAMSEFDIFINYIEAYMTMKIRN (SEQ ID NO: 20)

Human IL-12 subunit alpha mature form sequence
RNLPVATPDPGMFPCLHHSQNLLRAVSNMLQKARQTLEFYPCTSEEIDHEDITKDKTSTVEACL
PLELTKNESCLNSRETSFITNGSCLASRKTSFMMALCLSSIYEDLKMYQVEFKTMNAKLLMDPK
RQIFLDQNMLAVIDELMQALNFNSETVPQKSSLEEPDFYKTKIKLCILLHAFRIRAVTIDRVMSYL
NAS (SEQ ID NO: 21)

Human IL-12 subunit beta mature form sequence
IWELKKDVYVVELDWYPDAPGEMVVLTCDTPEEDGITWTLDQSSEVLGSGKTLTIQVKEFGDA
GQYTCHKGGEVLSHSLLLLHKKEDGIWSTDILKDQKEPKNKTFLRCEAKNYSGRFTCWWLTTIS
TDLTFSVKSSRGSSDPQGVTCGAATLSAERVRGDNKEYEYSVECQEDSACPAAEESLPIEVMV
DAVHKLKYENYTSSFFIRDIIKPDPPKNLQLKPLKNSRQVEVSWEYPDTWSTPHSYFSLTFCVQ
VQGKSKREKKDRVFTDKTSATVICRKNASISVRAQDRYYSSSWSEWASVPCS
(SEQ ID NO: 22)

Human IL-23 subunit alpha mature form sequence
RAVPGGSSPAWTQCQQLSQKLCTLAWSAHPLVGHMDLREEGDEETTNDVPHIQCGDGCDPQ
GLRDNSQFCLQRIHQGLIFYEKLLGSDIFTGEPSLLPDSPVGQLHASLLGLSQLLQPEGHHWET
QQIPSLSPSQPWQRLLLRFKILRSLQAFVAVAARVFAHGAATLSP (SEQ ID NO: 23)

Human TGF beta mature form sequence
ALDTNYCFSSTEKNCCVRQLYIDFRKDLGWKWIHEPKGYHANFCLGPCPYIWSLDTQY
SKVLALYNQHNPGASAAPCCVPQALEPLPIVYYVGRKPKVEQLSNMIVRSCKCS
(SEQ ID NO: 24)

P-0351
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGGSGGGGSNWVNVISD
LKKIEDLIQSMHIDATLYTESDVHPSCKVTAMKCFLLELQVISLESGDADIHDTVENLIILANNSLS
SNGNVTESGCKECEELEEKNIKEFLQSFVHIVQMFINTSGGGGSGGGGSITCPPPMSVEHADI
WVKSYSLYSRERYICNSGFKRKAGTSSLTECVLNKATNVAHWTTPSLKCIRDPALVHQRPAPP
(SEQ ID NO: 25)

P-0170 Hole chain
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPCREEMTKNQVSLSCAVKGFYPSDIAVEWESNGQPENNYKTTPPVLDSDGSFFLVSK
LTVDKSRWQQGNVFSCSVMHEALHNHYTQKSLSLSPGLGGSGRSANAILENWVNVISDLKKIE
DLIQSMHIDATLYTESDVHPSCKVTAMKCFLLELQVISLESGDASIHDTVENLIILANNSLSSNGN
VTESGCKECEELEEKNIKEFLQSFVHIVQMFINTSGSITCPPPMSVEHADIWVKSYSLYSRERYI
CNSGFKRKAGTSSLTECVLNKATNVAHWTTPSLKCIRDPALVHQRPAPP (SEQ ID NO: 26)

P-0172
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGLGGSGRSANAILENWVNVISDLKKIE
DLIQSMHIDATLYTESDVHPSCKVTAMKCFLLELQVISLESGDASIHDTVENLIILANNSLSSNGN
VTESGCKECEELEEKNIKEFLQSFVHIVQMFINTSGSITCPPPMSVEHADIWVKSYSLYSRERYI
CNSGFKRKAGTSSLTECVLNKATNVAHWTTPSLKCIRDPALVHQRPAPP (SEQ ID NO: 27)

P-0202
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGGSGGGGSLSGRSDNH
GGSGGGGSNWVNVISDLKKIEDLIQSMHIDATLYTESDVHPSCKVTAMKCFLLELQVISLESGD
ASIHDTVENLIILANNSLSSNGNVTESGCKECEELEEKNIKEFLQSFVHIVQMFINTSGSITCPPP
MSVEHADIWVKSYSLYSRERYICNSGFKRKAGTSSLTECVLNKATNVAHWTTPSLKCIRDPALV
HQRPAPP (SEQ ID NO: 28)

P-0203
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGGSGGGGSLGGSGRSAN
AILEGGSGGGGSNWVNVISDLKKIEDLIQSMHIDATLYTESDVHPSCKVTAMKCFLLELQVISLE
SGDASIHDTVENLIILANNSLSSNGNVTESGCKECEELEEKNIKEFLQSFVHIVQMFINTSGGGG
SGGGGSGGGGSITCPPPMSVEHADIWVKSYSLYSRERYICNSGFKRKAGTSSLTECVLNKATN
VAHWTTPSLKCIRDPALVHQRPAPP (SEQ ID NO: 29)

SEQUENCE LISTINGS

P-0204
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGGSLGGSGRSANAILEG
GGGSNWVNVISDLKKIEDLIQSMHIDATLYTESDVHPSCKVTAMKCFLLELQVISLESGDASIHD
TVENLIILANNSLSSNGNVTESGCKECEELEEKNIKEFLQSFVHIVQMFINTSGGGGSGGGGSG
GGGSITCPPPMSVEHADIWVKSYSLYSRERYICNSGFKRKAGTSSLTECVLNKATNVAHWTTP
SLKCIRDPALVHQRPAPP (SEQ ID NO: 30)

P-0205
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGGSLGGSGRSANAILEG
GGGSNWVNVISDLKKIEDLIQSMHIDATLYTESDVHPSCKVTAMKCFLLELQVISLESGDASIHD
TVENLIILANNSLSSNGNVTESGCKECEELEEKNIKEFLQSFVHIVQMFINTSGGGGSGGGGSIT
CPPPMSVEHADIWVKSYSLYSRERYICNSGFKRKAGTSSLTECVLNKATNVAHWTTPSLKCIRD
PALVHQRPAPP (SEQ ID NO: 31)

P-0206
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGGSLGGSGRSANAILEG
GGGSNWVNVISDLKKIEDLIQSMHIDATLYTESDVHPSCKVTAMKCFLLELQVISLESGDASIHD
TVENLIILANNSLSSNGNVTESGCKECEELEEKNIKEFLQSFVHIVQMFINTSGGGSITCPPPM
SVEHADIWVKSYSLYSRERYICNSGFKRKAGTSSLTECVLNKATNVAHWTTPSLKCIRDPALVH
QRPAPP (SEQ ID NO: 32)

P-0315
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSLGGSGRSANAILEGGSNWV
NVISDLKKIEDLIQSMHIDATLYTESDVHPSCKVTAMKCFLLELQVISLESGDADIHDTVENLIILAN
NSLSSNGNVTESGCKECEELEEKNIKEFLQSFVHIVQMFINTSGGPLGMLSQSITCPPPMSVEH
ADIWVKSYSLYSRERYICNSGFKRKAGTSSLTECVLNKATNVAHWTTPSLKCIRDPALVHQRPA
PP (SEQ ID NO: 33)

P-0316
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSLGGSGRSANAILEGGSNWV
NVISDLKKIEDLIQSMHIDATLYTESDVHPSCKVTAMKCFLLELQVISLESGDADIHDTVENLIILAN
NSLSSNGNVTESGCKECEELEEKNIKEFLQSFVHIVQMFINTSGGGPLGMLSQGGSITCPPPMS
VEHADIWVKSYSLYSRERYICNSGFKRKAGTSSLTECVLNKATNVAHWTTPSLKCIRDPALVHQ
RPAPP (SEQ ID NO: 34)

P-0350
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGGSGGGGSNWVNVISD
LKKIEDLIQSMHIDATLYTESDVHPSCKVTAMKCFLLELQVISLESGDADIHDTVENLIILANNSLS
SNGNVTESGCKECEELEEKNIKEFLQSFVHIVQMFINTSGGPLGMLSQSITCPPPMSVEHADIW
VKSYSLYSRERYICNSGFKRKAGTSSLTECVLNKATNVAHWTTPSLKCIRDPALVHQRPAPP
(SEQ ID NO: 35)

P-0354
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGSGPLGMLSQGGGSNWVNVISDL
KKIEDLIQSMHIDATLYTESDVHPSCKVTAMKCFLLELQVISLESGDADIHDTVENLIILANNSLSS
NGNVTESGCKECEELEEKNIKEFLQSFVHIVQMFINTSGGSGRSANAIITCPPPMSVEHADIWVK
SYSLYSRERYICNSGFKRKAGTSSLTECVLNKATNVAHWTTPSLKCIRDPALVHQRPAPP
(SEQ ID NO: 36)

P-0355
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGGSGGGGSNWVNVISD
LKKIEDLIQSMHIDATLYTESDVHPSCKVTAMKCFLLELQVISLESGDADIHDTVENLIILANNSLS

SEQUENCE LISTINGS

```
SNGNVTESGCKECEELEEKNIKEFLQSFVHIVQMFINTSGGSGRSANAIITCPPPMSVEHADIWV
KSYSLYSRERYICNSGFKRKAGTSSLTECVLNKATNVAHWTTPSLKCIRDPALVHQRPAPP
(SEQ ID NO: 37)

P-0385
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGGSLGGSGRSANAILEGGSNWV
NVISDLKKIEDLIQSMHIDATLYTESDVHPSCKVTAMKCFLLELQVISLESGDADIHDTVENLIILAN
NSLSSNGNVTESGCKECEELEEKNIKEFLQSFVHIVQMFINTSGPLGMLSQITCPPPMSVEHADI
WVKSYSLYSRERYICNSGFKRKAGTSSLTECVLNKATNVAHWTTPSLKCIRDPALVHQRPAPP
(SEQ ID NO: 38)

P-0386
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGGSLGGSGRSANAILEGGSNWV
NVISDLKKIEDLIQSMHIDATLYTESDVHPSCKVTAMKCFLLELQVISLESGDADIHDTVENLIILAN
NSLSSNGNVTESGCKECEELEEKNIKEFLQSFVHIVQMFINTSGGPLGMLSQSITCPPPMSVEH
ADIWVKSYSLYSRERYISNSGFKRKAGTSSLTECVLNKATNVAHWTTPSLKSIRDPALVHQRPA
PP (SEQ ID NO: 39)

P-0387
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGGSLGGSGRSANAILEGGSNW
VNVISDLKKIEDLIQSMHIDATLYTESDVHPSCKVTAMKCFLLELQVISLESGDADIHDTVENLIILA
NNSLSSNGNVTESGCKECEELEEKNIKEFLQSFVHIVQMFINTSGGPLGMLSQSITCPPPMSVE
HADIWVKSYSLYSREEYICNSGFKEKAGTSSLTECVLNKATNVAHWTTPSLKCIRDPALVHQRP
APP (SEQ ID NO: 40)

P-0388
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGGSLGGSGRSANAILEGGSNWV
NVISDLKKIEDLIQSMHIDATLYTESDVHPSCKVTAMKCFLLELQVISLESGDADIHDTVENLIILAN
NSLSSNGNVTESGCKECEELEEKNIKEFLQSFVHIVQMFINTSGGPLGMLSQSDCGLPPDVPN
AQPALEGRTSFPEDTVITYKCEESFVKIPGEKDSVICLKGSQWSDIEEFCNR (SEQ ID NO: 41)

P-0389
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGGSLGGSGRSANAILEGGSNWV
NVISDLKKIEDLIQSMHIDATLYTESDVHPSCKVTAMKCFLLELQVISLESGDADIHDTVENLIILAN
NSLSSNGNVTESGCKECEELEEKNIKEFLQSFVHIVQMFINTSGGPLGMLSQSELCDDDPPEIP
HATFKAMAYKEGTMLNCECKRGFRRIKSGSLYMLCTGNSSHSSWDNQCQCTSSATRNTTKQ
VTPQPEEQKERKTTEMQSPMQPVDQASLPGHCREPPPWENEATERIYHFVVGQMVYYQCVQ
GYRALHRGPAESVCKMTHGKTRWTQPQLICTG (SEQ ID NO: 42)

P-0397
ITCPPPMSVEHADIWVKSYSLYSRERYICNSGFKRKAGTSSLTECVLNKATNVAHWTTPSLKCI
RDPALVHQRPAPPGPLGMLSQSNWVNVISDLKKIEDLIQSMHIDATLYTESDVHPSCKVTAMK
CFLLELQVISLESGDADIHDTVENLIILANNSLSSNGNVTESGCKECEELEEKNIKEFLQSFVHIVQ
MFINTSGGGSLGGSGRSANAILEGGSCPPCPAPEAAGAPSVFLFPPKPKDTLMISRTPEVTC
VVVDVSHEDPEVKFNWYVDGVEVHNAKTKPREEQYNSTYRVVSVLTVLHQDWLNGKEYKCK
VSNKALPAPIEKTISKAKGQPREPQVYTLPPSRDELTKNQVSLTCLVKGFYPSDIAVEWESNGQ
PENNYKTIPPVLDSDGSFFLYSKLTVDKSRWQQGNVFSCSVMHEALHNHYTQKSLSLSPG
(SEQ ID NO: 43)

Hole-Fc-IL-15
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPCREEMTKNQVSLSCAVKGFYPSDIAVEWESNGQPENNYKTTPPVLDSDGSFFLVSK
LTVDKSRWQQGNVFSCSVMHEALHNHYTQKSLSLSPGEPKSSDKTHTSPPSPNWVNVISDLK
KIEDLIQSMHIDATLYTESDVHPSCKVTAMKCFLLELQVISLESGDASIHDTVENLIILANNSLSSN
GNVTESGCKECEELEEKNIKEFLQSFVHIVQMFINTS (SEQ ID NO: 44)

Knob-Fc-IL-15
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVCTLPPSREEMTKNQVSLWCLVKGFYPSDIAVEWESNGQPENNYKTTPPVLDSDGSFFLYS
KLTVDKSRWQQGNVFSCSVMHEALHNHYTQKSLSLSPGEPKSSDKTHTSPPSPNWVNVISDL
```

SEQUENCE LISTINGS

KKIEDLIQSMHIDATLYTESDVHPSCKVTAMKCFLLELQVISLESGDASIHDTVENLIILANNSLSS
NGNVTESGCKECEELEEKNIKEFLQSFVHIVQMFINTS (SEQ ID NO: 45)

Knob-Fc-IL-15Rα-Sushi+
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVCTLPPSREEMTKNQVSLWCLVKGFYPSDIAVEWESNGQPENNYKTTPPVLDSDGSFFLYS
KLTVDKSRWQQGNVFSCSVMHEALHNHYTQKSLSLSPGEPKSSDKTHTSPPSPITCPPPMSV
EHADIWVKSYSLYSRERYICNSGFKRKAGTSSLTECVLNKATNVAHWTTPSLKCIRDPALVHQR
PAPP (SEQ ID NO: 46)

Fc-IL-15 S58D
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGGSGGGGSNWVNVISD
LKKIEDLIQSMHIDATLYTESDVHPSCKVTAMKCFLLELQVISLESGDADIHDTVENLIILANNSLS
SNGNVTESGCKECEELEEKNIKEFLQSFVHIVQMFINTS (SEQ ID NO: 47)

P-0250
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGGSAPTSSSSIKKTQLQLEH
LLLDLQMILNGINNYKNPKLTRMLTFKFYMPKKATELKHLQCLEEEELKPLEEVLNLAQSKNFHLR
PRDLISNINIVIVLELKGSETTFMCEYADETATIVEFLNRWITFSQSIISTLT (SEQ ID NO: 48)

P-0320
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGGSLGGSGRSANAILEGGSAPT
SSSTKKTQLQLEHLLLDLQMILNGINNYKNPKLTRMLTFKFYMPKKATELKHLQCLEEEELKPLEE
VLNLAQSKNFHLRPRDLISNINIVIVLELKGSETTFMCEYADETATIVEFLNRWITFSQSIISTLTGG
GGSGGGGSGGGGSELCDDDPPEIPHATFKAMAYKEGTMLNCECKRGFRRIKSGSLYMLCTG
NSSHSSWDNQCQCTSSATRNTTKQVTPQPEEQKERKTTEMQSPMQPVDQASLPGHCREPPP
WENEATERIYHFVVGQMVYYQCVQGYRALHRGPAESVCKMTHGKTRWTQPQLICTG
(SEQ ID NO: 49)

P-0352
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGGSLGGSGRSANAILEGGSAPT
SSSTKKTQLQLEHLLLDLQMILNGINNYKNPKLTRMLTFKFYMPKKATELKHLQCLEEEELKPLEE
VLNLAQSKNFHLRPRDLISNINIVIVLELKGSETTFMCEYADETATIVEFLNRWITFSQSIISTLTGG
GGSGGGGSGGGGSELCDDDPPEIPHATFKAMAYKEGTMLNCECKRGFRRIESGSLYMLCTG
NSSHSSWDNQCQCTSSATRNTTKQVTPQPEEQKERKTTEMQSPMQPVDQASLPGHCREPPP
WENEATERIYHFVVGQMVYYQCVQGYRALHRGPAESVCKMTHGKTRWTQPQLICTG
(SEQ ID NO: 50)

P-0382
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGSAPTSSSIKKTQLQLEH
LLLDLQMILNGINNYKNPKLTRMLTFKFYMPKKATELKHLQCLEEEELKPLEEVLNLAQSKNFHLR
PRDLISNINIVIVLELKGSETTFMCEYADETATIVEFLNRWITFSQSIISTLTGGPLGMLSQSELCDD
DPPEIPHATFKAMAYKEGTMLNCECKRGFRRIKSGSLYMLCTGNSSHSSWDNQCQCTSSATR
NTTKQVTPQPEEQKERKTTEMQSPMQPVDQASLPGHCREPPPWENEATERIYHFVVGQMVY
YQCVQGYRALHRGPAESVCKMTHGKTRWTQPQLICTG (SEQ ID NO: 51)

P-0398
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGSGGGSAPTSSSIKKTQLQLEH
LLLDLQMILNGINNYKNPKLTRMLTFKFYMPKKATELKHLQCLEEEELKPLEEVLNLAQSKNFHLR
PRDLISNINIVIVLELKGSETTFMCEYADETATIVEFLNRWITFSQSIISTLTGGSGPLGMLSQGGG
SELCDDDPPEIPHATFKAMAYKEGTMLNCECKRGFRRIKSGSLYMLCTGNSSHSSWDNQCQC
TSSATRNTTKQVTPQPEEQKERKTTEMQSPMQPVDQASLPGHCREPPPWENEATERIYHFVV
GQMVYYQCVQGYRALHRGPAESVCKMTHGKTRWTQPQLICTG (SEQ ID NO: 52)

P-0362
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK

```
                            SEQUENCE LISTINGS

LTVDKSRWQQGNVFSCSVMHEALHNHYTQKSLSLSPGGGGSGGGSAPTSSSIKKTQLQLEH
LLLDLQMILNGINNYKNPKLTRMLTFKFYMPKKATELKHLQCLEEELKPLEEVLNLAQSKNFHLR
PRDLISNINVIVLELKGSETTFMCEYADETATIVEFLNRWITFSQSIISTLTGGPLGMLSQSELCDD
DPPEIPHATFKAMAYKEGTMLNCECKRGFRRIESGSLYMLCTGNSSHSSWDNQCQCTSSATR
NTTKQVTPQPEEQKERKTTEMQSPMQPVDQASLPGHCREPPPWENEATERIYHFVVGQMVY
YQCVQGYRALHRGPAESVCKMTHGKTRWTQPQLICTG (SEQ ID NO: 53)

P-0380
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGSAPTSSSIKKTQLQLEH
LLLDLQMILNGINNYKNPKLTRMLTFKFYMPKKATELKHLQCLEEELKPLEEVLNLAQSKNFHLR
PRDLISNINVIVLELKGSETTFMCEYADETATIVEFLNRWITFSQSIISTLTGGPLGMLSQSELCDD
DPPEIPHATFKAMAYKEGTMLNCECKRGFRRIESGSLAMLCTGNSSHSSWDNQCQCTSSATR
NTTKQVTPQPEEQKERKTTEMQSPMQPVDQASLPGHCREPPPWENEATERIYHFVVGQMVY
YQCVQGYRALHRGPAESVCKMTHGKTRWTQPQLICTG (SEQ ID NO: 54)

P-0384
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGSAPTSSSIKKTQLQLEH
LLLDLQMILNGINNYKNPKLTRMLTFKFYMPKKATELKHLQCLEEELKPLEEVLNLAQSKNFHLR
PRDLISNINVIVLELKGSETTFMCEYADETATIVEFLNRWITFSQSIISTLTGGPLGMLSQSELCDD
DPPEIPHATFKAMAYKEGTMLNCECKRGFRRIKSGSLAMLCTGNSSHSSWDNQCQCTSSATR
NTTKQVTPQPEEQKERKTTEMQSPMQPVDQASLPGHCREPPPWENEATERIYHFVVGQMVY
YQCVQGYRALHRGPAESVCKMTHGKTRWTQPQLICTG (SEQ ID NO: 55)

P-0400
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGSAPTSSSIKKTQLQLEH
LLNDLQMILNGINNYKNPKLTRMLTFKFYMPKKATELKHLQCLEEELKPLEEVLNLAQSKNFHLR
PRDLISNINVIVLELKGSETTFMCEYADETATIVEFLNRWITFSQSIISTLTGGPLGMLSQSELCDD
DPPEIPHATFKAMAYKEGTMLNCECKRGFRRIESGSLYMLCTGNSSHSSWDNQCQCTSSATR
NTTKQVTPQPEEQKERKTTEMQSPMQPVDQASLPGHCREPPPWENEATERIYHFVVGQMVY
YQCVQGYRALHRGPAESVCKMTHGKTRWTQPQLICTG (SEQ ID NO: 56)

P-0404
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGSAPTSSSTKKTQLQLEH
LLLELQMILNGINNYKNPKLTRMLTFKFYMPKKATELKHLQCLEEELKPLEEVLNLAQSKNFHLR
PRDLISNINVIVLELKGSETTFMCEYADETATIVEFLNRWITFSQSIISTLTGGPLGMLSQSELCDD
DPPEIPHATFKAMAYKEGTMLNCECKRGFRRIESGSLYMLCTGNSSHSSWDNQCQCTSSATR
NTTKQVTPQPEEQKERKTTEMQSPMQPVDQASLPGHCREPPPWENEATERIYHFVVGQMVY
YQCVQGYRALHRGPAESVCKMTHGKTRWTQPQLICTG (SEQ ID NO: 57)

P-0399
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGSAPTSSSTKKTQLQLEH
LLLDLQMILNGINNYKNPKLTRMLTFKFYMPKKATELKHLQCLEEELKPLEEVLNLAQSKNFHLR
PRDLISNINVIVLELKGSETTFMCEYADETATIVEFLNRWITFSQSIISTLTGGPLGMLSQSITCPP
PMSVEHADIWVKSYSLYSRERYICNSGFKRKAGTSSLTECVLNKATNVAHWTTPSLKCIRDPAL
VHQRPAPP (SEQ ID NO: 58)

P-0379
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGSAPTSSSTKKTQLQLEH
LLLDLQMILNGINNYKNPKLTRMLTAKFYMPKKATELKHLQCLEEELKPLEEVLNLAQSKNFHLR
PRDLISNINVIVLELKGSETTFMCEYADETATIVEFLNRWITFSQSIISTLTGGPLGMLSQSELCDD
DPPEIPHATFKAMAYKEGTMLNCECKRGFRRIKSGSLYMLCTGNSSHSSWDNQCQCTSSATR
NTTKQVTPQPEEQKERKTTEMQSPMQPVDQASLPGHCREPPPWENEATERIYHFVVGQMVY
YQCVQGYRALHRGPAESVCKMTHGKTRWTQPQLICTG (SEQ ID NO: 59)

P-0381
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGSAPTSSSTKKTQLQLEH
```

```
                              SEQUENCE LISTINGS

LLLDLQMILNGINNYKNPKLTEMLTAKFYMPKKATELKHLQCLEEELKPLEEVLNLAQSKNFHLR
PRDLISNINVIVLELKGSETTFMCEYADETATIVEFLNRWITFSQSIISTLTGGPLGMLSQSELCDD
DPPEIPHATFKAMAYKEGTMLNCECKRGFRRIKSGSLYMLCTGNSSHSSWDNQCQCTSSATR
NTTKQVTPQPEEQKERKTTEMQSPMQPVDQASLPGHCREPPPWENEATERIYHFVVGQMVY
YQCVQGYRALHRGPAESVCKMTHGKTRWTQPQLICTG (SEQ ID NO: 60)

P-0383
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGGSAPTSSSIKKTQLQLEH
LLLDLQMILNGINNYKNPKLTEMLTFKFYMPKKATELKHLQCLEEELKPLEEVLNLAQSKNFHLR
PRDLISNINVIVLELKGSETTFMCEYADETATIVEFLNRWITFSQSIISTLTGGPLGMLSQSELCDD
DPPEIPHATFKAMAYKEGTMLNCECKRGFRRIKSGSLYMLCTGNSSHSSWDNQCQCTSSATR
NTTKQVTPQPEEQKERKTTEMQSPMQPVDQASLPGHCREPPPWENEATERIYHFVVGQMVY
YQCVQGYRALHRGPAESVCKMTHGKTRWTQPQLICTG (SEQ ID NO: 61)

P-0329
ELCDDDPPEIPHATFKAMAYKEGTMLNCECKRGFRRIKSGSLYMLCTGNSSHSSWDNQCQCT
SSATRNTTKQVTPQPEEQKERKTTEMQSPMQPVDQASLPGHCREPPPWENEATERIYHFVVG
QMVYYQCVQGYRALHRGPAESVCKMTHGKTRWTQPQLICTGGGGSGGGGSGGGGSAPTS
SSTKKTQLQLEHLLLDLQMILNGINNYKNPKLTRMLTFKFYMPKKATELKHLQCLEEELKPLEEV
LNLAQSKNFHLRPRDLISNINVIVLELKGSETTFMCEYADETATIVEFLNRWITFSQSIISTLTGGG
GSLGGSGRSANAILEGGSCPPCPAPEAAGAPSVFLFPPKPKDTLMISRTPEVTCVVVDVSHED
PEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPG (SEQ ID NO: 62)

P-0401
ELCDDDPPEIPHATFKAMAYKEGTMLNCECKRGFRRIKSGSLYMLCTGNSSHSSWDNQCQCT
SSATRNTTKQVTPQPEEQKERKTTEMQSPMQPVDQASLPGHCREPPPWENEATERIYHFVVG
QMVYYQCVQGYRALHRGPAESVCKMTHGKTRWTQPQLICTGGGPLGMLSQSAPTSSSTKKT
QLQLEHLLLDLQMILNGINNYKNPKLTRMLTFKFYMPKKATELKHLQCLEEELKPLEEVLNLAQS
KNFHLRPRDLISNINVIVLELKGSETTFMCEYADETATIVEFLNRWITFSQSIISTLTGGGGSGGG
GSGGGGSGGGGSCPPCPAPEAAGAPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPG (SEQ ID NO: 63)

P-0402
ELCDDDPPEIPHATFKAMAYKEGTMLNCECKRGFRRIKSGSLYMLCTGNSSHSSWDNQCQCT
SSATRNTTKQVTPQPEEQKERKTTEMQSPMQPVDQASLPGHCREPPPWENEATERIYHFVVG
QMVYYQCVQGYRALHRGPAESVCKMTHGKTRWTQPQLICTGGGSGPLGMLSQGGGSAPTS
SSTKKTQLQLEHLLLDLQMILNGINNYKNPKLTRMLTFKFYMPKKATELKHLQCLEEELKPLEEV
LNLAQSKNFHLRPRDLISNINVIVLELKGSETTFMCEYADETATIVEFLNRWITFSQSIISTLTGGG
GSGGGGSGGGGSGGGGSCPPCPAPEAAGAPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPG (SEQ ID NO: 64)

P-0403
ELCDDDPPEIPHATFKAMAYKEGTMLNCECKRGFRRIKSGSLYMLCTGNSSHSSWDNQCQCT
SSATRNTTKQVTPQPEEQKERKTTEMQSPMQPVDQASLPGHCREPPPWENEATERIYHFVVG
QMVYYQCVQGYRALHRGPAESVCKMTHGKTRWTQPQLICTGGGPLGMLSQSAPTSSSTKKT
QLQLEHLLLDLQMILNGINNYKNPKLTRMLTFKFYMPKKATELKHLQCLEEELKPLEEVLNLAQS
KNFHLRPRDLISNINVIVLELKGSETTFMCEYADETATIVEFLNRWITFSQSIISTLTAEAAAKEAA
AKEAAAKACPPCPAPEAAGAPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTISKAKGQP
REPQVYTLPPSRDELTKNQVSLTCLVKGFYPSDIAVEWESNGQPENNYKTTPPVLDSDGSFFL
YSKLTVDKSRWQQGNVFSCSVMHEALHNHYTQKSLSLSPG (SEQ ID NO: 65)

Hole-Fc-15p1
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPCREEMTKNQVSLSCAVKGFYPSDIAVEWESNGQPENNYKTTPPVLDSDGSFFLVSK
LTVDKSRWQQGNVFSCSVMHEALHNHYTQKSLSLSPGEPKSSDKTHTSPPSPNWVNVISDLK
KIEDLIQSMHIDATLYTESDVHPSCKVTAMKCFLLELQVISLESGDASIHDTVENLIILANNSLSSN
GNVTESGCKECEELEEKNIKEFLQSFVHIVQMFINTGGGSLGGSGRSANAILEGGGSGGGSG
GGSIYNCEISQASHYFERHLCYSI (SEQ ID NO: 66)

Hole-Fc-15p2
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPCREEMTKNQVSLSCAVKGFYPSDIAVEWESNGQPENNYKTTPPVLDSDGSFFLVSK
LTVDKSRWQQGNVFSCSVMHEALHNHYTQKSLSLSPGEPKSSDKTHTSPPSPNWVNVISDLK
```

```
KIEDLIQSMHIDATLYTESDVHPSCKVTAMKCFLLELQVISLESGDASIHDTVENLIILANNSLSSN
GNVTESGCKECEELEEKNIKEFLQSFVHIVQMFINTSGGGSLGGSGRSANAILEGGGSGGGSG
GGSIYNCELHREFYHSAQSIEWCYSI (SEQ ID NO: 67)

Hole-Fc-15p3
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPCREEMTKNQVSLSCAVKGFYPSDIAVEWESNGQPENNYKTTPPVLDSDGSFFLVSK
LTVDKSRWQQGNVFSCSVMHEALHNHYTQKSLSLSPGEPKSSDKTHTSPPSPNWVNVISDLK
KIEDLIQSMHIDATLYTESDVHPSCKVTAMKCFLLELQVISLESGDASIHDTVENLIILANNSLSSN
GNVTESGCKECEELEEKNIKEFLQSFVHIVQMFINTSGGGSLGGSGRSANAILEGGGSGGGSG
GGSETHRCNISWEISQASHYFERHLEFEARTLCPGH (SEQ ID NO: 68)

p1'-15-Fc
QGQSGQCEISQASHYFERHLCYSIGSSGGSGGSGGSGLSGRSDNHGSSGTNWVNVISDLKKI
EDLIQSMHIDATLYTESDVHPSCKVTAMKCFLLELQVISLESGDASIHDTVENLIILANNSLSSNG
NVTESGCKECEELEEKNIKEFLQSFVHIVQMFINTSGCPPCPAPEAAGAPSVFLFPPKPKDTLMI
SRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPCREEMTKNQVSLSCAVKGFYPSDIAV
EWESNGQPENNYKTTPPVLDSDGSFFLVSKLTVDKSRWQQGNVFSCSVMHEALHNHYTQKS
LSLSPG (SEQ ID NO: 69)

p3'-15-Fc
QGQSGQCNISWEISQASHYFERHLEFEARTLCPGHGSSGGSGGSGGSGLSGRSDNHGSSGT
NWVNVISDLKKIEDLIQSMHIDATLYTESDVHPSCKVTAMKCFLLELQVISLESGDASIHDTVENLI
ILANNSLSSNGNVTESGCKECEELEEKNIKEFLQSFVHIVQMFINTSGCPPCPAPEAAGAPSVFL
FPPKPKDTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPCREEMTKNQVSLSCA
VKGFYPSDIAVEWESNGQPENNYKTTPPVLDSDGSFFLVSKLTVDKSRWQQGNVFSCSVMHE
ALHNHYTQKSLSLSPG (SEQ ID NO: 70)

Protease substrate peptide sequence
SPLGLAGS (SEQ ID NO: 71)

Protease substrate peptide sequence
EPLELRAG (SEQ ID NO: 72)

Protease substrate peptide sequence
LSGRSDNH (SEQ ID NO: 73)

Protease substrate peptide sequence
GPLGIAGQ (SEQ ID NO: 74)

Protease substrate peptide sequence
GTAHLMGG (SEQ ID NO: 75)

Protease substrate peptide sequence
RIGSLRTA (SEQ ID NO: 76)

Protease substrate peptide sequence
GPLGMLSQ (SEQ ID NO: 77)

Protease substrate peptide sequence
RPSASRSA (SEQ ID NO: 78)

Protease substrate peptide sequence
PLGLAG (SEQ ID NO: 79)

Protease substrate peptide sequence
LGGSGRSANAILE (SEQ ID NO: 80)

Protease substrate peptide sequence
GGSGRSANAI (SEQ ID NO: 81)

Protease substrate peptide sequence
SGRSA (SEQ ID NO: 82)

Protease substrate peptide sequence
AANL (SEQ ID NO: 83)

Protease substrate peptide sequence
GFFY (SEQ ID NO: 84)

Protease substrate peptide sequence
GPICFRLG (SEQ ID NO: 85)
```

SEQUENCE LISTINGS

Protease substrate peptide sequence
RQAGFSL (SEQ ID NO: 86)

Protease substrate peptide sequence
HSSKLQ (SEQ ID NO: 87)

Protease cleavable linker sequence
GGGSGGGGSGGGGSLSGRSDNHGGSGGGGS (SEQ ID NO: 88)

Protease cleavable linker sequence
GSSSGRSENIRTAGT (SEQ ID NO: 89)

Protease cleavable linker sequence
GGGGSGGGGSGGGSLGGSGRSANAILEGGSGGGGS (SEQ ID NO: 90)

Protease cleavable linker sequence
GGGGSGGGGSLGGSGRSANAILEGGGGS (SEQ ID NO: 91)

Protease cleavable linker sequence
GGGGSLGGSGRSANAILEGGS (SEQ ID NO: 92)

Protease cleavable linker sequence
GGGSGPTNKVRGGS (SEQ ID NO: 93)

Protease cleavable linker sequence
GGSGPLGMLSQGGGS (SEQ ID NO: 94)

Protease cleavable linker sequence
GGPLGMLSQS (SEQ ID NO: 95)

Protease cleavable linker sequence
GGGPLGMLSQGGS (SEQ ID NO: 96)

Peptide sequence
LGAPDSQKLTTVDIV (SEQ ID NO: 97)

Peptide sequence
EISQASHYFERHL (SEQ ID NO: 98)

Peptide sequence
CEISQASHYFERHLC (SEQ ID NO: 99)

Peptide sequence
LGAPDSQKLTTVDIVGGGGGGGGEISQASHYFERHL (SEQ ID NO: 100)

Peptide sequence
KPFENLRLMAPIS (SEQ ID NO: 101)

Peptide sequence
GGGSLGGSGRSANAILEGGGSGGGSGGGSIYNCEISQASHYFERHLCYSI (SEQ ID NO: 102)

Peptide sequence
GGGSLGGSGRSANAILEGGGSGGGSGGGSIYNCELHREFYHSAQSIEWCYSI
(SEQ ID NO: 103)

Peptide sequence
GGGSLGGSGRSANAILEGGGSGGGSGGGSETHRCNISWEISQASHYFERHLEFEARTLCPGH
(SEQ ID NO: 104)

Peptide sequence
QGQSGQCEISQASHYFERHLCYSIGSSGGSGGSGGSGLSGRSDNHGSSGT
(SEQ ID NO: 105)

Peptide sequence
QGQSGQCNISWEISQASHYFERHLEFEARTLCPGHGSSGGSGGSGGSGLSGRSDNHGSSGT
(SEQ ID NO: 106)

Non-cleavable linker sequence
EPKSSDKTHTSPPS (SEQ ID NO: 107)

Non-cleavable linker sequence
GGGSGGGSGGGS (SEQ ID NO: 108)

Non-cleavable linker sequence
GGGS (SEQ ID NO: 109)

SEQUENCE LISTINGS

Non-cleavable linker sequence
GSSGGSGGSGGSG (SEQ ID NO: 110)

Non-cleavable linker sequence
GSSGT (SEQ ID NO: 111)

Non-cleavable linker sequence
GGGGSGGGGSGGGGS (SEQ ID NO: 112)

Non-cleavable linker sequence
AEAAAKEAAAKEAAAKA (SEQ ID NO: 113)

Non-cleavable linker sequence
GGGGSGGGGSGGGGSGGGGS (SEQ ID NO: 114)

Non-cleavable linker sequence
GGGSGGGS (SEQ ID NO: 115)

Non-cleavable linker sequence
GS (SEQ ID NO: 116)

Non-cleavable linker sequence
GGS (SEQ ID NO: 117)

Non-cleavable linker sequence
GGGGS (SEQ ID NO: 118)

Non-cleavable linker sequence
GGSG (SEQ ID NO: 119)

Non-cleavable linker sequence
SGGG (SEQ ID NO: 120)

Non-cleavable linker sequence
GSGS (SEQ ID NO: 121)

Non-cleavable linker sequence
GSGSGS (SEQ ID NO: 122)

Non-cleavable linker sequence
GSGSGSGS (SEQ ID NO: 123)

Non-cleavable linker sequence
GSGSGSGSGS (SEQ ID NO: 124)

Non-cleavable linker sequence
GSGSGSGSGSGS (SEQ ID NO: 125)

Non-cleavable linker sequence
GGGGSGGGGS (SEQ ID NO: 126)

Non-cleavable linker sequence
GGGGSGGGGSGGGGS (SEQ ID NO: 127)

JS001-IL-15-VitoKine-HC
QGQLVQSGAEVKKPGASVKVSCKASGYTFTDYEMHWVRQAPGQGLEWMGVIESETGGTAYN
QKFKGRAKITADKSTSTAYMELSSLRSEDTAVYYCTREGITTVATTYYWYFDVWGQGTTVTVS
SASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPEAAGAPSVFLF
PPKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQGNVFSCSVMHEAL
HNHYTQKSLSLSPGGGGGSLGGSGRSANAILEGGSNWVNVISDLKKIEDLIQSMHIDATLYTES
DVHPSCKVTAMKCFLLELQVISLESGDADIHDTVENLIILANNSLSSNGNVTESGCKECEELEEK
NIKEFLQSFVHIVQMFINTSGGPLGMLSQSITCPPPMSVEHADIWVKSYSLYSRERYICNSGFKR
KAGTSSLTECVLNKATNVAHWTTPSLKCIRDPALVHQRPAPP (SEQ ID NO: 128)

J5001-Lκ
DVVMTQSPLSLPVTLGQPASISCRSSQSIVHSNGNTYLEWYLQKPGQSPQLLIYKVSNRFSGVP
DRFSGSGSGTDFTLKISRVEAEDVGVYYCFQGSHVPLTFGQGTKLEIKRTVAAPSVFIFPPSDE
QLKSGTASVVCLLNNFYPREAKVQWKVDNALQSGNSQESVTEQDSKDSTYSLSSTLTLSKADY
EKHKVYACEVTHQGLSSPVTKSFNRGEC (SEQ ID NO: 129)

Ipilimumab-IL-15-VitoKine-HC
QVQLVESGGGVVQPGRSLRLSCAASGFTFSSYTMHWVRQAPGKGLEWVTFISYDGNNKYYA
DSVKGRFTISRDNSKNTLYLQMNSLRAEDTAIYYCARTGWLGPFDYWGQGTLVTVSSASTKGP
SVFPLAPSSKSTSGGTAALGCLVKDYFPEPVTVSWNSGALTSGVHTFPAVLQSSGLYSLSSVV

```
TVPSSSLGTQTYICNVNHKPSNTKVDKKVEPKSCDKTHTCPPCPAPELLGGPSVFLFPPKPKDT
LMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELTKNQVSLTCLVKGFYPSD
lAVEWESNGQPENNYKTIPPVLDSDGSFFLYSKLTVDKSRWQQGNVFSCSVMHEALHNHYTQ
KSLSLSPGGGGSLGGSGRSANAILEGGSNWVNVISDLKKIEDLIQSMHIDATLYTESDVHPSC
KVTAMKCFLLELQVISLESGDADIHDTVENLIILANNSLSSNGNVTESGCKECEELEEKNIKEFLQ
SFVHIVQMFINTSGGPLGMLSQSITCPPPMSVEHADIWVKSYSLYSRERYICNSGFKRKAGTSS
LTECVLNKATNVAHWTTPSLKCIRDPALVHQRPAPP (SEQ ID NO: 130)

Ipilimumab-Lκ
EIVLTQSPGTLSLSPGERATLSCRASQSVGSSYLAWYQQKPGQAPRLLIYGAFSRATGIPDRFS
GSGSGTDFTLTISRLEPEDFAVYYCQQYGSSPWTFGQGTKVEIKRTVAAPSVFIFPPSDEQLKS
GTASVVCLLNNFYPREAKVQWKVDNALQSGNSQESVTEQDSKDSTYSLSSTLTLSKADYEKH
KVYACEVTHQGLSSPVTKSFNRGEC (SEQ ID NO: 131)

RO7009789-IL-15-VitoKine- HC
QVQLVQSGAEVKKPGASVKVSCKASGYTFTGYYMHWVRQAPGQGLEWMGWINPDSGGTNY
AQKFQGRVTMTRDTSISTAYMELNRLRSDDTAVYYCARDQPLGYCTNGVCSYFDYWGQGTLV
TVSSASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVSLT
CLVKGFYPSDIAVEWESNGQPENNYKTTPPVLDSDGSFFLYSKLTVDKSRWQQGNVFSCSVM
HEALHNHYTQKSLSLSPGGGGSLGGSGRSANAILEGGSNWVNVISDLKKIEDLIQSMHIDATL
YTESDVHPSCKVTAMKCFLLELQVISLESGDADIHDTVENLIILANNSLSSNGNVTESGCKECEE
LEEKNIKEFLQSFVHIVQMFINTSGGPLGMLSQSITCPPPMSVEHADIWVKSYSLYSRERYICNS
GFKRKAGTSSLTECVLNKATNVAHWTTPSLKCIRDPALVHQRPAPP (SEQ ID NO: 132)

RO7009789-Lκ
DIQMTQSPSSVSASVGDRVTITCRASQGIYSWLAWYQQKPGKAPNLLIYTASTLQSGVPSRFS
GSGSGTDFTLTISSLQPEDFATYYCQQANIFPLTFGGGTKVEIKRTVAAPSVFIFPPSDEQLKSG
TASVVCLLNNFYPREAKVQWKVDNALQSGNSQESVTEQDSKDSTYSLSSTLTLSKADYEKHKV
YACEVTHQGLSSPVTKSFNRGEC (SEQ ID NO: 133)

L19-IL-15-VitoKine-HC
EVQLLESGGGLVQPGGSLRLSCAASGFTFSSFSMSWVRQAPGKGLEWVSSISGSSGTTYYAD
SVKGRFTISRDSKNTLYLQMNSLRAEDTAVYYCAKPFPYFDYWGQGTLVTVSSASTKGPSVFP
LAPSSKSTSGGTAALGCLVKDYFPEPVTVSWNSGALTSGVHTFPAVLQSSGLYSLSSVVTVPS
SSLGTQTYICNVNHKPSNTKVDKKVEPKSCDKTHTCPPCPAPELLGGPSVFLFPPKPKDTLMIS
RTPEVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSRDELTKNQVSLTCLVKGFYPSDIAVE
WESNGQPENNYKTIPPVLDSDGSFFLYSKLTVDKSRWQQGNVFSCSVMHEALHNHYTQKSL
SLSPGGGGSLGGSGRSANAILEGGSNWVNVISDLKKIEDLIQSMHIDATLYTESDVHPSCKVT
AMKCFLLELQVISLESGDADIHDTVENLIILANNSLSSNGNVTESGCKECEELEEKNIKEFLQSFV
HIVQMFINTSGGPLGMLSQSITCPPPMSVEHADIWVKSYSLYSRERYICNSGFKRKAGTSSLTE
CVLNKATNVAHWTTPSLKCIRDPALVHQRPAPP (SEQ ID NO: 134)

L19-Lκ
EIVLTQSPGTLSLSPGERATLSCRASQSVSSSFLAWYQQKPGQAPRLLIYYASSRATGIPDRFS
GSGSGTDFTLTISRLEPEDFAVYYCQQTGRIPPTFGQGTKVEIKRTVAAPSVFIFPPSDEQLKSG
TASVVCLLNNFYPREAKVQWKVDNALQSGNSQESVTEQDSKDSTYSLSSTLTLSKADYEKHKV
YACEVTHQGLSSPVTKSFNRGEC (SEQ ID NO: 135)

Rituximab-IL-2-VitoKine-HC
QVQLQQPGAELVKPGASVKMSCKASGYTFTSYNMHWVKQTPGRGLEWIGAIYPGNGDTSYN
QKFKGKATLTADKSSSTAYMQLSSLTSEDSAVYYCARSTYYGGDWYFNVWGAGTTVTVSAAS
TKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKAEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHN
HYTQKSLSLSPGGGSGGGSAPTSSSTKKTQLQLEHLLLDLQMILNGINNYKNPKLTRMLTFKF
YMPKKATELKHLQCLEEELKPLEEVLNLAQSKNFHLRPRDLISNINVIVLELKGSETTFMCEYAD
ETATIVEFLNRWITFSQSIISTLTGGPLGMLSQSELCDDDPPEIPHATFKAMAYKEGTMLNCECK
RGFRRIKSGSLYMLCTGNSSHSSWDNQCQCTSSATRNTTKQVTPQPEEQKERKTTEMQSPM
QPVDQASLPGHCREPPPWENEATERIYHFVVGQMVYYQCVQGYRALHRGPAESVCKMTHGK
TRWTQPQLICTG (SEQ ID NO: 136)

Rituximab-Lκ
QIVLSQSPAILSASPGEKVTMTCRASSSVSYIHWFQQKPGSSPKPWIYATSNLASGVPVRFSGS
GSGTSYSLTISRVEAEDAATYYCQQWTSNPPTFGGGTKLEIKRTVAAPSVFIFPPSDEQLKSGT
ASVVCLLNNFYPREAKVQWKVDNALQSGNSQESVTEQDSKDSTYSLSSTLTLSKADYEKHKVY
ACEVTHQGLSSPVTKSFNRGEC (SEQ ID NO: 137)

Herceptin-IL-2-VitoKine-HC
EVQLVESGGGLVQPGGSLRLSCAASGFNIKDTYIHWVRQAPGKGLEWVARIYPTNGYTRYADS
VKGRFTISADTSKNTAYLQMNSLRAEDTAVYYCSRWGGDGFYAMDYWGQGTLVTVSSASTK
```

GPSVFPLAPSSKSTSGGTAALGCLVKDYFPEPVTVSWNSGALTSGVHTFPAVLQSSGLYSLSS
VVTVPSSSLGTQTYICNVNHKPSNTKVDKKVEPPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEALHNHY
TQKSLSLSPGGGSGGGSAPTSSSTKKTQLQLEHLLLDLQMILNGINNYKNPKLTRMLTFKFYM
PKKATELKHLQCLEEELKPLEEVLNLAQSKNFHLRPRDLISNINIVLELKGSETTFMCEYADETA
TIVEFLNRWITFSQSIISTLTGGPLGMLSQSELCDDDPPEIPHATFKAMAYKEGTMLNCECKRGF
RRIKSGSLYMLCTGNSSHSSWDNQCQCTSSATRNTTKQVTPQPEEQKERKTTEMQSPMQPV
DQASLPGHCREPPPWENEATERIYHFVVGQMVYYQCVQGYRALHRGPAESVCKMTHGKTRW
TQPQLICTG (SEQ ID NO: 138)

Herceptin-Lκ
DIQMTQSPSSLSASVGDRVTITCRASQDVNTAVAWYQQKPGKAPKLLIYSASFLYSGVPSRFS
GSRSGTDFTLTISSLQPEDFATYYCQQHYTTPPTFGQGTKVEIKRTVAAPSVFIFPPSDEQLKS
GTASVVCLLNNFYPREAKVQWKVDNALQSGNSQESVTEQDSKDSTYSLSSTLTLSKADYEKH
KVYACEVTHQGLSSPVTKSFNRGEC (SEQ ID NO: 139)

Cetuximab-IL-2-VitoKine-HC
QVQLKQSGPGLVQPSQSLSITCTVSGFSLTNYGVHWVRQSPGKGLEWLGVIWSGGNIDYNTP
FTSRLSINKDNSKSQVFFKMNSLQSNDTAIYYCARALTYYDYEFAYWGQGTLVTVSAASTKGP
SVFPLAPSSKSTSGGTAALGCLVKDYFPEPVTVSWNSGALTSGVHTFPAVLQSSGLYSLSSVV
TVPSSSLGTQTYICNVNHKPSNTKVDKKVEPKSCDKTHTCPPCPAPELLGGPSVFLFPPKPDT
LMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSRDELTKNQVSLTCLVKGFYPSD
IAVEWESNGQPENNYKTIPPVLDSDGSFFLYSKLTVDKSRWQQGNVFSCSVMHEALHNHYTQ
KSLSLSPGGGSGGGSAPTSSSTKKTQLQLEHLLLDLQMILNGINNYKNPKLTRMLTFKYMPK
KATELKHLQCLEEELKPLEEVLNLAQSKNFHLRPRDLISNINIVLELKGSETTFMCEYADETATI
VEFLNRWITFSQSIISTLTGGPLGMLSQSELCDDDPPEIPHATFKAMAYKEGTMLNCECKRGFR
RIKSGSLYMLCTGNSSHSSWDNQCQCTSSATRNTTKQVTPQPEEQKERKTTEMQSPMQPVD
QASLPGHCREPPPWENEATERIYHFVVGQMVYYQCVQGYRALHRGPAESVCKMTHGKTRWT
QPQLICTG (SEQ ID NO: 140)

Cetuximab-Lκ
DILLTQSPVILSVSPGERVSFSCRASQSIGTNIHWYQQRTNGSPRLL1KYASESISGIPSRFSGSG
SGTDFTLSINSVESEDIADYYCQQNNNWPTTFGAGTKLELKRTVAAPSVFIFPPSDEQLKSGTA
SVVCLLNNFYPREAKVQWKVDNALQSGNSQESVTEQDSKDSTYSLSSTLTLSKADYEKHKVYA
CEVTHQGLSSPVTKSFNRGEC (SEQ ID NO: 141)

JS001-1L-2-VitoKine-HC
QGQLVQSGAEVKKPGASVKVSCKASGYTFTDYEMHWVRQAPGQGLEWMGVIESETGGTAYN
QKFKGRAKITADKSTSTAYMELSSLRSEDTAVYYCTREGITTVATTYYWYFDVWGQGTTVTVS
SASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPEAAGAPSVFLF
PPKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQGNVFSCSVMHEAL
HNHYTQKSLSLSPGGGGSGGGSAPTSSSTKKTQLQLEHLLLDLQMILNGINNYKNPKLTRMLT
KFYMPKKATELKHLQCLEEELKPLEEVLNLAQSKNFHLRPRDLISNINIVLELKGSETTFMCEY
ADETATIVEFLNRWITFSQSIISTLTGGPLGMLSQSELCDDDPPEIPHATFKAMAYKEGTMLNCE
CKRGFRRIKSGSLYMLCTGNSSHSSWDNQCQCTSSATRNTTKQVTPQPEEQKERKTTEMQS
PMQPVDQASLPGHCREPPPWENEATERIYHFVVGQMVYYQCVQGYRALHRGPAESVCKMTH
GKTRWTQPQLICTG (SEQ ID NO: 142)

Vedolizumab-IL-2-VitoKine-HC
QVQLVQSGAEVKKPGASVKVSCKGSGYTFTSYWMHWVRQAPGQRLEWIGEIDPSESNTNYN
QKFKGRVTLTVDISASTAYMELSSLRSEDTAVYYCARGGYDGWDYAIDYWGQGTLVTVSSAST
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELAGAPSVFLFPPK
KDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEALHNHY
TQKSLSLSPGGGSGGGSAPTSSSTKKTQLQLEHLLLTLQMILNGINNYKNPKLTRMLTFKYM
PKKATELKHLQCLEEELKPLEEVLNLAQSKNFHLRPRDLISNINIVLELKGSETTFMCEYADETA
TIVEFLNRWITFSQSIISTLTGGPLGMLSQSELCDDDPPEIPHATFKAMAYKEGTMLNCECKRGF
RRIESGSLYMLCTGNSSHSSWDNQCQCTSSATRNTTKQVTPQPEEQKERKTTEMQSPMQPV
DQASLPGHCREPPPWENEATERIYHFVVGQMVYYQCVQGYRALHRGPAESVCKMTHGKTRW
TQPQLICTG (SEQ ID NO: 143)

Vedolizumab-Lκ
DVVMTQSPLSLPVTPGEPASISCRSSQSLAKSYGNTYLSWYLQKPGQSPQLLIYGISNRFSGVP
DRFSGSGSGTDFTLKISRVEAEDVGVYYCLQGTHQPYTFGQGTKVEIKRTVAAPSVFIFPPSDE
QLKSGTASVVCLLNNFYPREAKVQWKVDNALQSGNSQESVTEQDSKDSTYSLSSTLTLSKADY
EKHKVYACEVTHQGLSSPVTKSFNRGEC (SEQ ID NO: 144)

SEQUENCE LISTINGS

Humira-IL-2-VitoKine-HC
EVQLVESGGGLVQPGRSLRLSCAASGFTFDDYAMHWVRQAPGKGLEWVSAITWNSGHIDYA
DSVEGRFTISRDNAKNSLYLQMNSLRAEDTAVYYCAKVSYLSTASSLDYWGQGTLVTVSSAST
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEALHNHY
TQKSLSLSPGGGGSGGGSAPTSSSTKKTQLQLEHLLLTLQMILNGINNYKNPKLTRMLTFKFYM
PKKATELKHLQCLEEELKPLEEVLNLAQSKNFHLRPRDLISNINVIVLELKGSETTFMCEYADETA
TIVEFLNRWITFSQSIISTLTGGPLGMLSQSELCDDDPPEIPHATFKAMAYKEGTMLNCECKRGF
RRIESGSLYMLCTGNSSHSSWDNQCQCTSSATRNTTKQVTPQPEEQKERKTTEMQSPMQPV
DQASLPGHCREPPPWENEATERIYHFVVGQMVYYQCVQGYRALHRGPAESVCKMTHGKTRW
TQPQLICTG (SEQ ID NO: 145)

Humira-Lκ
DIQMTQSPSSLSASVGDRVTITCRASQGIRNYLAWYQQKPGKAPKLLIYAASTLQSGVPSRFSG
SGSGTDFTLTISSLQPEDVATYYCQRYNRAPYTFGQGTKVEIKRTVAAPSVFIFPPSDEQLKSG
TASVVCLLNNFYPREAKVQWKVDNALQSGNSQESVTEQDSKDSTYSLSSTLTLSKADYEKHKV
YACEVTHQGLSSPVTKSFNRGEC (SEQ ID NO: 146)

IL-2Rα domain swapped Sushi
GHCREPPPWENEATERIYHFVYKEGTMLNCECKRGFRRIKSGSLYMLCTGNSSHSSWDNQC
QCTSSATRN (SEQ ID NO: 147)

Hole-Fc-IL-15-2
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPCREEMTKNQVSLSCAVKGFYPSDIAVEWESNGQPENNYKTTPPVLDSDGSFFLVSK
LTVDKSRWQQGNVFSCSVMHEALHNHYTQKSLSLSPGGGGSGGGGSNWVNVISDLKKIED
LIQSMHIDATLYTESDVHPSCKVTAMKCFLLELQVISLESGDASIHDTVENLIILANNSLSSNGNV
TESGCKECEELEEKNIKEFLQSFVHIVQMFINTS (SEQ ID NO: 148)

Hole-Fc-IL-15-3
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPCREEMTKNQVSLSCAVKGFYPSDIAVEWESNGQPENNYKTTPPVLDSDGSFFLVSK
LTVDKSRWQQGNVFSCSVMHEALHNHYTQKSLSLSPGGGGSGGGGSGGGGSNWVNVISD
LKKIEDLIQSMHIDATLYTESDVHPSCKVTAMKCFLLELQVISLESGDASIHDTVENLIILANNSLS
SNGNVTESGCKECEELEEKNIKEFLQSFVHIVQMFINTS (SEQ ID NO: 149)

P-0420
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGSAPTSSSIKKTQLQLEH
LLLDLQMILNGINNYKNPKLTRMLTFKFYMPKKATELKHLQCLEEELKPLEEVLNLAQSKNFHLR
PRDLISRINVIVLELKGSETTFMCEYADETATIVEFLNRWITFSQSIISTLTGGPLGMLSQSELCDD
DPPEIPHATFKAMAYKEGTMLNCECKRGFRRIESGSLYMLCTGNSSHSSWDNQCQCTSSATR
NTTKQVTPQPEEQKERKTTEMQSPMQPVDQASLPGHCREPPPWENEATERIYHFVVGQMVY
YQCVQGYRALHRGPAESVCKMTHGKTRWTQPQLICTG (SEQ ID NO: 150)

P-0421
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGSAPTSSSIKKTQLQLEH
LLLTLQMILNGINNYKNPKLTRMLTFKFYMPKKATELKHLQCLEEELKPLEEVLNLAQSKNFHLR
PRDLISNINVIVLELKGSETTFMCEYADETATIVEFLNRWITFSQSIISTLTGGPLGMLSQSELCDD
DPPEIPHATFKAMAYKEGTMLNCECKRGFRRIESGSLYMLCTGNSSHSSWDNQCQCTSSATR
NTTKQVTPQPEEQKERKTTEMQSPMQPVDQASLPGHCREPPPWENEATERIYHFVVGQMVY
YQCVQGYRALHRGPAESVCKMTHGKTRWTQPQLICTG (SEQ ID NO: 151)

P-0423
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGSAPTSSSIKKTQLQLEH
LLLDLQMILNGINNYKNPKLTRMLTFKFYMPKKATELKHLQCLEEELKPLEEVLNLAQSKNFHLR
PRDLISNINVIVLELKGSETTFMCEYADETATIVEFLNRWITFSESIISTLTGGPLGMLSQSELCDD
DPPEIPHATFKAMAYKEGTMLNCECKRGFRRIESGSLYMLCTGNSSHSSWDNQCQCTSSATR
NTTKQVTPQPEEQKERKTTEMQSPMQPVDQASLPGHCREPPPWENEATERIYHFVVGQMVY
YQCVQGYRALHRGPAESVCKMTHGKTRWTQPQLICTG (SEQ ID NO: 152)

P-0424
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP

```
                          SEQUENCE LISTINGS
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGSAPTSSSIKKTQLQLEH
LLNDLQMILNGINNYKNPKLTRMLTFKFYMPKKATELKHLQCLEEELKPLEEVLNLAQSKNFHLR
PRDLISNINVIVLELKGSETTFMCEYADETATIVEFLNRWITFSESIISTLTGGPLGMLSQSELCDD
DPPEIPHATFKAMAYKEGTMLNCECKRGFRRIESGSLYMLCTGNSSHSSWDNQCQCTSSATR
NTTKQVTPQPEEQKERKTTEMQSPMQPVDQASLPGHCREPPPWENEATERIYHFVVGQMVY
YQCVQGYRALHRGPAESVCKMTHGKTRWTQPQLICTG    (SEQ ID NO: 153)

P-0425
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGSAPTSSSTKKTQLQLEH
LLRDLQMILNGINNYKNPKLTRMLTFKFYMPKKATELKHLQCLEEELKPLEEVLNLAQSKNFHLR
PRDLISNINVIVLELKGSETTFMCEYADETATIVEFLNRWITFSESIISTLTGGPLGMLSQSELCDD
DPPEIPHATFKAMAYKEGTMLNCECKRGFRRIESGSLYMLCTGNSSHSSWDNQCQCTSSATR
NTTKQVTPQPEEQKERKTTEMQSPMQPVDQASLPGHCREPPPWENEATERIYHFVVGQMVY
YQCVQGYRALHRGPAESVCKMTHGKTRWTQPQLICTG    (SEQ ID NO: 154)

P-0426
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGSAPTSSSTKKTQLQLEH
LLHDLQMILNGINNYKNPKLTRMLTFKFYMPKKATELKHLQCLEEELKPLEEVLNLAQSKNFHLR
PRDLISNINVIVLELKGSETTFMCEYADETATIVEFLNRWITFIESIISTLTGGSGPLGMLSQGGGS
ELCDDDPPEIPHATFKAMAYKEGTMLNCECKRGFRRIESGSLYMLCTGNSSHSSWDNQCQCT
SSATRNTTKQVTPQPEEQKERKTTEMQSPMQPVDQASLPGHCREPPPWENEATERIYHFVVG
QMVYYQCVQGYRALHRGPAESVCKMTHGKTRWTQPQLICTG    (SEQ ID NO: 155)

Human IgG1-Fc with reduced/abolished effector function and extended half-life
DKTHTCPPCPAPEAAGGPSVFLFPPKPKDTLYITREPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPG    (SEQ ID NO: 156)

Protease substrate peptide sequence
SGRSENIRTA    (SEQ ID NO: 157)

Protease substrate peptide sequence
GPTNKVR    (SEQ ID NO: 158)

Protease substrate peptide sequence
RQARAVGG    (SEQ ID NO: 159)

Protease cleavable linker sequence
GGPTNKVRGS    (SEQ ID NO: 160)

Protease cleavable linker sequence
GRQARAVGGS    (SEQ ID NO: 161)

P-0660
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGSSSGRSENIRTAGTNWVNVISDLK
KIEDLIQSMHIDATLYTESDVHPSCKVTAMKCFLLELQVISLESGDADIHDTVENLIILANNSLSSN
GNVTESGCKECEELEEKNIKEFLQSFVHIVQMFINTSGGPLGMLSQSITCPPPMSVEHADIWVK
SYSLYSRERYICNSGFKRKAGTSSLTECVLNKATNVAHWTTPSLKCIRDPALVHQRPAPP
(SEQ ID NO: 162)

P-0488
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGGGGSGGGGSNWVNVISD
LKKIEDLIQSMHIDATLYTESDVHPSCKVTAMKCFLLELQVISLESGDADIHDTVENLIILANNSLS
SNGNVTESGCKECEELEEKNIKEFLQSFVHIVQMFINTSGRSENIRTAITCPPPMSVEHADIWV
KSYSLYSRERYICNSGFKRKAGTSSLTECVLNKATNVAHWTTPSLKCIRDPALVHQRPAPP
(SEQ ID NO: 163)

P-0489
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGGSGGGGSGGGGSNWVNVISD
LKKIEDLIQSMHIDATLYTESDVHPSCKVTAMKCFLLELQVISLESGDADIHDTVENLIILANNSLS
```

SEQUENCE LISTINGS

```
SNGNVTESGCKECEELEEKNIKEFLQSFVHIVQMFINTSGGPTNKVRGSITCPPPMSVEHADIW
VKSYSLYSRERYICNSGFKRKAGTSSLTECVLNKATNVAHWTTPSLKCIRDPALVHQRPAPP
(SEQ ID NO: 164)

P-0661
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGSGPTNKVRGGSNWVNVISDLK
KIEDLIQSMHIDATLYTESDVHPSCKVTAMKCFLLELQVISLESGDADIHDTVENLIILANNSLSSN
GNVTESGCKECEELEEKNIKEFLQSFVHIVQMFINTSGGPLGMLSQSITCPPPMSVEHADIWVK
SYSLYSRERYICNSGFKRKAGTSSLTECVLNKATNVAHWTTPSLKCIRDPALVHQRPAPP
(SEQ ID NO: 165)

Human IgG1-Fc with reduced/abolished effector function and extended in vivo half-life
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHAHYTQKSLSLSPG (SEQ ID NO: 166)

Knob-Fc with extended in vivo half-life
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVCTLPPSREEMTKNQVSLWCLVKGFYPSDIAVEWESNGQPENNYKTTPPVLDSDGSFFLYS
KLTVDKSRWQQGNVFSCSVMHEALHAHYTQKSLSLSPG (SEQ ID NO: 167)

Hole-Fc with extended in vivo half-life
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVCTLPPCREEMTKNQVSLSCAVKGFYPSDIAVEWESNGQPENNYKTTPPVLDSDGSFFLVSK
LTVDKSRWQQGNVFSCSVMHEALHAHYTQKSLSLSPG (SEQ ID NO: 168)

P-0650
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHAHYTQKSLSLSPGGGGGSGGGGSGGGGSNWVNVISD
LKKIEDLIQSMHIDATLYTESDVHPSCKVTAMKCFLLELQVISLESGDADIHDTVENLIILANNSLS
SNGNVTESGCKECEELEEKNIKEFLQSFVHIVQMFINTSGGPLGMLSQSITCPPPMSVEHADIW
VKSYSLYSRERYICNSGFKRKAGTSSLTECVLNKATNVAHWTTPSLKCIRDPALVHQRPAPP
(SEQ ID NO: 169)

P-0651
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHAHYTQKSLSLSPGGGGGSGGGGSGGGGSNWVNVISD
LKKIEDLIQSMHIDATLYTESDVHPSCKVTAMKCFLLELQVISLESGDADIHDTVENLIILANNSLS
SNGNVTESGCKECEELEEKNIKEFLQSFVHIVQMFINTSGGGSGGGGSITCPPPMSVEHADI
WVKSYSLYSRERYICNSGFKRKAGTSSLTECVLNKATNVAHWTTPSLKCIRDPALVHQRPAPP
(SEQ ID NO: 170)

P-0662 Hole Chain
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPCREEMTKNQVSLSCAVKGFYPSDIAVEWESNGQPENNYKTTPPVLDSDGSFFLVSK
LTVDKSRWQQGNVFSCSVMHEALHNHYTQKSLSLSPGGGGGSLGGSGRSANAILEGGSNWV
NVISDLKKIEDLIQSMHIDATLYTESDVHPSCKVTAMKCFLLELQVISLESGDADIHDTVENLIILAN
NSLSSNGNVTESGCKECEELEEKNIKEFLQSFVHIVQMFINTSGGPLGMLSQSITCPPPMSVEH
ADIWVKSYSLYSRERYICNSGFKRKAGTSSLTECVLNKATNVAHWTTPSLKCIRDPALVHQRPA
PP (SEQ ID NO: 171)

P-0663 Hole Chain with extended half-life
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPCREEMTKNQVSLSCAVKGFYPSDIAVEWESNGQPENNYKTTPPVLDSDGSFFLVSK
LTVDKSRWQQGNVFSCSVMHEALHAHYTQKSLSLSPGGGGGSLGGSGRSANAILEGGSNWV
NVISDLKKIEDLIQSMHIDATLYTESDVHPSCKVTAMKCFLLELQVISLESGDADIHDTVENLIILAN
NSLSSNGNVTESGCKECEELEEKNIKEFLQSFVHIVQMFINTSGGPLGMLSQSITCPPPMSVEH
ADIWVKSYSLYSRERYICNSGFKRKAGTSSLTECVLNKATNVAHWTTPSLKCIRDPALVHQRPA
PP (SEQ ID NO: 172)

P-0664 Hole chain with extended half-life
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPCREEMTKNQVSLSCAVKGFYPSDIAVEWESNGQPENNYKTTPPVLDSDGSFFLVSK
LTVDKSRWQQGNVFSCSVMHEALHAHYTQKSLSLSPGGGGGSGGGGSGGGGSNWVNVISD
```

```
LKKIEDLIQSMHIDATLYTESDVHPSCKVTAMKCFLLELQVISLESGDADIHDTVENLIILANNSLS
SNGNVTESGCKECEELEEKNIKEFLQSFVHIVQMFINTSGGPLGMLSQSITCPPPMSVEHADIW
VKSYSLYSRERYICNSGFKRKAGTSSLTECVLNKATNVAHWTTPSLKCIRDPALVHQRPAPP
(SEQ ID NO: 173)

P-0665 Hole chain with extended half-life
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPCREEMTKNQVSLSCAVKGFYPSDIAVEWESNGQPENNYKTTPPVLDSDGSFFLVSK
LTVDKSRWQQGNVFSCSVMHEALHAHYTQKSLSLSPGGSSSGRSENIRTAGTNWVNVISDLK
KIEDLIQSMHIDATLYTESDVHPSCKVTAMKCFLLELQVISLESGDADIHDTVENLIILANNSLSSN
GNVTESGCKECEELEEKNIKEFLQSFVHIVQMFINTSGGPLGMLSQSITCPPPMSVEHADIWVK
SYSLYSRERYICNSGFKRKAGTSSLTECVLNKATNVAHWTTPSLKCIRDPALVHQRPAPP
(SEQ ID NO: 174)

P-0156 Knob-chain
ITCPPPMSVEHADIWVKSYSLYSRERYICNSGFKRKAGTSSLTECVLNKATNVAHWTTPSLKCI
RDPALVHQRPAPPGCPPCPAPEAAGAPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIEKTIS
KAKGQPREPQVCTLPPSREEMTKNQVSLWCLVKGFYPSDIAVEWESNGQPENNYKTTPPVLD
SDGSFFLYSKLTVDKSRWQQGNVFSCSVMHEALHNHYTQKSLSLSPG (SEQ ID NO: 175)

P-0156 hole-chain
NWVNVISDLKKIEDLIQSMHIDATLYTESDVHPSCKVTAMKCFLLELQVISLESGDASIHDTVENLI
ILANNSLSSNGNVTESGCKECEELEEKNIKEFLQSFVHIVQMFINTSGCPPCPAPEAAGAPSVFL
FPPKPKDTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPCREEMTKNQVSLSCA
VKGFYPSDIAVEWESNGQPENNYKTTPPVLDSDGSFFLVSKLTVDKSRWQQGNVFSCSVMHE
ALHNHYTQKSLSLSPG (SEQ ID NO: 176)

Benchmark chain 1
NWVNVISDLKKIEDLIQSMHIDATLYTESNVHPSCKVTAMKCFLLELQVISLESGDASIHDTVQDL
IILANNSLSSNGNVTESGCKECEELEEKNIKEFLQSFVHIVQMFINTSGGGGSEPKSSDKTHTCP
PCPAPPVAGPSVFLFPPKPKDTLMISRTPEVTCVVVDVKHEDPEVKFNWYVDGVEVHNAKTKP
REEEYNSTYRVVSVLTVLHQDWLNGKEYKCKVSNKALPAPIEKTISKAKGQPREPQVYTLPPSR
EEMTKNQVSLTCDVSGFYPSDIAVEWESDGQPENNYKTTPPVLDSDGSFFLYSKLTVDKSRW
EQGDVFSCSVLHEALHSHYTQKSLSLSPGK (SEQ ID NO: 177)

Benchmark chain 2
ITCPPPMSVEHADIWVKSYSLYSRERYICNSGFKRKAGTSSLTECVLNKATNVAHWTTPSLKCI
RGGGGSEPKSSDKTHTCPPCPAPPVAGPSVFLFPPKPKDTLMISRTPEVTCVVVDVKHEDPEV
KFNWYVDGVEVHNAKTKPREEQYNSTYRVVSVLTVLHQDWLNGKEYKCKVSNKALPAPIEKTI
SKAKGQPREPQVYTLPPSREQMTKNQVKLTCLVKGFYPSDIAVEWESNGQPENNYKTTPPVL
DSDGSFFLYSKLTVDKSRWQQGNVFSCSVLHEALHSHYTQKSLSLSPGK (SEQ ID NO: 178)

P-0321
DKTHTCPPCPAPEAAGAPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSRDELTKNQVSLTCLVKGFYPSDIAVEWESNGQPENNYKTTPPVLDSDGSFFLYSK
LTVDKSRWQQGNVFSCSVMHEALHNHYTQKSLSLSPGGGGGSLGGSGRSANAILEGGSAPT
SSSTKKTQLQLEHLLLDLQMILNGINNYKNPKLTRMLTFKFYMPKKATELKHLQCLEEELKPLEE
VLNLAQSKNFHLRPRDLISNINVIVLELKGSETTFMCEYADETATIVEFLNRWITFSQS1ISTLTGG
GGSGGGGSGGGGSGHCREPPPWENEATERIYHFVYKEGTMLNCECKRGFRRIKSGSLYMLC
TGNSSHSSWDNQCQCTSSATRN (SEQ ID NO: 179)

Tecentriq-IL-15-VitoKineHC
EVQLVESGGGLVQPGGSLRLSCAASGFTFSDSWIHWVRQAPGKGLEWVAWISPYGGSTYYA
DSVKGRFTISADTSKNTAYLQMNSLRAEDTAVYYCARRHWPGGFDYWGQGTLVTVSSASTKG
PSVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPEAAGAPSVFLFPPKPK
DTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMHEALHNHYT
QKSLSLSPGGGGSLGGSGRSANAILEGGSNWVNVISDLKKIEDLIQSMHIDATLYTESDVHPS
CKVTAMKCFLLELQVISLESGDADIHDTVENLIILANNSLSSNGNVTESGCKECEELEEKNIKEFL
QSFVHIVQMFINTSGGPLGMLSQSITCPPPMSVEHADIWVKSYSLYSRERYICNSGFKRKAGTS
SLTECVLNKATNVAHWTTPSLKCIRDPALVHQRPAPP (SEQ ID NO: 180)

Tecentriq-Lκ
DIQMTQSPSSLSASVGDRVTITCRASQDVSTAVAWYQQKPGKAPKLLIYSASFLYSGVPSRFS
GSGSGTDFTLTISSLQPEDFATYYCQQYLYHPATFGQGTKVEIKRTVAAPSVFIFPPSDEQLKS
GTASVVCLLNNFYPREAKVQWKVDNALQSGNSQESVTEQDSKDSTYSLSSTLTLSKADYEKH
KVYACEVTHQGLSSPVTKSFNRGEC (SEQ ID NO: 181)

P-0315
atggatatgcgggtgcctgctcagctgctgggcctgctgctgctgtggctgcgaggggctagatgtgataaaactcatacttgtcctccat
gcccagcacctgaggcagcaggcgccccatccgtgttcctgtttccccctaagcccaaggacacactgatgatctcccgtacgccag
```

SEQUENCE LISTINGS aggtgacatgcgtggtggtggacgtgagccacgaggaccccgaggtgaagtttaactggtacgtggacggcgtggaggtgcacaat
gccaagacaaagcctagggaggagcagtacaattctacctatcgcgtggtgagcgtgctgacagtgctgcaccaggattggctgaa
cggcaaggagtataagtgcaaggtgtccaataaggccctgcctgccccaatcgagaagaccatctctaaggccaagggccagccc
agagagcctcaggtgtacacactgcctccaagcagagacgagctgaccaagaaccaggtgtccctgacatgtctggtgaagggctt
ctatcccctctgatatcgccgtggagtgggagagcaatggccagcctgagaacaattacaagaccacaccccctgtgctggacagcg
atggctccttctttctgtattccaagctgaccgtggataagtctcggtggcagcagggcaacgtgttttcctgctctgtgatgcacgaagca
ctgcataaccactacacccagaagagcctgagcctgtcccccgggggcggcggaggaagtctgggagggagtgggcgaagtgc
caacgctattctggagggcggaagtaactgggtcaatgtgattagtgatctgaagaagatcgaggacctgatccagagcatgcacat
cgatgccaccctgtacacagagtccgacgtgcaccccctcttgcaaggtgaccgccatgaagtgtttcctgctggagctgcaggtcatc
agcctggagagcggcgacgccgatatccacgataccgtggagaacctgatcatcctggccaacaattctctgagctccaacggcaa
tgtgacagagagcggctgcaaggagtgtgaggagctggaggagaagaacatcaaggagttcctgcagtccttgtgcacatcgtgc
agatgttcatcaatacctctggaggaccactgggaatgctgtcccagtctatcacatgcccactccaatgtccgtggagcacgcaga
catctgggtgaagagctactcccctgtatagccgggagagatatatctgcaattccggctttaagcggaaggccggcacctctagcctg
acagagtgcgtgctgaacaaggccaccaatgtggcccactggacaaccccaagcctgaaatgtattcgcgaccctgccctggtcca
ccagcgccctgccccccc (SEQ ID NO: 182)

P-0350
<u>atggatatgcgggtgcctgctcagctgctgggcctgctgctgctgtggctgcgagggggctagatgtgataaaactcatacttgtcctccat</u>
gcccagcacctgaggcagcaggcgccccatccgtgttcctgtttccccctaagcccaaggacacactgatgatctcccgtacgccag
aggtgacatgcgtggtggtggacgtgagccacgaggaccccgaggtgaagtttaactggtacgtggacggcgtggaggtgcacaat
gccaagacaaagcctagggaggagcagtacaattctacctatcgcgtggtgagcgtgctgacagtgctgcaccaggattggctgaa
cggcaaggagtataagtgcaaggtgtccaataaggccctgcctgccccaatcgagaagaccatctctaaggccaagggccagccc
agagagcctcaggtgtacacactgcctccaagcagagacgagctgaccaagaaccaggtgtccctgacatgtctggtgaagggctt
ctatcccctctgatatcgccgtggagtgggagagcaatggccagcctgagaacaattacaagaccacaccccctgtgctggacagcg
atggctccttctttctgtattccaagctgaccgtggataagtctcggtggcagcagggcaacgtgttttcctgctctgtgatgcacgaagca
ctgcataaccactacacccagaagagcctgagcctgtcccccgggggcggcggaggaagtggcgaggaggctctggcggagg
cggaagtaactgggtcaatgtgattagtgatctgaagaagatcgaggacctgatccagagcatgcacatcgatgccaccctgtacac
agagtccgacgtgcaccccctcttgcaaggtgaccgccatgaagtgtttcctgctggagctgcaggtcatcagcctggagtccggcgac
gccgatatccacgataccgtggagaacctgatcatcctggccaacaattctctgagctccaacggcaatgtgacagagagcggctg
caaggagtgtgaggagctggaggagaagaacatcaaggagttcctgcagtccttgtgcacatcgtgcagatgttcatcaatacctct
ggaggaccactgggaatgctgtcccagtctatcacatgcccacctccaatgtccgtggagcacgcagacatctgggtgaagagctac
tcccctgtatagccgggagagatatatctgcaattccggctttaagcggaaggccggcacctctagcctgacagagtgcgtgctgaaca
aggccaccaatgtggcccactggacaaccccaagcctgaaatgtattcgcgaccctgccctggtccaccagcgccctgccccccc
(SEQ ID NO: 183)

P-0351
<u>atggatatgcgggtgcctgctcagctgctgggcctgctgctgctgtggctgcgagggggctagatgtgataaaactcatacttgtcctccat</u>
gcccagcacctgaggcagcaggcgccccatccgtgttcctgtttccccctaagcccaaggacacactgatgatctcccgtacgccag
aggtgacatgcgtggtggtggacgtgagccacgaggaccccgaggtgaagtttaactggtacgtggacggcgtggaggtgcacaat
gccaagacaaagcctagggaggagcagtacaattctacctatcgcgtggtgagcgtgctgacagtgctgcaccaggattggctgaa
cggcaaggagtataagtgcaaggtgtccaataaggccctgcctgccccaatcgagaagaccatctctaaggccaagggccagccc
agagagcctcaggtgtacacactgcctccaagcagagacgagctgaccaagaaccaggtgtccctgacatgtctggtgaagggctt
ctatcccctctgatatcgccgtggagtgggagagcaatggccagcctgagaacaattacaagaccacaccccctgtgctggacagcg
atggctccttctttctgtattccaagctgaccgtggataagtctcggtggcagcagggcaacgtgttttcctgctctgtgatgcacgaagca
ctgcataaccactacacccagaagagcctgagcctgtcccccgggggcggcggaggaagtctgggaggaggagtggcgaggtg
aggctccaactgggtgaatgtgatctctgacctgaagaagatcgaggatctgatccagagcatgcacatcgacgccaccctgtacac
agagtctgatgtgcaccctagctgcaaggtgaccgccatgaagtgtttcctgctggagctgcaggtcatcagcctggagtccggcgac
gccgatatccacgacaccgtggagaacctgatcatcctggccaacaatagcctgagctccaacggcaatgtgacagagtccggctg
caaggagtgtgaggagctggaggagaagaacatcaaggagttcctgcagtcctttgtgcacatcgtgcagatgttcatcaatacctcc
ggaggaggaggctctggcggcggaggcagcatacatgcccccctccaatgtctgtggagcacgccgacatctgggtgaagtccta
ctctctgtacagccgggagcggtacatctgcaattctggctttaagcggaaggccggcacctctagcctgacagagtgcgtgctgaac
aaggccacaaatgtggcccactggaccacacccagcctgaagtgtatccgggaccccgccctggtgcaccagcgccccgccccc
cct (SEQ ID NO: 184)

P-0650
<u>atggatatgcgggtgcctgctcagctgctgggcctgctgctgctgtggctgcgagggggctagatgtgataaaactcatacttgtcctccat</u>
gcccagcacctgaggcagcaggcgccccatccgtgttcctgtttccccctaagcccaaggacacactgatgatctcccgtacgccag
aggtgacatgcgtggtggtggacgtgagccacgaggaccccgaggtgaagtttaactggtacgtggacggcgtggaggtgcacaat
gccaagacaaagcctagggaggagcagtacaattctacctatcgcgtggtgagcgtgctgacagtgctgcaccaggattggctgaa
cggcaaggagtataagtgcaaggtgtccaataaggccctgcctgccccaatcgagaagaccatctctaaggccaagggccagccc
agagagcctcaggtgtacacactgcctccaagcagagacgagctgaccaagaaccaggtgtccctgacatgtctggtgaagggctt
ctatcccctctgatatcgccgtggagtgggagagcaatggccagcctgagaacaattacaagaccacaccccctgtgctggacagcg
atggctccttctttctgtattccaagctgaccgtggataagtctcggtggcagcagggcaacgtgttttcctgctctgtgatgcacgaagca
ctgcatgctcactacacccagaagagcctgagcctgtcccccgggggcggcggaggaagtggcgaggaggctctggcggaggc
ggaagtaactgggtcaatgtgattagtgatctgaagaagatcgaggacctgatccagagcatgcacatcgatgccaccctgtacaca
gagtccgacgtgcaccccctcttgcaaggtgaccgccatgaagtgtttcctgctggagctgcaggtcatcagcctggagagcggcgac
gccgatatccacgataccgtggagaacctgatcatcctggccaacaattctctgagctccaacggcaatgtgacagagagcggctgc
aaggagtgtgaggagctggaggagaagaacatcaaggagttcctgcagtcctttgtgcacatcgtgcagatgttcatcaatacctctg
gaggaccactgggaatgctgtcccagtctatcacatgcccacctccaatgtccgtggagcacgcagacatctgggtgaagagctact
cccctgtatagccgggagagatatatctgcaattccggctttaagcggaaggccggcacctctagcctgacagagtgcgtgctgaaca
aggccaccaatgtggcccactggacaaccccaagcctgaaatgtattcgcgaccctgccctggtccaccagcgccctgccccccc
(SEQ ID NO: 185)

P-0651
<u>atggatatgcgggtgcctgctcagctgctgggcctgctgctgctgtggctgcgagggggctagatgtgataaaactcatacttgtcctccat</u>
gcccagcacctgaggcagcaggcgccccatccgtgttcctgtttccccctaagcccaaggacacactgatgatctcccgtacgccag
aggtgacatgcgtggtggtggacgtgagccacgaggaccccgaggtgaagtttaactggtacgtggacggcgtggaggtgcacaat

SEQUENCE LISTINGS

```
gccaagacaaagcctagggaggagcagtacaattctacctatcgcgtggtgagcgtgctgacagtgctgcaccaggattggctgaa
cggcaaggagtataagtgcaaggtgtccaataaggccctgcctgccccaatcgagaagaccatctctaaggccaagggccagccc
agagagcctcaggtgtacacactgcctccaagcagagacgagctgaccaagaaccaggtgtccctgacatgtctggtgaagggctt
ctatccctctgatatcgccgtggagtgggagagcaatggccagcctgagaacaattacaagaccacacccctgtgctggacagcg
atggctccttctttctgtattccaagctgaccgtggataagctcggtggcagcagggcaacgtgttttcctgctctgtgatgcacgaagca
ctgcatgctcactacacccagaagagcctgagcctgtcccccggggggcggcggcggctctggaggaggaggcagcggcggagg
aggctccaactgggtgaatgtgatctctgacctgaagaagatcgaggatctgatccagagcatgcacatcgacgccaccctgtacac
agagtctgatgtgcaccctagctgcaaggtgaccgccatgaagtgtttcctgctggagctgcaggtcatcagcctggagtccggcgac
gccgatatccacgacaccgtggagaacctgatcatcctggccaacaatagcctgagctccaacggcaatgtgacagagtccggctg
caaggagtgtgaggagctggaggagaagaacatcaaggagttcctgcagtcctttgtgcacatcgtgcagatgttcatcaatacctcc
ggaggaggaggctctggcggcggaggcagcatcacatgccccctccaatgtctgtggagcacgccgacatctgggtgaagtccta
ctctctgtacagccgggagcggtacatctgcaattctggctttaagcggaaggccggcacctctagcctgacagagtgcgtgctgaac
aaggccacaaatgtggcccactggaccacacccagcctgaagtgtatccgggaccccgccctggtgcaccagcgccccgccccc
cct (SEQ ID NO: 186)

P-0662 Chain 1
atggatatgcgggtgcctgctcagctgctgggcctgctgctgctgtggctgcgaggggctagatgtgataaaactcatacctatcctcca
tgcccagcacctgaggcagcaggcgcccatccglgttcctgtttcccctaagcccaaggacaccctgatgatctctcgtacgccg
aggtgacatgcgtggtggtggacgtgagccacgaggaccccgaggtgaagttcaactggtacgtggatggcgtggaggtgcacaat
gccaagacaaagcctcgggaggagcagtacaactccacctatagagtggtgtctgtgctgacagtgctgcaccaggactggctgaa
cggcaaggagtacaagtgcaaggtgtccaataaggccctgccagccccatcgagaagaccatcagcaaggccaagggccagc
ctagggagccacaggtgtataccctgccaccctgccgcgaggagatgacaaagaaccaggtgtccctgtcttgtgccgtgaagggct
tctaccccttctgacatcgccgtggagtgggagagcaatggccagccagagaacaattataagaccacacctccagtgctggactctg
atggcagcttctttctggtgagcaagctgaccgtggataagtccaggtggcagcagggcaacgtgttttagctgttcctgatgcacgag
gccctgcacaatcactacacacagaagtctctgagcctgtcccccggggcggcggaggaagtctgggagggagtgggcgaagt
gccaacgctattctggagggcggaagtaactgggtcaatgtgattagtgatctgaagaagatcgaggacctgatccagagcatgcac
atcgatgccaccctgtacacagagtccgacgtgcaccctcttgcaaggtgaccgccatgaagtgtttcclgctggagctgcaggtcat
cagcctggagagcggcgacgccgalatccacgataccgtggaaactgatcatcctggccaacaattctclgagctccaacggca
atgtgacagagagcggctgcaaggagtgtgaggagctggaggagaagaacatcaaggagttcctgcagtcctttgtgcacatcgtg
cagatgttcatcaatacctctggaggaccactgggaatgctgtcccagtctatcacatgcccacctccaatgtccgtggagcacgcag
acatctgggtgaagagctactccctgtatagccgggagagatatatctgcaattccggctttaagcggaaggccggcacctctagcct
gacagagtgcgtgctgaacaaggccaccaatgtggcccactggacaaccccaagcctgaaatgtattcgcgaccctgccctggtcc
accagcgccctgccccccc (SEQ ID NO: 187)

P-0662 Chain 2
atggatatgcgggtgcctgctcagctgctgggcctgctgctgctgtggctgcgaggggctagatgtgataaaactcatacttgtcctccat
gcccagcacctgaggcagcaggcgccccatccgtgttcctgtttcccctaagcccaaggacacactgatgatctcccgtacgccag
aggtgacatgcgtggtggtggacgtctcacgaggaccccgaggtgaagttcaactggtacgtggatggcgtggaggtgcacaatg
ccaagaccaagcccagggaggagcagtacaacagcacctatcgcgtggtgtccgtgctgacagtgctgcaccaggactggctgaa
cggcaaggagtataagtgcaaggtgtccaataaggccctgccagccccatcgagaagaccatcagcaaggcaaagggacagc
ctcgggagccacaggtgcacccctgccaccctctagagaggagatgacaaagaaccaggtgtgtctgtctggtgaaggg
cttctaccccttccgacatcgccgtggagtgggagtctaatggccagccagagaacaattacaagaccacacctccagtgctggactct
gatgcagccttctttctgtattctaagctgaccgtggataagagcaggtggcagcagggcaacgtgttttcctgctctgtgatgcacgag
gccctgcacaatcactacacacagaagagcctgtccctgtctcccggg (SEQ ID NO: 188)

P-0663 Chain 1
atggatatgcgggtgccgctcagctgctgggcctgctgctgctgtggctgcgaggggctagatgtgataaaactcatacctgtcctcca
tgcccagcacctgaggcagcaggcgcccatccgtgttcctgtttcccctaagcccaaggacaccctgatgatctctcgtacgccg
aggtgacatgcgtggtggtggacgtgagccacgaggaccccgaggtgaagttcaactggtacgtggatggcgtggaggtgcacaat
gccaagacaaagcctcgggaggagcagtacaactccacctatagagtggtgtctgtgctgacagtgctgcaccaggactggctgaa
cggcaaggagtacaagtgcaaggtgtccaataaggccctgccagccccatcgagaagaccatcagcaaggccaagggccagc
ctagggagccacaggtgtataccctgccaccctgccgcgaggagatgacaaagaaccaggtgtccctgtcttgtgccgtgaagggct
tctaccccttctgacatcgccgtggagtgggagagcaatggccagccagagaacaattataagaccacacctccagtgctggactctg
atggcagcttctttctggtgagcaagctgaccgtggataagtccaggtggcagcagggcaacgtgtttagctgttcctgatgcacgag
gccctgcacgctcactacacacagaagtctctgagcctgtccccggggcggcggaggaagtctgggagggagtgggcgaagt
gccaacgctattctggagggcggaagtaactgggtcaatgtgattagtgatctgaagaagatcgaggacctgatccagagcatgcac
atcgatgccaccctgtacacagagtccgacgtgcaccctcttgcaaggtgaccgccatgaagtgtttcctgctggagctgcaggtcat
cagcctggagagcggcgacgccgatatccacgataccgtggaaactgatcatcctgagctccaacaattctctgagctccaacggca
atgtgacagagagcggctgcaaggagtgtgaggagctggaggagaagaacatcaaggagttcctgcagtcctttgtgcacatcgtg
cagatgttcatcaatacctctggaggaccactgggaatgctgtcccagtctatcacatgcccacctccaatgtccgtggagcacgcag
acatctgggtgaagagctactccctgtatagccgggagagatatatctgcaattccggctttaagcggaaggccggcacctctagcct
gacagagtgcgtgctgaacaaggccaccaatgtggcccactggacaaccccaagcctgaaatgtattcgcgaccctgccctggtcc
accagcgccctgccccccc (SEQ ID NO: 189)

P-0664 Chain 1
atggatatgcgggtgcctgctcagctgctgggcctgctgctgctgtggctgcgaggggctagatgtgataaaactcatacctgtcctcca
tgcccagcacctgaggcagcaggcgcccatccgtgttcctgtttcccctaagcccaaggacaccctgatgatctctcgtacgccg
aggtgacatgcgtggtggtggacgtgagccacgaggaccccgaggtgaagttcaactggtacgtggatggcgtggaggtgcacaat
gccaagacaaagcctcgggaggagcagtacaactccacctatagagtggtgtctgtgctgacagtgctgcaccaggactggctgaa
cggcaaggagtacaagtgcaaggtgtccaataaggccctgccagccccatcgagaagaccatcagcaaggccaagggccagc
ctagggagccacaggtgtataccctgccaccctgccgcgaggagatgacaaagaaccaggtgtccctgtcttgtgccgtgaagggct
tctaccccttctgacatcgccgtggagtgggagagcaatggccagccagagaacaattataagaccacacctccagtgctggactctg
atggcagcttctttctggtgagcaagctgaccgtggataagtccaggtggcagcagggcaacgtgtttagctgttcctgatgcacgag
gccctgcacgctcactacacacagaagtctctgagcctgtccccggggcggcggaggaagtggcggaggaggctctggcgga
ggcggaagtaactgggtcaatgtgattagtgatctgaagaagatcgaggacctgatccagagcatgcacatcgatgccaccctgtac
acagagtccgacgtgcaccctcttgcaaggtgaccgccatgaagtgtttcctgctggagctgcaggtcatcagcctggagagcggc
gacgccgatatccacgataccgtggaaactgatcatcctgagctccaacaattctctgagctccaacggcaatgtgacagagagcgg
```

SEQUENCE LISTINGS ctgcaaggagtgtgaggagctggaggagaagaacatcaaggagttcctgcagtcctttgtgcacatcgtgcagatgttcatcaatacc
tctggaggaccactgggaatgctgtcccagtctatcacatgcccacctccaatgtccgtggagcacgcagacatctggtgaagagct
actccctgtatagccgggagagatatatctgcaattccggctttaagcggaaggccggcacctctagcctgacagagtgcgtgctgaa
caaggccaccaatgtggcccactggacaaccccaagcctgaaatgtattcgcgaccctgccctggtccaccagcgccctgccccccc
cc (SEQ ID NO: 190)

P-0665 Chain 1
<u>atggatatgcgggtgcctgctcagctgctgggcctgctgctgctgtggctgcgaggggctagatgt</u>gataaaactcatacctgtcctcca
tgcccagcacctgaggcagcaggcgccccatccgtgttcctgtttcccccctaagcccaaggacaccctgatgatctctcgtacgccg
aggtgacatgcgtggtggtggacgtgagccacgaggaccccgaggtgaagttcaactggtacgtggatggcgtggaggtgcacaat
gccaagacaaagcctcgggaggagcagtacaactccacctatagagtggtgtctgtgctgacagtgctgcaccaggactggctgaa
cggcaaggagtacaagtgcaaggtgtccaataaggccctgccagcccccatcgagaagaccatcagcaaggcaagggccagc
ctagggagccacaggtgtatacctgccaccctgccgcgaggagatgacaaagaaccaggtgtccctgtcttgtgccgtgaagggct
tctacccttctgacatcgccgtggagtgggagagcaatggccagccagagaacaattataagaccacacctccagtgctggactctg
atggcagcttctttctggtgagcaagctgaccgtggataagtccaggtggcagcagggcaacgtgtttagctgttccgtgatgcacgag
gccctgcacgctcactacacacagaagagtctctgagcctgtccccgcaggtccgagaagcggcaggtccgagaatatccga
ccgccggaacaaactgggctcaatgtgattagtgatctgaagaagatcgaggacctgatccagagcatgcacatcgatgccaccctgt
acacagagtccgacgtgcacccctcttgcaaggtgaccgccatgaagtgtttcctgctggagctgcaggtcatcagcctggagagcg
gcgacgccgatatccacgataccgtggagaacctgatcatcctggccaacaattctctgagctcaacggcaatgtgacagagagc
ggctgcaaggagtgtgaggagctggaggagaagaacatcaaggagttcctgcagtcctttgtgcacatcgtgcagatgttcatcaata
cctctgaggaccactgggaatgctgtcccagtctatcacatgcccacctccaatgtccgtggagcacgcagacatctgggtgaaga
gctactccctgtatagccgggagagatatatctgcaattccggctttaagcggaaggccggcacctctagcctgacagagtgcgtgct
gaacaaggccaccaatgtggcccactggacaaccccaagcctgaaatgtattcgcgaccctgccctggtccaccagcgccctgccc
ccccc (SEQ ID NO: 191)

P-0663/P-0664/P-0665 Chain 2
<u>atggatatgcgggtgcctgctcagctgctgggcctgctgctgctgtggctgcgaggggctagatgt</u>gataaaactcatacttgtcctccat
gcccagcacctgaggcagcaggcgccccatccgtgttcctgtttcccccctaagcccaaggacacactgatgatctcccgtacgccag
aggtgacatgcgtggtggtgacgtgctctcacgaggaccccgaggtgaagttcaactggtacgtggatggcgtggaggtgcacaatg
ccaagaccaagcccagggaggagcagtacaacagcacctatcgcgtggtgtccgtgctgacagtgctgcaccaggactggctgaa
cggcaaggagtataagtgcaaggtgtccaataaggccctgccagcccccatcgagaagaccatcagcaaggcaaagggacagc
ctcgggagccacaggtgtgcaccctgccaccctctagagaggagatgacaaagaaccaggtgagcctgtggtgtctggtgaaggg
cttctacccttccgacatcgccgtggagtgggagtctaatggccagccagagaacaattacaagaccacacctccagtgctggactct
gatggcagcttcttttctgtattctaagctgaccgtggataagagcaggtggcagcagggcaacgtgttttcctgctctgtgatgcacgag
gccctgcacgctcactacacacagaagagcctgtccctgtctcccggg (SEQ ID NO: 192)

What is claimed is:

1. A bioactivatable polypeptide drug construct comprising, in an N- to C-terminal direction (D1-D2-D3): 1) a functional moiety D1 domain (D1), 2) a bioactivatable moiety D2 domain (D2), and 3) a concealing moiety D3 domain (D3); wherein the D1 domain is an Fc domain comprising an amino acid sequence selected from the group consisting of the amino acid sequences set forth in SEQ ID NO: 14, SEQ ID NO: 15, SEQ ID NO: 16, SEQ ID NO: 156, and SEQ ID NOS: 166-168; wherein the D2 domain is an interleukin-15 (IL-15) polypeptide comprising an amino acid sequence selected from the group consisting of the amino acid sequences set forth in SEQ ID NOS: 2-3; wherein the D3 domain is a cognate receptor/binding partner for IL-15 comprising an amino acid sequence selected from the group consisting of the amino acid sequences set forth in SEQ ID NOS: 4-5; wherein D1 is attached to D2 by a peptide linker (L1) selected from the group consisting of a protease cleavable peptide linker and a non-cleavable peptide linker; wherein D2 is attached to D3 by a peptide linker (L2) selected from the group consisting of a protease cleavable peptide linker and a non-cleavable peptide linker; and wherein D3 conceals the activity of D2 until activated.

2. The construct according to claim 1, wherein the construct is selected from the group of constructs wherein L1 and L2 are both protease cleavable peptide linkers, wherein L1 and L2 are both non-cleavable peptide linkers, wherein L1 is a protease cleavable peptide linker and L2 is a non-cleavable peptide linker, and wherein L1 is a non-cleavable peptide linker and L2 is a protease cleavable peptide linker.

3. The construct according to claim 1, wherein the construct is selected from the group consisting of a construct wherein the D1, D2 and D3 domains of the construct are each in the form of a monomer, a construct wherein the D1, D2 and D3 domains of the construct are each in the form of a dimer, or a construct wherein the D1, D2 and D3 domains of the construct are collectively in the form of a combination of dimer and monomer.

4. The construct according to claim 1, wherein the D1 domain is an Fc domain comprising the amino acid sequence of SEQ ID NO: 14; wherein the D2 domain is an IL-15 polypeptide an comprising the amino acid sequence of SEQ IQ NO: 3; and wherein the D3 domain is a cognate receptor/binding partner for IL-15 comprising the amino acid sequence of SEQ ID NO: 5.

5. The construct according to claim 1, wherein D2 is attached to D1 by a peptide linker selected from the group consisting of a protease cleavable peptide linker selected from the group of sequences set forth in SEQ ID NOs: 71-96 and 157-161, and a non-cleavable peptide linker selected from the group of sequences set forth in SEQ ID NOs: 107-127; and wherein D2 is attached to D3 by a peptide linker selected from the group consisting of a protease cleavable peptide linker selected from the group of sequences set forth in SEQ ID NOs: 71-96 and 157-161, and a non-cleavable peptide linker selected from the group of sequences set forth in SEQ ID NOs: 107-127.

6. The construct according to claim 1, wherein the D1 domain is an Fc domain comprising the amino acid sequence of SEQ ID NO: 14; wherein the D2 domain is an IL-15 polypeptide comprising the amino acid sequence of SEQ IQ NO: 3; and wherein the D3 domain is a cognate receptor/binding partner for IL-15 comprising the amino acid sequence of SEQ ID NO: 5; wherein D1 is attached to D2 by a peptide linker comprising the amino acid sequence of SEQ ID NO: 92 and wherein D2 is attached to D3 by a peptide linker comprising the amino acid sequence of SEQ ID NO: 95.

7. The construct according to claim 1, wherein the construct is selected from the group of constructs comprising the amino acid sequences set forth in SEQ ID NOs: 25-38, 162-165, and 169-174.

8. The construct according to claim 7, wherein the construct is selected from the group of constructs comprising the amino acid sequences set forth in SEQ ID NO: 25, SEQ ID NO: 33 and SEQ ID NO: 29.

9. A pharmaceutical composition comprising a construct according to claim 1 in admixture with a pharmaceutically acceptable carrier.

* * * * *

SEQUENCE LISTING

<160> NUMBER OF SEQ ID NOS: 192

<210> SEQ ID NO 1
<211> LENGTH: 162
<212> TYPE: PRT
<213> ORGANISM: Homo sapiens

<400> SEQUENCE: 1

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

```
Lys Glu Phe Leu Gln Ser Phe Val His Ile Val Gln Met Phe Ile Asn
145                 150                 155                 160

Thr Ser

<210> SEQ ID NO 2
<211> LENGTH: 114
<212> TYPE: PRT
<213> ORGANISM: Homo sapiens

<400> SEQUENCE: 2

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser

<210> SEQ ID NO 3
<211> LENGTH: 114
<212> TYPE: PRT
<213> ORGANISM: Artificial
<220> FEATURE:
<223> OTHER INFORMATION: IL-15 S58D mutein

<400> SEQUENCE: 3

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Asp Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser

<210> SEQ ID NO 4
<211> LENGTH: 267
<212> TYPE: PRT
<213> ORGANISM: Homo sapiens

<400> SEQUENCE: 4

Met Ala Pro Arg Arg Ala Arg Gly Cys Arg Thr Leu Gly Leu Pro Ala
```

```
              1               5                  10                 15
            Leu Leu Leu Leu Leu Leu Leu Arg Pro Pro Ala Thr Arg Gly Ile Thr
                            20                  25                 30

Cys Pro Pro Pro Met Ser Val Glu His Ala Asp Ile Trp Val Lys Ser
                            35                  40                 45

Tyr Ser Leu Tyr Ser Arg Glu Arg Tyr Ile Cys Asn Ser Gly Phe Lys
                            50                  55                 60

Arg Lys Ala Gly Thr Ser Ser Leu Thr Glu Cys Val Leu Asn Lys Ala
             65             70                  75                 80

Thr Asn Val Ala His Trp Thr Thr Pro Ser Leu Lys Cys Ile Arg Asp
                                85                  90                 95

Pro Ala Leu Val His Gln Arg Pro Ala Pro Pro Ser Thr Val Thr Thr
                           100                 105                110

Ala Gly Val Thr Pro Gln Pro Glu Ser Leu Ser Pro Ser Gly Lys Glu
                           115                 120                125

Pro Ala Ala Ser Ser Pro Ser Ser Asn Asn Thr Ala Ala Thr Thr Ala
                           130                 135                140

Ala Ile Val Pro Gly Ser Gln Leu Met Pro Ser Lys Ser Pro Ser Thr
             145                150                 155                160

Gly Thr Thr Glu Ile Ser Ser His Glu Ser Ser His Gly Thr Pro Ser
                           165                 170                175

Gln Thr Thr Ala Lys Asn Trp Glu Leu Thr Ala Ser Ala Ser His Gln
                           180                 185                190

Pro Pro Gly Val Tyr Pro Gln Gly His Ser Asp Thr Thr Val Ala Ile
                           195                 200                205

Ser Thr Ser Thr Val Leu Leu Cys Gly Leu Ser Ala Val Ser Leu Leu
             210                215                 220

Ala Cys Tyr Leu Lys Ser Arg Gln Thr Pro Pro Leu Ala Ser Val Glu
             225                230                 235                240

Met Glu Ala Met Glu Ala Leu Pro Val Thr Trp Gly Thr Ser Ser Arg
                           245                 250                255

Asp Glu Asp Leu Glu Asn Cys Ser His His Leu
                           260                 265

<210> SEQ ID NO 5
<211> LENGTH: 77
<212> TYPE: PRT
<213> ORGANISM: Homo sapiens

<400> SEQUENCE: 5

Ile Thr Cys Pro Pro Pro Met Ser Val Glu His Ala Asp Ile Trp Val
 1               5                  10                 15

Lys Ser Tyr Ser Leu Tyr Ser Arg Glu Arg Tyr Ile Cys Asn Ser Gly
                20                  25                 30

Phe Lys Arg Lys Ala Gly Thr Ser Ser Leu Thr Glu Cys Val Leu Asn
                35                  40                 45

Lys Ala Thr Asn Val Ala His Trp Thr Thr Pro Ser Leu Lys Cys Ile
         50                  55                 60

Arg Asp Pro Ala Leu Val His Gln Arg Pro Ala Pro Pro
 65                 70                 75

<210> SEQ ID NO 6
<211> LENGTH: 153
<212> TYPE: PRT
<213> ORGANISM: Homo sapiens
```

<400> SEQUENCE: 6

Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
        130                 135                 140

Cys Gln Ser Ile Ile Ser Thr Leu Thr
145                 150

<210> SEQ ID NO 7
<211> LENGTH: 133
<212> TYPE: PRT
<213> ORGANISM: Homo sapiens

<400> SEQUENCE: 7

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
    130

<210> SEQ ID NO 8
<211> LENGTH: 133
<212> TYPE: PRT
<213> ORGANISM: Homo sapiens

<400> SEQUENCE: 8

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys

```
            20                  25                  30
Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 9
<211> LENGTH: 272
<212> TYPE: PRT
<213> ORGANISM: Homo sapiens

<400> SEQUENCE: 9

Met Asp Ser Tyr Leu Leu Met Trp Gly Leu Leu Thr Phe Ile Met Val
1               5                   10                  15

Pro Gly Cys Gln Ala Glu Leu Cys Asp Asp Asp Pro Pro Glu Ile Pro
            20                  25                  30

His Ala Thr Phe Lys Ala Met Ala Tyr Lys Glu Gly Thr Met Leu Asn
        35                  40                  45

Cys Glu Cys Lys Arg Gly Phe Arg Arg Ile Lys Ser Gly Ser Leu Tyr
50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
            85                  90                  95

Gln Pro Glu Glu Gln Lys Glu Arg Lys Thr Thr Glu Met Gln Ser Pro
                100                 105                 110

Met Gln Pro Val Asp Gln Ala Ser Leu Pro Gly His Cys Arg Glu Pro
            115                 120                 125

Pro Pro Trp Glu Asn Glu Ala Thr Glu Arg Ile Tyr His Phe Val Val
        130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
            180                 185                 190

Phe Pro Gly Glu Glu Lys Pro Gln Ala Ser Pro Glu Gly Arg Pro Glu
        195                 200                 205

Ser Glu Thr Ser Cys Leu Val Thr Thr Thr Asp Phe Gln Ile Gln Thr
    210                 215                 220

Glu Met Ala Ala Thr Met Glu Thr Ser Ile Phe Thr Thr Glu Tyr Gln
225                 230                 235                 240

Val Ala Val Ala Gly Cys Val Phe Leu Leu Ile Ser Val Leu Leu Leu
                245                 250                 255
```

```
Ser Gly Leu Thr Trp Gln Arg Arg Gln Arg Lys Ser Arg Thr Ile
        260                 265                 270

<210> SEQ ID NO 10
<211> LENGTH: 165
<212> TYPE: PRT
<213> ORGANISM: Homo sapiens

<400> SEQUENCE: 10

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly
                165

<210> SEQ ID NO 11
<211> LENGTH: 551
<212> TYPE: PRT
<213> ORGANISM: Homo sapiens

<400> SEQUENCE: 11

Met Ala Ala Pro Ala Leu Ser Trp Arg Leu Pro Leu Leu Ile Leu Leu
1               5                   10                  15

Leu Pro Leu Ala Thr Ser Trp Ala Ser Ala Ala Val Asn Gly Thr Ser
            20                  25                  30

Gln Phe Thr Cys Phe Tyr Asn Ser Arg Ala Asn Ile Ser Cys Val Trp
        35                  40                  45

Ser Gln Asp Gly Ala Leu Gln Asp Thr Ser Cys Gln Val His Ala Trp
    50                  55                  60

Pro Asp Arg Arg Arg Trp Asn Gln Thr Cys Glu Leu Leu Pro Val Ser
65                  70                  75                  80

Gln Ala Ser Trp Ala Cys Asn Leu Ile Leu Gly Ala Pro Asp Ser Gln
                85                  90                  95

Lys Leu Thr Thr Val Asp Ile Val Thr Leu Arg Val Leu Cys Arg Glu
            100                 105                 110

Gly Val Arg Trp Arg Val Met Ala Ile Gln Asp Phe Lys Pro Phe Glu
        115                 120                 125

Asn Leu Arg Leu Met Ala Pro Ile Ser Leu Gln Val Val His Val Glu
    130                 135                 140
```

```
Thr His Arg Cys Asn Ile Ser Trp Glu Ile Ser Gln Ala Ser His Tyr
145                 150                 155                 160

Phe Glu Arg His Leu Glu Phe Glu Ala Arg Thr Leu Ser Pro Gly His
                165                 170                 175

Thr Trp Glu Glu Ala Pro Leu Leu Thr Leu Lys Gln Lys Gln Glu Trp
                180                 185                 190

Ile Cys Leu Glu Thr Leu Thr Pro Asp Thr Gln Tyr Glu Phe Gln Val
                195                 200                 205

Arg Val Lys Pro Leu Gln Gly Glu Phe Thr Thr Trp Ser Pro Trp Ser
                210                 215                 220

Gln Pro Leu Ala Phe Arg Thr Lys Pro Ala Ala Leu Gly Lys Asp Thr
225                 230                 235                 240

Ile Pro Trp Leu Gly His Leu Leu Val Gly Leu Ser Gly Ala Phe Gly
                245                 250                 255

Phe Ile Ile Leu Val Tyr Leu Leu Ile Asn Cys Arg Asn Thr Gly Pro
                260                 265                 270

Trp Leu Lys Lys Val Leu Lys Cys Asn Thr Pro Asp Pro Ser Lys Phe
                275                 280                 285

Phe Ser Gln Leu Ser Ser Glu His Gly Gly Asp Val Gln Lys Trp Leu
                290                 295                 300

Ser Ser Pro Phe Pro Ser Ser Ser Phe Ser Pro Gly Gly Leu Ala Pro
305                 310                 315                 320

Glu Ile Ser Pro Leu Glu Val Leu Glu Arg Asp Lys Val Thr Gln Leu
                325                 330                 335

Leu Leu Gln Gln Asp Lys Val Pro Glu Pro Ala Ser Leu Ser Ser Asn
                340                 345                 350

His Ser Leu Thr Ser Cys Phe Thr Asn Gln Gly Tyr Phe Phe Phe His
                355                 360                 365

Leu Pro Asp Ala Leu Glu Ile Glu Ala Cys Gln Val Tyr Phe Thr Tyr
                370                 375                 380

Asp Pro Tyr Ser Glu Glu Asp Pro Asp Glu Gly Val Ala Gly Ala Pro
385                 390                 395                 400

Thr Gly Ser Ser Pro Gln Pro Leu Gln Pro Leu Ser Gly Glu Asp Asp
                405                 410                 415

Ala Tyr Cys Thr Phe Pro Ser Arg Asp Asp Leu Leu Leu Phe Ser Pro
                420                 425                 430

Ser Leu Leu Gly Gly Pro Ser Pro Pro Ser Thr Ala Pro Gly Gly Ser
                435                 440                 445

Gly Ala Gly Glu Glu Arg Met Pro Pro Ser Leu Gln Glu Arg Val Pro
450                 455                 460

Arg Asp Trp Asp Pro Gln Pro Leu Gly Pro Pro Thr Pro Gly Val Pro
465                 470                 475                 480

Asp Leu Val Asp Phe Gln Pro Pro Glu Leu Val Leu Arg Glu Ala
                485                 490                 495

Gly Glu Glu Val Pro Asp Ala Gly Pro Arg Gly Val Ser Phe Pro
                500                 505                 510

Trp Ser Arg Pro Pro Gly Gln Gly Glu Phe Arg Ala Leu Asn Ala Arg
                515                 520                 525

Leu Pro Leu Asn Thr Asp Ala Tyr Leu Ser Leu Gln Glu Leu Gln Gly
                530                 535                 540

Gln Asp Pro Thr His Leu Val
545                 550
```

```
<210> SEQ ID NO 12
<211> LENGTH: 214
<212> TYPE: PRT
<213> ORGANISM: Homo sapiens

<400> SEQUENCE: 12

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Thr His Arg Cys Asn Ile Ser Trp Glu Ile
        115                 120                 125

Ser Gln Ala Ser His Tyr Phe Glu Arg His Leu Glu Phe Glu Ala Arg
130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr
210

<210> SEQ ID NO 13
<211> LENGTH: 226
<212> TYPE: PRT
<213> ORGANISM: Homo sapiens

<400> SEQUENCE: 13

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
```

```
              115                 120                 125
Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 14
<211> LENGTH: 226
<212> TYPE: PRT
<213> ORGANISM: Artificial
<220> FEATURE:
<223> OTHER INFORMATION: IgG1-Fc with reduced/abolished effector
      function

<400> SEQUENCE: 14

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225
```

<210> SEQ ID NO 15
<211> LENGTH: 226
<212> TYPE: PRT
<213> ORGANISM: Artificial
<220> FEATURE:
<223> OTHER INFORMATION: Knob-Fc

<400> SEQUENCE: 15

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225
```

<210> SEQ ID NO 16
<211> LENGTH: 226
<212> TYPE: PRT
<213> ORGANISM: Artificial
<220> FEATURE:
<223> OTHER INFORMATION: Hole-Fc

<400> SEQUENCE: 16

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80
```

```
Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 17
<211> LENGTH: 129
<212> TYPE: PRT
<213> ORGANISM: Homo sapiens

<400> SEQUENCE: 17

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser

<210> SEQ ID NO 18
<211> LENGTH: 152
<212> TYPE: PRT
<213> ORGANISM: Homo sapiens

<400> SEQUENCE: 18

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30
```

```
Asn Cys Leu Asn Asn Glu Phe Asn Phe Phe Lys Arg His Ile Cys Asp
            35                  40                  45

Ala Asn Lys Glu Gly Met Phe Leu Phe Arg Ala Ala Arg Lys Leu Arg
 50                  55                  60

Gln Phe Leu Lys Met Asn Ser Thr Gly Asp Phe Asp Leu His Leu Leu
 65                  70                  75                  80

Lys Val Ser Glu Gly Thr Thr Ile Leu Leu Asn Cys Thr Gly Gln Val
                 85                  90                  95

Lys Gly Arg Lys Pro Ala Ala Leu Gly Glu Ala Gln Pro Thr Lys Ser
                100                 105                 110

Leu Glu Glu Asn Lys Ser Leu Lys Glu Gln Lys Lys Leu Asn Asp Leu
                115                 120                 125

Cys Phe Leu Lys Arg Leu Leu Gln Glu Ile Lys Thr Cys Trp Asn Lys
                130                 135                 140

Ile Leu Met Gly Thr Lys Glu His
145                 150
```

<210> SEQ ID NO 19
<211> LENGTH: 126
<212> TYPE: PRT
<213> ORGANISM: Homo sapiens

<400> SEQUENCE: 19

```
Gln Gly Cys Pro Thr Leu Ala Gly Ile Leu Asp Ile Asn Phe Leu Ile
 1               5                  10                  15

Asn Lys Met Gln Glu Asp Pro Ala Ser Lys Cys His Cys Ser Ala Asn
                20                  25                  30

Val Thr Ser Cys Leu Cys Leu Gly Ile Pro Ser Asp Asn Cys Thr Arg
                35                  40                  45

Pro Cys Phe Ser Glu Arg Leu Ser Gln Met Thr Asn Thr Thr Met Gln
 50                  55                  60

Thr Arg Tyr Pro Leu Ile Phe Ser Arg Val Lys Lys Ser Val Glu Val
 65                  70                  75                  80

Leu Lys Asn Asn Lys Cys Pro Tyr Phe Ser Cys Glu Gln Pro Cys Asn
                 85                  90                  95

Gln Thr Thr Ala Gly Asn Ala Leu Thr Phe Leu Lys Ser Leu Leu Glu
                100                 105                 110

Ile Phe Gln Lys Glu Lys Met Arg Gly Met Arg Gly Lys Ile
                115                 120                 125
```

<210> SEQ ID NO 20
<211> LENGTH: 160
<212> TYPE: PRT
<213> ORGANISM: Homo sapiens

<400> SEQUENCE: 20

```
Ser Pro Gly Gln Gly Thr Gln Ser Glu Asn Ser Cys Thr His Phe Pro
 1               5                  10                  15

Gly Asn Leu Pro Asn Met Leu Arg Asp Leu Arg Asp Ala Phe Ser Arg
                20                  25                  30

Val Lys Thr Phe Phe Gln Met Lys Asp Gln Leu Asp Asn Leu Leu Leu
                35                  40                  45

Lys Glu Ser Leu Leu Glu Asp Phe Lys Gly Tyr Leu Gly Cys Gln Ala
 50                  55                  60

Leu Ser Glu Met Ile Gln Phe Tyr Leu Glu Glu Val Met Pro Gln Ala
 65                  70                  75                  80
```

```
Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
            115                 120                 125

Asn Lys Leu Gln Glu Lys Gly Ile Tyr Lys Ala Met Ser Glu Phe Asp
130                 135                 140

Ile Phe Ile Asn Tyr Ile Glu Ala Tyr Met Thr Met Lys Ile Arg Asn
145                 150                 155                 160

<210> SEQ ID NO 21
<211> LENGTH: 197
<212> TYPE: PRT
<213> ORGANISM: Homo sapiens

<400> SEQUENCE: 21

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195

<210> SEQ ID NO 22
<211> LENGTH: 306
<212> TYPE: PRT
<213> ORGANISM: Homo sapiens

<400> SEQUENCE: 22

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45
```

-continued

```
Ser Gly Lys Thr Leu Thr Ile Gln Val Lys Glu Phe Gly Asp Ala Gly
 50                  55                  60

Gln Tyr Thr Cys His Lys Gly Glu Val Leu Ser His Ser Leu Leu
 65                  70                  75                  80

Leu Leu His Lys Lys Glu Asp Gly Ile Trp Ser Thr Asp Ile Leu Lys
                 85                  90                  95

Asp Gln Lys Glu Pro Lys Asn Lys Thr Phe Leu Arg Cys Glu Ala Lys
             100                 105                 110

Asn Tyr Ser Gly Arg Phe Thr Cys Trp Trp Leu Thr Thr Ile Ser Thr
         115                 120                 125

Asp Leu Thr Phe Ser Val Lys Ser Ser Arg Gly Ser Ser Asp Pro Gln
130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                 165                 170                 175

Cys Pro Ala Ala Glu Glu Ser Leu Pro Ile Glu Val Met Val Asp Ala
             180                 185                 190

Val His Lys Leu Lys Tyr Glu Asn Tyr Thr Ser Ser Phe Phe Ile Arg
         195                 200                 205

Asp Ile Ile Lys Pro Asp Pro Pro Lys Asn Leu Gln Leu Lys Pro Leu
210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                 245                 250                 255

Gly Lys Ser Lys Arg Glu Lys Lys Asp Arg Val Phe Thr Asp Lys Thr
             260                 265                 270

Ser Ala Thr Val Ile Cys Arg Lys Asn Ala Ser Ile Ser Val Arg Ala
         275                 280                 285

Gln Asp Arg Tyr Tyr Ser Ser Trp Ser Glu Trp Ala Ser Val Pro
290                 295                 300

Cys Ser
305
```

<210> SEQ ID NO 23
<211> LENGTH: 170
<212> TYPE: PRT
<213> ORGANISM: Homo sapiens

<400> SEQUENCE: 23

```
Arg Ala Val Pro Gly Gly Ser Ser Pro Ala Trp Thr Gln Cys Gln Gln
 1                   5                  10                  15

Leu Ser Gln Lys Leu Cys Thr Leu Ala Trp Ser Ala His Pro Leu Val
                 20                  25                  30

Gly His Met Asp Leu Arg Glu Glu Gly Asp Glu Glu Thr Thr Asn Asp
             35                  40                  45

Val Pro His Ile Gln Cys Gly Asp Gly Cys Asp Pro Gln Gly Leu Arg
 50                  55                  60

Asp Asn Ser Gln Phe Cys Leu Gln Arg Ile His Gln Gly Leu Ile Phe
 65                  70                  75                  80

Tyr Glu Lys Leu Leu Gly Ser Asp Ile Phe Thr Gly Glu Pro Ser Leu
                 85                  90                  95

Leu Pro Asp Ser Pro Val Gly Gln Leu His Ala Ser Leu Leu Gly Leu
             100                 105                 110
```

```
Ser Gln Leu Leu Gln Pro Glu Gly His His Trp Glu Thr Gln Gln Ile
        115                 120                 125
Pro Ser Leu Ser Pro Ser Gln Pro Trp Gln Arg Leu Leu Arg Phe
    130                 135                 140
Lys Ile Leu Arg Ser Leu Gln Ala Phe Val Ala Val Ala Ala Arg Val
145                 150                 155                 160
Phe Ala His Gly Ala Ala Thr Leu Ser Pro
                165                 170

<210> SEQ ID NO 24
<211> LENGTH: 112
<212> TYPE: PRT
<213> ORGANISM: Homo sapiens

<400> SEQUENCE: 24

Ala Leu Asp Thr Asn Tyr Cys Phe Ser Ser Thr Glu Lys Asn Cys Cys
1               5                   10                  15
Val Arg Gln Leu Tyr Ile Asp Phe Arg Lys Asp Leu Gly Trp Lys Trp
                20                  25                  30
Ile His Glu Pro Lys Gly Tyr His Ala Asn Phe Cys Leu Gly Pro Cys
            35                  40                  45
Pro Tyr Ile Trp Ser Leu Asp Thr Gln Tyr Ser Lys Val Leu Ala Leu
        50                  55                  60
Tyr Asn Gln His Asn Pro Gly Ala Ser Ala Ala Pro Cys Cys Val Pro
65                  70                  75                  80
Gln Ala Leu Glu Pro Leu Pro Ile Val Tyr Tyr Val Gly Arg Lys Pro
                85                  90                  95
Lys Val Glu Gln Leu Ser Asn Met Ile Val Arg Ser Cys Lys Cys Ser
            100                 105                 110

<210> SEQ ID NO 25
<211> LENGTH: 442
<212> TYPE: PRT
<213> ORGANISM: Artificial
<220> FEATURE:
<223> OTHER INFORMATION: P-0351

<400> SEQUENCE: 25

Asp Lys Thr His Thr Cys Pro Pro Cys Pro Ala Pro Glu Ala Ala Gly
1               5                   10                  15
Ala Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
            35                  40                  45
Glu Asp Pro Glu Val Lys Phe Asn Trp Tyr Val Asp Gly Val Glu Val
        50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
        130                 135                 140
```

```
Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Gly Ser Gly Gly Gly Gly
225                 230                 235                 240

Ser Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
                260                 265                 270

His Pro Ser Cys Lys Val Thr Ala Met Lys Cys Phe Leu Leu Glu Leu
            275                 280                 285

Gln Val Ile Ser Leu Glu Ser Gly Asp Ala Asp Ile His Asp Thr Val
290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
                340                 345                 350

Asn Thr Ser Gly Gly Gly Gly Ser Gly Gly Gly Gly Ser Ile Thr Cys
                355                 360                 365

Pro Pro Pro Met Ser Val Glu His Ala Asp Ile Trp Val Lys Ser Tyr
            370                 375                 380

Ser Leu Tyr Ser Arg Glu Arg Tyr Ile Cys Asn Ser Gly Phe Lys Arg
385                 390                 395                 400

Lys Ala Gly Thr Ser Ser Leu Thr Glu Cys Val Leu Asn Lys Ala Thr
                405                 410                 415

Asn Val Ala His Trp Thr Thr Pro Ser Leu Lys Cys Ile Arg Asp Pro
            420                 425                 430

Ala Leu Val His Gln Arg Pro Ala Pro Pro
            435                 440

<210> SEQ ID NO 26
<211> LENGTH: 432
<212> TYPE: PRT
<213> ORGANISM: Artificial
<220> FEATURE:
<223> OTHER INFORMATION: P-0170 Hole chain

<400> SEQUENCE: 26

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60
```

```
His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
             85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Leu Gly Gly Ser Gly Arg Ser Ala Asn Ala Ile Leu Glu Asn
225                 230                 235                 240

Trp Val Asn Val Ile Ser Asp Leu Lys Lys Ile Glu Asp Leu Ile Gln
                245                 250                 255

Ser Met His Ile Asp Ala Thr Leu Tyr Thr Glu Ser Asp Val His Pro
            260                 265                 270

Ser Cys Lys Val Thr Ala Met Lys Cys Phe Leu Leu Glu Leu Gln Val
        275                 280                 285

Ile Ser Leu Glu Ser Gly Asp Ala Ser Ile His Asp Thr Val Glu Asn
290                 295                 300

Leu Ile Ile Leu Ala Asn Asn Ser Leu Ser Ser Asn Gly Asn Val Thr
305                 310                 315                 320

Glu Ser Gly Cys Lys Glu Cys Glu Glu Leu Glu Glu Lys Asn Ile Lys
                325                 330                 335

Glu Phe Leu Gln Ser Phe Val His Ile Val Gln Met Phe Ile Asn Thr
            340                 345                 350

Ser Gly Ser Ile Thr Cys Pro Pro Met Ser Val Glu His Ala Asp
        355                 360                 365

Ile Trp Val Lys Ser Tyr Ser Leu Tyr Ser Arg Glu Arg Tyr Ile Cys
370                 375                 380

Asn Ser Gly Phe Lys Arg Lys Ala Gly Thr Ser Ser Leu Thr Glu Cys
385                 390                 395                 400

Val Leu Asn Lys Ala Thr Asn Val Ala His Trp Thr Thr Pro Ser Leu
                405                 410                 415

Lys Cys Ile Arg Asp Pro Ala Leu Val His Gln Arg Pro Ala Pro Pro
            420                 425                 430
```

<210> SEQ ID NO 27
<211> LENGTH: 432
<212> TYPE: PRT
<213> ORGANISM: Artificial
<220> FEATURE:
<223> OTHER INFORMATION: P-0172

<400> SEQUENCE: 27

-continued

```
Asp Lys Thr His Thr Cys Pro Pro Cys Pro Ala Pro Glu Ala Ala Gly
1               5                   10                  15
Ala Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Leu Gly Gly Ser Gly Arg Ser Ala Asn Ala Ile Leu Glu Asn
225                 230                 235                 240
Trp Val Asn Val Ile Ser Asp Leu Lys Lys Ile Glu Asp Leu Ile Gln
                245                 250                 255
Ser Met His Ile Asp Ala Thr Leu Tyr Thr Glu Ser Asp Val His Pro
            260                 265                 270
Ser Cys Lys Val Thr Ala Met Lys Cys Phe Leu Leu Glu Leu Gln Val
        275                 280                 285
Ile Ser Leu Glu Ser Gly Asp Ala Ser Ile His Asp Thr Val Glu Asn
    290                 295                 300
Leu Ile Ile Leu Ala Asn Asn Ser Leu Ser Ser Asn Gly Asn Val Thr
305                 310                 315                 320
Glu Ser Gly Cys Lys Glu Cys Glu Glu Leu Glu Glu Lys Asn Ile Lys
                325                 330                 335
Glu Phe Leu Gln Ser Phe Val His Ile Val Gln Met Phe Ile Asn Thr
            340                 345                 350
Ser Gly Ser Ile Thr Cys Pro Pro Met Ser Val Glu His Ala Asp
        355                 360                 365
Ile Trp Val Lys Ser Tyr Ser Leu Tyr Ser Arg Glu Arg Tyr Ile Cys
    370                 375                 380
Asn Ser Gly Phe Lys Arg Lys Ala Gly Thr Ser Ser Leu Thr Glu Cys
385                 390                 395                 400
Val Leu Asn Lys Ala Thr Asn Val Ala His Trp Thr Thr Pro Ser Leu
                405                 410                 415
Lys Cys Ile Arg Asp Pro Ala Leu Val His Gln Arg Pro Ala Pro Pro
```

```
                      420                 425                 430

<210> SEQ ID NO 28
<211> LENGTH: 450
<212> TYPE: PRT
<213> ORGANISM: Artificial
<220> FEATURE:
<223> OTHER INFORMATION: P-0202

<400> SEQUENCE: 28

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Gly Ser Gly Gly Gly Gly
225                 230                 235                 240

Ser Leu Ser Gly Arg Ser Asp Asn His Gly Ser Gly Gly Gly Gly
                245                 250                 255

Ser Asn Trp Val Asn Val Ile Ser Asp Leu Lys Lys Ile Glu Asp Leu
            260                 265                 270

Ile Gln Ser Met His Ile Asp Ala Thr Leu Tyr Thr Glu Ser Asp Val
        275                 280                 285

His Pro Ser Cys Lys Val Thr Ala Met Lys Cys Phe Leu Leu Glu Leu
    290                 295                 300

Gln Val Ile Ser Leu Glu Ser Gly Asp Ala Ser Ile His Asp Thr Val
305                 310                 315                 320

Glu Asn Leu Ile Ile Leu Ala Asn Asn Ser Leu Ser Asn Gly Asn
                325                 330                 335

Val Thr Glu Ser Gly Cys Lys Glu Cys Glu Glu Leu Glu Glu Lys Asn
            340                 345                 350

Ile Lys Glu Phe Leu Gln Ser Phe Val His Ile Val Gln Met Phe Ile
```

```
                    355                 360                 365
Asn Thr Ser Gly Ser Ile Thr Cys Pro Pro Met Ser Val Glu His
    370                 375                 380

Ala Asp Ile Trp Val Lys Ser Tyr Ser Leu Tyr Ser Arg Glu Arg Tyr
385                 390                 395                 400

Ile Cys Asn Ser Gly Phe Lys Arg Lys Ala Gly Thr Ser Ser Leu Thr
                405                 410                 415

Glu Cys Val Leu Asn Lys Ala Thr Asn Val Ala His Trp Thr Thr Pro
                420                 425                 430

Ser Leu Lys Cys Ile Arg Asp Pro Ala Leu Val His Gln Arg Pro Ala
                435                 440                 445

Pro Pro
    450

<210> SEQ ID NO 29
<211> LENGTH: 467
<212> TYPE: PRT
<213> ORGANISM: Artificial
<220> FEATURE:
<223> OTHER INFORMATION: P-0203

<400> SEQUENCE: 29

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Ser Gly Gly Gly Ser
225                 230                 235                 240

Leu Gly Gly Ser Gly Arg Ser Ala Asn Ala Ile Leu Glu Gly Gly Ser
                245                 250                 255

Gly Gly Gly Gly Ser Asn Trp Val Asn Val Ile Ser Asp Leu Lys Lys
```

-continued

```
                260                 265                 270
Ile Glu Asp Leu Ile Gln Ser Met His Ile Asp Ala Thr Leu Tyr Thr
            275                 280                 285

Glu Ser Asp Val His Pro Ser Cys Lys Val Thr Ala Met Lys Cys Phe
        290                 295                 300

Leu Leu Glu Leu Gln Val Ile Ser Leu Glu Ser Gly Asp Ala Ser Ile
305                 310                 315                 320

His Asp Thr Val Glu Asn Leu Ile Ile Leu Ala Asn Asn Ser Leu Ser
                325                 330                 335

Ser Asn Gly Asn Val Thr Glu Ser Gly Cys Lys Glu Cys Glu Glu Leu
            340                 345                 350

Glu Glu Lys Asn Ile Lys Glu Phe Leu Gln Ser Phe Val His Ile Val
        355                 360                 365

Gln Met Phe Ile Asn Thr Ser Gly Gly Gly Ser Gly Gly Gly Gly
370                 375                 380

Ser Gly Gly Gly Gly Ser Ile Thr Cys Pro Pro Pro Met Ser Val Glu
385                 390                 395                 400

His Ala Asp Ile Trp Val Lys Ser Tyr Ser Leu Tyr Ser Arg Glu Arg
                405                 410                 415

Tyr Ile Cys Asn Ser Gly Phe Lys Arg Lys Ala Gly Thr Ser Ser Leu
            420                 425                 430

Thr Glu Cys Val Leu Asn Lys Ala Thr Asn Val Ala His Trp Thr Thr
        435                 440                 445

Pro Ser Leu Lys Cys Ile Arg Asp Pro Ala Leu Val His Gln Arg Pro
450                 455                 460

Ala Pro Pro
465

<210> SEQ ID NO 30
<211> LENGTH: 460
<212> TYPE: PRT
<213> ORGANISM: Artificial
<220> FEATURE:
<223> OTHER INFORMATION: P-0204

<400> SEQUENCE: 30

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
```

```
            145                 150                 155                 160
        Trp Glu Ser Asn Gly Gln Pro Glu Asn Tyr Lys Thr Thr Pro Pro
                        165                 170                 175

Val Leu Asp Ser Asp Gly Ser Phe Phe Leu Tyr Ser Lys Leu Thr Val
                        180                 185                 190

Asp Lys Ser Arg Trp Gln Gln Gly Asn Val Phe Ser Cys Ser Val Met
                        195                 200                 205

His Glu Ala Leu His Asn His Tyr Thr Gln Lys Ser Leu Ser Leu Ser
                    210                 215                 220

Pro Gly Gly Gly Gly Ser Gly Gly Gly Gly Ser Leu Gly Gly Ser
        225                 230                 235                 240

Gly Arg Ser Ala Asn Ala Ile Leu Glu Gly Gly Gly Ser Asn Trp
                        245                 250                 255

Val Asn Val Ile Ser Asp Leu Lys Lys Ile Glu Asp Leu Ile Gln Ser
                        260                 265                 270

Met His Ile Asp Ala Thr Leu Tyr Thr Glu Ser Asp Val His Pro Ser
                    275                 280                 285

Cys Lys Val Thr Ala Met Lys Cys Phe Leu Leu Glu Leu Gln Val Ile
                290                 295                 300

Ser Leu Glu Ser Gly Asp Ala Ser Ile His Asp Thr Val Glu Asn Leu
        305                 310                 315                 320

Ile Ile Leu Ala Asn Asn Ser Leu Ser Ser Asn Gly Asn Val Thr Glu
                        325                 330                 335

Ser Gly Cys Lys Glu Cys Glu Glu Leu Glu Glu Lys Asn Ile Lys Glu
                    340                 345                 350

Phe Leu Gln Ser Phe Val His Ile Val Gln Met Phe Ile Asn Thr Ser
                    355                 360                 365

Gly Gly Gly Gly Ser Gly Gly Gly Gly Ser Gly Gly Gly Gly Ser Ile
                    370                 375                 380

Thr Cys Pro Pro Pro Met Ser Val Glu His Ala Asp Ile Trp Val Lys
        385                 390                 395                 400

Ser Tyr Ser Leu Tyr Ser Arg Glu Arg Tyr Ile Cys Asn Ser Gly Phe
                        405                 410                 415

Lys Arg Lys Ala Gly Thr Ser Ser Leu Thr Glu Cys Val Leu Asn Lys
                    420                 425                 430

Ala Thr Asn Val Ala His Trp Thr Thr Pro Ser Leu Lys Cys Ile Arg
                    435                 440                 445

Asp Pro Ala Leu Val His Gln Arg Pro Ala Pro
                450                 455                 460

<210> SEQ ID NO 31
<211> LENGTH: 455
<212> TYPE: PRT
<213> ORGANISM: Artificial
<220> FEATURE:
<223> OTHER INFORMATION: P-0205

<400> SEQUENCE: 31

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
```

```
            50                  55                  60
His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Gly Ser Leu Gly Gly Ser
225                 230                 235                 240

Gly Arg Ser Ala Asn Ala Ile Leu Glu Gly Gly Gly Ser Asn Trp
                245                 250                 255

Val Asn Val Ile Ser Asp Leu Lys Lys Ile Glu Asp Leu Ile Gln Ser
            260                 265                 270

Met His Ile Asp Ala Thr Leu Tyr Thr Glu Ser Asp Val His Pro Ser
        275                 280                 285

Cys Lys Val Thr Ala Met Lys Cys Phe Leu Leu Glu Leu Gln Val Ile
    290                 295                 300

Ser Leu Glu Ser Gly Asp Ala Ser Ile His Asp Thr Val Glu Asn Leu
305                 310                 315                 320

Ile Ile Leu Ala Asn Asn Ser Leu Ser Ser Asn Gly Asn Val Thr Glu
                325                 330                 335

Ser Gly Cys Lys Glu Cys Glu Glu Leu Glu Glu Lys Asn Ile Lys Glu
            340                 345                 350

Phe Leu Gln Ser Phe Val His Ile Val Gln Met Phe Ile Asn Thr Ser
        355                 360                 365

Gly Gly Gly Gly Ser Gly Gly Gly Gly Ser Ile Thr Cys Pro Pro Pro
    370                 375                 380

Met Ser Val Glu His Ala Asp Ile Trp Val Lys Ser Tyr Ser Leu Tyr
385                 390                 395                 400

Ser Arg Glu Arg Tyr Ile Cys Asn Ser Gly Phe Lys Arg Lys Ala Gly
                405                 410                 415

Thr Ser Ser Leu Thr Glu Cys Val Leu Asn Lys Ala Thr Asn Val Ala
            420                 425                 430

His Trp Thr Thr Pro Ser Leu Lys Cys Ile Arg Asp Pro Ala Leu Val
        435                 440                 445

His Gln Arg Pro Ala Pro Pro
    450                 455

<210> SEQ ID NO 32
```

```
<211> LENGTH: 450
<212> TYPE: PRT
<213> ORGANISM: Artificial
<220> FEATURE:
<223> OTHER INFORMATION: P-0206

<400> SEQUENCE: 32
```

| | | | | | | | | | | | | | | |
|---|---|---|---|---|---|---|---|---|---|---|---|---|---|---|
| Asp | Lys | Thr | His | Thr | Cys | Pro | Pro | Cys | Pro | Ala | Pro | Glu | Ala | Ala | Gly
| 1 | | | | 5 | | | | | 10 | | | | | 15 |

| | | | | | | | | | | | | | | |
|---|---|---|---|---|---|---|---|---|---|---|---|---|---|---|
| Ala | Pro | Ser | Val | Phe | Leu | Phe | Pro | Pro | Lys | Pro | Lys | Asp | Thr | Leu | Met
| | | | 20 | | | | | 25 | | | | | 30 | |

| | | | | | | | | | | | | | | |
|---|---|---|---|---|---|---|---|---|---|---|---|---|---|---|
| Ile | Ser | Arg | Thr | Pro | Glu | Val | Thr | Cys | Val | Val | Val | Asp | Val | Ser | His
| | | | 35 | | | | | 40 | | | | | 45 | |

| | | | | | | | | | | | | | | |
|---|---|---|---|---|---|---|---|---|---|---|---|---|---|---|
| Glu | Asp | Pro | Glu | Val | Lys | Phe | Asn | Trp | Tyr | Val | Asp | Gly | Val | Glu | Val
| 50 | | | | | 55 | | | | | 60 | | | | | |

| | | | | | | | | | | | | | | |
|---|---|---|---|---|---|---|---|---|---|---|---|---|---|---|
| His | Asn | Ala | Lys | Thr | Lys | Pro | Arg | Glu | Glu | Gln | Tyr | Asn | Ser | Thr | Tyr
| 65 | | | | | 70 | | | | | 75 | | | | | 80 |

| | | | | | | | | | | | | | | |
|---|---|---|---|---|---|---|---|---|---|---|---|---|---|---|
| Arg | Val | Val | Ser | Val | Leu | Thr | Val | Leu | His | Gln | Asp | Trp | Leu | Asn | Gly
| | | | | 85 | | | | | 90 | | | | | 95 | |

| | | | | | | | | | | | | | | |
|---|---|---|---|---|---|---|---|---|---|---|---|---|---|---|
| Lys | Glu | Tyr | Lys | Cys | Lys | Val | Ser | Asn | Lys | Ala | Leu | Pro | Ala | Pro | Ile
| | | | | 100 | | | | | 105 | | | | | 110 | |

| | | | | | | | | | | | | | | |
|---|---|---|---|---|---|---|---|---|---|---|---|---|---|---|
| Glu | Lys | Thr | Ile | Ser | Lys | Ala | Lys | Gly | Gln | Pro | Arg | Glu | Pro | Gln | Val
| | | | 115 | | | | | 120 | | | | | 125 | | |

| | | | | | | | | | | | | | | |
|---|---|---|---|---|---|---|---|---|---|---|---|---|---|---|
| Tyr | Thr | Leu | Pro | Pro | Ser | Arg | Asp | Glu | Leu | Thr | Lys | Asn | Gln | Val | Ser
| | 130 | | | | | 135 | | | | | 140 | | | | |

| | | | | | | | | | | | | | | |
|---|---|---|---|---|---|---|---|---|---|---|---|---|---|---|
| Leu | Thr | Cys | Leu | Val | Lys | Gly | Phe | Tyr | Pro | Ser | Asp | Ile | Ala | Val | Glu
| 145 | | | | | 150 | | | | | 155 | | | | | 160 |

| | | | | | | | | | | | | | | |
|---|---|---|---|---|---|---|---|---|---|---|---|---|---|---|
| Trp | Glu | Ser | Asn | Gly | Gln | Pro | Glu | Asn | Asn | Tyr | Lys | Thr | Thr | Pro | Pro
| | | | | 165 | | | | | 170 | | | | | 175 | |

| | | | | | | | | | | | | | | |
|---|---|---|---|---|---|---|---|---|---|---|---|---|---|---|
| Val | Leu | Asp | Ser | Asp | Gly | Ser | Phe | Phe | Leu | Tyr | Ser | Lys | Leu | Thr | Val
| | | | 180 | | | | | 185 | | | | | 190 | | |

| | | | | | | | | | | | | | | |
|---|---|---|---|---|---|---|---|---|---|---|---|---|---|---|
| Asp | Lys | Ser | Arg | Trp | Gln | Gln | Gly | Asn | Val | Phe | Ser | Cys | Ser | Val | Met
| | | 195 | | | | | 200 | | | | | 205 | | | |

| | | | | | | | | | | | | | | |
|---|---|---|---|---|---|---|---|---|---|---|---|---|---|---|
| His | Glu | Ala | Leu | His | Asn | His | Tyr | Thr | Gln | Lys | Ser | Leu | Ser | Leu | Ser
| 210 | | | | | 215 | | | | | 220 | | | | | |

| | | | | | | | | | | | | | | |
|---|---|---|---|---|---|---|---|---|---|---|---|---|---|---|
| Pro | Gly | Gly | Gly | Gly | Ser | Gly | Gly | Gly | Gly | Ser | Leu | Gly | Gly | Ser
| 225 | | | | 230 | | | | | 235 | | | | | 240 |

| | | | | | | | | | | | | | | |
|---|---|---|---|---|---|---|---|---|---|---|---|---|---|---|
| Gly | Arg | Ser | Ala | Asn | Ala | Ile | Leu | Glu | Gly | Gly | Gly | Ser | Asn | Trp
| | | | | 245 | | | | | 250 | | | | | 255 |

| | | | | | | | | | | | | | | |
|---|---|---|---|---|---|---|---|---|---|---|---|---|---|---|
| Val | Asn | Val | Ile | Ser | Asp | Leu | Lys | Lys | Ile | Glu | Asp | Leu | Ile | Gln | Ser
| | | | 260 | | | | | 265 | | | | | 270 | | |

| | | | | | | | | | | | | | | |
|---|---|---|---|---|---|---|---|---|---|---|---|---|---|---|
| Met | His | Ile | Asp | Ala | Thr | Leu | Tyr | Thr | Glu | Ser | Asp | Val | His | Pro | Ser
| | | 275 | | | | | 280 | | | | | 285 | | | |

| | | | | | | | | | | | | | | |
|---|---|---|---|---|---|---|---|---|---|---|---|---|---|---|
| Cys | Lys | Val | Thr | Ala | Met | Lys | Cys | Phe | Leu | Leu | Glu | Leu | Gln | Val | Ile
| | 290 | | | | | 295 | | | | | 300 | | | | |

| | | | | | | | | | | | | | | |
|---|---|---|---|---|---|---|---|---|---|---|---|---|---|---|
| Ser | Leu | Glu | Ser | Gly | Asp | Ala | Ser | Ile | His | Asp | Thr | Val | Glu | Asn | Leu
| 305 | | | | | 310 | | | | | 315 | | | | | 320 |

| | | | | | | | | | | | | | | |
|---|---|---|---|---|---|---|---|---|---|---|---|---|---|---|
| Ile | Ile | Leu | Ala | Asn | Asn | Ser | Leu | Ser | Ser | Asn | Gly | Asn | Val | Thr | Glu
| | | | | 325 | | | | | 330 | | | | | 335 | |

| | | | | | | | | | | | | | | |
|---|---|---|---|---|---|---|---|---|---|---|---|---|---|---|
| Ser | Gly | Cys | Lys | Glu | Cys | Glu | Glu | Leu | Glu | Glu | Lys | Asn | Ile | Lys | Glu
| | | | 340 | | | | | 345 | | | | | 350 | | |

| | | | | | | | | | | | | | | |
|---|---|---|---|---|---|---|---|---|---|---|---|---|---|---|
| Phe | Leu | Gln | Ser | Phe | Val | His | Ile | Val | Gln | Met | Phe | Ile | Asn | Thr | Ser
| | | 355 | | | | | 360 | | | | | 365 | | | |

| | | | | | | | | | | | | | | |
|---|---|---|---|---|---|---|---|---|---|---|---|---|---|---|
| Gly | Gly | Gly | Gly | Ser | Ile | Thr | Cys | Pro | Pro | Pro | Met | Ser | Val | Glu | His
| | 370 | | | | | 375 | | | | | 380 | | | | |

```
Ala Asp Ile Trp Val Lys Ser Tyr Ser Leu Tyr Ser Arg Glu Arg Tyr
385                 390                 395                 400

Ile Cys Asn Ser Gly Phe Lys Arg Lys Ala Gly Thr Ser Ser Leu Thr
                405                 410                 415

Glu Cys Val Leu Asn Lys Ala Thr Asn Val Ala His Trp Thr Thr Pro
            420                 425                 430

Ser Leu Lys Cys Ile Arg Asp Pro Ala Leu Val His Gln Arg Pro Ala
        435                 440                 445

Pro Pro
    450

<210> SEQ ID NO 33
<211> LENGTH: 448
<212> TYPE: PRT
<213> ORGANISM: Artificial
<220> FEATURE:
<223> OTHER INFORMATION: P-0315

<400> SEQUENCE: 33

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Leu Gly Gly Ser Gly Arg Ser Ala Asn
225                 230                 235                 240

Ala Ile Leu Glu Gly Gly Ser Asn Trp Val Asn Val Ile Ser Asp Leu
                245                 250                 255

Lys Lys Ile Glu Asp Leu Ile Gln Ser Met His Ile Asp Ala Thr Leu
            260                 265                 270

Tyr Thr Glu Ser Asp Val His Pro Ser Cys Lys Val Thr Ala Met Lys
        275                 280                 285
```

-continued

```
Cys Phe Leu Leu Glu Leu Gln Val Ile Ser Leu Ser Gly Asp Ala
    290                 295                 300

Asp Ile His Asp Thr Val Glu Asn Leu Ile Ile Leu Ala Asn Asn Ser
305                 310                 315                 320

Leu Ser Ser Asn Gly Asn Val Thr Glu Ser Gly Cys Lys Glu Cys Glu
                325                 330                 335

Glu Leu Glu Glu Lys Asn Ile Lys Glu Phe Leu Gln Ser Phe Val His
                340                 345                 350

Ile Val Gln Met Phe Ile Asn Thr Ser Gly Gly Pro Leu Gly Met Leu
                355                 360                 365

Ser Gln Ser Ile Thr Cys Pro Pro Met Ser Val Glu His Ala Asp
    370                 375                 380

Ile Trp Val Lys Ser Tyr Ser Leu Tyr Ser Arg Glu Arg Tyr Ile Cys
385                 390                 395                 400

Asn Ser Gly Phe Lys Arg Lys Ala Gly Thr Ser Ser Leu Thr Glu Cys
                405                 410                 415

Val Leu Asn Lys Ala Thr Asn Val Ala His Trp Thr Thr Pro Ser Leu
                420                 425                 430

Lys Cys Ile Arg Asp Pro Ala Leu Val His Gln Arg Pro Ala Pro Pro
                435                 440                 445
```

<210> SEQ ID NO 34
<211> LENGTH: 451
<212> TYPE: PRT
<213> ORGANISM: Artificial
<220> FEATURE:
<223> OTHER INFORMATION: P-0316

<400> SEQUENCE: 34

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205
```

```
His Glu Ala Leu His Asn His Tyr Thr Gln Lys Ser Leu Ser Leu Ser
        210                 215                 220

Pro Gly Gly Gly Gly Ser Leu Gly Gly Ser Gly Arg Ser Ala Asn
225                 230                 235                 240

Ala Ile Leu Glu Gly Gly Ser Asn Trp Val Asn Val Ile Ser Asp Leu
                245                 250                 255

Lys Lys Ile Glu Asp Leu Ile Gln Ser Met His Ile Asp Ala Thr Leu
                260                 265                 270

Tyr Thr Glu Ser Asp Val His Pro Ser Cys Lys Val Thr Ala Met Lys
            275                 280                 285

Cys Phe Leu Leu Glu Leu Gln Val Ile Ser Leu Glu Ser Gly Asp Ala
            290                 295                 300

Asp Ile His Asp Thr Val Glu Asn Leu Ile Ile Leu Ala Asn Asn Ser
305                 310                 315                 320

Leu Ser Ser Asn Gly Asn Val Thr Glu Ser Gly Cys Lys Glu Cys Glu
                325                 330                 335

Glu Leu Glu Glu Lys Asn Ile Lys Glu Phe Leu Gln Ser Phe Val His
            340                 345                 350

Ile Val Gln Met Phe Ile Asn Thr Ser Gly Gly Pro Leu Gly Met
            355                 360                 365

Leu Ser Gln Gly Gly Ser Ile Thr Cys Pro Pro Met Ser Val Glu
370                 375                 380

His Ala Asp Ile Trp Val Lys Ser Tyr Ser Leu Tyr Ser Arg Glu Arg
385                 390                 395                 400

Tyr Ile Cys Asn Ser Gly Phe Lys Arg Lys Ala Gly Thr Ser Ser Leu
                405                 410                 415

Thr Glu Cys Val Leu Asn Lys Ala Thr Asn Val Ala His Trp Thr Thr
            420                 425                 430

Pro Ser Leu Lys Cys Ile Arg Asp Pro Ala Leu Val His Gln Arg Pro
            435                 440                 445

Ala Pro Pro
    450

<210> SEQ ID NO 35
<211> LENGTH: 442
<212> TYPE: PRT
<213> ORGANISM: Artificial
<220> FEATURE:
<223> OTHER INFORMATION: P-0350

<400> SEQUENCE: 35

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110
```

```
Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Gly Gly Gly Ser Gly Gly Gly Ser Gly Gly Gly Gly
225                 230                 235                 240

Ser Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
            260                 265                 270

His Pro Ser Cys Lys Val Thr Ala Met Lys Cys Phe Leu Leu Glu Leu
            275                 280                 285

Gln Val Ile Ser Leu Glu Ser Gly Asp Ala Asp Ile His Asp Thr Val
            290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
            340                 345                 350

Asn Thr Ser Gly Gly Pro Leu Gly Met Leu Ser Gln Ser Ile Thr Cys
            355                 360                 365

Pro Pro Pro Met Ser Val Glu His Ala Asp Ile Trp Val Lys Ser Tyr
            370                 375                 380

Ser Leu Tyr Ser Arg Glu Arg Tyr Ile Cys Asn Ser Gly Phe Lys Arg
385                 390                 395                 400

Lys Ala Gly Thr Ser Ser Leu Thr Glu Cys Val Leu Asn Lys Ala Thr
                405                 410                 415

Asn Val Ala His Trp Thr Thr Pro Ser Leu Lys Cys Ile Arg Asp Pro
            420                 425                 430

Ala Leu Val His Gln Arg Pro Ala Pro Pro
            435                 440

<210> SEQ ID NO 36
<211> LENGTH: 442
<212> TYPE: PRT
<213> ORGANISM: Artificial
<220> FEATURE:
<223> OTHER INFORMATION: P-0354

<400> SEQUENCE: 36

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
                20                  25                  30
```

```
Ile Ser Arg Thr Pro Glu Val Thr Cys Val Val Val Asp Val Ser His
         35                  40                  45
Glu Asp Pro Glu Val Lys Phe Asn Trp Tyr Val Asp Gly Val Glu Val
     50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Gln Val
                115                 120                 125
Tyr Thr Leu Pro Pro Ser Arg Asp Glu Leu Thr Lys Asn Gln Val Ser
        130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
                180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
        210                 215                 220
Pro Gly Gly Gly Ser Gly Pro Leu Gly Met Leu Ser Gln Gly Gly Gly
225                 230                 235                 240
Ser Asn Trp Val Asn Val Ile Ser Asp Leu Lys Lys Ile Glu Asp Leu
                245                 250                 255
Ile Gln Ser Met His Ile Asp Ala Thr Leu Tyr Thr Glu Ser Asp Val
                260                 265                 270
His Pro Ser Cys Lys Val Thr Ala Met Lys Cys Phe Leu Leu Glu Leu
        275                 280                 285
Gln Val Ile Ser Leu Glu Ser Gly Asp Ala Asp Ile His Asp Thr Val
        290                 295                 300
Glu Asn Leu Ile Ile Leu Ala Asn Asn Ser Leu Ser Ser Asn Gly Asn
305                 310                 315                 320
Val Thr Glu Ser Gly Cys Lys Glu Cys Glu Glu Leu Glu Glu Lys Asn
                325                 330                 335
Ile Lys Glu Phe Leu Gln Ser Phe Val His Ile Val Gln Met Phe Ile
                340                 345                 350
Asn Thr Ser Gly Gly Ser Gly Arg Ser Ala Asn Ala Ile Ile Thr Cys
                355                 360                 365
Pro Pro Pro Met Ser Val Glu His Ala Asp Ile Trp Val Lys Ser Tyr
        370                 375                 380
Ser Leu Tyr Ser Arg Glu Arg Tyr Ile Cys Asn Ser Gly Phe Lys Arg
385                 390                 395                 400
Lys Ala Gly Thr Ser Ser Leu Thr Glu Cys Val Leu Asn Lys Ala Thr
                405                 410                 415
Asn Val Ala His Trp Thr Thr Pro Ser Leu Lys Cys Ile Arg Asp Pro
                420                 425                 430
Ala Leu Val His Gln Arg Pro Ala Pro Pro
        435                 440
```

<210> SEQ ID NO 37
<211> LENGTH: 442
<212> TYPE: PRT
<213> ORGANISM: Artificial
<220> FEATURE:
<223> OTHER INFORMATION: P-0355

<400> SEQUENCE: 37

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Gly Ser Gly Gly Gly Gly
225                 230                 235                 240

Ser Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
            260                 265                 270

His Pro Ser Cys Lys Val Thr Ala Met Lys Cys Phe Leu Leu Glu Leu
        275                 280                 285

Gln Val Ile Ser Leu Glu Ser Gly Asp Ala Asp Ile His Asp Thr Val
    290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
            340                 345                 350

Asn Thr Ser Gly Gly Ser Gly Arg Ser Ala Asn Ala Ile Ile Thr Cys
        355                 360                 365
```

Pro Pro Pro Met Ser Val Glu His Ala Asp Ile Trp Val Lys Ser Tyr
        370             375             380

Ser Leu Tyr Ser Arg Glu Arg Tyr Ile Cys Asn Ser Gly Phe Lys Arg
385             390             395             400

Lys Ala Gly Thr Ser Ser Leu Thr Glu Cys Val Leu Asn Lys Ala Thr
                405             410             415

Asn Val Ala His Trp Thr Thr Pro Ser Leu Lys Cys Ile Arg Asp Pro
            420             425             430

Ala Leu Val His Gln Arg Pro Ala Pro Pro
            435             440

<210> SEQ ID NO 38
<211> LENGTH: 446
<212> TYPE: PRT
<213> ORGANISM: Artificial
<220> FEATURE:
<223> OTHER INFORMATION: P-0385

<400> SEQUENCE: 38

Asp Lys Thr His Thr Cys Pro Pro Cys Pro Ala Pro Glu Ala Ala Gly
1               5                   10                  15

Ala Pro Ser Val Phe Leu Phe Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Leu Gly Gly Gly Arg Ser Ala Asn
225                 230                 235                 240

Ala Ile Leu Glu Gly Gly Ser Asn Trp Val Asn Val Ile Ser Asp Leu
                245                 250                 255

Lys Lys Ile Glu Asp Leu Ile Gln Ser Met His Ile Asp Ala Thr Leu
            260                 265                 270

Tyr Thr Glu Ser Asp Val His Pro Ser Cys Lys Val Thr Ala Met Lys
        275                 280                 285

```
Cys Phe Leu Glu Leu Gln Val Ile Ser Leu Glu Ser Gly Asp Ala
    290                 295                 300

Asp Ile His Asp Thr Val Glu Asn Leu Ile Ile Leu Ala Asn Asn Ser
305                 310                 315                 320

Leu Ser Ser Asn Gly Asn Val Thr Glu Ser Gly Cys Lys Glu Cys Glu
                325                 330                 335

Glu Leu Glu Glu Lys Asn Ile Lys Glu Phe Leu Gln Ser Phe Val His
            340                 345                 350

Ile Val Gln Met Phe Ile Asn Thr Ser Gly Pro Leu Gly Met Leu Ser
                355                 360                 365

Gln Ile Thr Cys Pro Pro Met Ser Val Glu His Ala Asp Ile Trp
    370                 375                 380

Val Lys Ser Tyr Ser Leu Tyr Ser Arg Glu Arg Tyr Ile Cys Asn Ser
385                 390                 395                 400

Gly Phe Lys Arg Lys Ala Gly Thr Ser Ser Leu Thr Glu Cys Val Leu
                405                 410                 415

Asn Lys Ala Thr Asn Val Ala His Trp Thr Thr Pro Ser Leu Lys Cys
                420                 425                 430

Ile Arg Asp Pro Ala Leu Val His Gln Arg Pro Ala Pro Pro
    435                 440                 445

<210> SEQ ID NO 39
<211> LENGTH: 448
<212> TYPE: PRT
<213> ORGANISM: Artificial
<220> FEATURE:
<223> OTHER INFORMATION: P-0386

<400> SEQUENCE: 39

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205
```

```
His Glu Ala Leu His Asn His Tyr Thr Gln Lys Ser Leu Ser Leu Ser
    210                 215                 220
Pro Gly Gly Gly Gly Ser Leu Gly Gly Ser Gly Arg Ser Ala Asn
225                 230                 235                 240
Ala Ile Leu Glu Gly Gly Ser Asn Trp Val Asn Val Ile Ser Asp Leu
                245                 250                 255
Lys Lys Ile Glu Asp Leu Ile Gln Ser Met His Ile Asp Ala Thr Leu
                260                 265                 270
Tyr Thr Glu Ser Asp Val His Pro Ser Cys Lys Val Thr Ala Met Lys
                275                 280                 285
Cys Phe Leu Leu Glu Leu Gln Val Ile Ser Leu Glu Ser Gly Asp Ala
    290                 295                 300
Asp Ile His Asp Thr Val Glu Asn Leu Ile Ile Leu Ala Asn Asn Ser
305                 310                 315                 320
Leu Ser Ser Asn Gly Asn Val Thr Glu Ser Gly Cys Lys Glu Cys Glu
                325                 330                 335
Glu Leu Glu Glu Lys Asn Ile Lys Glu Phe Leu Gln Ser Phe Val His
                340                 345                 350
Ile Val Gln Met Phe Ile Asn Thr Ser Gly Gly Pro Leu Gly Met Leu
    355                 360                 365
Ser Gln Ser Ile Thr Cys Pro Pro Pro Met Ser Val Glu His Ala Asp
    370                 375                 380
Ile Trp Val Lys Ser Tyr Ser Leu Tyr Ser Arg Glu Arg Tyr Ile Ser
385                 390                 395                 400
Asn Ser Gly Phe Lys Arg Lys Ala Gly Thr Ser Ser Leu Thr Glu Cys
                405                 410                 415
Val Leu Asn Lys Ala Thr Asn Val Ala His Trp Thr Thr Pro Ser Leu
                420                 425                 430
Lys Ser Ile Arg Asp Pro Ala Leu Val His Gln Arg Pro Ala Pro Pro
                435                 440                 445

<210> SEQ ID NO 40
<211> LENGTH: 448
<212> TYPE: PRT
<213> ORGANISM: Artificial
<220> FEATURE:
<223> OTHER INFORMATION: P-0387

<400> SEQUENCE: 40

Asp Lys Thr His Thr Cys Pro Pro Cys Pro Ala Pro Glu Ala Ala Gly
1               5                   10                  15
Ala Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
                35                  40                  45
Glu Asp Pro Glu Val Lys Phe Asn Trp Tyr Val Asp Gly Val Glu Val
            50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Gln Val
            115                 120                 125
```

Tyr Thr Leu Pro Pro Ser Arg Asp Glu Leu Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Gly Gly Gly Ser Leu Gly Gly Ser Gly Arg Ser Ala Asn
225                 230                 235                 240

Ala Ile Leu Glu Gly Gly Ser Asn Trp Val Asn Val Ile Ser Asp Leu
                245                 250                 255

Lys Lys Ile Glu Asp Leu Ile Gln Ser Met His Ile Asp Ala Thr Leu
            260                 265                 270

Tyr Thr Glu Ser Asp Val His Pro Ser Cys Lys Val Thr Ala Met Lys
        275                 280                 285

Cys Phe Leu Leu Glu Leu Gln Val Ile Ser Leu Glu Ser Gly Asp Ala
290                 295                 300

Asp Ile His Asp Thr Val Glu Asn Leu Ile Ile Leu Ala Asn Asn Ser
305                 310                 315                 320

Leu Ser Ser Asn Gly Asn Val Thr Glu Ser Gly Cys Lys Glu Cys Glu
                325                 330                 335

Glu Leu Glu Glu Lys Asn Ile Lys Glu Phe Leu Gln Ser Phe Val His
            340                 345                 350

Ile Val Gln Met Phe Ile Asn Thr Ser Gly Gly Pro Leu Gly Met Leu
        355                 360                 365

Ser Gln Ser Ile Thr Cys Pro Pro Met Ser Val Glu His Ala Asp
370                 375                 380

Ile Trp Val Lys Ser Tyr Ser Leu Tyr Ser Arg Glu Glu Tyr Ile Cys
385                 390                 395                 400

Asn Ser Gly Phe Lys Glu Lys Ala Gly Thr Ser Ser Leu Thr Glu Cys
                405                 410                 415

Val Leu Asn Lys Ala Thr Asn Val Ala His Trp Thr Thr Pro Ser Leu
            420                 425                 430

Lys Cys Ile Arg Asp Pro Ala Leu Val His Gln Arg Pro Ala Pro Pro
        435                 440                 445

<210> SEQ ID NO 41
<211> LENGTH: 433
<212> TYPE: PRT
<213> ORGANISM: Artificial
<220> FEATURE:
<223> OTHER INFORMATION: P-0388

<400> SEQUENCE: 41

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

```
Glu Asp Pro Glu Val Lys Phe Asn Trp Tyr Val Asp Gly Val Glu Val
 50                  55                  60
His Asn Ala Lys Thr Lys Pro Arg Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
            115                 120                 125
Tyr Thr Leu Pro Pro Ser Arg Asp Glu Leu Thr Lys Asn Gln Val Ser
130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
            195                 200                 205
His Glu Ala Leu His Asn His Tyr Thr Gln Lys Ser Leu Ser Leu Ser
210                 215                 220
Pro Gly Gly Gly Gly Ser Leu Gly Gly Ser Gly Arg Ser Ala Asn
225                 230                 235                 240
Ala Ile Leu Glu Gly Gly Ser Asn Trp Val Asn Val Ile Ser Asp Leu
                245                 250                 255
Lys Lys Ile Glu Asp Leu Ile Gln Ser Met His Ile Asp Ala Thr Leu
            260                 265                 270
Tyr Thr Glu Ser Asp Val His Pro Ser Cys Lys Val Thr Ala Met Lys
            275                 280                 285
Cys Phe Leu Leu Glu Leu Gln Val Ile Ser Leu Glu Ser Gly Asp Ala
            290                 295                 300
Asp Ile His Asp Thr Val Glu Asn Leu Ile Ile Leu Ala Asn Asn Ser
305                 310                 315                 320
Leu Ser Ser Asn Gly Asn Val Thr Glu Ser Gly Cys Lys Glu Cys Glu
                325                 330                 335
Glu Leu Glu Glu Lys Asn Ile Lys Glu Phe Leu Gln Ser Phe Val His
            340                 345                 350
Ile Val Gln Met Phe Ile Asn Thr Ser Gly Gly Pro Leu Gly Met Leu
            355                 360                 365
Ser Gln Ser Asp Cys Gly Leu Pro Pro Asp Val Pro Asn Ala Gln Pro
370                 375                 380
Ala Leu Glu Gly Arg Thr Ser Phe Pro Glu Asp Thr Val Ile Thr Tyr
385                 390                 395                 400
Lys Cys Glu Glu Ser Phe Val Lys Ile Pro Gly Glu Lys Asp Ser Val
                405                 410                 415
Ile Cys Leu Lys Gly Ser Gln Trp Ser Asp Ile Glu Glu Phe Cys Asn
            420                 425                 430
Arg
```

<210> SEQ ID NO 42
<211> LENGTH: 536
<212> TYPE: PRT
<213> ORGANISM: Artificial

<220> FEATURE:
<223> OTHER INFORMATION: P-0389

<400> SEQUENCE: 42

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Leu Gly Gly Ser Gly Arg Ser Ala Asn
225                 230                 235                 240

Ala Ile Leu Glu Gly Gly Ser Asn Trp Val Asn Val Ile Ser Asp Leu
                245                 250                 255

Lys Lys Ile Glu Asp Leu Ile Gln Ser Met His Ile Asp Ala Thr Leu
            260                 265                 270

Tyr Thr Glu Ser Asp Val His Pro Ser Cys Lys Val Thr Ala Met Lys
        275                 280                 285

Cys Phe Leu Leu Glu Leu Gln Val Ile Ser Leu Glu Ser Gly Asp Ala
    290                 295                 300

Asp Ile His Asp Thr Val Glu Asn Leu Ile Ile Leu Ala Asn Asn Ser
305                 310                 315                 320

Leu Ser Ser Asn Gly Asn Val Thr Glu Ser Gly Cys Lys Glu Cys Glu
                325                 330                 335

Glu Leu Glu Glu Lys Asn Ile Lys Glu Phe Leu Gln Ser Phe Val His
            340                 345                 350

Ile Val Gln Met Phe Ile Asn Thr Ser Gly Pro Leu Gly Met Leu
        355                 360                 365

Ser Gln Ser Glu Leu Cys Asp Asp Pro Pro Glu Ile Pro His Ala
    370                 375                 380

Thr Phe Lys Ala Met Ala Tyr Lys Glu Gly Thr Met Leu Asn Cys Glu
385                 390                 395                 400
```

```
Cys Lys Arg Gly Phe Arg Arg Ile Lys Ser Gly Ser Leu Tyr Met Leu
            405                 410                 415

Cys Thr Gly Asn Ser Ser His Ser Ser Trp Asp Asn Gln Cys Gln Cys
            420                 425                 430

Thr Ser Ser Ala Thr Arg Asn Thr Thr Lys Gln Val Thr Pro Gln Pro
            435                 440                 445

Glu Glu Gln Lys Glu Arg Lys Thr Thr Glu Met Gln Ser Pro Met Gln
        450                 455                 460

Pro Val Asp Gln Ala Ser Leu Pro Gly His Cys Arg Glu Pro Pro Pro
465                 470                 475                 480

Trp Glu Asn Glu Ala Thr Glu Arg Ile Tyr His Phe Val Val Gly Gln
            485                 490                 495

Met Val Tyr Tyr Gln Cys Val Gln Gly Tyr Arg Ala Leu His Arg Gly
            500                 505                 510

Pro Ala Glu Ser Val Cys Lys Met Thr His Gly Lys Thr Arg Trp Thr
            515                 520                 525

Gln Pro Gln Leu Ile Cys Thr Gly
        530                 535

<210> SEQ ID NO 43
<211> LENGTH: 443
<212> TYPE: PRT
<213> ORGANISM: Artificial
<220> FEATURE:
<223> OTHER INFORMATION: P-0397

<400> SEQUENCE: 43

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Gly Gly Pro
65                  70                  75                  80

Leu Gly Met Leu Ser Gln Ser Asn Trp Val Asn Val Ile Ser Asp Leu
                85                  90                  95

Lys Lys Ile Glu Asp Leu Ile Gln Ser Met His Ile Asp Ala Thr Leu
            100                 105                 110

Tyr Thr Glu Ser Asp Val His Pro Ser Cys Lys Val Thr Ala Met Lys
        115                 120                 125

Cys Phe Leu Leu Glu Leu Gln Val Ile Ser Leu Glu Ser Gly Asp Ala
    130                 135                 140

Asp Ile His Asp Thr Val Glu Asn Leu Ile Ile Leu Ala Asn Asn Ser
145                 150                 155                 160

Leu Ser Ser Asn Gly Asn Val Thr Glu Ser Gly Cys Lys Glu Cys Glu
                165                 170                 175

Glu Leu Glu Glu Lys Asn Ile Lys Glu Phe Leu Gln Ser Phe Val His
            180                 185                 190

Ile Val Gln Met Phe Ile Asn Thr Ser Gly Gly Gly Ser Leu Gly
        195                 200                 205

Gly Ser Gly Arg Ser Ala Asn Ala Ile Leu Glu Gly Gly Ser Cys Pro
    210                 215                 220
```

```
Pro Cys Pro Ala Pro Glu Ala Ala Gly Ala Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440

<210> SEQ ID NO 44
<211> LENGTH: 355
<212> TYPE: PRT
<213> ORGANISM: Artificial
<220> FEATURE:
<223> OTHER INFORMATION: Hole-Fc-IL-15

<400> SEQUENCE: 44

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140
```

```
Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Glu Pro Lys Ser Ser Asp Lys Thr His Thr Ser Pro Pro Ser
225                 230                 235                 240

Pro Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
            260                 265                 270

His Pro Ser Cys Lys Val Thr Ala Met Lys Cys Phe Leu Leu Glu Leu
        275                 280                 285

Gln Val Ile Ser Leu Glu Ser Gly Asp Ala Ser Ile His Asp Thr Val
290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
            340                 345                 350

Asn Thr Ser
        355

<210> SEQ ID NO 45
<211> LENGTH: 355
<212> TYPE: PRT
<213> ORGANISM: Artificial
<220> FEATURE:
<223> OTHER INFORMATION: Knob-Fc-IL-15

<400> SEQUENCE: 45

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
130                 135                 140
```

```
Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Glu Pro Lys Ser Ser Asp Lys Thr His Thr Ser Pro Pro Ser
225                 230                 235                 240

Pro Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
            260                 265                 270

His Pro Ser Cys Lys Val Thr Ala Met Lys Cys Phe Leu Leu Glu Leu
        275                 280                 285

Gln Val Ile Ser Leu Glu Ser Gly Asp Ala Ser Ile His Asp Thr Val
    290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
            340                 345                 350

Asn Thr Ser
        355

<210> SEQ ID NO 46
<211> LENGTH: 318
<212> TYPE: PRT
<213> ORGANISM: Artificial
<220> FEATURE:
<223> OTHER INFORMATION: Knob-Fc-IL-15Rα?-Sushi+

<400> SEQUENCE: 46

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
    130                 135                 140
```

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Glu Pro Lys Ser Ser Asp Lys Thr His Thr Ser Pro Pro Ser
225                 230                 235                 240

Pro Ile Thr Cys Pro Pro Met Ser Val Glu His Ala Asp Ile Trp
            245                 250                 255

Val Lys Ser Tyr Ser Leu Tyr Ser Arg Glu Arg Tyr Ile Cys Asn Ser
                260                 265                 270

Gly Phe Lys Arg Lys Ala Gly Thr Ser Ser Leu Thr Glu Cys Val Leu
            275                 280                 285

Asn Lys Ala Thr Asn Val Ala His Trp Thr Thr Pro Ser Leu Lys Cys
        290                 295                 300

Ile Arg Asp Pro Ala Leu Val His Gln Arg Pro Ala Pro Pro
305                 310                 315

<210> SEQ ID NO 47
<211> LENGTH: 355
<212> TYPE: PRT
<213> ORGANISM: Artificial
<220> FEATURE:
<223> OTHER INFORMATION: Fc-IL-15 S58D

<400> SEQUENCE: 47

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

```
Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Gly Gly Gly Ser Gly Gly Gly Ser Gly Gly Gly Gly
225                 230                 235                 240

Ser Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
            260                 265                 270

His Pro Ser Cys Lys Val Thr Ala Met Lys Cys Phe Leu Leu Glu Leu
        275                 280                 285

Gln Val Ile Ser Leu Glu Ser Gly Asp Ala Asp Ile His Asp Thr Val
290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
            340                 345                 350

Asn Thr Ser
        355

<210> SEQ ID NO 48
<211> LENGTH: 367
<212> TYPE: PRT
<213> ORGANISM: Artificial
<220> FEATURE:
<223> OTHER INFORMATION: P-0250

<400> SEQUENCE: 48

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190
```

```
Asp Lys Ser Arg Trp Gln Gln Gly Asn Val Phe Ser Cys Ser Val Met
            195                 200                 205
His Glu Ala Leu His Asn His Tyr Thr Gln Lys Ser Leu Ser Leu Ser
        210                 215                 220
Pro Gly Gly Gly Ser Gly Gly Gly Ser Ala Pro Thr Ser Ser Ser
225                 230                 235                 240
Thr Lys Lys Thr Gln Leu Gln Leu Glu His Leu Leu Leu Asp Leu Gln
                245                 250                 255
Met Ile Leu Asn Gly Ile Asn Asn Tyr Lys Asn Pro Lys Leu Thr Arg
            260                 265                 270
Met Leu Thr Phe Lys Phe Tyr Met Pro Lys Lys Ala Thr Glu Leu Lys
        275                 280                 285
His Leu Gln Cys Leu Glu Glu Glu Leu Lys Pro Leu Glu Glu Val Leu
    290                 295                 300
Asn Leu Ala Gln Ser Lys Asn Phe His Leu Arg Pro Arg Asp Leu Ile
305                 310                 315                 320
Ser Asn Ile Asn Val Ile Val Leu Glu Leu Lys Gly Ser Glu Thr Thr
                325                 330                 335
Phe Met Cys Glu Tyr Ala Asp Glu Thr Ala Thr Ile Val Glu Phe Leu
            340                 345                 350
Asn Arg Trp Ile Thr Phe Ser Gln Ser Ile Ile Ser Thr Leu Thr
        355                 360                 365

<210> SEQ ID NO 49
<211> LENGTH: 560
<212> TYPE: PRT
<213> ORGANISM: Artificial
<220> FEATURE:
<223> OTHER INFORMATION: P-0320

<400> SEQUENCE: 49

Asp Lys Thr His Thr Cys Pro Pro Cys Pro Ala Pro Glu Ala Ala Gly
1               5                   10                  15
Ala Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
```

```
Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Gly Gly Gly Ser Leu Gly Ser Gly Arg Ser Ala Asn
225                 230                 235                 240

Ala Ile Leu Glu Gly Ser Ala Pro Thr Ser Ser Thr Lys Lys
            245                 250                 255

Thr Gln Leu Gln Leu Glu His Leu Leu Leu Asp Leu Gln Met Ile Leu
            260                 265                 270

Asn Gly Ile Asn Asn Tyr Lys Asn Pro Lys Leu Thr Arg Met Leu Thr
            275                 280                 285

Phe Lys Phe Tyr Met Pro Lys Lys Ala Thr Glu Leu Lys His Leu Gln
        290                 295                 300

Cys Leu Glu Glu Glu Leu Lys Pro Leu Glu Glu Val Leu Asn Leu Ala
305                 310                 315                 320

Gln Ser Lys Asn Phe His Leu Arg Pro Arg Asp Leu Ile Ser Asn Ile
            325                 330                 335

Asn Val Ile Val Leu Glu Leu Lys Gly Ser Glu Thr Thr Phe Met Cys
            340                 345                 350

Glu Tyr Ala Asp Glu Thr Ala Thr Ile Val Glu Phe Leu Asn Arg Trp
        355                 360                 365

Ile Thr Phe Ser Gln Ser Ile Ile Ser Thr Leu Thr Gly Gly Gly Gly
        370                 375                 380

Ser Gly Gly Gly Gly Ser Gly Gly Gly Ser Glu Leu Cys Asp Asp
385                 390                 395                 400

Asp Pro Pro Glu Ile Pro His Ala Thr Phe Lys Ala Met Ala Tyr Lys
            405                 410                 415

Glu Gly Thr Met Leu Asn Cys Glu Cys Lys Arg Gly Phe Arg Arg Ile
        420                 425                 430

Lys Ser Gly Ser Leu Tyr Met Leu Cys Thr Gly Asn Ser Ser His Ser
        435                 440                 445

Ser Trp Asp Asn Gln Cys Gln Cys Thr Ser Ser Ala Thr Arg Asn Thr
        450                 455                 460

Thr Lys Gln Val Thr Pro Gln Pro Glu Glu Gln Lys Glu Arg Lys Thr
465                 470                 475                 480

Thr Glu Met Gln Ser Pro Met Gln Pro Val Asp Gln Ala Ser Leu Pro
            485                 490                 495

Gly His Cys Arg Glu Pro Pro Trp Glu Asn Glu Ala Thr Glu Arg
        500                 505                 510

Ile Tyr His Phe Val Val Gly Gln Met Val Tyr Tyr Gln Cys Val Gln
        515                 520                 525

Gly Tyr Arg Ala Leu His Arg Gly Pro Ala Glu Ser Val Cys Lys Met
        530                 535                 540

Thr His Gly Lys Thr Arg Trp Thr Gln Pro Gln Leu Ile Cys Thr Gly
545                 550                 555                 560
```

<210> SEQ ID NO 50
<211> LENGTH: 560
<212> TYPE: PRT
<213> ORGANISM: Artificial
<220> FEATURE:
<223> OTHER INFORMATION: P-0352

<400> SEQUENCE: 50

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Leu Gly Ser Gly Arg Ser Ala Asn
225                 230                 235                 240

Ala Ile Leu Glu Gly Gly Ser Ala Pro Thr Ser Ser Thr Lys Lys
                245                 250                 255

Thr Gln Leu Gln Leu Glu His Leu Leu Leu Asp Leu Gln Met Ile Leu
        260                 265                 270

Asn Gly Ile Asn Asn Tyr Lys Asn Pro Lys Leu Thr Arg Met Leu Thr
    275                 280                 285

Phe Lys Phe Tyr Met Pro Lys Lys Ala Thr Glu Leu Lys His Leu Gln
290                 295                 300

Cys Leu Glu Glu Glu Leu Lys Pro Leu Glu Val Leu Asn Leu Ala
305                 310                 315                 320

Gln Ser Lys Asn Phe His Leu Arg Pro Arg Asp Leu Ile Ser Asn Ile
                325                 330                 335

Asn Val Ile Val Leu Glu Leu Lys Gly Ser Glu Thr Thr Phe Met Cys
        340                 345                 350

Glu Tyr Ala Asp Glu Thr Ala Thr Ile Val Glu Phe Leu Asn Arg Trp
    355                 360                 365

Ile Thr Phe Ser Gln Ser Ile Ile Ser Thr Leu Thr Gly Gly Gly Gly
370                 375                 380

Ser Gly Gly Gly Gly Ser Gly Gly Gly Ser Glu Leu Cys Asp Asp
385                 390                 395                 400

Asp Pro Pro Glu Ile Pro His Ala Thr Phe Lys Ala Met Ala Tyr Lys
            405                 410                 415
```

```
Glu Gly Thr Met Leu Asn Cys Glu Cys Lys Arg Gly Phe Arg Arg Ile
            420                 425                 430

Glu Ser Gly Ser Leu Tyr Met Leu Cys Thr Gly Asn Ser Ser His Ser
        435                 440                 445

Ser Trp Asp Asn Gln Cys Gln Cys Thr Ser Ser Ala Thr Arg Asn Thr
450                 455                 460

Thr Lys Gln Val Thr Pro Gln Pro Glu Glu Gln Lys Glu Arg Lys Thr
465                 470                 475                 480

Thr Glu Met Gln Ser Pro Met Gln Pro Val Asp Gln Ala Ser Leu Pro
                485                 490                 495

Gly His Cys Arg Glu Pro Pro Trp Glu Asn Glu Ala Thr Glu Arg
            500                 505                 510

Ile Tyr His Phe Val Val Gly Gln Met Val Tyr Tyr Gln Cys Val Gln
            515                 520                 525

Gly Tyr Arg Ala Leu His Arg Gly Pro Ala Glu Ser Val Cys Lys Met
        530                 535                 540

Thr His Gly Lys Thr Arg Trp Thr Gln Pro Gln Leu Ile Cys Thr Gly
545                 550                 555                 560

<210> SEQ ID NO 51
<211> LENGTH: 542
<212> TYPE: PRT
<213> ORGANISM: Artificial
<220> FEATURE:
<223> OTHER INFORMATION: P-0382

<400> SEQUENCE: 51

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220
```

Pro Gly Gly Gly Gly Ser Gly Gly Gly Ser Ala Pro Thr Ser Ser Ser
225                 230                 235                 240

Thr Lys Lys Thr Gln Leu Gln Leu Glu His Leu Leu Leu Asp Leu Gln
            245                 250                 255

Met Ile Leu Asn Gly Ile Asn Asn Tyr Lys Asn Pro Lys Leu Thr Arg
        260                 265                 270

Met Leu Thr Phe Lys Phe Tyr Met Pro Lys Lys Ala Thr Glu Leu Lys
    275                 280                 285

His Leu Gln Cys Leu Glu Glu Glu Leu Lys Pro Leu Glu Glu Val Leu
290                 295                 300

Asn Leu Ala Gln Ser Lys Asn Phe His Leu Arg Pro Arg Asp Leu Ile
305                 310                 315                 320

Ser Asn Ile Asn Val Ile Val Leu Glu Leu Lys Gly Ser Glu Thr Thr
                325                 330                 335

Phe Met Cys Glu Tyr Ala Asp Glu Thr Ala Thr Ile Val Glu Phe Leu
            340                 345                 350

Asn Arg Trp Ile Thr Phe Ser Gln Ser Ile Ile Ser Thr Leu Thr Gly
        355                 360                 365

Gly Pro Leu Gly Met Leu Ser Gln Ser Glu Leu Cys Asp Asp Asp Pro
    370                 375                 380

Pro Glu Ile Pro His Ala Thr Phe Lys Ala Met Ala Tyr Lys Glu Gly
385                 390                 395                 400

Thr Met Leu Asn Cys Glu Cys Lys Arg Gly Phe Arg Arg Ile Lys Ser
                405                 410                 415

Gly Ser Leu Tyr Met Leu Cys Thr Gly Asn Ser Ser His Ser Ser Trp
            420                 425                 430

Asp Asn Gln Cys Gln Cys Thr Ser Ser Ala Thr Arg Asn Thr Thr Lys
        435                 440                 445

Gln Val Thr Pro Gln Pro Glu Glu Gln Lys Glu Arg Lys Thr Thr Glu
    450                 455                 460

Met Gln Ser Pro Met Gln Pro Val Asp Gln Ala Ser Leu Pro Gly His
465                 470                 475                 480

Cys Arg Glu Pro Pro Pro Trp Glu Asn Glu Ala Thr Glu Arg Ile Tyr
                485                 490                 495

His Phe Val Val Gly Gln Met Val Tyr Tyr Gln Cys Val Gln Gly Tyr
            500                 505                 510

Arg Ala Leu His Arg Gly Pro Ala Glu Ser Val Cys Lys Met Thr His
        515                 520                 525

Gly Lys Thr Arg Trp Thr Gln Pro Gln Leu Ile Cys Thr Gly
    530                 535                 540

<210> SEQ ID NO 52
<211> LENGTH: 547
<212> TYPE: PRT
<213> ORGANISM: Artificial
<220> FEATURE:
<223> OTHER INFORMATION: P-0398

<400> SEQUENCE: 52

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

-continued

Glu Asp Pro Glu Val Lys Phe Asn Trp Tyr Val Asp Gly Val Glu Val
 50                  55                  60

His Asn Ala Lys Thr Lys Pro Arg Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Gly Gly Gly Ser Gly Gly Gly Ser Ala Pro Thr Ser Ser Ser
225                 230                 235                 240

Thr Lys Lys Thr Gln Leu Gln Leu Glu His Leu Leu Leu Asp Leu Gln
                245                 250                 255

Met Ile Leu Asn Gly Ile Asn Asn Tyr Lys Asn Pro Lys Leu Thr Arg
            260                 265                 270

Met Leu Thr Phe Lys Phe Tyr Met Pro Lys Lys Ala Thr Glu Leu Lys
        275                 280                 285

His Leu Gln Cys Leu Glu Glu Leu Lys Pro Leu Glu Glu Val Leu
290                 295                 300

Asn Leu Ala Gln Ser Lys Asn Phe His Leu Arg Pro Arg Asp Leu Ile
305                 310                 315                 320

Ser Asn Ile Asn Val Ile Val Leu Glu Leu Lys Gly Ser Glu Thr Thr
                325                 330                 335

Phe Met Cys Glu Tyr Ala Asp Glu Thr Ala Thr Ile Val Glu Phe Leu
            340                 345                 350

Asn Arg Trp Ile Thr Phe Ser Gln Ser Ile Ile Ser Thr Leu Thr Gly
        355                 360                 365

Gly Ser Gly Pro Leu Gly Met Leu Ser Gln Gly Gly Gly Ser Glu Leu
370                 375                 380

Cys Asp Asp Asp Pro Pro Glu Ile Pro His Ala Thr Phe Lys Ala Met
385                 390                 395                 400

Ala Tyr Lys Glu Gly Thr Met Leu Asn Cys Glu Cys Lys Arg Gly Phe
                405                 410                 415

Arg Arg Ile Lys Ser Gly Ser Leu Tyr Met Leu Cys Thr Gly Asn Ser
            420                 425                 430

Ser His Ser Ser Trp Asp Asn Gln Cys Gln Cys Thr Ser Ser Ala Thr
        435                 440                 445

Arg Asn Thr Thr Lys Gln Val Thr Pro Gln Pro Glu Glu Gln Lys Glu
450                 455                 460

Arg Lys Thr Thr Glu Met Gln Ser Pro Met Gln Pro Val Asp Gln Ala

```
465             470             475             480
Ser Leu Pro Gly His Cys Arg Glu Pro Pro Trp Glu Asn Glu Ala
                485             490             495

Thr Glu Arg Ile Tyr His Phe Val Val Gly Gln Met Val Tyr Tyr Gln
                500             505             510

Cys Val Gln Gly Tyr Arg Ala Leu His Arg Gly Pro Ala Glu Ser Val
                515             520             525

Cys Lys Met Thr His Gly Lys Thr Arg Trp Thr Gln Pro Gln Leu Ile
                530             535             540

Cys Thr Gly
545

<210> SEQ ID NO 53
<211> LENGTH: 542
<212> TYPE: PRT
<213> ORGANISM: Artificial
<220> FEATURE:
<223> OTHER INFORMATION: P-0362

<400> SEQUENCE: 53

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Ser Arg Asp Glu Leu Thr Lys Asn Gln Val Ser
                130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
                210                 215                 220

Pro Gly Gly Gly Gly Ser Gly Gly Gly Ser Ala Pro Thr Ser Ser Ser
225                 230                 235                 240

Thr Lys Lys Thr Gln Leu Gln Leu Glu His Leu Leu Leu Asp Leu Gln
                245                 250                 255

Met Ile Leu Asn Gly Ile Asn Asn Tyr Lys Asn Pro Lys Leu Thr Arg
                260                 265                 270

Met Leu Thr Phe Lys Phe Tyr Met Pro Lys Lys Ala Thr Glu Leu Lys
```

```
              275                 280                 285
His Leu Gln Cys Leu Glu Glu Glu Leu Lys Pro Leu Glu Glu Val Leu
290                 295                 300
Asn Leu Ala Gln Ser Lys Asn Phe His Leu Arg Pro Arg Asp Leu Ile
305                 310                 315                 320
Ser Asn Ile Asn Val Ile Val Leu Glu Leu Lys Gly Ser Glu Thr Thr
                325                 330                 335
Phe Met Cys Glu Tyr Ala Asp Glu Thr Ala Thr Ile Val Glu Phe Leu
            340                 345                 350
Asn Arg Trp Ile Thr Phe Ser Gln Ser Ile Ile Ser Thr Leu Thr Gly
                355                 360                 365
Gly Pro Leu Gly Met Leu Ser Gln Ser Glu Leu Cys Asp Asp Asp Pro
            370                 375                 380
Pro Glu Ile Pro His Ala Thr Phe Lys Ala Met Ala Tyr Lys Glu Gly
385                 390                 395                 400
Thr Met Leu Asn Cys Glu Cys Lys Arg Gly Phe Arg Arg Ile Glu Ser
                405                 410                 415
Gly Ser Leu Tyr Met Leu Cys Thr Gly Asn Ser Ser His Ser Ser Trp
                420                 425                 430
Asp Asn Gln Cys Gln Cys Thr Ser Ser Ala Thr Arg Asn Thr Thr Lys
            435                 440                 445
Gln Val Thr Pro Gln Pro Glu Glu Gln Lys Glu Arg Lys Thr Thr Glu
        450                 455                 460
Met Gln Ser Pro Met Gln Pro Val Asp Gln Ala Ser Leu Pro Gly His
465                 470                 475                 480
Cys Arg Glu Pro Pro Pro Trp Glu Asn Glu Ala Thr Glu Arg Ile Tyr
                485                 490                 495
His Phe Val Val Gly Gln Met Val Tyr Tyr Gln Cys Val Gln Gly Tyr
                500                 505                 510
Arg Ala Leu His Arg Gly Pro Ala Glu Ser Val Cys Lys Met Thr His
            515                 520                 525
Gly Lys Thr Arg Trp Thr Gln Pro Gln Leu Ile Cys Thr Gly
        530                 535                 540

<210> SEQ ID NO 54
<211> LENGTH: 542
<212> TYPE: PRT
<213> ORGANISM: Artificial
<220> FEATURE:
<223> OTHER INFORMATION: P-0380

<400> SEQUENCE: 54

Asp Lys Thr His Thr Cys Pro Pro Cys Pro Ala Pro Glu Ala Ala Gly
1               5                   10                  15
Ala Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
            35                  40                  45
Glu Asp Pro Glu Val Lys Phe Asn Trp Tyr Val Asp Gly Val Glu Val
        50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
```

-continued

```
               100                 105                 110
Glu Lys Thr Ile Ser Lys Ala Lys Gly Gln Pro Arg Glu Pro Gln Val
               115                 120                 125

Tyr Thr Leu Pro Pro Ser Arg Asp Glu Leu Thr Lys Asn Gln Val Ser
           130                 135             140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                       165                 170                 175

Val Leu Asp Ser Asp Gly Ser Phe Phe Leu Tyr Ser Lys Leu Thr Val
               180                 185                 190

Asp Lys Ser Arg Trp Gln Gln Gly Asn Val Phe Ser Cys Ser Val Met
           195                 200                 205

His Glu Ala Leu His Asn His Tyr Thr Gln Lys Ser Leu Ser Leu Ser
       210                 215                 220

Pro Gly Gly Gly Gly Ser Gly Gly Gly Ser Ala Pro Thr Ser Ser Ser
225                 230                 235                 240

Thr Lys Lys Thr Gln Leu Gln Leu Glu His Leu Leu Leu Asp Leu Gln
                       245                 250                 255

Met Ile Leu Asn Gly Ile Asn Asn Tyr Lys Asn Pro Lys Leu Thr Arg
               260                 265                 270

Met Leu Thr Phe Lys Phe Tyr Met Pro Lys Lys Ala Thr Glu Leu Lys
           275                 280                 285

His Leu Gln Cys Leu Glu Glu Glu Leu Lys Pro Leu Glu Glu Val Leu
       290                 295                 300

Asn Leu Ala Gln Ser Lys Asn Phe His Leu Arg Pro Arg Asp Leu Ile
305                 310                 315                 320

Ser Asn Ile Asn Val Ile Val Leu Glu Leu Lys Gly Ser Glu Thr Thr
                       325                 330                 335

Phe Met Cys Glu Tyr Ala Asp Glu Thr Ala Thr Ile Val Glu Phe Leu
               340                 345                 350

Asn Arg Trp Ile Thr Phe Ser Gln Ser Ile Ile Ser Thr Leu Thr Gly
           355                 360                 365

Gly Pro Leu Gly Met Leu Ser Gln Ser Glu Leu Cys Asp Asp Asp Pro
       370                 375                 380

Pro Glu Ile Pro His Ala Thr Phe Lys Ala Met Ala Tyr Lys Glu Gly
385                 390                 395                 400

Thr Met Leu Asn Cys Glu Cys Lys Arg Gly Phe Arg Arg Ile Glu Ser
                       405                 410                 415

Gly Ser Leu Ala Met Leu Cys Thr Gly Asn Ser Ser His Ser Ser Trp
               420                 425                 430

Asp Asn Gln Cys Gln Cys Thr Ser Ser Ala Thr Arg Asn Thr Thr Lys
           435                 440                 445

Gln Val Thr Pro Gln Pro Glu Glu Gln Lys Glu Arg Lys Thr Thr Glu
       450                 455                 460

Met Gln Ser Pro Met Gln Pro Val Asp Gln Ala Ser Leu Pro Gly His
465                 470                 475                 480

Cys Arg Glu Pro Pro Trp Glu Asn Glu Ala Thr Glu Arg Ile Tyr
                       485                 490                 495

His Phe Val Val Gly Gln Met Val Tyr Tyr Gln Cys Val Gln Gly Tyr
               500                 505                 510

Arg Ala Leu His Arg Gly Pro Ala Glu Ser Val Cys Lys Met Thr His
           515                 520                 525
```

```
Gly Lys Thr Arg Trp Thr Gln Pro Gln Leu Ile Cys Thr Gly
    530                 535                 540

<210> SEQ ID NO 55
<211> LENGTH: 542
<212> TYPE: PRT
<213> ORGANISM: Artificial
<220> FEATURE:
<223> OTHER INFORMATION: P-0384

<400> SEQUENCE: 55

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Ser Ala Pro Thr Ser Ser Ser
225                 230                 235                 240

Thr Lys Lys Thr Gln Leu Gln Leu Glu His Leu Leu Asp Leu Gln
                245                 250                 255

Met Ile Leu Asn Gly Ile Asn Asn Tyr Lys Asn Pro Lys Leu Thr Arg
            260                 265                 270

Met Leu Thr Phe Lys Phe Tyr Met Pro Lys Lys Ala Thr Glu Leu Lys
        275                 280                 285

His Leu Gln Cys Leu Glu Glu Glu Leu Lys Pro Leu Glu Glu Val Leu
    290                 295                 300

Asn Leu Ala Gln Ser Lys Asn Phe His Leu Arg Pro Arg Asp Leu Ile
305                 310                 315                 320

Ser Asn Ile Asn Val Ile Val Leu Glu Leu Lys Gly Ser Glu Thr Thr
                325                 330                 335

Phe Met Cys Glu Tyr Ala Asp Glu Thr Ala Thr Ile Val Glu Phe Leu
            340                 345                 350
```

-continued

```
Asn Arg Trp Ile Thr Phe Ser Gln Ser Ile Ser Thr Leu Thr Gly
        355                 360                 365
Gly Pro Leu Gly Met Leu Ser Gln Ser Glu Leu Cys Asp Asp Pro
    370                 375                 380
Pro Glu Ile Pro His Ala Thr Phe Lys Ala Met Ala Tyr Lys Glu Gly
385                 390                 395                 400
Thr Met Leu Asn Cys Glu Cys Lys Arg Gly Phe Arg Arg Ile Lys Ser
                405                 410                 415
Gly Ser Leu Ala Met Leu Cys Thr Gly Asn Ser Ser His Ser Ser Trp
            420                 425                 430
Asp Asn Gln Cys Gln Cys Thr Ser Ser Ala Thr Arg Asn Thr Thr Lys
            435                 440                 445
Gln Val Thr Pro Gln Pro Glu Glu Gln Lys Glu Arg Lys Thr Thr Glu
    450                 455                 460
Met Gln Ser Pro Met Gln Pro Val Asp Gln Ala Ser Leu Pro Gly His
465                 470                 475                 480
Cys Arg Glu Pro Pro Pro Trp Glu Asn Glu Ala Thr Glu Arg Ile Tyr
                485                 490                 495
His Phe Val Val Gly Gln Met Val Tyr Tyr Gln Cys Val Gln Gly Tyr
            500                 505                 510
Arg Ala Leu His Arg Gly Pro Ala Glu Ser Val Cys Lys Met Thr His
        515                 520                 525
Gly Lys Thr Arg Trp Thr Gln Pro Gln Leu Ile Cys Thr Gly
    530                 535                 540

<210> SEQ ID NO 56
<211> LENGTH: 542
<212> TYPE: PRT
<213> ORGANISM: Artificial
<220> FEATURE:
<223> OTHER INFORMATION: P-0400

<400> SEQUENCE: 56

Asp Lys Thr His Thr Cys Pro Pro Cys Pro Ala Pro Glu Ala Ala Gly
1               5                   10                  15
Ala Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
```

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Gly Gly Ser Gly Gly Gly Ser Ala Pro Thr Ser Ser Ser
225                 230                 235                 240

Thr Lys Lys Thr Gln Leu Gln Leu Glu His Leu Leu Asn Asp Leu Gln
            245                 250                 255

Met Ile Leu Asn Gly Ile Asn Asn Tyr Lys Asn Pro Lys Leu Thr Arg
            260                 265                 270

Met Leu Thr Phe Lys Phe Tyr Met Pro Lys Lys Ala Thr Glu Leu Lys
            275                 280                 285

His Leu Gln Cys Leu Glu Glu Glu Leu Lys Pro Leu Glu Glu Val Leu
            290                 295                 300

Asn Leu Ala Gln Ser Lys Asn Phe His Leu Arg Pro Arg Asp Leu Ile
305                 310                 315                 320

Ser Asn Ile Asn Val Ile Val Leu Glu Leu Lys Gly Ser Glu Thr Thr
            325                 330                 335

Phe Met Cys Glu Tyr Ala Asp Glu Thr Ala Thr Ile Val Glu Phe Leu
            340                 345                 350

Asn Arg Trp Ile Thr Phe Ser Gln Ser Ile Ile Ser Thr Leu Thr Gly
            355                 360                 365

Gly Pro Leu Gly Met Leu Ser Gln Ser Glu Leu Cys Asp Asp Pro
            370                 375                 380

Pro Glu Ile Pro His Ala Thr Phe Lys Ala Met Ala Tyr Lys Glu Gly
385                 390                 395                 400

Thr Met Leu Asn Cys Glu Cys Lys Arg Gly Phe Arg Arg Ile Glu Ser
            405                 410                 415

Gly Ser Leu Tyr Met Leu Cys Thr Gly Asn Ser Ser His Ser Ser Trp
            420                 425                 430

Asp Asn Gln Cys Gln Cys Thr Ser Ser Ala Thr Arg Asn Thr Thr Lys
            435                 440                 445

Gln Val Thr Pro Gln Pro Glu Glu Gln Lys Glu Arg Lys Thr Thr Glu
            450                 455                 460

Met Gln Ser Pro Met Gln Pro Val Asp Gln Ala Ser Leu Pro Gly His
465                 470                 475                 480

Cys Arg Glu Pro Pro Pro Trp Glu Asn Glu Ala Thr Glu Arg Ile Tyr
            485                 490                 495

His Phe Val Val Gly Gln Met Val Tyr Tyr Gln Cys Val Gln Gly Tyr
            500                 505                 510

Arg Ala Leu His Arg Gly Pro Ala Glu Ser Val Cys Lys Met Thr His
            515                 520                 525

Gly Lys Thr Arg Trp Thr Gln Pro Gln Leu Ile Cys Thr Gly
            530                 535                 540

<210> SEQ ID NO 57
<211> LENGTH: 542
<212> TYPE: PRT
<213> ORGANISM: Artificial
<220> FEATURE:
<223> OTHER INFORMATION: P-0404

<400> SEQUENCE: 57

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Gly Gly Gly Ser Gly Gly Gly Ser Ala Pro Thr Ser Ser Ser
225                 230                 235                 240

Thr Lys Lys Thr Gln Leu Gln Leu Glu His Leu Leu Leu Asp Leu Gln
                245                 250                 255

Met Ile Leu Asn Gly Ile Asn Asn Tyr Lys Asn Pro Lys Leu Thr Arg
                260                 265                 270

Met Leu Thr Phe Lys Phe Tyr Met Pro Lys Lys Ala Thr Glu Leu Lys
            275                 280                 285

His Leu Gln Cys Leu Glu Glu Glu Leu Lys Pro Leu Glu Glu Val Leu
        290                 295                 300

Asn Leu Ala Gln Ser Lys Asn Phe His Leu Arg Pro Arg Asp Leu Ile
305                 310                 315                 320

Ser Asn Ile Asn Val Ile Val Leu Glu Leu Lys Gly Ser Glu Thr Thr
                325                 330                 335

Phe Met Cys Glu Tyr Ala Asp Glu Thr Ala Thr Ile Val Glu Phe Leu
                340                 345                 350

Asn Arg Trp Ile Thr Phe Ser Gln Ser Ile Ile Ser Thr Leu Thr Gly
            355                 360                 365

Gly Pro Leu Gly Met Leu Ser Gln Ser Glu Leu Cys Asp Asp Asp Pro
        370                 375                 380

Pro Glu Ile Pro His Ala Thr Phe Lys Ala Met Ala Tyr Lys Glu Gly
385                 390                 395                 400

Thr Met Leu Asn Cys Glu Cys Lys Arg Gly Phe Arg Arg Ile Glu Ser
                405                 410                 415
```

Gly Ser Leu Tyr Met Leu Cys Thr Gly Asn Ser Ser His Ser Ser Trp
            420                 425                 430

Asp Asn Gln Cys Gln Cys Thr Ser Ser Ala Thr Arg Asn Thr Thr Lys
435                 440                 445

Gln Val Thr Pro Gln Pro Glu Glu Gln Lys Glu Arg Lys Thr Thr Glu
    450                 455                 460

Met Gln Ser Pro Met Gln Pro Val Asp Gln Ala Ser Leu Pro Gly His
465                 470                 475                 480

Cys Arg Glu Pro Pro Pro Trp Glu Asn Glu Ala Thr Glu Arg Ile Tyr
                485                 490                 495

His Phe Val Val Gly Gln Met Val Tyr Tyr Gln Cys Val Gln Gly Tyr
            500                 505                 510

Arg Ala Leu His Arg Gly Pro Ala Glu Ser Val Cys Lys Met Thr His
        515                 520                 525

Gly Lys Thr Arg Trp Thr Gln Pro Gln Leu Ile Cys Thr Gly
    530                 535                 540

<210> SEQ ID NO 58
<211> LENGTH: 454
<212> TYPE: PRT
<213> ORGANISM: Artificial
<220> FEATURE:
<223> OTHER INFORMATION: P-0399

<400> SEQUENCE: 58

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Ser Ala Pro Thr Ser Ser Ser
225                 230                 235                 240

```
Thr Lys Lys Thr Gln Leu Gln Leu Glu His Leu Leu Leu Asp Leu Gln
                245                 250                 255

Met Ile Leu Asn Gly Ile Asn Asn Tyr Lys Asn Pro Lys Leu Thr Arg
            260                 265                 270

Met Leu Thr Phe Lys Phe Tyr Met Pro Lys Lys Ala Thr Glu Leu Lys
        275                 280                 285

His Leu Gln Cys Leu Glu Glu Leu Lys Pro Leu Glu Glu Val Leu
    290                 295                 300

Asn Leu Ala Gln Ser Lys Asn Phe His Leu Arg Pro Arg Asp Leu Ile
305                 310                 315                 320

Ser Asn Ile Asn Val Ile Val Leu Glu Leu Lys Gly Ser Glu Thr Thr
                325                 330                 335

Phe Met Cys Glu Tyr Ala Asp Glu Thr Ala Thr Ile Val Glu Phe Leu
            340                 345                 350

Asn Arg Trp Ile Thr Phe Ser Gln Ser Ile Ile Ser Thr Leu Thr Gly
        355                 360                 365

Gly Pro Leu Gly Met Leu Ser Gln Ser Ile Thr Cys Pro Pro Pro Met
    370                 375                 380

Ser Val Glu His Ala Asp Ile Trp Val Lys Ser Tyr Ser Leu Tyr Ser
385                 390                 395                 400

Arg Glu Arg Tyr Ile Cys Asn Ser Gly Phe Lys Arg Lys Ala Gly Thr
                405                 410                 415

Ser Ser Leu Thr Glu Cys Val Leu Asn Lys Ala Thr Asn Val Ala His
            420                 425                 430

Trp Thr Thr Pro Ser Leu Lys Cys Ile Arg Asp Pro Ala Leu Val His
        435                 440                 445

Gln Arg Pro Ala Pro Pro
    450

<210> SEQ ID NO 59
<211> LENGTH: 542
<212> TYPE: PRT
<213> ORGANISM: Artificial
<220> FEATURE:
<223> OTHER INFORMATION: P-0379

<400> SEQUENCE: 59

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140
```

```
Leu Thr Cys Leu Val Lys Gly Phe Tyr Pro Ser Asp Ile Ala Val Glu
145                 150                 155                 160

Trp Glu Ser Asn Gly Gln Pro Glu Asn Tyr Lys Thr Thr Pro Pro
            165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Gly Gly Ser Gly Gly Gly Ser Ala Pro Thr Ser Ser Ser
225                 230                 235                 240

Thr Lys Lys Thr Gln Leu Gln Leu Glu His Leu Leu Leu Asp Leu Gln
                245                 250                 255

Met Ile Leu Asn Gly Ile Asn Asn Tyr Lys Asn Pro Lys Leu Thr Arg
            260                 265                 270

Met Leu Thr Ala Lys Phe Tyr Met Pro Lys Lys Ala Thr Glu Leu Lys
            275                 280                 285

His Leu Gln Cys Leu Glu Glu Glu Leu Lys Pro Leu Glu Glu Val Leu
290                 295                 300

Asn Leu Ala Gln Ser Lys Asn Phe His Leu Arg Pro Arg Asp Leu Ile
305                 310                 315                 320

Ser Asn Ile Asn Val Ile Val Leu Glu Leu Lys Gly Ser Glu Thr Thr
                325                 330                 335

Phe Met Cys Glu Tyr Ala Asp Glu Thr Ala Thr Ile Val Glu Phe Leu
            340                 345                 350

Asn Arg Trp Ile Thr Phe Ser Gln Ser Ile Ile Ser Thr Leu Thr Gly
            355                 360                 365

Gly Pro Leu Gly Met Leu Ser Gln Ser Glu Leu Cys Asp Asp Asp Pro
370                 375                 380

Pro Glu Ile Pro His Ala Thr Phe Lys Ala Met Ala Tyr Lys Glu Gly
385                 390                 395                 400

Thr Met Leu Asn Cys Glu Cys Lys Arg Gly Phe Arg Arg Ile Lys Ser
                405                 410                 415

Gly Ser Leu Tyr Met Leu Cys Thr Gly Asn Ser Ser His Ser Ser Trp
            420                 425                 430

Asp Asn Gln Cys Gln Cys Thr Ser Ser Ala Thr Arg Asn Thr Thr Lys
            435                 440                 445

Gln Val Thr Pro Gln Pro Glu Glu Gln Lys Glu Arg Lys Thr Thr Glu
450                 455                 460

Met Gln Ser Pro Met Gln Pro Val Asp Gln Ala Ser Leu Pro Gly His
465                 470                 475                 480

Cys Arg Glu Pro Pro Pro Trp Glu Asn Glu Ala Thr Glu Arg Ile Tyr
                485                 490                 495

His Phe Val Val Gly Gln Met Val Tyr Tyr Gln Cys Val Gln Gly Tyr
            500                 505                 510

Arg Ala Leu His Arg Gly Pro Ala Glu Ser Val Cys Lys Met Thr His
            515                 520                 525

Gly Lys Thr Arg Trp Thr Gln Pro Gln Leu Ile Cys Thr Gly
530                 535                 540

<210> SEQ ID NO 60
<211> LENGTH: 542
<212> TYPE: PRT
```

<213> ORGANISM: Artificial
<220> FEATURE:
<223> OTHER INFORMATION: P-0381

<400> SEQUENCE: 60

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Ser Ala Pro Thr Ser Ser Ser
225                 230                 235                 240

Thr Lys Lys Thr Gln Leu Gln Leu Glu His Leu Leu Leu Asp Leu Gln
                245                 250                 255

Met Ile Leu Asn Gly Ile Asn Asn Tyr Lys Asn Pro Lys Leu Thr Glu
            260                 265                 270

Met Leu Thr Ala Lys Phe Tyr Met Pro Lys Lys Ala Thr Glu Leu Lys
        275                 280                 285

His Leu Gln Cys Leu Glu Glu Glu Leu Lys Pro Leu Glu Glu Val Leu
    290                 295                 300

Asn Leu Ala Gln Ser Lys Asn Phe His Leu Arg Pro Arg Asp Leu Ile
305                 310                 315                 320

Ser Asn Ile Asn Val Ile Val Leu Glu Leu Lys Gly Ser Glu Thr Thr
                325                 330                 335

Phe Met Cys Glu Tyr Ala Asp Glu Thr Ala Thr Ile Val Glu Phe Leu
            340                 345                 350

Asn Arg Trp Ile Thr Phe Ser Gln Ser Ile Ile Ser Thr Leu Thr Gly
        355                 360                 365

Gly Pro Leu Gly Met Leu Ser Gln Ser Glu Leu Cys Asp Asp Pro
370                 375                 380

Pro Glu Ile Pro His Ala Thr Phe Lys Ala Met Ala Tyr Lys Glu Gly
```

```
                385                 390                 395                 400
Thr Met Leu Asn Cys Glu Cys Lys Arg Gly Phe Arg Arg Ile Lys Ser
                    405                 410                 415

Gly Ser Leu Tyr Met Leu Cys Thr Gly Asn Ser Ser His Ser Ser Trp
                420                 425                 430

Asp Asn Gln Cys Gln Cys Thr Ser Ser Ala Thr Arg Asn Thr Thr Lys
                435                 440                 445

Gln Val Thr Pro Gln Pro Glu Glu Lys Glu Arg Lys Thr Thr Glu
        450                 455                 460

Met Gln Ser Pro Met Gln Pro Val Asp Gln Ala Ser Leu Pro Gly His
465                 470                 475                 480

Cys Arg Glu Pro Pro Pro Trp Glu Asn Glu Ala Thr Glu Arg Ile Tyr
                    485                 490                 495

His Phe Val Val Gly Gln Met Val Tyr Tyr Gln Cys Val Gln Gly Tyr
                500                 505                 510

Arg Ala Leu His Arg Gly Pro Ala Glu Ser Val Cys Lys Met Thr His
                515                 520                 525

Gly Lys Thr Arg Trp Thr Gln Pro Gln Leu Ile Cys Thr Gly
        530                 535                 540

<210> SEQ ID NO 61
<211> LENGTH: 542
<212> TYPE: PRT
<213> ORGANISM: Artificial
<220> FEATURE:
<223> OTHER INFORMATION: P-0383

<400> SEQUENCE: 61

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
```

|     |     |     |     |     | 210 |     |     |     |     | 215 |     |     |     |     | 220 |     |     |

Pro Gly Gly Gly Ser Gly Gly Ser Ala Pro Thr Ser Ser Ser
225                 230                 235                 240

Thr Lys Lys Thr Gln Leu Gln Leu Glu His Leu Leu Leu Asp Leu Gln
                245                 250                 255

Met Ile Leu Asn Gly Ile Asn Asn Tyr Lys Asn Pro Lys Leu Thr Glu
            260                 265                 270

Met Leu Thr Phe Lys Phe Tyr Met Pro Lys Lys Ala Thr Glu Leu Lys
        275                 280                 285

His Leu Gln Cys Leu Glu Glu Glu Leu Lys Pro Leu Glu Glu Val Leu
    290                 295                 300

Asn Leu Ala Gln Ser Lys Asn Phe His Leu Arg Pro Arg Asp Leu Ile
305                 310                 315                 320

Ser Asn Ile Asn Val Ile Val Leu Glu Leu Lys Gly Ser Glu Thr Thr
                325                 330                 335

Phe Met Cys Glu Tyr Ala Asp Glu Thr Ala Thr Ile Val Glu Phe Leu
            340                 345                 350

Asn Arg Trp Ile Thr Phe Ser Gln Ser Ile Ile Ser Thr Leu Thr Gly
        355                 360                 365

Gly Pro Leu Gly Met Leu Ser Gln Ser Glu Leu Cys Asp Asp Asp Pro
    370                 375                 380

Pro Glu Ile Pro His Ala Thr Phe Lys Ala Met Ala Tyr Lys Glu Gly
385                 390                 395                 400

Thr Met Leu Asn Cys Glu Cys Lys Arg Gly Phe Arg Arg Ile Lys Ser
                405                 410                 415

Gly Ser Leu Tyr Met Leu Cys Thr Gly Asn Ser Ser His Ser Ser Trp
            420                 425                 430

Asp Asn Gln Cys Gln Cys Thr Ser Ser Ala Thr Arg Asn Thr Thr Lys
        435                 440                 445

Gln Val Thr Pro Gln Pro Glu Glu Gln Lys Glu Arg Lys Thr Thr Glu
    450                 455                 460

Met Gln Ser Pro Met Gln Pro Val Asp Gln Ala Ser Leu Pro Gly His
465                 470                 475                 480

Cys Arg Glu Pro Pro Pro Trp Glu Asn Glu Ala Thr Glu Arg Ile Tyr
                485                 490                 495

His Phe Val Val Gly Gln Met Val Tyr Tyr Gln Cys Val Gln Gly Tyr
            500                 505                 510

Arg Ala Leu His Arg Gly Pro Ala Glu Ser Val Cys Lys Met Thr His
        515                 520                 525

Gly Lys Thr Arg Trp Thr Gln Pro Gln Leu Ile Cys Thr Gly
    530                 535                 540

<210> SEQ ID NO 62
<211> LENGTH: 555
<212> TYPE: PRT
<213> ORGANISM: Artificial
<220> FEATURE:
<223> OTHER INFORMATION: P-0329

<400> SEQUENCE: 62

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly

```
            35                  40                  45
Asn Ser Ser His Ser Ser Trp Asp Asn Gln Cys Gln Cys Thr Ser Ser
 50                  55                  60

Ala Thr Arg Asn Thr Thr Lys Gln Val Thr Pro Gln Pro Glu Glu Gln
 65                  70                  75                  80

Lys Glu Arg Lys Thr Thr Glu Met Gln Ser Pro Met Gln Pro Val Asp
                 85                  90                  95

Gln Ala Ser Leu Pro Gly His Cys Arg Glu Pro Pro Pro Trp Glu Asn
                100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
        130                 135                 140

Ser Val Cys Lys Met Thr His Gly Lys Thr Arg Trp Thr Gln Pro Gln
145                 150                 155                 160

Leu Ile Cys Thr Gly Gly Gly Gly Ser Gly Gly Gly Ser Gly
                165                 170                 175

Gly Gly Gly Ser Ala Pro Thr Ser Ser Ser Thr Lys Lys Thr Gln Leu
            180                 185                 190

Gln Leu Glu His Leu Leu Leu Asp Leu Gln Met Ile Leu Asn Gly Ile
        195                 200                 205

Asn Asn Tyr Lys Asn Pro Lys Leu Thr Arg Met Leu Thr Phe Lys Phe
    210                 215                 220

Tyr Met Pro Lys Lys Ala Thr Glu Leu Lys His Leu Gln Cys Leu Glu
225                 230                 235                 240

Glu Glu Leu Lys Pro Leu Glu Glu Val Leu Asn Leu Ala Gln Ser Lys
                245                 250                 255

Asn Phe His Leu Arg Pro Arg Asp Leu Ile Ser Asn Ile Asn Val Ile
            260                 265                 270

Val Leu Glu Leu Lys Gly Ser Glu Thr Thr Phe Met Cys Glu Tyr Ala
        275                 280                 285

Asp Glu Thr Ala Thr Ile Val Glu Phe Leu Asn Arg Trp Ile Thr Phe
    290                 295                 300

Ser Gln Ser Ile Ile Ser Thr Leu Thr Gly Gly Gly Gly Ser Leu Gly
305                 310                 315                 320

Gly Ser Gly Arg Ser Ala Asn Ala Ile Leu Glu Gly Gly Ser Cys Pro
                325                 330                 335

Pro Cys Pro Ala Pro Glu Ala Ala Gly Ala Pro Ser Val Phe Leu Phe
            340                 345                 350

Pro Pro Lys Pro Lys Asp Thr Leu Met Ile Ser Arg Thr Pro Glu Val
        355                 360                 365

Thr Cys Val Val Val Asp Val Ser His Glu Asp Pro Glu Val Lys Phe
    370                 375                 380

Asn Trp Tyr Val Asp Gly Val Glu Val His Asn Ala Lys Thr Lys Pro
385                 390                 395                 400

Arg Glu Glu Gln Tyr Asn Ser Thr Tyr Arg Val Val Ser Val Leu Thr
                405                 410                 415

Val Leu His Gln Asp Trp Leu Asn Gly Lys Glu Tyr Lys Cys Lys Val
            420                 425                 430

Ser Asn Lys Ala Leu Pro Ala Pro Ile Glu Lys Thr Ile Ser Lys Ala
        435                 440                 445

Lys Gly Gln Pro Arg Glu Pro Gln Val Tyr Thr Leu Pro Pro Ser Arg
    450                 455                 460
```

```
Asp Glu Leu Thr Lys Asn Gln Val Ser Leu Thr Cys Leu Val Lys Gly
465                 470                 475                 480

Phe Tyr Pro Ser Asp Ile Ala Val Glu Trp Glu Ser Asn Gly Gln Pro
                485                 490                 495

Glu Asn Asn Tyr Lys Thr Thr Pro Pro Val Leu Asp Ser Asp Gly Ser
            500                 505                 510

Phe Phe Leu Tyr Ser Lys Leu Thr Val Asp Lys Ser Arg Trp Gln Gln
        515                 520                 525

Gly Asn Val Phe Ser Cys Ser Val Met His Glu Ala Leu His Asn His
    530                 535                 540

Tyr Thr Gln Lys Ser Leu Ser Leu Ser Pro Gly
545                 550                 555

<210> SEQ ID NO 63
<211> LENGTH: 549
<212> TYPE: PRT
<213> ORGANISM: Artificial
<220> FEATURE:
<223> OTHER INFORMATION: P-0401

<400> SEQUENCE: 63

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
                20                  25                  30

Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Gly Gly Pro Leu Gly Met Leu Ser Gln Ser Ala
                165                 170                 175

Pro Thr Ser Ser Ser Thr Lys Lys Thr Gln Leu Gln Leu Glu His Leu
            180                 185                 190

Leu Leu Asp Leu Gln Met Ile Leu Asn Gly Ile Asn Asn Tyr Lys Asn
        195                 200                 205

Pro Lys Leu Thr Arg Met Leu Thr Phe Lys Phe Tyr Met Pro Lys Lys
    210                 215                 220

Ala Thr Glu Leu Lys His Leu Gln Cys Leu Glu Glu Glu Leu Lys Pro
225                 230                 235                 240

Leu Glu Glu Val Leu Asn Leu Ala Gln Ser Lys Asn Phe His Leu Arg
                245                 250                 255

Pro Arg Asp Leu Ile Ser Asn Ile Asn Val Ile Val Leu Glu Leu Lys
            260                 265                 270
```

Gly Ser Glu Thr Thr Phe Met Cys Glu Tyr Ala Asp Glu Thr Ala Thr
        275                 280                 285

Ile Val Glu Phe Leu Asn Arg Trp Ile Thr Phe Ser Gln Ser Ile Ile
290                 295                 300

Ser Thr Leu Thr Gly Gly Gly Ser Gly Gly Gly Ser Gly Gly
305                 310                 315                 320

Gly Gly Ser Gly Gly Gly Gly Ser Cys Pro Pro Cys Pro Ala Pro Glu
                325                 330                 335

Ala Ala Gly Ala Pro Ser Val Phe Leu Phe Pro Pro Lys Pro Lys Asp
                340                 345                 350

Thr Leu Met Ile Ser Arg Thr Pro Glu Val Thr Cys Val Val Val Asp
            355                 360                 365

Val Ser His Glu Asp Pro Glu Val Lys Phe Asn Trp Tyr Val Asp Gly
        370                 375                 380

Val Glu Val His Asn Ala Lys Thr Lys Pro Arg Glu Glu Gln Tyr Asn
385                 390                 395                 400

Ser Thr Tyr Arg Val Val Ser Val Leu Thr Val Leu His Gln Asp Trp
                405                 410                 415

Leu Asn Gly Lys Glu Tyr Lys Cys Lys Val Ser Asn Lys Ala Leu Pro
            420                 425                 430

Ala Pro Ile Glu Lys Thr Ile Ser Lys Ala Lys Gly Gln Pro Arg Glu
        435                 440                 445

Pro Gln Val Tyr Thr Leu Pro Pro Ser Arg Asp Glu Leu Thr Lys Asn
    450                 455                 460

Gln Val Ser Leu Thr Cys Leu Val Lys Gly Phe Tyr Pro Ser Asp Ile
465                 470                 475                 480

Ala Val Glu Trp Glu Ser Asn Gly Gln Pro Glu Asn Asn Tyr Lys Thr
                485                 490                 495

Thr Pro Pro Val Leu Asp Ser Asp Gly Ser Phe Phe Leu Tyr Ser Lys
            500                 505                 510

Leu Thr Val Asp Lys Ser Arg Trp Gln Gln Gly Asn Val Phe Ser Cys
        515                 520                 525

Ser Val Met His Glu Ala Leu His Asn His Tyr Thr Gln Lys Ser Leu
    530                 535                 540

Ser Leu Ser Pro Gly
545

<210> SEQ ID NO 64
<211> LENGTH: 554
<212> TYPE: PRT
<213> ORGANISM: Artificial
<220> FEATURE:
<223> OTHER INFORMATION: P-0402

<400> SEQUENCE: 64

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
                20                  25                  30

Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser Ser
        50                  55                  60

Ala Thr Arg Asn Thr Thr Lys Gln Val Thr Pro Gln Pro Glu Glu Gln
65                  70                  75                  80

```
Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
        130                 135                 140

Ser Val Cys Lys Met Thr His Gly Lys Thr Arg Trp Thr Gln Pro Gln
145                 150                 155                 160

Leu Ile Cys Thr Gly Gly Ser Gly Pro Leu Gly Met Leu Ser Gln
                165                 170                 175

Gly Gly Gly Ser Ala Pro Thr Ser Ser Ser Thr Lys Lys Thr Gln Leu
            180                 185                 190

Gln Leu Glu His Leu Leu Leu Asp Leu Gln Met Ile Leu Asn Gly Ile
        195                 200                 205

Asn Asn Tyr Lys Asn Pro Lys Leu Thr Arg Met Leu Thr Phe Lys Phe
    210                 215                 220

Tyr Met Pro Lys Lys Ala Thr Glu Leu Lys His Leu Gln Cys Leu Glu
225                 230                 235                 240

Glu Glu Leu Lys Pro Leu Glu Glu Val Leu Asn Leu Ala Gln Ser Lys
                245                 250                 255

Asn Phe His Leu Arg Pro Arg Asp Leu Ile Ser Asn Ile Asn Val Ile
            260                 265                 270

Val Leu Glu Leu Lys Gly Ser Glu Thr Thr Phe Met Cys Glu Tyr Ala
        275                 280                 285

Asp Glu Thr Ala Thr Ile Val Glu Phe Leu Asn Arg Trp Ile Thr Phe
    290                 295                 300

Ser Gln Ser Ile Ile Ser Thr Leu Thr Gly Gly Gly Ser Gly Gly
305                 310                 315                 320

Gly Gly Ser Gly Gly Gly Ser Gly Gly Gly Ser Cys Pro Pro
                325                 330                 335

Cys Pro Ala Pro Glu Ala Ala Gly Ala Pro Ser Val Phe Leu Phe Pro
            340                 345                 350

Pro Lys Pro Lys Asp Thr Leu Met Ile Ser Arg Thr Pro Glu Val Thr
        355                 360                 365

Cys Val Val Val Asp Val Ser His Glu Asp Pro Glu Val Lys Phe Asn
    370                 375                 380

Trp Tyr Val Asp Gly Val Glu Val His Asn Ala Lys Thr Lys Pro Arg
385                 390                 395                 400

Glu Glu Gln Tyr Asn Ser Thr Tyr Arg Val Val Ser Val Leu Thr Val
                405                 410                 415

Leu His Gln Asp Trp Leu Asn Gly Lys Glu Tyr Lys Cys Lys Val Ser
            420                 425                 430

Asn Lys Ala Leu Pro Ala Pro Ile Glu Lys Thr Ile Ser Lys Ala Lys
        435                 440                 445

Gly Gln Pro Arg Glu Pro Gln Val Tyr Thr Leu Pro Pro Ser Arg Asp
    450                 455                 460

Glu Leu Thr Lys Asn Gln Val Ser Leu Thr Cys Leu Val Lys Gly Phe
465                 470                 475                 480

Tyr Pro Ser Asp Ile Ala Val Glu Trp Glu Ser Asn Gly Gln Pro Glu
                485                 490                 495
```

```
Asn Asn Tyr Lys Thr Thr Pro Pro Val Leu Asp Ser Asp Gly Ser Phe
            500             505             510

Phe Leu Tyr Ser Lys Leu Thr Val Asp Lys Ser Arg Trp Gln Gln Gly
        515             520             525

Asn Val Phe Ser Cys Ser Val Met His Glu Ala Leu His Asn His Tyr
    530             535             540

Thr Gln Lys Ser Leu Ser Leu Ser Pro Gly
545             550

<210> SEQ ID NO 65
<211> LENGTH: 546
<212> TYPE: PRT
<213> ORGANISM: Artificial
<220> FEATURE:
<223> OTHER INFORMATION: P-0403

<400> SEQUENCE: 65

Glu Leu Cys Asp Asp Pro Pro Glu Ile Pro His Ala Thr Phe Lys
1               5               10              15

Ala Met Ala Tyr Lys Glu Gly Thr Met Leu Asn Cys Glu Cys Lys Arg
            20              25              30

Gly Phe Arg Arg Ile Lys Ser Gly Ser Leu Tyr Met Leu Cys Thr Gly
        35              40              45

Asn Ser Ser His Ser Ser Trp Asp Asn Gln Cys Gln Cys Thr Ser Ser
    50              55              60

Ala Thr Arg Asn Thr Thr Lys Gln Val Thr Pro Gln Pro Glu Glu Gln
65              70              75              80

Lys Glu Arg Lys Thr Thr Glu Met Gln Ser Pro Met Gln Pro Val Asp
            85              90              95

Gln Ala Ser Leu Pro Gly His Cys Arg Glu Pro Pro Pro Trp Glu Asn
        100             105             110

Glu Ala Thr Glu Arg Ile Tyr His Phe Val Val Gly Gln Met Val Tyr
    115             120             125

Tyr Gln Cys Val Gln Gly Tyr Arg Ala Leu His Arg Gly Pro Ala Glu
    130             135             140

Ser Val Cys Lys Met Thr His Gly Lys Thr Arg Trp Thr Gln Pro Gln
145             150             155             160

Leu Ile Cys Thr Gly Gly Gly Pro Leu Gly Met Leu Ser Gln Ser Ala
            165             170             175

Pro Thr Ser Ser Ser Thr Lys Lys Thr Gln Leu Gln Leu Glu His Leu
        180             185             190

Leu Leu Asp Leu Gln Met Ile Leu Asn Gly Ile Asn Asn Tyr Lys Asn
    195             200             205

Pro Lys Leu Thr Arg Met Leu Thr Phe Lys Phe Tyr Met Pro Lys Lys
    210             215             220

Ala Thr Glu Leu Lys His Leu Gln Cys Leu Glu Glu Glu Leu Lys Pro
225             230             235             240

Leu Glu Glu Val Leu Asn Leu Ala Gln Ser Lys Asn Phe His Leu Arg
            245             250             255

Pro Arg Asp Leu Ile Ser Asn Ile Asn Val Ile Val Leu Glu Leu Lys
        260             265             270

Gly Ser Glu Thr Thr Phe Met Cys Glu Tyr Ala Asp Glu Thr Ala Thr
    275             280             285

Ile Val Glu Phe Leu Asn Arg Trp Ile Thr Phe Ser Gln Ser Ile Ile
    290             295             300
```

-continued

Ser Thr Leu Thr Ala Glu Ala Ala Lys Glu Ala Ala Lys Glu
305                 310                 315                 320

Ala Ala Ala Lys Ala Cys Pro Pro Cys Pro Ala Pro Glu Ala Ala Gly
                325                 330                 335

Ala Pro Ser Val Phe Leu Phe Pro Pro Lys Pro Lys Asp Thr Leu Met
            340                 345                 350

Ile Ser Arg Thr Pro Glu Val Thr Cys Val Val Val Asp Val Ser His
        355                 360                 365

Glu Asp Pro Glu Val Lys Phe Asn Trp Tyr Val Asp Gly Val Glu Val
    370                 375                 380

His Asn Ala Lys Thr Lys Pro Arg Glu Glu Gln Tyr Asn Ser Thr Tyr
385                 390                 395                 400

Arg Val Val Ser Val Leu Thr Val Leu His Gln Asp Trp Leu Asn Gly
                405                 410                 415

Lys Glu Tyr Lys Cys Lys Val Ser Asn Lys Ala Leu Pro Ala Pro Ile
            420                 425                 430

Glu Lys Thr Ile Ser Lys Ala Lys Gly Gln Pro Arg Glu Pro Gln Val
        435                 440                 445

Tyr Thr Leu Pro Pro Ser Arg Asp Glu Leu Thr Lys Asn Gln Val Ser
    450                 455                 460

Leu Thr Cys Leu Val Lys Gly Phe Tyr Pro Ser Asp Ile Ala Val Glu
465                 470                 475                 480

Trp Glu Ser Asn Gly Gln Pro Glu Asn Asn Tyr Lys Thr Thr Pro Pro
                485                 490                 495

Val Leu Asp Ser Asp Gly Ser Phe Phe Leu Tyr Ser Lys Leu Thr Val
            500                 505                 510

Asp Lys Ser Arg Trp Gln Gln Gly Asn Val Phe Ser Cys Ser Val Met
        515                 520                 525

His Glu Ala Leu His Asn His Tyr Thr Gln Lys Ser Leu Ser Leu Ser
    530                 535                 540

Pro Gly
545

<210> SEQ ID NO 66
<211> LENGTH: 405
<212> TYPE: PRT
<213> ORGANISM: Artificial
<220> FEATURE:
<223> OTHER INFORMATION: Hole-Fc-15p1

<400> SEQUENCE: 66

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Glu Pro Lys Ser Ser Asp Lys Thr His Thr Ser Pro Pro Ser
225                 230                 235                 240

Pro Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
            260                 265                 270

His Pro Ser Cys Lys Val Thr Ala Met Lys Cys Phe Leu Leu Glu Leu
        275                 280                 285

Gln Val Ile Ser Leu Glu Ser Gly Asp Ala Ser Ile His Asp Thr Val
    290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
            340                 345                 350

Asn Thr Ser Gly Gly Gly Ser Leu Gly Gly Ser Gly Arg Ser Ala Asn
        355                 360                 365

Ala Ile Leu Glu Gly Gly Gly Ser Gly Gly Ser Gly Gly Gly Gly Ser
370                 375                 380

Ile Tyr Asn Cys Glu Ile Ser Gln Ala Ser His Tyr Phe Glu Arg His
385                 390                 395                 400

Leu Cys Tyr Ser Ile
                405

<210> SEQ ID NO 67
<211> LENGTH: 407
<212> TYPE: PRT
<213> ORGANISM: Artificial
<220> FEATURE:
<223> OTHER INFORMATION: Hole-Fc-15p2

<400> SEQUENCE: 67

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Glu Pro Lys Ser Ser Asp Lys Thr His Thr Ser Pro Pro Ser
225                 230                 235                 240

Pro Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
            260                 265                 270

His Pro Ser Cys Lys Val Thr Ala Met Lys Cys Phe Leu Leu Glu Leu
        275                 280                 285

Gln Val Ile Ser Leu Glu Ser Gly Asp Ala Ser Ile His Asp Thr Val
    290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
            340                 345                 350

Asn Thr Ser Gly Gly Ser Leu Gly Gly Ser Gly Arg Ser Ala Asn
        355                 360                 365

Ala Ile Leu Glu Gly Gly Ser Gly Gly Ser Gly Gly Ser
370                 375                 380

Ile Tyr Asn Cys Glu Leu His Arg Glu Phe Tyr His Ser Ala Gln Ser
385                 390                 395                 400

Ile Glu Trp Cys Tyr Ser Ile
            405

<210> SEQ ID NO 68
<211> LENGTH: 417
<212> TYPE: PRT
<213> ORGANISM: Artificial
<220> FEATURE:
<223> OTHER INFORMATION: Hole-Fc-15p3

<400> SEQUENCE: 68

Asp Lys Thr His Thr Cys Pro Pro Cys Pro Ala Pro Glu Ala Ala Gly
1               5                   10                  15

```
Ala Pro Ser Val Phe Leu Phe Pro Lys Pro Lys Asp Thr Leu Met
             20                  25                  30

Ile Ser Arg Thr Pro Glu Val Thr Cys Val Val Asp Val Ser His
         35                  40                  45

Glu Asp Pro Glu Val Lys Phe Asn Trp Tyr Val Asp Gly Val Glu Val
 50                      55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
             100                 105                 110

Glu Lys Thr Ile Ser Lys Ala Lys Gly Gln Pro Arg Glu Pro Gln Val
         115                 120                 125

Tyr Thr Leu Pro Pro Cys Arg Glu Glu Met Thr Lys Asn Gln Val Ser
         130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                 165                 170                 175

Val Leu Asp Ser Asp Gly Ser Phe Phe Leu Val Ser Lys Leu Thr Val
             180                 185                 190

Asp Lys Ser Arg Trp Gln Gln Gly Asn Val Phe Ser Cys Ser Val Met
         195                 200                 205

His Glu Ala Leu His Asn His Tyr Thr Gln Lys Ser Leu Ser Leu Ser
 210                 215                 220

Pro Gly Glu Pro Lys Ser Ser Asp Lys Thr His Thr Ser Pro Pro Ser
225                 230                 235                 240

Pro Asn Trp Val Asn Val Ile Ser Asp Leu Lys Lys Ile Glu Asp Leu
                 245                 250                 255

Ile Gln Ser Met His Ile Asp Ala Thr Leu Tyr Thr Glu Ser Asp Val
             260                 265                 270

His Pro Ser Cys Lys Val Thr Ala Met Lys Cys Phe Leu Leu Glu Leu
         275                 280                 285

Gln Val Ile Ser Leu Glu Ser Gly Asp Ala Ser Ile His Asp Thr Val
 290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                 325                 330                 335

Ile Lys Glu Phe Leu Gln Ser Phe Val His Ile Val Gln Met Phe Ile
             340                 345                 350

Asn Thr Ser Gly Gly Gly Ser Leu Gly Gly Ser Gly Arg Ser Ala Asn
         355                 360                 365

Ala Ile Leu Glu Gly Gly Ser Gly Gly Ser Gly Gly Ser
 370                 375                 380

Glu Thr His Arg Cys Asn Ile Ser Trp Glu Ile Ser Gln Ala Ser His
385                 390                 395                 400

Tyr Phe Glu Arg His Leu Glu Phe Glu Ala Arg Thr Leu Cys Pro Gly
                 405                 410                 415

His

<210> SEQ ID NO 69
```

```
<211> LENGTH: 386
<212> TYPE: PRT
<213> ORGANISM: Artificial
<220> FEATURE:
<223> OTHER INFORMATION: p1'-15-Fc

<400> SEQUENCE: 69

Gln Gly Gln Ser Gly Gln Cys Glu Ile Ser Gln Ala Ser His Tyr Phe
1               5                   10                  15

Glu Arg His Leu Cys Tyr Ser Ile Gly Ser Ser Gly Ser Gly Gly
            20                  25                  30

Ser Gly Gly Ser Gly Leu Ser Gly Arg Ser Asp Asn His Gly Ser Ser
        35                  40                  45

Gly Thr Asn Trp Val Asn Val Ile Ser Asp Leu Lys Lys Ile Glu Asp
    50                  55                  60

Leu Ile Gln Ser Met His Ile Asp Ala Thr Leu Tyr Thr Glu Ser Asp
65                  70                  75                  80

Val His Pro Ser Cys Lys Val Thr Ala Met Lys Cys Phe Leu Leu Glu
                85                  90                  95

Leu Gln Val Ile Ser Leu Glu Ser Gly Asp Ala Ser Ile His Asp Thr
            100                 105                 110

Val Glu Asn Leu Ile Ile Leu Ala Asn Asn Ser Leu Ser Ser Asn Gly
        115                 120                 125

Asn Val Thr Glu Ser Gly Cys Lys Glu Cys Glu Glu Leu Glu Glu Lys
130                 135                 140

Asn Ile Lys Glu Phe Leu Gln Ser Phe Val His Ile Val Gln Met Phe
145                 150                 155                 160

Ile Asn Thr Ser Gly Cys Pro Pro Cys Pro Ala Pro Glu Ala Ala Gly
                165                 170                 175

Ala Pro Ser Val Phe Leu Phe Pro Pro Lys Pro Lys Asp Thr Leu Met
            180                 185                 190

Ile Ser Arg Thr Pro Glu Val Thr Cys Val Val Val Asp Val Ser His
        195                 200                 205

Glu Asp Pro Glu Val Lys Phe Asn Trp Tyr Val Asp Gly Val Glu Val
    210                 215                 220

His Asn Ala Lys Thr Lys Pro Arg Glu Glu Gln Tyr Asn Ser Thr Tyr
225                 230                 235                 240

Arg Val Val Ser Val Leu Thr Val Leu His Gln Asp Trp Leu Asn Gly
                245                 250                 255

Lys Glu Tyr Lys Cys Lys Val Ser Asn Lys Ala Leu Pro Ala Pro Ile
            260                 265                 270

Glu Lys Thr Ile Ser Lys Ala Lys Gly Gln Pro Arg Glu Pro Gln Val
        275                 280                 285

Tyr Thr Leu Pro Pro Cys Arg Glu Glu Met Thr Lys Asn Gln Val Ser
    290                 295                 300

Leu Ser Cys Ala Val Lys Gly Phe Tyr Pro Ser Asp Ile Ala Val Glu
305                 310                 315                 320

Trp Glu Ser Asn Gly Gln Pro Glu Asn Asn Tyr Lys Thr Thr Pro Pro
                325                 330                 335

Val Leu Asp Ser Asp Gly Ser Phe Phe Leu Val Ser Lys Leu Thr Val
            340                 345                 350

Asp Lys Ser Arg Trp Gln Gln Gly Asn Val Phe Ser Cys Ser Val Met
        355                 360                 365

His Glu Ala Leu His Asn His Tyr Thr Gln Lys Ser Leu Ser Leu Ser
    370                 375                 380
```

```
Pro Gly
385

<210> SEQ ID NO 70
<211> LENGTH: 397
<212> TYPE: PRT
<213> ORGANISM: Artificial
<220> FEATURE:
<223> OTHER INFORMATION: p3'-15-Fc

<400> SEQUENCE: 70

Gln Gly Gln Ser Gly Gln Cys Asn Ile Ser Trp Glu Ile Ser Gln Ala
1               5                   10                  15

Ser His Tyr Phe Glu Arg His Leu Glu Phe Glu Ala Arg Thr Leu Cys
            20                  25                  30

Pro Gly His Gly Ser Ser Gly Gly Ser Gly Gly Ser Gly Gly Ser Gly
        35                  40                  45

Leu Ser Gly Arg Ser Asp Asn His Gly Ser Ser Gly Thr Asn Trp Val
    50                  55                  60

Asn Val Ile Ser Asp Leu Lys Lys Ile Glu Asp Leu Ile Gln Ser Met
65                  70                  75                  80

His Ile Asp Ala Thr Leu Tyr Thr Glu Ser Asp Val His Pro Ser Cys
                85                  90                  95

Lys Val Thr Ala Met Lys Cys Phe Leu Leu Glu Leu Gln Val Ile Ser
            100                 105                 110

Leu Glu Ser Gly Asp Ala Ser Ile His Asp Thr Val Glu Asn Leu Ile
        115                 120                 125

Ile Leu Ala Asn Asn Ser Leu Ser Ser Asn Gly Asn Val Thr Glu Ser
    130                 135                 140

Gly Cys Lys Glu Cys Glu Glu Leu Glu Glu Lys Asn Ile Lys Glu Phe
145                 150                 155                 160

Leu Gln Ser Phe Val His Ile Val Gln Met Phe Ile Asn Thr Ser Gly
                165                 170                 175

Cys Pro Pro Cys Pro Ala Pro Glu Ala Ala Gly Ala Pro Ser Val Phe
            180                 185                 190

Leu Phe Pro Pro Lys Pro Lys Asp Thr Leu Met Ile Ser Arg Thr Pro
        195                 200                 205

Glu Val Thr Cys Val Val Val Asp Val Ser His Glu Asp Pro Glu Val
    210                 215                 220

Lys Phe Asn Trp Tyr Val Asp Gly Val Glu Val His Asn Ala Lys Thr
225                 230                 235                 240

Lys Pro Arg Glu Glu Gln Tyr Asn Ser Thr Tyr Arg Val Val Ser Val
                245                 250                 255

Leu Thr Val Leu His Gln Asp Trp Leu Asn Gly Lys Glu Tyr Lys Cys
            260                 265                 270

Lys Val Ser Asn Lys Ala Leu Pro Ala Pro Ile Glu Lys Thr Ile Ser
        275                 280                 285

Lys Ala Lys Gly Gln Pro Arg Glu Pro Gln Val Tyr Thr Leu Pro Pro
    290                 295                 300

Cys Arg Glu Glu Met Thr Lys Asn Gln Val Ser Leu Ser Cys Ala Val
305                 310                 315                 320

Lys Gly Phe Tyr Pro Ser Asp Ile Ala Val Glu Trp Glu Ser Asn Gly
                325                 330                 335

Gln Pro Glu Asn Asn Tyr Lys Thr Thr Pro Pro Val Leu Asp Ser Asp
            340                 345                 350
```

```
Gly Ser Phe Phe Leu Val Ser Lys Leu Thr Val Asp Lys Ser Arg Trp
        355                 360                 365

Gln Gln Gly Asn Val Phe Ser Cys Ser Val Met His Glu Ala Leu His
    370                 375                 380

Asn His Tyr Thr Gln Lys Ser Leu Ser Leu Ser Pro Gly
385                 390                 395

<210> SEQ ID NO 71
<211> LENGTH: 8
<212> TYPE: PRT
<213> ORGANISM: Artificial
<220> FEATURE:
<223> OTHER INFORMATION: Protease substrate peptide sequence

<400> SEQUENCE: 71

Ser Pro Leu Gly Leu Ala Gly Ser
1               5

<210> SEQ ID NO 72
<211> LENGTH: 8
<212> TYPE: PRT
<213> ORGANISM: Artificial
<220> FEATURE:
<223> OTHER INFORMATION: Protease substrate peptide sequence

<400> SEQUENCE: 72

Glu Pro Leu Glu Leu Arg Ala Gly
1               5

<210> SEQ ID NO 73
<211> LENGTH: 8
<212> TYPE: PRT
<213> ORGANISM: Artificial
<220> FEATURE:
<223> OTHER INFORMATION: Protease substrate peptide sequence

<400> SEQUENCE: 73

Leu Ser Gly Arg Ser Asp Asn His
1               5

<210> SEQ ID NO 74
<211> LENGTH: 8
<212> TYPE: PRT
<213> ORGANISM: Artificial
<220> FEATURE:
<223> OTHER INFORMATION: Protease substrate peptide sequence

<400> SEQUENCE: 74

Gly Pro Leu Gly Ile Ala Gly Gln
1               5

<210> SEQ ID NO 75
<211> LENGTH: 8
<212> TYPE: PRT
<213> ORGANISM: Artificial
<220> FEATURE:
<223> OTHER INFORMATION: Protease substrate peptide sequence

<400> SEQUENCE: 75

Gly Thr Ala His Leu Met Gly Gly
1               5

<210> SEQ ID NO 76
<211> LENGTH: 8
<212> TYPE: PRT
```

```
<213> ORGANISM: Artificial
<220> FEATURE:
<223> OTHER INFORMATION: Protease substrate peptide sequence

<400> SEQUENCE: 76

Arg Ile Gly Ser Leu Arg Thr Ala
1               5

<210> SEQ ID NO 77
<211> LENGTH: 8
<212> TYPE: PRT
<213> ORGANISM: Artificial
<220> FEATURE:
<223> OTHER INFORMATION: Protease substrate peptide sequence

<400> SEQUENCE: 77

Gly Pro Leu Gly Met Leu Ser Gln
1               5

<210> SEQ ID NO 78
<211> LENGTH: 8
<212> TYPE: PRT
<213> ORGANISM: Artificial
<220> FEATURE:
<223> OTHER INFORMATION: Protease substrate peptide sequence

<400> SEQUENCE: 78

Arg Pro Ser Ala Ser Arg Ser Ala
1               5

<210> SEQ ID NO 79
<211> LENGTH: 6
<212> TYPE: PRT
<213> ORGANISM: Artificial
<220> FEATURE:
<223> OTHER INFORMATION: Protease substrate peptide sequence

<400> SEQUENCE: 79

Pro Leu Gly Leu Ala Gly
1               5

<210> SEQ ID NO 80
<211> LENGTH: 13
<212> TYPE: PRT
<213> ORGANISM: Artificial
<220> FEATURE:
<223> OTHER INFORMATION: Protease substrate peptide sequence

<400> SEQUENCE: 80

Leu Gly Gly Ser Gly Arg Ser Ala Asn Ala Ile Leu Glu
1               5                   10

<210> SEQ ID NO 81
<211> LENGTH: 10
<212> TYPE: PRT
<213> ORGANISM: Artificial
<220> FEATURE:
<223> OTHER INFORMATION: Protease substrate peptide sequence

<400> SEQUENCE: 81

Gly Gly Ser Gly Arg Ser Ala Asn Ala Ile
1               5                   10

<210> SEQ ID NO 82
<211> LENGTH: 5
<212> TYPE: PRT
<213> ORGANISM: Artificial
```

```
<220> FEATURE:
<223> OTHER INFORMATION: Protease substrate peptide sequence

<400> SEQUENCE: 82

Ser Gly Arg Ser Ala
1               5

<210> SEQ ID NO 83
<211> LENGTH: 4
<212> TYPE: PRT
<213> ORGANISM: Artificial
<220> FEATURE:
<223> OTHER INFORMATION: Protease substrate peptide sequence

<400> SEQUENCE: 83

Ala Ala Asn Leu
1

<210> SEQ ID NO 84
<211> LENGTH: 4
<212> TYPE: PRT
<213> ORGANISM: Artificial
<220> FEATURE:
<223> OTHER INFORMATION: Protease substrate peptide sequence

<400> SEQUENCE: 84

Gly Phe Phe Tyr
1

<210> SEQ ID NO 85
<211> LENGTH: 8
<212> TYPE: PRT
<213> ORGANISM: Artificial
<220> FEATURE:
<223> OTHER INFORMATION: Protease substrate peptide sequence

<400> SEQUENCE: 85

Gly Pro Ile Cys Phe Arg Leu Gly
1               5

<210> SEQ ID NO 86
<211> LENGTH: 7
<212> TYPE: PRT
<213> ORGANISM: Artificial
<220> FEATURE:
<223> OTHER INFORMATION: Protease substrate peptide sequence

<400> SEQUENCE: 86

Arg Gln Ala Gly Phe Ser Leu
1               5

<210> SEQ ID NO 87
<211> LENGTH: 6
<212> TYPE: PRT
<213> ORGANISM: Artificial
<220> FEATURE:
<223> OTHER INFORMATION: Protease substrate peptide sequence

<400> SEQUENCE: 87

His Ser Ser Lys Leu Gln
1               5

<210> SEQ ID NO 88
<211> LENGTH: 30
<212> TYPE: PRT
<213> ORGANISM: Artificial
<220> FEATURE:
```

<223> OTHER INFORMATION: Protease cleavable linker sequence

<400> SEQUENCE: 88

Gly Gly Gly Ser Gly Gly Gly Ser Gly Gly Gly Ser Leu Ser
1               5                   10                  15
Gly Arg Ser Asp Asn His Gly Ser Gly Gly Gly Ser
            20                  25                  30

<210> SEQ ID NO 89
<211> LENGTH: 15
<212> TYPE: PRT
<213> ORGANISM: Artificial
<220> FEATURE:
<223> OTHER INFORMATION: Protease cleavable linker sequence

<400> SEQUENCE: 89

Gly Ser Ser Ser Gly Arg Ser Glu Asn Ile Arg Thr Ala Gly Thr
1               5                   10                  15

<210> SEQ ID NO 90
<211> LENGTH: 35
<212> TYPE: PRT
<213> ORGANISM: Artificial
<220> FEATURE:
<223> OTHER INFORMATION: Protease cleavable linker sequence

<400> SEQUENCE: 90

Gly Gly Gly Gly Ser Gly Gly Gly Gly Ser Gly Gly Gly Ser Leu Gly
1               5                   10                  15
Gly Ser Gly Arg Ser Ala Asn Ala Ile Leu Glu Gly Ser Gly Gly
            20                  25                  30
Gly Gly Ser
        35

<210> SEQ ID NO 91
<211> LENGTH: 28
<212> TYPE: PRT
<213> ORGANISM: Artificial
<220> FEATURE:
<223> OTHER INFORMATION: Protease cleavable linker sequence

<400> SEQUENCE: 91

Gly Gly Gly Gly Ser Gly Gly Gly Gly Ser Leu Gly Ser Gly Arg
1               5                   10                  15
Ser Ala Asn Ala Ile Leu Glu Gly Gly Gly Ser
            20                  25

<210> SEQ ID NO 92
<211> LENGTH: 21
<212> TYPE: PRT
<213> ORGANISM: Artificial
<220> FEATURE:
<223> OTHER INFORMATION: Protease cleavable linker sequence

<400> SEQUENCE: 92

Gly Gly Gly Gly Ser Leu Gly Gly Ser Gly Arg Ser Ala Asn Ala Ile
1               5                   10                  15
Leu Glu Gly Gly Ser
            20

<210> SEQ ID NO 93
<211> LENGTH: 14
<212> TYPE: PRT
<213> ORGANISM: Artificial

```
<220> FEATURE:
<223> OTHER INFORMATION: Protease cleavable linker sequence

<400> SEQUENCE: 93

Gly Gly Gly Ser Gly Pro Thr Asn Lys Val Arg Gly Gly Ser
1               5                   10

<210> SEQ ID NO 94
<211> LENGTH: 15
<212> TYPE: PRT
<213> ORGANISM: Artificial
<220> FEATURE:
<223> OTHER INFORMATION: Protease cleavable linker sequence

<400> SEQUENCE: 94

Gly Gly Ser Gly Pro Leu Gly Met Leu Ser Gln Gly Gly Gly Ser
1               5                   10                  15

<210> SEQ ID NO 95
<211> LENGTH: 10
<212> TYPE: PRT
<213> ORGANISM: Artificial
<220> FEATURE:
<223> OTHER INFORMATION: Protease cleavable linker sequence

<400> SEQUENCE: 95

Gly Gly Pro Leu Gly Met Leu Ser Gln Ser
1               5                   10

<210> SEQ ID NO 96
<211> LENGTH: 13
<212> TYPE: PRT
<213> ORGANISM: Artificial
<220> FEATURE:
<223> OTHER INFORMATION: Protease cleavable linker sequence

<400> SEQUENCE: 96

Gly Gly Gly Pro Leu Gly Met Leu Ser Gln Gly Gly Ser
1               5                   10

<210> SEQ ID NO 97
<211> LENGTH: 15
<212> TYPE: PRT
<213> ORGANISM: Artificial
<220> FEATURE:
<223> OTHER INFORMATION: Peptide sequence

<400> SEQUENCE: 97

Leu Gly Ala Pro Asp Ser Gln Lys Leu Thr Thr Val Asp Ile Val
1               5                   10                  15

<210> SEQ ID NO 98
<211> LENGTH: 13
<212> TYPE: PRT
<213> ORGANISM: Artificial
<220> FEATURE:
<223> OTHER INFORMATION: Peptide sequence

<400> SEQUENCE: 98

Glu Ile Ser Gln Ala Ser His Tyr Phe Glu Arg His Leu
1               5                   10

<210> SEQ ID NO 99
<211> LENGTH: 15
<212> TYPE: PRT
<213> ORGANISM: Artificial
<220> FEATURE:
```

```
<223> OTHER INFORMATION: Peptide sequence

<400> SEQUENCE: 99

Cys Glu Ile Ser Gln Ala Ser His Tyr Phe Glu Arg His Leu Cys
1               5                   10                  15

<210> SEQ ID NO 100
<211> LENGTH: 36
<212> TYPE: PRT
<213> ORGANISM: Artificial
<220> FEATURE:
<223> OTHER INFORMATION: Peptide sequence

<400> SEQUENCE: 100

Leu Gly Ala Pro Asp Ser Gln Lys Leu Thr Thr Val Asp Ile Val Gly
1               5                   10                  15

Gly Gly Gly Gly Gly Gly Glu Ile Ser Gln Ala Ser His Tyr Phe
            20                  25                  30

Glu Arg His Leu
        35

<210> SEQ ID NO 101
<211> LENGTH: 13
<212> TYPE: PRT
<213> ORGANISM: Artificial
<220> FEATURE:
<223> OTHER INFORMATION: Peptide sequence

<400> SEQUENCE: 101

Lys Pro Phe Glu Asn Leu Arg Leu Met Ala Pro Ile Ser
1               5                   10

<210> SEQ ID NO 102
<211> LENGTH: 50
<212> TYPE: PRT
<213> ORGANISM: Artificial
<220> FEATURE:
<223> OTHER INFORMATION: Peptide sequence

<400> SEQUENCE: 102

Gly Gly Gly Ser Leu Gly Gly Ser Gly Arg Ser Ala Asn Ala Ile Leu
1               5                   10                  15

Glu Gly Gly Gly Ser Gly Gly Gly Ser Gly Gly Gly Ser Ile Tyr Asn
            20                  25                  30

Cys Glu Ile Ser Gln Ala Ser His Tyr Phe Glu Arg His Leu Cys Tyr
        35                  40                  45

Ser Ile
    50

<210> SEQ ID NO 103
<211> LENGTH: 52
<212> TYPE: PRT
<213> ORGANISM: Artificial
<220> FEATURE:
<223> OTHER INFORMATION: Peptide sequence

<400> SEQUENCE: 103

Gly Gly Gly Ser Leu Gly Gly Ser Gly Arg Ser Ala Asn Ala Ile Leu
1               5                   10                  15

Glu Gly Gly Gly Ser Gly Gly Gly Ser Gly Gly Gly Ser Ile Tyr Asn
            20                  25                  30

Cys Glu Leu His Arg Glu Phe Tyr His Ser Ala Gln Ser Ile Glu Trp
        35                  40                  45
```

Cys Tyr Ser Ile
    50

<210> SEQ ID NO 104
<211> LENGTH: 62
<212> TYPE: PRT
<213> ORGANISM: Artificial
<220> FEATURE:
<223> OTHER INFORMATION: Peptide sequence

<400> SEQUENCE: 104

Gly Gly Gly Ser Leu Gly Gly Ser Gly Arg Ser Ala Asn Ala Ile Leu
1               5                   10                  15

Glu Gly Gly Gly Ser Gly Gly Gly Ser Gly Gly Gly Ser Glu Thr His
            20                  25                  30

Arg Cys Asn Ile Ser Trp Glu Ile Ser Gln Ala Ser His Tyr Phe Glu
        35                  40                  45

Arg His Leu Glu Phe Glu Ala Arg Thr Leu Cys Pro Gly His
    50                  55                  60

<210> SEQ ID NO 105
<211> LENGTH: 50
<212> TYPE: PRT
<213> ORGANISM: Artificial
<220> FEATURE:
<223> OTHER INFORMATION: Peptide sequence

<400> SEQUENCE: 105

Gln Gly Gln Ser Gly Gln Cys Glu Ile Ser Gln Ala Ser His Tyr Phe
1               5                   10                  15

Glu Arg His Leu Cys Tyr Ser Ile Gly Ser Ser Gly Ser Gly Gly
            20                  25                  30

Ser Gly Gly Ser Gly Leu Ser Gly Arg Ser Asp Asn His Gly Ser Ser
        35                  40                  45

Gly Thr
    50

<210> SEQ ID NO 106
<211> LENGTH: 61
<212> TYPE: PRT
<213> ORGANISM: Artificial
<220> FEATURE:
<223> OTHER INFORMATION: Peptide sequence

<400> SEQUENCE: 106

Gln Gly Gln Ser Gly Gln Cys Asn Ile Ser Trp Glu Ile Ser Gln Ala
1               5                   10                  15

Ser His Tyr Phe Glu Arg His Leu Glu Phe Glu Ala Arg Thr Leu Cys
            20                  25                  30

Pro Gly His Gly Ser Ser Gly Ser Gly Gly Ser Gly Gly Ser Gly
        35                  40                  45

Leu Ser Gly Arg Ser Asp Asn His Gly Ser Ser Gly Thr
    50                  55                  60

<210> SEQ ID NO 107
<211> LENGTH: 14
<212> TYPE: PRT
<213> ORGANISM: Artificial
<220> FEATURE:
<223> OTHER INFORMATION: Non-cleavable linker sequence

<400> SEQUENCE: 107

Glu Pro Lys Ser Ser Asp Lys Thr His Thr Ser Pro Pro Ser
1               5                   10

<210> SEQ ID NO 108
<211> LENGTH: 12
<212> TYPE: PRT
<213> ORGANISM: Artificial
<220> FEATURE:
<223> OTHER INFORMATION: Non-cleavable linker sequence

<400> SEQUENCE: 108

Gly Gly Gly Ser Gly Gly Gly Ser Gly Gly Gly Ser
1               5                   10

<210> SEQ ID NO 109
<211> LENGTH: 4
<212> TYPE: PRT
<213> ORGANISM: Artificial
<220> FEATURE:
<223> OTHER INFORMATION: Non-cleavable linker sequence

<400> SEQUENCE: 109

Gly Gly Gly Ser
1

<210> SEQ ID NO 110
<211> LENGTH: 13
<212> TYPE: PRT
<213> ORGANISM: Artificial
<220> FEATURE:
<223> OTHER INFORMATION: Non-cleavable linker sequence

<400> SEQUENCE: 110

Gly Ser Ser Gly Gly Ser Gly Gly Ser Gly Gly Ser Gly
1               5                   10

<210> SEQ ID NO 111
<211> LENGTH: 5
<212> TYPE: PRT
<213> ORGANISM: Artificial
<220> FEATURE:
<223> OTHER INFORMATION: Non-cleavable linker sequence

<400> SEQUENCE: 111

Gly Ser Ser Gly Thr
1               5

<210> SEQ ID NO 112
<211> LENGTH: 15
<212> TYPE: PRT
<213> ORGANISM: Artificial
<220> FEATURE:
<223> OTHER INFORMATION: Non-cleavable linker sequence

<400> SEQUENCE: 112

Gly Gly Gly Gly Ser Gly Gly Gly Gly Ser Gly Gly Gly Gly Ser
1               5                   10                  15

<210> SEQ ID NO 113
<211> LENGTH: 17
<212> TYPE: PRT
<213> ORGANISM: Artificial
<220> FEATURE:
<223> OTHER INFORMATION: Non-cleavable linker sequence

<400> SEQUENCE: 113

```
Ala Glu Ala Ala Ala Lys Glu Ala Ala Lys Glu Ala Ala Lys
1               5                   10                  15

Ala

<210> SEQ ID NO 114
<211> LENGTH: 20
<212> TYPE: PRT
<213> ORGANISM: Artificial
<220> FEATURE:
<223> OTHER INFORMATION: Non-cleavable linker sequence

<400> SEQUENCE: 114

Gly Gly Gly Gly Ser Gly Gly Gly Gly Ser Gly Gly Gly Gly Ser Gly
1               5                   10                  15

Gly Gly Gly Ser
            20

<210> SEQ ID NO 115
<211> LENGTH: 8
<212> TYPE: PRT
<213> ORGANISM: Artificial
<220> FEATURE:
<223> OTHER INFORMATION: Non-cleavable linker sequence

<400> SEQUENCE: 115

Gly Gly Gly Ser Gly Gly Gly Ser
1               5

<210> SEQ ID NO 116
<211> LENGTH: 2
<212> TYPE: PRT
<213> ORGANISM: Artificial
<220> FEATURE:
<223> OTHER INFORMATION: Non-cleavable linker sequence

<400> SEQUENCE: 116

Gly Ser
1

<210> SEQ ID NO 117
<211> LENGTH: 3
<212> TYPE: PRT
<213> ORGANISM: Artificial
<220> FEATURE:
<223> OTHER INFORMATION: Non-cleavable linker sequence

<400> SEQUENCE: 117

Gly Gly Ser
1

<210> SEQ ID NO 118
<211> LENGTH: 5
<212> TYPE: PRT
<213> ORGANISM: Artificial
<220> FEATURE:
<223> OTHER INFORMATION: Non-cleavable linker sequence

<400> SEQUENCE: 118

Gly Gly Gly Gly Ser
1               5

<210> SEQ ID NO 119
<211> LENGTH: 4
<212> TYPE: PRT
<213> ORGANISM: Artificial
<220> FEATURE:
```

```
<223> OTHER INFORMATION: Non-cleavable linker sequence

<400> SEQUENCE: 119

Gly Gly Ser Gly
1

<210> SEQ ID NO 120
<211> LENGTH: 4
<212> TYPE: PRT
<213> ORGANISM: Artificial
<220> FEATURE:
<223> OTHER INFORMATION: Non-cleavable linker sequence

<400> SEQUENCE: 120

Ser Gly Gly Gly
1

<210> SEQ ID NO 121
<211> LENGTH: 4
<212> TYPE: PRT
<213> ORGANISM: Artificial
<220> FEATURE:
<223> OTHER INFORMATION: Non-cleavable linker sequence

<400> SEQUENCE: 121

Gly Ser Gly Ser
1

<210> SEQ ID NO 122
<211> LENGTH: 6
<212> TYPE: PRT
<213> ORGANISM: Artificial
<220> FEATURE:
<223> OTHER INFORMATION: Non-cleavable linker sequence

<400> SEQUENCE: 122

Gly Ser Gly Ser Gly Ser
1               5

<210> SEQ ID NO 123
<211> LENGTH: 8
<212> TYPE: PRT
<213> ORGANISM: Artificial
<220> FEATURE:
<223> OTHER INFORMATION: Non-cleavable linker sequence

<400> SEQUENCE: 123

Gly Ser Gly Ser Gly Ser Gly Ser
1               5

<210> SEQ ID NO 124
<211> LENGTH: 10
<212> TYPE: PRT
<213> ORGANISM: Artificial
<220> FEATURE:
<223> OTHER INFORMATION: Non-cleavable linker sequence

<400> SEQUENCE: 124

Gly Ser Gly Ser Gly Ser Gly Ser Gly Ser
1               5                   10

<210> SEQ ID NO 125
<211> LENGTH: 12
<212> TYPE: PRT
<213> ORGANISM: Artificial
<220> FEATURE:
<223> OTHER INFORMATION: Non-cleavable linker sequence
```

```
<400> SEQUENCE: 125

Gly Ser Gly Ser Gly Ser Gly Ser Gly Ser
1               5                   10

<210> SEQ ID NO 126
<211> LENGTH: 10
<212> TYPE: PRT
<213> ORGANISM: Artificial
<220> FEATURE:
<223> OTHER INFORMATION: Non-cleavable linker sequence

<400> SEQUENCE: 126

Gly Gly Gly Gly Ser Gly Gly Gly Gly Ser
1               5                   10

<210> SEQ ID NO 127
<211> LENGTH: 15
<212> TYPE: PRT
<213> ORGANISM: Artificial
<220> FEATURE:
<223> OTHER INFORMATION: Non-cleavable linker sequence

<400> SEQUENCE: 127

Gly Gly Gly Gly Ser Gly Gly Gly Gly Ser Gly Gly Gly Gly Ser
1               5                   10                  15

<210> SEQ ID NO 128
<211> LENGTH: 676
<212> TYPE: PRT
<213> ORGANISM: Artificial
<220> FEATURE:
<223> OTHER INFORMATION: JS001-IL-15-VitoKine- HC

<400> SEQUENCE: 128

Gln Gly Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Val Ile Glu Ser Glu Thr Gly Thr Ala Tyr Asn Gln Lys Phe
        50                  55                  60

Lys Gly Arg Ala Lys Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Ile Thr Thr Val Ala Thr Thr Tyr Tyr Trp Tyr Phe
                100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
```

195                 200                 205
Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Ala Ala Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Gly Gly Gly Ser Leu Gly Gly Ser Gly
    450                 455                 460

Arg Ser Ala Asn Ala Ile Leu Glu Gly Gly Ser Asn Trp Val Asn Val
465                 470                 475                 480

Ile Ser Asp Leu Lys Lys Ile Glu Asp Leu Ile Gln Ser Met His Ile
                485                 490                 495

Asp Ala Thr Leu Tyr Thr Glu Ser Asp Val His Pro Ser Cys Lys Val
            500                 505                 510

Thr Ala Met Lys Cys Phe Leu Leu Glu Leu Gln Val Ile Ser Leu Glu
        515                 520                 525

Ser Gly Asp Ala Asp Ile His Asp Thr Val Glu Asn Leu Ile Ile Leu
    530                 535                 540

Ala Asn Asn Ser Leu Ser Ser Asn Gly Asn Val Thr Glu Ser Gly Cys
545                 550                 555                 560

Lys Glu Cys Glu Glu Leu Glu Glu Lys Asn Ile Lys Glu Phe Leu Gln
                565                 570                 575

Ser Phe Val His Ile Val Gln Met Phe Ile Asn Thr Ser Gly Gly Pro
            580                 585                 590

Leu Gly Met Leu Ser Gln Ser Ile Thr Cys Pro Pro Met Ser Val
    595                 600                 605

Glu His Ala Asp Ile Trp Val Lys Ser Tyr Ser Leu Tyr Ser Arg Glu
610                 615                 620

Arg Tyr Ile Cys Asn Ser Gly Phe Lys Arg Lys Ala Gly Thr Ser Ser
625                 630                 635                 640

Leu Thr Glu Cys Val Leu Asn Lys Ala Thr Asn Val Ala His Trp Thr
                645                 650                 655

Thr Pro Ser Leu Lys Cys Ile Arg Asp Pro Ala Leu Val His Gln Arg
            660                 665                 670

Pro Ala Pro Pro
        675

<210> SEQ ID NO 129
<211> LENGTH: 219
<212> TYPE: PRT
<213> ORGANISM: Artificial
<220> FEATURE:
<223> OTHER INFORMATION: JS001-L

<400> SEQUENCE: 129

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 130
<211> LENGTH: 669
<212> TYPE: PRT
<213> ORGANISM: Artificial
<220> FEATURE:
<223> OTHER INFORMATION: Ipilimumab-IL-15-VitoKine -HC

<400> SEQUENCE: 130

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr

```
                     20                  25                  30
Thr Met His Trp Val Arg Gln Ala Pro Gly Lys Gly Leu Glu Trp Val
            35                  40                  45
Thr Phe Ile Ser Tyr Asp Gly Asn Asn Lys Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Ile Tyr Tyr Cys
                85                  90                  95
Ala Arg Thr Gly Trp Leu Gly Pro Phe Asp Tyr Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
        210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Gly
        435                 440                 445
```

```
Gly Gly Gly Ser Leu Gly Ser Gly Arg Ser Ala Asn Ala Ile Leu
        450                 455                 460
Glu Gly Gly Ser Asn Trp Val Asn Val Ile Ser Asp Leu Lys Lys Ile
465                 470                 475                 480
Glu Asp Leu Ile Gln Ser Met His Ile Asp Ala Thr Leu Tyr Thr Glu
                485                 490                 495
Ser Asp Val His Pro Ser Cys Lys Val Thr Ala Met Lys Cys Phe Leu
                500                 505                 510
Leu Glu Leu Gln Val Ile Ser Leu Glu Ser Gly Asp Ala Asp Ile His
                515                 520                 525
Asp Thr Val Glu Asn Leu Ile Ile Leu Ala Asn Asn Ser Leu Ser Ser
530                 535                 540
Asn Gly Asn Val Thr Glu Ser Gly Cys Lys Glu Cys Glu Glu Leu Glu
545                 550                 555                 560
Glu Lys Asn Ile Lys Glu Phe Leu Gln Ser Phe Val His Ile Val Gln
                565                 570                 575
Met Phe Ile Asn Thr Ser Gly Gly Pro Leu Gly Met Leu Ser Gln Ser
                580                 585                 590
Ile Thr Cys Pro Pro Pro Met Ser Val Glu His Ala Asp Ile Trp Val
                595                 600                 605
Lys Ser Tyr Ser Leu Tyr Ser Arg Glu Arg Tyr Ile Cys Asn Ser Gly
                610                 615                 620
Phe Lys Arg Lys Ala Gly Thr Ser Ser Leu Thr Glu Cys Val Leu Asn
625                 630                 635                 640
Lys Ala Thr Asn Val Ala His Trp Thr Thr Pro Ser Leu Lys Cys Ile
                645                 650                 655
Arg Asp Pro Ala Leu Val His Gln Arg Pro Ala Pro
                660                 665

<210> SEQ ID NO 131
<211> LENGTH: 215
<212> TYPE: PRT
<213> ORGANISM: Artificial
<220> FEATURE:
<223> OTHER INFORMATION: Ipilimumab-L

<400> SEQUENCE: 131

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Gly Ser Ser
                20                  25                  30
Tyr Leu Ala Trp Tyr Gln Gln Lys Pro Gly Gln Ala Pro Arg Leu Leu
            35                  40                  45
Ile Tyr Gly Ala Phe Ser Arg Ala Thr Gly Ile Pro Asp Arg Phe Ser
        50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Trp Thr Phe Gly Gln Gly Thr Lys Val Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
    130                 135                 140
```

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
        180                 185                 190

Tyr Ala Cys Glu Val Thr His Gln Gly Leu Ser Ser Pro Val Thr Lys
    195                 200                 205

Ser Phe Asn Arg Gly Glu Cys
    210                 215

<210> SEQ ID NO 132
<211> LENGTH: 677
<212> TYPE: PRT
<213> ORGANISM: Artificial
<220> FEATURE:
<223> OTHER INFORMATION: RO7009789-IL-15-VitoKine- HC

<400> SEQUENCE: 132

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Leu Gly Tyr Cys Thr Asn Gly Val Cys Ser Tyr
            100                 105                 110

Phe Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
        180                 185                 190

Ser Val Val Thr Val Pro Ser Ser Leu Gly Thr Gln Thr Tyr Ile
    195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285
```

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Gly Gly Gly Ser Leu Gly Gly Ser
450                 455                 460

Gly Arg Ser Ala Asn Ala Ile Leu Glu Gly Gly Ser Asn Trp Val Asn
465                 470                 475                 480

Val Ile Ser Asp Leu Lys Lys Ile Glu Asp Leu Ile Gln Ser Met His
                485                 490                 495

Ile Asp Ala Thr Leu Tyr Thr Glu Ser Asp Val His Pro Ser Cys Lys
            500                 505                 510

Val Thr Ala Met Lys Cys Phe Leu Leu Glu Leu Gln Val Ile Ser Leu
        515                 520                 525

Glu Ser Gly Asp Ala Asp Ile His Asp Thr Val Glu Asn Leu Ile Ile
530                 535                 540

Leu Ala Asn Asn Ser Leu Ser Ser Asn Gly Asn Val Thr Glu Ser Gly
545                 550                 555                 560

Cys Lys Glu Cys Glu Glu Leu Glu Glu Lys Asn Ile Lys Glu Phe Leu
                565                 570                 575

Gln Ser Phe Val His Ile Val Gln Met Phe Ile Asn Thr Ser Gly Gly
            580                 585                 590

Pro Leu Gly Met Leu Ser Gln Ser Ile Thr Cys Pro Pro Met Ser
        595                 600                 605

Val Glu His Ala Asp Ile Trp Val Lys Ser Tyr Ser Leu Tyr Ser Arg
610                 615                 620

Glu Arg Tyr Ile Cys Asn Ser Gly Phe Lys Arg Lys Ala Gly Thr Ser
625                 630                 635                 640

Ser Leu Thr Glu Cys Val Leu Asn Lys Ala Thr Asn Val Ala His Trp
                645                 650                 655

Thr Thr Pro Ser Leu Lys Cys Ile Arg Asp Pro Ala Leu Val His Gln
            660                 665                 670

Arg Pro Ala Pro Pro
        675

<210> SEQ ID NO 133
<211> LENGTH: 214

```
<212> TYPE: PRT
<213> ORGANISM: Artificial
<220> FEATURE:
<223> OTHER INFORMATION: RO7009789-L

<400> SEQUENCE: 133
```

| | | | | | | | | | | | | | | | |
|---|---|---|---|---|---|---|---|---|---|---|---|---|---|---|---|
| Asp | Ile | Gln | Met | Thr | Gln | Ser | Pro | Ser | Ser | Val | Ser | Ala | Ser | Val | Gly |
| 1 | | | | 5 | | | | | 10 | | | | | 15 | |
| Asp | Arg | Val | Thr | Ile | Thr | Cys | Arg | Ala | Ser | Gln | Gly | Ile | Tyr | Ser | Trp |
| | | | 20 | | | | | 25 | | | | | 30 | | |
| Leu | Ala | Trp | Tyr | Gln | Gln | Lys | Pro | Gly | Lys | Ala | Pro | Asn | Leu | Leu | Ile |
| | | | 35 | | | | | 40 | | | | | 45 | | |
| Tyr | Thr | Ala | Ser | Thr | Leu | Gln | Ser | Gly | Val | Pro | Ser | Arg | Phe | Ser | Gly |
| | 50 | | | | | 55 | | | | | 60 | | | | |
| Ser | Gly | Ser | Gly | Thr | Asp | Phe | Thr | Leu | Thr | Ile | Ser | Ser | Leu | Gln | Pro |
| 65 | | | | | 70 | | | | | 75 | | | | | 80 |
| Glu | Asp | Phe | Ala | Thr | Tyr | Tyr | Cys | Gln | Gln | Ala | Asn | Ile | Phe | Pro | Leu |
| | | | | 85 | | | | | 90 | | | | | 95 | |
| Thr | Phe | Gly | Gly | Gly | Thr | Lys | Val | Glu | Ile | Lys | Arg | Thr | Val | Ala | Ala |
| | | | | 100 | | | | | 105 | | | | | 110 | |
| Pro | Ser | Val | Phe | Ile | Phe | Pro | Pro | Ser | Asp | Glu | Gln | Leu | Lys | Ser | Gly |
| | | | | 115 | | | | | 120 | | | | | 125 | |
| Thr | Ala | Ser | Val | Val | Cys | Leu | Leu | Asn | Asn | Phe | Tyr | Pro | Arg | Glu | Ala |
| | 130 | | | | | 135 | | | | | 140 | | | | |
| Lys | Val | Gln | Trp | Lys | Val | Asp | Asn | Ala | Leu | Gln | Ser | Gly | Asn | Ser | Gln |
| 145 | | | | | 150 | | | | | 155 | | | | | 160 |
| Glu | Ser | Val | Thr | Glu | Gln | Asp | Ser | Lys | Asp | Ser | Thr | Tyr | Ser | Leu | Ser |
| | | | | 165 | | | | | 170 | | | | | 175 | |
| Ser | Thr | Leu | Thr | Leu | Ser | Lys | Ala | Asp | Tyr | Glu | Lys | His | Lys | Val | Tyr |
| | | | 180 | | | | | 185 | | | | | 190 | | |
| Ala | Cys | Glu | Val | Thr | His | Gln | Gly | Leu | Ser | Ser | Pro | Val | Thr | Lys | Ser |
| | | | 195 | | | | | 200 | | | | | 205 | | |
| Phe | Asn | Arg | Gly | Glu | Cys | | | | | | | | | | |
| | | | 210 | | | | | | | | | | | | |

```
<210> SEQ ID NO 134
<211> LENGTH: 666
<212> TYPE: PRT
<213> ORGANISM: Artificial
<220> FEATURE:
<223> OTHER INFORMATION: L19-IL-15-VitoKine- HC

<400> SEQUENCE: 134
```

| | | | | | | | | | | | | | | | |
|---|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | Phe |
| | | | 20 | | | | | 25 | | | | | 30 | | |
| Ser | Met | Ser | Trp | Val | Arg | Gln | Ala | Pro | Gly | Lys | Gly | Leu | Glu | Trp | Val |
| | | | 35 | | | | | 40 | | | | | 45 | | |
| Ser | Ser | Ile | Ser | Gly | Ser | Ser | Gly | Thr | Thr | Tyr | Tyr | Ala | Asp | Ser | Val |
| | 50 | | | | | 55 | | | | | 60 | | | | |
| Lys | Gly | Arg | Phe | Thr | Ile | Ser | Arg | Asp | Ser | Lys | Asn | Thr | Leu | Tyr | Leu |
| 65 | | | | | 70 | | | | | 75 | | | | | 80 |
| Gln | Met | Asn | Ser | Leu | Arg | Ala | Glu | Asp | Thr | Ala | Val | Tyr | Tyr | Cys | Ala |
| | | | | 85 | | | | | 90 | | | | | 95 | |
| Lys | Pro | Phe | Pro | Tyr | Phe | Asp | Tyr | Trp | Gly | Gln | Gly | Thr | Leu | Val | Thr |
| | | | | 100 | | | | | 105 | | | | | 110 | |

```
Val Ser Ser Ala Ser Thr Lys Gly Pro Ser Val Phe Pro Leu Ala Pro
    115                 120                 125

Ser Ser Lys Ser Thr Ser Gly Gly Thr Ala Ala Leu Gly Cys Leu Val
130             135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Gly Gly Gly Gly
        435                 440                 445

Ser Leu Gly Gly Ser Gly Arg Ser Ala Asn Ala Ile Leu Glu Gly Gly
    450                 455                 460

Ser Asn Trp Val Asn Val Ile Ser Asp Leu Lys Lys Ile Glu Asp Leu
465                 470                 475                 480

Ile Gln Ser Met His Ile Asp Ala Thr Leu Tyr Thr Glu Ser Asp Val
                485                 490                 495

His Pro Ser Cys Lys Val Thr Ala Met Lys Cys Phe Leu Leu Glu Leu
            500                 505                 510

Gln Val Ile Ser Leu Glu Ser Gly Asp Ala Asp Ile His Asp Thr Val
        515                 520                 525
```

Glu Asn Leu Ile Ile Leu Ala Asn Asn Ser Leu Ser Ser Asn Gly Asn
            530                 535                 540

Val Thr Glu Ser Gly Cys Lys Glu Cys Glu Glu Leu Glu Glu Lys Asn
545                 550                 555                 560

Ile Lys Glu Phe Leu Gln Ser Phe Val His Ile Val Gln Met Phe Ile
                565                 570                 575

Asn Thr Ser Gly Gly Pro Leu Gly Met Leu Ser Gln Ser Ile Thr Cys
            580                 585                 590

Pro Pro Pro Met Ser Val Glu His Ala Asp Ile Trp Val Lys Ser Tyr
            595                 600                 605

Ser Leu Tyr Ser Arg Glu Arg Tyr Ile Cys Asn Ser Gly Phe Lys Arg
610                 615                 620

Lys Ala Gly Thr Ser Ser Leu Thr Glu Cys Val Leu Asn Lys Ala Thr
625                 630                 635                 640

Asn Val Ala His Trp Thr Thr Pro Ser Leu Lys Cys Ile Arg Asp Pro
                645                 650                 655

Ala Leu Val His Gln Arg Pro Ala Pro Pro
            660                 665

<210> SEQ ID NO 135
<211> LENGTH: 215
<212> TYPE: PRT
<213> ORGANISM: Artificial
<220> FEATURE:
<223> OTHER INFORMATION: L19-L

<400> SEQUENCE: 135

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Tyr Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Gly Arg Ile Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 136
<211> LENGTH: 766
<212> TYPE: PRT
<213> ORGANISM: Artificial
<220> FEATURE:
<223> OTHER INFORMATION: Rituximab-IL-2-VitoKine -HC

<400> SEQUENCE: 136

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365
```

-continued

```
Leu Thr Cys Leu Val Lys Gly Phe Tyr Pro Ser Asp Ile Ala Val Glu
    370                 375                 380

Trp Glu Ser Asn Gly Gln Pro Glu Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Gly Gly Gly Ser Gly Gly Gly Ser Ala Pro Thr Ser Ser Ser
    450                 455                 460

Thr Lys Lys Thr Gln Leu Gln Leu Glu His Leu Leu Leu Asp Leu Gln
465                 470                 475                 480

Met Ile Leu Asn Gly Ile Asn Asn Tyr Lys Asn Pro Lys Leu Thr Arg
                485                 490                 495

Met Leu Thr Phe Lys Phe Tyr Met Pro Lys Lys Ala Thr Glu Leu Lys
            500                 505                 510

His Leu Gln Cys Leu Glu Glu Glu Leu Lys Pro Leu Glu Glu Val Leu
        515                 520                 525

Asn Leu Ala Gln Ser Lys Asn Phe His Leu Arg Pro Arg Asp Leu Ile
530                 535                 540

Ser Asn Ile Asn Val Ile Val Leu Glu Leu Lys Gly Ser Glu Thr Thr
545                 550                 555                 560

Phe Met Cys Glu Tyr Ala Asp Glu Thr Ala Thr Ile Val Glu Phe Leu
                565                 570                 575

Asn Arg Trp Ile Thr Phe Ser Gln Ser Ile Ile Ser Thr Leu Thr Gly
                580                 585                 590

Gly Pro Leu Gly Met Leu Ser Gln Ser Glu Leu Cys Asp Asp Asp Pro
        595                 600                 605

Pro Glu Ile Pro His Ala Thr Phe Lys Ala Met Ala Tyr Lys Glu Gly
    610                 615                 620

Thr Met Leu Asn Cys Glu Cys Lys Arg Gly Phe Arg Arg Ile Lys Ser
625                 630                 635                 640

Gly Ser Leu Tyr Met Leu Cys Thr Gly Asn Ser Ser His Ser Ser Trp
                645                 650                 655

Asp Asn Gln Cys Gln Cys Thr Ser Ser Ala Thr Arg Asn Thr Thr Lys
                660                 665                 670

Gln Val Thr Pro Gln Pro Glu Glu Gln Lys Glu Arg Lys Thr Thr Glu
            675                 680                 685

Met Gln Ser Pro Met Gln Pro Val Asp Gln Ala Ser Leu Pro Gly His
    690                 695                 700

Cys Arg Glu Pro Pro Pro Trp Glu Asn Glu Ala Thr Glu Arg Ile Tyr
705                 710                 715                 720

His Phe Val Val Gly Gln Met Val Tyr Tyr Gln Cys Val Gln Gly Tyr
                725                 730                 735

Arg Ala Leu His Arg Gly Pro Ala Glu Ser Val Cys Lys Met Thr His
                740                 745                 750

Gly Lys Thr Arg Trp Thr Gln Pro Gln Leu Ile Cys Thr Gly
                755                 760                 765

<210> SEQ ID NO 137
<211> LENGTH: 213
<212> TYPE: PRT
```

<213> ORGANISM: Artificial
<220> FEATURE:
<223> OTHER INFORMATION: Rituximab-L

<400> SEQUENCE: 137

| | | | | | | | | | | | | | | |
|---|---|---|---|---|---|---|---|---|---|---|---|---|---|---|
| Gln | Ile | Val | Leu | Ser | Gln | Ser | Pro | Ala | Ile | Leu | Ser | Ala | Ser | Pro | Gly |
| 1 | | | | 5 | | | | | 10 | | | | | 15 | |
| Glu | Lys | Val | Thr | Met | Thr | Cys | Arg | Ala | Ser | Ser | Ser | Val | Ser | Tyr | Ile |
| | | | 20 | | | | | 25 | | | | | 30 | | |
| His | Trp | Phe | Gln | Gln | Lys | Pro | Gly | Ser | Ser | Pro | Lys | Pro | Trp | Ile | Tyr |
| | | | 35 | | | | | 40 | | | | | 45 | | |
| Ala | Thr | Ser | Asn | Leu | Ala | Ser | Gly | Val | Pro | Val | Arg | Phe | Ser | Gly | Ser |
| | 50 | | | | | 55 | | | | | 60 | | | | |
| Gly | Ser | Gly | Thr | Ser | Tyr | Ser | Leu | Thr | Ile | Ser | Arg | Val | Glu | Ala | Glu |
| 65 | | | | | 70 | | | | | 75 | | | | | 80 |
| Asp | Ala | Ala | Thr | Tyr | Tyr | Cys | Gln | Gln | Trp | Thr | Ser | Asn | Pro | Pro | Thr |
| | | | | 85 | | | | | 90 | | | | | 95 | |
| Phe | Gly | Gly | Gly | Thr | Lys | Leu | Glu | Ile | Lys | Arg | Thr | Val | Ala | Ala | Pro |
| | | | | 100 | | | | | 105 | | | | | 110 | |
| Ser | Val | Phe | Ile | Phe | Pro | Pro | Ser | Asp | Glu | Gln | Leu | Lys | Ser | Gly | Thr |
| | | | 115 | | | | | 120 | | | | | 125 | | |
| Ala | Ser | Val | Val | Cys | Leu | Leu | Asn | Asn | Phe | Tyr | Pro | Arg | Glu | Ala | Lys |
| | 130 | | | | | 135 | | | | | 140 | | | | |
| Val | Gln | Trp | Lys | Val | Asp | Asn | Ala | Leu | Gln | Ser | Gly | Asn | Ser | Gln | Glu |
| 145 | | | | | 150 | | | | | 155 | | | | | 160 |
| Ser | Val | Thr | Glu | Gln | Asp | Ser | Lys | Asp | Ser | Thr | Tyr | Ser | Leu | Ser | Ser |
| | | | | 165 | | | | | 170 | | | | | 175 | |
| Thr | Leu | Thr | Leu | Ser | Lys | Ala | Asp | Tyr | Glu | Lys | His | Lys | Val | Tyr | Ala |
| | | | 180 | | | | | 185 | | | | | 190 | | |
| Cys | Glu | Val | Thr | His | Gln | Gly | Leu | Ser | Ser | Pro | Val | Thr | Lys | Ser | Phe |
| | | | 195 | | | | | 200 | | | | | 205 | | |
| Asn | Arg | Gly | Glu | Cys | | | | | | | | | | | |
| | | 210 | | | | | | | | | | | | | |

<210> SEQ ID NO 138
<211> LENGTH: 766
<212> TYPE: PRT
<213> ORGANISM: Artificial
<220> FEATURE:
<223> OTHER INFORMATION: Herceptin-IL-2-VitoKine -HC

<400> SEQUENCE: 138

| | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Asn | Ile | Lys | Asp | Thr |
| | | | 20 | | | | | 25 | | | | | 30 | | |
| Tyr | Ile | His | Trp | Val | Arg | Gln | Ala | Pro | Gly | Lys | Gly | Leu | Glu | Trp | Val |
| | | | 35 | | | | | 40 | | | | | 45 | | |
| Ala | Arg | Ile | Tyr | Pro | Thr | Asn | Gly | Tyr | Thr | Arg | Tyr | Ala | Asp | Ser | Val |
| | 50 | | | | | 55 | | | | | 60 | | | | |
| Lys | Gly | Arg | Phe | Thr | Ile | Ser | Ala | Asp | Thr | Ser | Lys | Asn | Thr | Ala | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ser | Arg | Trp | Gly | Gly | Asp | Gly | Phe | Tyr | Ala | Met | Asp | Tyr | Trp | Gly | Gln |
| | | | | 100 | | | | | 105 | | | | | 110 | |

```
Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Gly Gly Ser Gly Gly Gly Ser Ala Pro Thr Ser Ser Ser
450                 455                 460

Thr Lys Lys Thr Gln Leu Gln Leu Glu His Leu Leu Leu Asp Leu Gln
465                 470                 475                 480

Met Ile Leu Asn Gly Ile Asn Asn Tyr Lys Asn Pro Lys Leu Thr Arg
                485                 490                 495

Met Leu Thr Phe Lys Phe Tyr Met Pro Lys Lys Ala Thr Glu Leu Lys
            500                 505                 510

His Leu Gln Cys Leu Glu Glu Glu Leu Lys Pro Leu Glu Glu Val Leu
            515                 520                 525

Asn Leu Ala Gln Ser Lys Asn Phe His Leu Arg Pro Arg Asp Leu Ile
```

```
                530                 535                 540
Ser Asn Ile Asn Val Ile Val Leu Glu Leu Lys Gly Ser Glu Thr Thr
545                 550                 555                 560

Phe Met Cys Glu Tyr Ala Asp Glu Thr Ala Thr Ile Val Glu Phe Leu
                565                 570                 575

Asn Arg Trp Ile Thr Phe Ser Gln Ser Ile Ile Ser Thr Leu Thr Gly
                580                 585                 590

Gly Pro Leu Gly Met Leu Ser Gln Ser Glu Leu Cys Asp Asp Asp Pro
                595                 600                 605

Pro Glu Ile Pro His Ala Thr Phe Lys Ala Met Ala Tyr Lys Glu Gly
                610                 615                 620

Thr Met Leu Asn Cys Glu Cys Lys Arg Gly Phe Arg Arg Ile Lys Ser
625                 630                 635                 640

Gly Ser Leu Tyr Met Leu Cys Thr Gly Asn Ser Ser His Ser Ser Trp
                645                 650                 655

Asp Asn Gln Cys Gln Cys Thr Ser Ser Ala Thr Arg Asn Thr Thr Lys
                660                 665                 670

Gln Val Thr Pro Gln Pro Glu Glu Gln Lys Glu Arg Lys Thr Thr Glu
                675                 680                 685

Met Gln Ser Pro Met Gln Pro Val Asp Gln Ala Ser Leu Pro Gly His
                690                 695                 700

Cys Arg Glu Pro Pro Trp Glu Asn Glu Ala Thr Glu Arg Ile Tyr
705                 710                 715                 720

His Phe Val Val Gly Gln Met Val Tyr Tyr Gln Cys Val Gln Gly Tyr
                725                 730                 735

Arg Ala Leu His Arg Gly Pro Ala Glu Ser Val Cys Lys Met Thr His
                740                 745                 750

Gly Lys Thr Arg Trp Thr Gln Pro Gln Leu Ile Cys Thr Gly
                755                 760                 765

<210> SEQ ID NO 139
<211> LENGTH: 214
<212> TYPE: PRT
<213> ORGANISM: Artificial
<220> FEATURE:
<223> OTHER INFORMATION: Herceptin-L

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
                35                  40                  45

Tyr Ser Ala Ser Phe Leu Tyr Ser Gly Val Pro Ser Arg Phe Ser Gly
                50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
```

```
              130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 140
<211> LENGTH: 764
<212> TYPE: PRT
<213> ORGANISM: Artificial
<220> FEATURE:
<223> OTHER INFORMATION: Cetuximab-IL-2-VitoKine -HC

<400> SEQUENCE: 140

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
```

```
                275                 280                 285
Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Gly Gly Gly Ser Gly Gly Gly Ser Ala Pro Thr Ser Ser Ser Thr Lys
450                 455                 460

Lys Thr Gln Leu Gln Leu Glu His Leu Leu Leu Asp Leu Gln Met Ile
465                 470                 475                 480

Leu Asn Gly Ile Asn Asn Tyr Lys Asn Pro Lys Leu Thr Arg Met Leu
                485                 490                 495

Thr Phe Lys Phe Tyr Met Pro Lys Lys Ala Thr Glu Leu Lys His Leu
                500                 505                 510

Gln Cys Leu Glu Glu Glu Leu Lys Pro Leu Glu Glu Val Leu Asn Leu
                515                 520                 525

Ala Gln Ser Lys Asn Phe His Leu Arg Pro Arg Asp Leu Ile Ser Asn
                530                 535                 540

Ile Asn Val Ile Val Leu Glu Leu Lys Gly Ser Glu Thr Thr Phe Met
545                 550                 555                 560

Cys Glu Tyr Ala Asp Glu Thr Ala Thr Ile Val Glu Phe Leu Asn Arg
                565                 570                 575

Trp Ile Thr Phe Ser Gln Ser Ile Ile Ser Thr Leu Thr Gly Gly Pro
                580                 585                 590

Leu Gly Met Leu Ser Gln Ser Glu Leu Cys Asp Asp Pro Pro Glu
                595                 600                 605

Ile Pro His Ala Thr Phe Lys Ala Met Ala Tyr Lys Glu Gly Thr Met
610                 615                 620

Leu Asn Cys Glu Cys Lys Arg Gly Phe Arg Arg Ile Lys Ser Gly Ser
625                 630                 635                 640

Leu Tyr Met Leu Cys Thr Gly Asn Ser Ser His Ser Ser Trp Asp Asn
                645                 650                 655

Gln Cys Gln Cys Thr Ser Ser Ala Thr Arg Asn Thr Thr Lys Gln Val
                660                 665                 670

Thr Pro Gln Pro Glu Glu Gln Lys Glu Arg Lys Thr Thr Glu Met Gln
                675                 680                 685

Ser Pro Met Gln Pro Val Asp Gln Ala Ser Leu Pro Gly His Cys Arg
690                 695                 700
```

Glu Pro Pro Trp Glu Asn Glu Ala Thr Glu Arg Ile Tyr His Phe
705                 710                 715                 720

Val Val Gly Gln Met Val Tyr Tyr Gln Cys Val Gln Gly Tyr Arg Ala
                725                 730                 735

Leu His Arg Gly Pro Ala Glu Ser Val Cys Lys Met Thr His Gly Lys
            740                 745                 750

Thr Arg Trp Thr Gln Pro Gln Leu Ile Cys Thr Gly
        755                 760

<210> SEQ ID NO 141
<211> LENGTH: 214
<212> TYPE: PRT
<213> ORGANISM: Artificial
<220> FEATURE:
<223> OTHER INFORMATION: Cetuximab-L

<400> SEQUENCE: 141

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 142
<211> LENGTH: 770
<212> TYPE: PRT
<213> ORGANISM: Artificial
<220> FEATURE:
<223> OTHER INFORMATION: JS001-IL-2-VitoKine -HC

<400> SEQUENCE: 142

Gln Gly Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr

-continued

```
                20                  25                  30
Glu Met His Trp Val Arg Gln Ala Pro Gly Gln Gly Leu Glu Trp Met
             35                  40                  45
Gly Val Ile Glu Ser Glu Thr Gly Thr Ala Tyr Asn Gln Lys Phe
 50                  55                  60
Lys Gly Arg Ala Lys Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
             85                  90                  95
Thr Arg Glu Gly Ile Thr Thr Val Ala Thr Thr Tyr Tyr Trp Tyr Phe
             100                 105                 110
Asp Val Trp Gly Gln Gly Thr Thr Val Thr Val Ser Ser Ala Ser Thr
             115                 120                 125
Lys Gly Pro Ser Val Phe Pro Leu Ala Pro Ser Ser Lys Ser Thr Ser
             130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
             165                 170                 175
Thr Phe Pro Ala Val Leu Gln Ser Ser Gly Leu Tyr Ser Leu Ser Ser
             180                 185                 190
Val Val Thr Val Pro Ser Ser Ser Leu Gly Thr Gln Thr Tyr Ile Cys
             195                 200                 205
Asn Val Asn His Lys Pro Ser Asn Thr Lys Val Asp Lys Lys Val Glu
             210                 215                 220
Pro Lys Ser Cys Asp Lys Thr His Thr Cys Pro Pro Cys Pro Ala Pro
225                 230                 235                 240
Glu Ala Ala Gly Ala Pro Ser Val Phe Leu Phe Pro Pro Lys Pro Lys
             245                 250                 255
Asp Thr Leu Met Ile Ser Arg Thr Pro Glu Val Thr Cys Val Val Val
             260                 265                 270
Asp Val Ser His Glu Asp Pro Glu Val Lys Phe Asn Trp Tyr Val Asp
             275                 280                 285
Gly Val Glu Val His Asn Ala Lys Thr Lys Pro Arg Glu Glu Gln Tyr
             290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
             325                 330                 335
Pro Ala Pro Ile Glu Lys Thr Ile Ser Lys Ala Lys Gly Gln Pro Arg
             340                 345                 350
Glu Pro Gln Val Tyr Thr Leu Pro Pro Ser Arg Asp Glu Leu Thr Lys
             355                 360                 365
Asn Gln Val Ser Leu Thr Cys Leu Val Lys Gly Phe Tyr Pro Ser Asp
             370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
             405                 410                 415
Lys Leu Thr Val Asp Lys Ser Arg Trp Gln Gln Gly Asn Val Phe Ser
             420                 425                 430
Cys Ser Val Met His Glu Ala Leu His Asn His Tyr Thr Gln Lys Ser
             435                 440                 445
```

```
Leu Ser Leu Ser Pro Gly Gly Gly Ser Gly Gly Ser Ala Pro
    450             455             460

Thr Ser Ser Ser Thr Lys Lys Thr Gln Leu Gln Leu Glu His Leu Leu
465                 470                 475                 480

Leu Asp Leu Gln Met Ile Leu Asn Gly Ile Asn Asn Tyr Lys Asn Pro
                485                 490                 495

Lys Leu Thr Arg Met Leu Thr Phe Lys Phe Tyr Met Pro Lys Lys Ala
            500                 505                 510

Thr Glu Leu Lys His Leu Gln Cys Leu Glu Glu Glu Leu Lys Pro Leu
        515                 520                 525

Glu Glu Val Leu Asn Leu Ala Gln Ser Lys Asn Phe His Leu Arg Pro
530                 535                 540

Arg Asp Leu Ile Ser Asn Ile Asn Val Ile Val Leu Glu Leu Lys Gly
545                 550                 555                 560

Ser Glu Thr Thr Phe Met Cys Glu Tyr Ala Asp Glu Thr Ala Thr Ile
                565                 570                 575

Val Glu Phe Leu Asn Arg Trp Ile Thr Phe Ser Gln Ser Ile Ile Ser
            580                 585                 590

Thr Leu Thr Gly Gly Pro Leu Gly Met Leu Ser Gln Ser Glu Leu Cys
        595                 600                 605

Asp Asp Asp Pro Pro Glu Ile Pro His Ala Thr Phe Lys Ala Met Ala
610                 615                 620

Tyr Lys Glu Gly Thr Met Leu Asn Cys Glu Cys Lys Arg Gly Phe Arg
625                 630                 635                 640

Arg Ile Lys Ser Gly Ser Leu Tyr Met Leu Cys Thr Gly Asn Ser Ser
                645                 650                 655

His Ser Ser Trp Asp Asn Gln Cys Gln Cys Thr Ser Ser Ala Thr Arg
            660                 665                 670

Asn Thr Thr Lys Gln Val Thr Pro Gln Pro Glu Glu Gln Lys Glu Arg
        675                 680                 685

Lys Thr Thr Glu Met Gln Ser Pro Met Gln Pro Val Asp Gln Ala Ser
690                 695                 700

Leu Pro Gly His Cys Arg Glu Pro Pro Trp Glu Asn Glu Ala Thr
705                 710                 715                 720

Glu Arg Ile Tyr His Phe Val Val Gly Gln Met Val Tyr Tyr Gln Cys
                725                 730                 735

Val Gln Gly Tyr Arg Ala Leu His Arg Gly Pro Ala Glu Ser Val Cys
            740                 745                 750

Lys Met Thr His Gly Lys Thr Arg Trp Thr Gln Pro Gln Leu Ile Cys
        755                 760                 765

Thr Gly
    770

<210> SEQ ID NO 143
<211> LENGTH: 766
<212> TYPE: PRT
<213> ORGANISM: Artificial
<220> FEATURE:
<223> OTHER INFORMATION: Vedolizumab-IL-2-VitoKine -HC

<400> SEQUENCE: 143

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Ser Tyr
                20                  25                  30
```

```
Trp Met His Trp Val Arg Gln Ala Pro Gly Gln Arg Leu Glu Trp Ile
        35                  40                  45

Gly Glu Ile Asp Pro Ser Glu Ser Asn Thr Asn Tyr Asn Gln Lys Phe
        50                  55                  60

Lys Gly Arg Val Thr Leu Thr Val Asp Ile Ser Ala Ser Thr Ala Tyr
65                      70                  75                  80

Met Glu Leu Ser Ser Leu Arg Ser Glu Asp Thr Ala Val Tyr Tyr Cys
                    85                  90                  95

Ala Arg Gly Gly Tyr Asp Gly Trp Asp Tyr Ala Ile Asp Tyr Trp Gly
                    100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                    165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Ala Gly
225                 230                 235                 240

Ala Pro Ser Val Phe Leu Phe Pro Pro Lys Pro Lys Asp Thr Leu Met
                    245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                    325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                    405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445
```

Pro Gly Gly Gly Ser Gly Gly Ser Ala Pro Thr Ser Ser Ser
    450             455             460
Thr Lys Lys Thr Gln Leu Gln Leu Glu His Leu Leu Thr Leu Gln
465                 470                 475                 480
Met Ile Leu Asn Gly Ile Asn Asn Tyr Lys Asn Pro Lys Leu Thr Arg
                485                 490                 495
Met Leu Thr Phe Lys Phe Tyr Met Pro Lys Lys Ala Thr Glu Leu Lys
            500                 505                 510
His Leu Gln Cys Leu Glu Glu Glu Leu Lys Pro Leu Glu Glu Val Leu
        515                 520                 525
Asn Leu Ala Gln Ser Lys Asn Phe His Leu Arg Pro Arg Asp Leu Ile
    530                 535                 540
Ser Asn Ile Asn Val Ile Val Leu Glu Leu Lys Gly Ser Glu Thr Thr
545                 550                 555                 560
Phe Met Cys Glu Tyr Ala Asp Glu Thr Ala Thr Ile Val Glu Phe Leu
                565                 570                 575
Asn Arg Trp Ile Thr Phe Ser Gln Ser Ile Ile Ser Thr Leu Thr Gly
            580                 585                 590
Gly Pro Leu Gly Met Leu Ser Gln Ser Glu Leu Cys Asp Asp Asp Pro
        595                 600                 605
Pro Glu Ile Pro His Ala Thr Phe Lys Ala Met Ala Tyr Lys Glu Gly
    610                 615                 620
Thr Met Leu Asn Cys Glu Cys Lys Arg Gly Phe Arg Arg Ile Glu Ser
625                 630                 635                 640
Gly Ser Leu Tyr Met Leu Cys Thr Gly Asn Ser Ser His Ser Ser Trp
                645                 650                 655
Asp Asn Gln Cys Gln Cys Thr Ser Ser Ala Thr Arg Asn Thr Thr Lys
            660                 665                 670
Gln Val Thr Pro Gln Pro Glu Glu Gln Lys Glu Arg Lys Thr Thr Glu
        675                 680                 685
Met Gln Ser Pro Met Gln Pro Val Asp Gln Ala Ser Leu Pro Gly His
    690                 695                 700
Cys Arg Glu Pro Pro Pro Trp Glu Asn Glu Ala Thr Glu Arg Ile Tyr
705                 710                 715                 720
His Phe Val Val Gly Gln Met Val Tyr Tyr Gln Cys Val Gln Gly Tyr
                725                 730                 735
Arg Ala Leu His Arg Gly Pro Ala Glu Ser Val Cys Lys Met Thr His
            740                 745                 750
Gly Lys Thr Arg Trp Thr Gln Pro Gln Leu Ile Cys Thr Gly
        755                 760                 765

<210> SEQ ID NO 144
<211> LENGTH: 219
<212> TYPE: PRT
<213> ORGANISM: Artificial
<220> FEATURE:
<223> OTHER INFORMATION: Vedolizumab-L

<400> SEQUENCE: 144

Asp Val Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Ala Lys Ser
            20                  25                  30
Tyr Gly Asn Thr Tyr Leu Ser Trp Tyr Leu Gln Lys Pro Gly Gln Ser
        35                  40                  45

```
Pro Gln Leu Leu Ile Tyr Gly Ile Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Leu Gln Gly
                 85                  90                  95

Thr His Gln Pro Tyr Thr Phe Gly Gln Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
210                 215

<210> SEQ ID NO 145
<211> LENGTH: 766
<212> TYPE: PRT
<213> ORGANISM: Artificial
<220> FEATURE:
<223> OTHER INFORMATION: Humira-IL-2-VitoKine -HC

<400> SEQUENCE: 145

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
             35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190
```

-continued

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Gly Gly Gly Ser Gly Gly Gly Ser Ala Pro Thr Ser Ser Ser
    450                 455                 460

Thr Lys Lys Thr Gln Leu Gln Leu Glu His Leu Leu Leu Thr Leu Gln
465                 470                 475                 480

Met Ile Leu Asn Gly Ile Asn Asn Tyr Lys Asn Pro Lys Leu Thr Arg
                485                 490                 495

Met Leu Thr Phe Lys Phe Tyr Met Pro Lys Lys Ala Thr Glu Leu Lys
            500                 505                 510

His Leu Gln Cys Leu Glu Glu Glu Leu Lys Pro Leu Glu Glu Val Leu
        515                 520                 525

Asn Leu Ala Gln Ser Lys Asn Phe His Leu Arg Pro Arg Asp Leu Ile
    530                 535                 540

Ser Asn Ile Asn Val Ile Val Leu Glu Leu Lys Gly Ser Glu Thr Thr
545                 550                 555                 560

Phe Met Cys Glu Tyr Ala Asp Glu Thr Ala Thr Ile Val Glu Phe Leu
                565                 570                 575

Asn Arg Trp Ile Thr Phe Ser Gln Ser Ile Ile Ser Thr Leu Thr Gly
            580                 585                 590

Gly Pro Leu Gly Met Leu Ser Gln Ser Glu Leu Cys Asp Asp Asp Pro
        595                 600                 605

Pro Glu Ile Pro His Ala Thr Phe Lys Ala Met Ala Tyr Lys Glu Gly

```
                    610                 615                 620
Thr Met Leu Asn Cys Glu Cys Lys Arg Gly Phe Arg Arg Ile Glu Ser
625                 630                 635                 640

Gly Ser Leu Tyr Met Leu Cys Thr Gly Asn Ser Ser His Ser Ser Trp
            645                 650                 655

Asp Asn Gln Cys Gln Cys Thr Ser Ser Ala Thr Arg Asn Thr Thr Lys
                660                 665                 670

Gln Val Thr Pro Gln Pro Glu Glu Lys Glu Arg Lys Thr Thr Glu
            675                 680                 685

Met Gln Ser Pro Met Gln Pro Val Asp Gln Ala Ser Leu Pro Gly His
            690                 695                 700

Cys Arg Glu Pro Pro Trp Glu Asn Glu Ala Thr Glu Arg Ile Tyr
705                 710                 715                 720

His Phe Val Val Gly Gln Met Val Tyr Tyr Gln Cys Val Gln Gly Tyr
                725                 730                 735

Arg Ala Leu His Arg Gly Pro Ala Glu Ser Val Cys Lys Met Thr His
            740                 745                 750

Gly Lys Thr Arg Trp Thr Gln Pro Gln Leu Ile Cys Thr Gly
            755                 760                 765

<210> SEQ ID NO 146
<211> LENGTH: 214
<212> TYPE: PRT
<213> ORGANISM: Artificial
<220> FEATURE:
<223> OTHER INFORMATION: Humira-L

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

-continued

```
<210> SEQ ID NO 147
<211> LENGTH: 70
<212> TYPE: PRT
<213> ORGANISM: Artificial
<220> FEATURE:
<223> OTHER INFORMATION: IL-2R domain swapped Sushi

<400> SEQUENCE: 147

Gly His Cys Arg Glu Pro Pro Trp Glu Asn Glu Ala Thr Glu Arg
1               5                   10                  15

Ile Tyr His Phe Val Tyr Lys Glu Gly Thr Met Leu Asn Cys Glu Cys
            20                  25                  30

Lys Arg Gly Phe Arg Arg Ile Lys Ser Gly Ser Leu Tyr Met Leu Cys
        35                  40                  45

Thr Gly Asn Ser Ser His Ser Ser Trp Asp Asn Gln Cys Gln Cys Thr
    50                  55                  60

Ser Ser Ala Thr Arg Asn
65                  70

<210> SEQ ID NO 148
<211> LENGTH: 350
<212> TYPE: PRT
<213> ORGANISM: Artificial
<220> FEATURE:
<223> OTHER INFORMATION: Hole-Fc-IL-15-2

<400> SEQUENCE: 148

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220
```

```
Pro Gly Gly Gly Gly Ser Gly Gly Gly Ser Asn Trp Val Asn
225             230             235             240

Val Ile Ser Asp Leu Lys Lys Ile Glu Asp Leu Ile Gln Ser Met His
        245             250             255

Ile Asp Ala Thr Leu Tyr Thr Glu Ser Asp Val His Pro Ser Cys Lys
            260             265             270

Val Thr Ala Met Lys Cys Phe Leu Leu Glu Leu Gln Val Ile Ser Leu
        275             280             285

Glu Ser Gly Asp Ala Ser Ile His Asp Thr Val Glu Asn Leu Ile Ile
290             295             300

Leu Ala Asn Asn Ser Leu Ser Ser Asn Gly Asn Val Thr Glu Ser Gly
305             310             315             320

Cys Lys Glu Cys Glu Glu Leu Glu Glu Lys Asn Ile Lys Glu Phe Leu
        325             330             335

Gln Ser Phe Val His Ile Val Gln Met Phe Ile Asn Thr Ser
            340             345             350
```

<210> SEQ ID NO 149
<211> LENGTH: 355
<212> TYPE: PRT
<213> ORGANISM: Artificial
<220> FEATURE:
<223> OTHER INFORMATION: Hole-Fc-IL-15-3

<400> SEQUENCE: 149

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Gly Gly Gly Ser Gly Gly Gly Gly Ser Gly Gly Gly Gly
225                 230                 235                 240
```

```
Ser Asn Trp Val Asn Val Ile Ser Asp Leu Lys Lys Ile Glu Asp Leu
            245                 250                 255

Ile Gln Ser Met His Ile Asp Ala Thr Leu Tyr Thr Glu Ser Asp Val
        260                 265                 270

His Pro Ser Cys Lys Val Thr Ala Met Lys Cys Phe Leu Leu Glu Leu
        275                 280                 285

Gln Val Ile Ser Leu Glu Ser Gly Asp Ala Ser Ile His Asp Thr Val
        290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
            340                 345                 350

Asn Thr Ser
        355

<210> SEQ ID NO 150
<211> LENGTH: 542
<212> TYPE: PRT
<213> ORGANISM: Artificial
<220> FEATURE:
<223> OTHER INFORMATION: P-0420

<400> SEQUENCE: 150

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Ser Ala Pro Thr Ser Ser Ser
225                 230                 235                 240
```

-continued

```
Thr Lys Lys Thr Gln Leu Gln Leu Glu His Leu Leu Asp Leu Gln
                245                 250                 255

Met Ile Leu Asn Gly Ile Asn Asn Tyr Lys Asn Pro Lys Leu Thr Arg
        260                 265                 270

Met Leu Thr Phe Lys Phe Tyr Met Pro Lys Lys Ala Thr Glu Leu Lys
    275                 280                 285

His Leu Gln Cys Leu Glu Glu Glu Leu Lys Pro Leu Glu Glu Val Leu
290                 295                 300

Asn Leu Ala Gln Ser Lys Asn Phe His Leu Arg Pro Arg Asp Leu Ile
305                 310                 315                 320

Ser Arg Ile Asn Val Ile Val Leu Glu Leu Lys Gly Ser Glu Thr Thr
                325                 330                 335

Phe Met Cys Glu Tyr Ala Asp Glu Thr Ala Thr Ile Val Glu Phe Leu
            340                 345                 350

Asn Arg Trp Ile Thr Phe Ser Gln Ser Ile Ile Ser Thr Leu Thr Gly
        355                 360                 365

Gly Pro Leu Gly Met Leu Ser Gln Ser Glu Leu Cys Asp Asp Asp Pro
    370                 375                 380

Pro Glu Ile Pro His Ala Thr Phe Lys Ala Met Ala Tyr Lys Glu Gly
385                 390                 395                 400

Thr Met Leu Asn Cys Glu Cys Lys Arg Gly Phe Arg Arg Ile Glu Ser
                405                 410                 415

Gly Ser Leu Tyr Met Leu Cys Thr Gly Asn Ser Ser His Ser Ser Trp
            420                 425                 430

Asp Asn Gln Cys Gln Cys Thr Ser Ser Ala Thr Arg Asn Thr Thr Lys
        435                 440                 445

Gln Val Thr Pro Gln Pro Glu Glu Gln Lys Glu Arg Lys Thr Thr Glu
    450                 455                 460

Met Gln Ser Pro Met Gln Pro Val Asp Gln Ala Ser Leu Pro Gly His
465                 470                 475                 480

Cys Arg Glu Pro Pro Pro Trp Glu Asn Glu Ala Thr Glu Arg Ile Tyr
                485                 490                 495

His Phe Val Val Gly Gln Met Val Tyr Tyr Gln Cys Val Gln Gly Tyr
            500                 505                 510

Arg Ala Leu His Arg Gly Pro Ala Glu Ser Val Cys Lys Met Thr His
        515                 520                 525

Gly Lys Thr Arg Trp Thr Gln Pro Gln Leu Ile Cys Thr Gly
    530                 535                 540

<210> SEQ ID NO 151
<211> LENGTH: 542
<212> TYPE: PRT
<213> ORGANISM: Artificial
<220> FEATURE:
<223> OTHER INFORMATION: P-0421

<400> SEQUENCE: 151

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60
```

```
His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Ser Ala Pro Thr Ser Ser Ser
225                 230                 235                 240

Thr Lys Lys Thr Gln Leu Gln Leu Glu His Leu Leu Leu Thr Leu Gln
                245                 250                 255

Met Ile Leu Asn Gly Ile Asn Asn Tyr Lys Asn Pro Lys Leu Thr Arg
            260                 265                 270

Met Leu Thr Phe Lys Phe Tyr Met Pro Lys Lys Ala Thr Glu Leu Lys
        275                 280                 285

His Leu Gln Cys Leu Glu Glu Glu Leu Lys Pro Leu Glu Glu Val Leu
    290                 295                 300

Asn Leu Ala Gln Ser Lys Asn Phe His Leu Arg Pro Arg Asp Leu Ile
305                 310                 315                 320

Ser Asn Ile Asn Val Ile Val Leu Glu Leu Lys Gly Ser Glu Thr Thr
                325                 330                 335

Phe Met Cys Glu Tyr Ala Asp Glu Thr Ala Thr Ile Val Glu Phe Leu
            340                 345                 350

Asn Arg Trp Ile Thr Phe Ser Gln Ser Ile Ile Ser Thr Leu Thr Gly
        355                 360                 365

Gly Pro Leu Gly Met Leu Ser Gln Ser Glu Leu Cys Asp Asp Pro
    370                 375                 380

Pro Glu Ile Pro His Ala Thr Phe Lys Ala Met Ala Tyr Lys Glu Gly
385                 390                 395                 400

Thr Met Leu Asn Cys Glu Cys Lys Arg Gly Phe Arg Arg Ile Glu Ser
                405                 410                 415

Gly Ser Leu Tyr Met Leu Cys Thr Gly Asn Ser Ser His Ser Ser Trp
            420                 425                 430

Asp Asn Gln Cys Gln Cys Thr Ser Ser Ala Thr Arg Asn Thr Thr Lys
        435                 440                 445

Gln Val Thr Pro Gln Pro Glu Glu Gln Lys Glu Arg Lys Thr Thr Glu
    450                 455                 460

Met Gln Ser Pro Met Gln Pro Val Asp Gln Ala Ser Leu Pro Gly His
465                 470                 475                 480

Cys Arg Glu Pro Pro Pro Trp Glu Asn Glu Ala Thr Glu Arg Ile Tyr
```

```
                485                 490                 495
His Phe Val Val Gly Gln Met Val Tyr Tyr Gln Cys Val Gln Gly Tyr
                500                 505                 510

Arg Ala Leu His Arg Gly Pro Ala Glu Ser Val Cys Lys Met Thr His
                515                 520                 525

Gly Lys Thr Arg Trp Thr Gln Pro Gln Leu Ile Cys Thr Gly
                530                 535                 540
```

<210> SEQ ID NO 152
<211> LENGTH: 542
<212> TYPE: PRT
<213> ORGANISM: Artificial
<220> FEATURE:
<223> OTHER INFORMATION: P-0423

<400> SEQUENCE: 152

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Ser Ala Pro Thr Ser Ser Ser
225                 230                 235                 240

Thr Lys Lys Thr Gln Leu Gln Leu Glu His Leu Leu Leu Asp Leu Gln
                245                 250                 255

Met Ile Leu Asn Gly Ile Asn Asn Tyr Lys Asn Pro Lys Leu Thr Arg
            260                 265                 270

Met Leu Thr Phe Lys Phe Tyr Met Pro Lys Lys Ala Thr Glu Leu Lys
        275                 280                 285

His Leu Gln Cys Leu Glu Glu Glu Leu Lys Pro Leu Glu Glu Val Leu
    290                 295                 300

Asn Leu Ala Gln Ser Lys Asn Phe His Leu Arg Pro Arg Asp Leu Ile
```

-continued

```
            305                 310                 315                 320
Ser Asn Ile Asn Val Ile Val Leu Glu Leu Lys Gly Ser Glu Thr Thr
                325                 330                 335

Phe Met Cys Glu Tyr Ala Asp Glu Thr Ala Thr Ile Val Glu Phe Leu
                340                 345                 350

Asn Arg Trp Ile Thr Phe Ser Glu Ser Ile Ile Ser Thr Leu Thr Gly
                355                 360                 365

Gly Pro Leu Gly Met Leu Ser Gln Ser Glu Leu Cys Asp Asp Asp Pro
            370                 375                 380

Pro Glu Ile Pro His Ala Thr Phe Lys Ala Met Ala Tyr Lys Glu Gly
385                 390                 395                 400

Thr Met Leu Asn Cys Glu Cys Lys Arg Gly Phe Arg Arg Ile Glu Ser
                405                 410                 415

Gly Ser Leu Tyr Met Leu Cys Thr Gly Asn Ser Ser His Ser Ser Trp
            420                 425                 430

Asp Asn Gln Cys Gln Cys Thr Ser Ser Ala Thr Arg Asn Thr Thr Lys
            435                 440                 445

Gln Val Thr Pro Gln Pro Glu Glu Gln Lys Glu Arg Lys Thr Thr Glu
        450                 455                 460

Met Gln Ser Pro Met Gln Pro Val Asp Gln Ala Ser Leu Pro Gly His
465                 470                 475                 480

Cys Arg Glu Pro Pro Trp Glu Asn Glu Ala Thr Glu Arg Ile Tyr
                485                 490                 495

His Phe Val Val Gly Gln Met Val Tyr Tyr Gln Cys Val Gln Gly Tyr
                500                 505                 510

Arg Ala Leu His Arg Gly Pro Ala Glu Ser Val Cys Lys Met Thr His
            515                 520                 525

Gly Lys Thr Arg Trp Thr Gln Pro Gln Leu Ile Cys Thr Gly
        530                 535                 540

<210> SEQ ID NO 153
<211> LENGTH: 542
<212> TYPE: PRT
<213> ORGANISM: Artificial
<220> FEATURE:
<223> OTHER INFORMATION: P-0424

<400> SEQUENCE: 153

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
```

```
                130                 135                 140
Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
            210                 215                 220

Pro Gly Gly Gly Gly Ser Gly Gly Gly Ser Ala Pro Thr Ser Ser Ser
225                 230                 235                 240

Thr Lys Lys Thr Gln Leu Gln Leu Glu His Leu Leu Asn Asp Leu Gln
                245                 250                 255

Met Ile Leu Asn Gly Ile Asn Asn Tyr Lys Asn Pro Lys Leu Thr Arg
                260                 265                 270

Met Leu Thr Phe Lys Phe Tyr Met Pro Lys Lys Ala Thr Glu Leu Lys
            275                 280                 285

His Leu Gln Cys Leu Glu Glu Glu Leu Lys Pro Leu Glu Glu Val Leu
            290                 295                 300

Asn Leu Ala Gln Ser Lys Asn Phe His Leu Arg Pro Arg Asp Leu Ile
305                 310                 315                 320

Ser Asn Ile Asn Val Ile Val Leu Glu Leu Lys Gly Ser Glu Thr Thr
                325                 330                 335

Phe Met Cys Glu Tyr Ala Asp Glu Thr Ala Thr Ile Val Glu Phe Leu
                340                 345                 350

Asn Arg Trp Ile Thr Phe Ser Glu Ser Ile Ile Ser Thr Leu Thr Gly
            355                 360                 365

Gly Pro Leu Gly Met Leu Ser Gln Ser Glu Leu Cys Asp Asp Asp Pro
            370                 375                 380

Pro Glu Ile Pro His Ala Thr Phe Lys Ala Met Ala Tyr Lys Glu Gly
385                 390                 395                 400

Thr Met Leu Asn Cys Glu Cys Lys Arg Gly Phe Arg Arg Ile Glu Ser
                405                 410                 415

Gly Ser Leu Tyr Met Leu Cys Thr Gly Asn Ser Ser His Ser Ser Trp
            420                 425                 430

Asp Asn Gln Cys Gln Cys Thr Ser Ser Ala Thr Arg Asn Thr Thr Lys
            435                 440                 445

Gln Val Thr Pro Gln Pro Glu Glu Gln Lys Glu Arg Lys Thr Thr Glu
450                 455                 460

Met Gln Ser Pro Met Gln Pro Val Asp Gln Ala Ser Leu Pro Gly His
465                 470                 475                 480

Cys Arg Glu Pro Pro Pro Trp Glu Asn Glu Ala Thr Glu Arg Ile Tyr
                485                 490                 495

His Phe Val Val Gly Gln Met Val Tyr Tyr Gln Cys Val Gln Gly Tyr
            500                 505                 510

Arg Ala Leu His Arg Gly Pro Ala Glu Ser Val Cys Lys Met Thr His
            515                 520                 525

Gly Lys Thr Arg Trp Thr Gln Pro Gln Leu Ile Cys Thr Gly
530                 535                 540

<210> SEQ ID NO 154
```

<211> LENGTH: 542
<212> TYPE: PRT
<213> ORGANISM: Artificial
<220> FEATURE:
<223> OTHER INFORMATION: P-0425

<400> SEQUENCE: 154

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Ser Ala Pro Thr Ser Ser Ser
225                 230                 235                 240

Thr Lys Lys Thr Gln Leu Gln Leu Glu His Leu Leu Arg Asp Leu Gln
                245                 250                 255

Met Ile Leu Asn Gly Ile Asn Asn Tyr Lys Asn Pro Lys Leu Thr Arg
            260                 265                 270

Met Leu Thr Phe Lys Phe Tyr Met Pro Lys Lys Ala Thr Glu Leu Lys
        275                 280                 285

His Leu Gln Cys Leu Glu Glu Glu Leu Lys Pro Leu Glu Glu Val Leu
    290                 295                 300

Asn Leu Ala Gln Ser Lys Asn Phe His Leu Arg Pro Arg Asp Leu Ile
305                 310                 315                 320

Ser Asn Ile Asn Val Ile Val Leu Glu Leu Lys Gly Ser Glu Thr Thr
                325                 330                 335

Phe Met Cys Glu Tyr Ala Asp Glu Thr Ala Thr Ile Val Glu Phe Leu
            340                 345                 350

Asn Arg Trp Ile Thr Phe Ser Glu Ser Ile Ile Ser Thr Leu Thr Gly
        355                 360                 365

Gly Pro Leu Gly Met Leu Ser Gln Ser Glu Leu Cys Asp Asp Asp Pro
    370                 375                 380
```

```
Pro Glu Ile Pro His Ala Thr Phe Lys Ala Met Ala Tyr Lys Glu Gly
385                 390                 395                 400

Thr Met Leu Asn Cys Glu Cys Lys Arg Gly Phe Arg Arg Ile Glu Ser
                405                 410                 415

Gly Ser Leu Tyr Met Leu Cys Thr Gly Asn Ser Ser His Ser Ser Trp
            420                 425                 430

Asp Asn Gln Cys Gln Cys Thr Ser Ser Ala Thr Arg Asn Thr Thr Lys
        435                 440                 445

Gln Val Thr Pro Gln Pro Glu Glu Gln Lys Glu Arg Lys Thr Thr Glu
    450                 455                 460

Met Gln Ser Pro Met Gln Pro Val Asp Gln Ala Ser Leu Pro Gly His
465                 470                 475                 480

Cys Arg Glu Pro Pro Trp Glu Asn Glu Ala Thr Glu Arg Ile Tyr
                485                 490                 495

His Phe Val Val Gly Gln Met Val Tyr Tyr Gln Cys Val Gln Gly Tyr
            500                 505                 510

Arg Ala Leu His Arg Gly Pro Ala Glu Ser Val Cys Lys Met Thr His
        515                 520                 525

Gly Lys Thr Arg Trp Thr Gln Pro Gln Leu Ile Cys Thr Gly
530                 535                 540

<210> SEQ ID NO 155
<211> LENGTH: 547
<212> TYPE: PRT
<213> ORGANISM: Artificial
<220> FEATURE:
<223> OTHER INFORMATION: P-0426

<400> SEQUENCE: 155

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
        100                 105                 110

Glu Lys Thr Ile Ser Lys Ala Lys Gly Gln Pro Arg Glu Pro Gln Val
    115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205
```

His Glu Ala Leu His Asn His Tyr Thr Gln Lys Ser Leu Ser Leu Ser
             210                 215                 220

Pro Gly Gly Gly Gly Ser Gly Gly Gly Ser Ala Pro Thr Ser Ser Ser
225                 230                 235                 240

Thr Lys Lys Thr Gln Leu Gln Leu Glu His Leu Leu His Asp Leu Gln
             245                 250                 255

Met Ile Leu Asn Gly Ile Asn Asn Tyr Lys Asn Pro Lys Leu Thr Arg
             260                 265                 270

Met Leu Thr Phe Lys Phe Tyr Met Pro Lys Lys Ala Thr Glu Leu Lys
             275                 280                 285

His Leu Gln Cys Leu Glu Glu Glu Leu Lys Pro Leu Glu Glu Val Leu
             290                 295                 300

Asn Leu Ala Gln Ser Lys Asn Phe His Leu Arg Pro Arg Asp Leu Ile
305                 310                 315                 320

Ser Asn Ile Asn Val Ile Val Leu Glu Leu Lys Gly Ser Glu Thr Thr
             325                 330                 335

Phe Met Cys Glu Tyr Ala Asp Glu Thr Ala Thr Ile Val Glu Phe Leu
             340                 345                 350

Asn Arg Trp Ile Thr Phe Ile Glu Ser Ile Ile Ser Thr Leu Thr Gly
             355                 360                 365

Gly Ser Gly Pro Leu Gly Met Leu Ser Gln Gly Gly Gly Ser Glu Leu
             370                 375                 380

Cys Asp Asp Asp Pro Pro Glu Ile Pro His Ala Thr Phe Lys Ala Met
385                 390                 395                 400

Ala Tyr Lys Glu Gly Thr Met Leu Asn Cys Glu Cys Lys Arg Gly Phe
             405                 410                 415

Arg Arg Ile Glu Ser Gly Ser Leu Tyr Met Leu Cys Thr Gly Asn Ser
             420                 425                 430

Ser His Ser Ser Trp Asp Asn Gln Cys Gln Cys Thr Ser Ser Ala Thr
             435                 440                 445

Arg Asn Thr Thr Lys Gln Val Thr Pro Gln Pro Glu Glu Gln Lys Glu
             450                 455                 460

Arg Lys Thr Thr Glu Met Gln Ser Pro Met Gln Pro Val Asp Gln Ala
465                 470                 475                 480

Ser Leu Pro Gly His Cys Arg Glu Pro Pro Pro Trp Glu Asn Glu Ala
             485                 490                 495

Thr Glu Arg Ile Tyr His Phe Val Val Gly Gln Met Val Tyr Tyr Gln
             500                 505                 510

Cys Val Gln Gly Tyr Arg Ala Leu His Arg Gly Pro Ala Glu Ser Val
             515                 520                 525

Cys Lys Met Thr His Gly Lys Thr Arg Trp Thr Gln Pro Gln Leu Ile
530                 535                 540

Cys Thr Gly
545

<210> SEQ ID NO 156
<211> LENGTH: 226
<212> TYPE: PRT
<213> ORGANISM: Artificial
<220> FEATURE:
<223> OTHER INFORMATION: IgG1-Fc with reduced/abolished effector
      function and extended half-life

<400> SEQUENCE: 156

Asp Lys Thr His Thr Cys Pro Pro Cys Pro Ala Pro Glu Ala Ala Gly

```
1               5                   10                  15
Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly
225

<210> SEQ ID NO 157
<211> LENGTH: 10
<212> TYPE: PRT
<213> ORGANISM: Artificial
<220> FEATURE:
<223> OTHER INFORMATION: Protease substrate peptide sequence

<400> SEQUENCE: 157

Ser Gly Arg Ser Glu Asn Ile Arg Thr Ala
1               5                   10

<210> SEQ ID NO 158
<211> LENGTH: 7
<212> TYPE: PRT
<213> ORGANISM: Artificial
<220> FEATURE:
<223> OTHER INFORMATION: Protease substrate peptide sequence

<400> SEQUENCE: 158

Gly Pro Thr Asn Lys Val Arg
1               5

<210> SEQ ID NO 159
<211> LENGTH: 8
<212> TYPE: PRT
<213> ORGANISM: Artificial
<220> FEATURE:
<223> OTHER INFORMATION: Protease substrate peptide sequence

<400> SEQUENCE: 159
```

```
Arg Gln Ala Arg Ala Val Gly Gly
1               5
```

<210> SEQ ID NO 160
<211> LENGTH: 10
<212> TYPE: PRT
<213> ORGANISM: Artificial
<220> FEATURE:
<223> OTHER INFORMATION: Protease cleavable linker sequence

<400> SEQUENCE: 160

```
Gly Gly Pro Thr Asn Lys Val Arg Gly Ser
1               5                   10
```

<210> SEQ ID NO 161
<211> LENGTH: 10
<212> TYPE: PRT
<213> ORGANISM: Artificial
<220> FEATURE:
<223> OTHER INFORMATION: Protease cleavable linker sequence

<400> SEQUENCE: 161

```
Gly Arg Gln Ala Arg Ala Val Gly Gly Ser
1               5                   10
```

<210> SEQ ID NO 162
<211> LENGTH: 442
<212> TYPE: PRT
<213> ORGANISM: Artificial
<220> FEATURE:
<223> OTHER INFORMATION: P-0660

<400> SEQUENCE: 162

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205
```

```
His Glu Ala Leu His Asn His Tyr Thr Gln Lys Ser Leu Ser Leu Ser
210                 215                 220

Pro Gly Gly Ser Ser Gly Arg Ser Glu Asn Ile Arg Thr Ala Gly
225                 230                 235                 240

Thr Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
            260                 265                 270

His Pro Ser Cys Lys Val Thr Ala Met Lys Cys Phe Leu Leu Glu Leu
        275                 280                 285

Gln Val Ile Ser Leu Glu Ser Gly Asp Ala Asp Ile His Asp Thr Val
290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
            340                 345                 350

Asn Thr Ser Gly Gly Pro Leu Gly Met Leu Ser Gln Ser Ile Thr Cys
        355                 360                 365

Pro Pro Pro Met Ser Val Glu His Ala Asp Ile Trp Val Lys Ser Tyr
370                 375                 380

Ser Leu Tyr Ser Arg Glu Arg Tyr Ile Cys Asn Ser Gly Phe Lys Arg
385                 390                 395                 400

Lys Ala Gly Thr Ser Ser Leu Thr Glu Cys Val Leu Asn Lys Ala Thr
                405                 410                 415

Asn Val Ala His Trp Thr Thr Pro Ser Leu Lys Cys Ile Arg Asp Pro
            420                 425                 430

Ala Leu Val His Gln Arg Pro Ala Pro Pro
        435                 440

<210> SEQ ID NO 163
<211> LENGTH: 442
<212> TYPE: PRT
<213> ORGANISM: Artificial
<220> FEATURE:
<223> OTHER INFORMATION: P-0488

<400> SEQUENCE: 163

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125
```

Tyr Thr Leu Pro Pro Ser Arg Asp Glu Leu Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Gly Gly Gly Ser Gly Gly Gly Ser Gly Gly Gly Gly
225                 230                 235                 240

Ser Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
            260                 265                 270

His Pro Ser Cys Lys Val Thr Ala Met Lys Cys Phe Leu Leu Glu Leu
            275                 280                 285

Gln Val Ile Ser Leu Glu Ser Gly Asp Ala Asp Ile His Asp Thr Val
            290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
            340                 345                 350

Asn Thr Ser Ser Gly Arg Ser Glu Asn Ile Arg Thr Ala Ile Thr Cys
            355                 360                 365

Pro Pro Pro Met Ser Val Glu His Ala Asp Ile Trp Val Lys Ser Tyr
            370                 375                 380

Ser Leu Tyr Ser Arg Glu Arg Tyr Ile Cys Asn Ser Gly Phe Lys Arg
385                 390                 395                 400

Lys Ala Gly Thr Ser Ser Leu Thr Glu Cys Val Leu Asn Lys Ala Thr
                405                 410                 415

Asn Val Ala His Trp Thr Thr Pro Ser Leu Lys Cys Ile Arg Asp Pro
            420                 425                 430

Ala Leu Val His Gln Arg Pro Ala Pro
            435                 440

<210> SEQ ID NO 164
<211> LENGTH: 442
<212> TYPE: PRT
<213> ORGANISM: Artificial
<220> FEATURE:
<223> OTHER INFORMATION: P-0489

<400> SEQUENCE: 164

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

```
Glu Asp Pro Glu Val Lys Phe Asn Trp Tyr Val Asp Gly Val Glu Val
 50                  55                  60

His Asn Ala Lys Thr Lys Pro Arg Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Gly Gly Gly Ser Gly Gly Gly Gly Ser Gly Gly Gly Gly
225                 230                 235                 240

Ser Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
            260                 265                 270

His Pro Ser Cys Lys Val Thr Ala Met Lys Cys Phe Leu Leu Glu Leu
        275                 280                 285

Gln Val Ile Ser Leu Glu Ser Gly Asp Ala Asp Ile His Asp Thr Val
290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
            340                 345                 350

Asn Thr Ser Gly Gly Pro Thr Asn Lys Val Arg Gly Ser Ile Thr Cys
        355                 360                 365

Pro Pro Pro Met Ser Val Glu His Ala Asp Ile Trp Val Lys Ser Tyr
370                 375                 380

Ser Leu Tyr Ser Arg Glu Arg Tyr Ile Cys Asn Ser Gly Phe Lys Arg
385                 390                 395                 400

Lys Ala Gly Thr Ser Ser Leu Thr Glu Cys Val Leu Asn Lys Ala Thr
                405                 410                 415

Asn Val Ala His Trp Thr Thr Pro Ser Leu Lys Cys Ile Arg Asp Pro
            420                 425                 430

Ala Leu Val His Gln Arg Pro Ala Pro Pro
        435                 440

<210> SEQ ID NO 165
<211> LENGTH: 441
<212> TYPE: PRT
```

<213> ORGANISM: Artificial
<220> FEATURE:
<223> OTHER INFORMATION: P-0661

<400> SEQUENCE: 165

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Pro Thr Asn Lys Val Arg Gly Gly Ser
225                 230                 235                 240

Asn Trp Val Asn Val Ile Ser Asp Leu Lys Lys Ile Glu Asp Leu Ile
                245                 250                 255

Gln Ser Met His Ile Asp Ala Thr Leu Tyr Thr Glu Ser Asp Val His
            260                 265                 270

Pro Ser Cys Lys Val Thr Ala Met Lys Cys Phe Leu Leu Glu Leu Gln
        275                 280                 285

Val Ile Ser Leu Glu Ser Gly Asp Ala Asp Ile His Asp Thr Val Glu
    290                 295                 300

Asn Leu Ile Ile Leu Ala Asn Asn Ser Leu Ser Ser Asn Gly Asn Val
305                 310                 315                 320

Thr Glu Ser Gly Cys Lys Glu Cys Glu Glu Leu Glu Glu Lys Asn Ile
                325                 330                 335

Lys Glu Phe Leu Gln Ser Phe Val His Ile Val Gln Met Phe Ile Asn
            340                 345                 350

Thr Ser Gly Gly Pro Leu Gly Met Leu Ser Gln Ser Ile Thr Cys Pro
        355                 360                 365

Pro Pro Met Ser Val Glu His Ala Asp Ile Trp Val Lys Ser Tyr Ser
    370                 375                 380

Leu Tyr Ser Arg Glu Arg Tyr Ile Cys Asn Ser Gly Phe Lys Arg Lys
```

```
                385                 390                 395                 400
Ala Gly Thr Ser Ser Leu Thr Glu Cys Val Leu Asn Lys Ala Thr Asn
                    405                 410                 415

Val Ala His Trp Thr Thr Pro Ser Leu Lys Cys Ile Arg Asp Pro Ala
                420                 425                 430

Leu Val His Gln Arg Pro Ala Pro Pro
                435                 440

<210> SEQ ID NO 166
<211> LENGTH: 226
<212> TYPE: PRT
<213> ORGANISM: Artificial
<220> FEATURE:
<223> OTHER INFORMATION: IgG1-Fc with reduced/abolished effector
      function and extended in vivo half-life

<400> SEQUENCE: 166

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Ala His Tyr Thr Gln Lys Ser Leu Ser Leu Ser
    210                 215                 220

Pro Gly
225

<210> SEQ ID NO 167
<211> LENGTH: 226
<212> TYPE: PRT
<213> ORGANISM: Artificial
<220> FEATURE:
<223> OTHER INFORMATION: Knob-Fc with extended in vivo half-life

<400> SEQUENCE: 167

Asp Lys Thr His Thr Cys Pro Pro Cys Pro Ala Pro Glu Ala Ala Gly
1               5                   10                  15
```

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Ala His Tyr Thr Gln Lys Ser Leu Ser Leu Ser
    210                 215                 220

Pro Gly
225

<210> SEQ ID NO 168
<211> LENGTH: 226
<212> TYPE: PRT
<213> ORGANISM: Artificial
<220> FEATURE:
<223> OTHER INFORMATION: Hole-Fc with extended in vivo half-life

<400> SEQUENCE: 168

Asp Lys Thr His Thr Cys Pro Pro Cys Pro Ala Pro Glu Ala Ala Gly
 1               5                  10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
130                 135                 140

```
Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Ala His Tyr Thr Gln Lys Ser Leu Ser Leu Ser
    210                 215                 220

Pro Gly
225

<210> SEQ ID NO 169
<211> LENGTH: 442
<212> TYPE: PRT
<213> ORGANISM: Artificial
<220> FEATURE:
<223> OTHER INFORMATION: P-0650

<400> SEQUENCE: 169

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Ala His Tyr Thr Gln Lys Ser Leu Ser Leu Ser
    210                 215                 220

Pro Gly Gly Gly Gly Ser Gly Gly Gly Ser Gly Gly Gly Gly
225                 230                 235                 240

Ser Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
            260                 265                 270
```

```
His Pro Ser Cys Lys Val Thr Ala Met Lys Cys Phe Leu Leu Glu Leu
            275                 280                 285

Gln Val Ile Ser Leu Glu Ser Gly Asp Ala Asp Ile His Asp Thr Val
        290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
            340                 345                 350

Asn Thr Ser Gly Gly Pro Leu Gly Met Leu Ser Gln Ser Ile Thr Cys
        355                 360                 365

Pro Pro Pro Met Ser Val Glu His Ala Asp Ile Trp Val Lys Ser Tyr
    370                 375                 380

Ser Leu Tyr Ser Arg Glu Arg Tyr Ile Cys Asn Ser Gly Phe Lys Arg
385                 390                 395                 400

Lys Ala Gly Thr Ser Ser Leu Thr Glu Cys Val Leu Asn Lys Ala Thr
                405                 410                 415

Asn Val Ala His Trp Thr Thr Pro Ser Leu Lys Cys Ile Arg Asp Pro
            420                 425                 430

Ala Leu Val His Gln Arg Pro Ala Pro Pro
        435                 440

<210> SEQ ID NO 170
<211> LENGTH: 442
<212> TYPE: PRT
<213> ORGANISM: Artificial
<220> FEATURE:
<223> OTHER INFORMATION: P-0651

<400> SEQUENCE: 170

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190
```

-continued

```
Asp Lys Ser Arg Trp Gln Gln Gly Asn Val Phe Ser Cys Ser Val Met
            195                 200                 205

His Glu Ala Leu His Ala His Tyr Thr Gln Lys Ser Leu Ser Leu Ser
        210                 215                 220

Pro Gly Gly Gly Gly Ser Gly Gly Gly Ser Gly Gly Gly Gly
225                 230                 235                 240

Ser Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
            260                 265                 270

His Pro Ser Cys Lys Val Thr Ala Met Lys Cys Phe Leu Leu Glu Leu
        275                 280                 285

Gln Val Ile Ser Leu Glu Ser Gly Asp Ala Asp Ile His Asp Thr Val
    290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
            340                 345                 350

Asn Thr Ser Gly Gly Gly Gly Ser Gly Gly Gly Gly Ser Ile Thr Cys
        355                 360                 365

Pro Pro Pro Met Ser Val Glu His Ala Asp Ile Trp Val Lys Ser Tyr
370                 375                 380

Ser Leu Tyr Ser Arg Glu Arg Tyr Ile Cys Asn Ser Gly Phe Lys Arg
385                 390                 395                 400

Lys Ala Gly Thr Ser Ser Leu Thr Glu Cys Val Leu Asn Lys Ala Thr
                405                 410                 415

Asn Val Ala His Trp Thr Thr Pro Ser Leu Lys Cys Ile Arg Asp Pro
            420                 425                 430

Ala Leu Val His Gln Arg Pro Ala Pro Pro
        435                 440
```

<210> SEQ ID NO 171
<211> LENGTH: 448
<212> TYPE: PRT
<213> ORGANISM: Artificial
<220> FEATURE:
<223> OTHER INFORMATION: P-0662 Hole Chain

<400> SEQUENCE: 171

```
Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110
```

```
Glu Lys Thr Ile Ser Lys Ala Lys Gly Gln Pro Arg Glu Pro Gln Val
            115                 120                 125

Tyr Thr Leu Pro Pro Cys Arg Glu Glu Met Thr Lys Asn Gln Val Ser
        130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Gly Gly Gly Ser Leu Gly Gly Ser Gly Arg Ser Ala Asn
225                 230                 235                 240

Ala Ile Leu Glu Gly Gly Ser Asn Trp Val Asn Val Ile Ser Asp Leu
                245                 250                 255

Lys Lys Ile Glu Asp Leu Ile Gln Ser Met His Ile Asp Ala Thr Leu
            260                 265                 270

Tyr Thr Glu Ser Asp Val His Pro Ser Cys Lys Val Thr Ala Met Lys
        275                 280                 285

Cys Phe Leu Leu Glu Leu Gln Val Ile Ser Leu Glu Ser Gly Asp Ala
            290                 295                 300

Asp Ile His Asp Thr Val Glu Asn Leu Ile Ile Leu Ala Asn Asn Ser
305                 310                 315                 320

Leu Ser Ser Asn Gly Asn Val Thr Glu Ser Gly Cys Lys Glu Cys Glu
                325                 330                 335

Glu Leu Glu Glu Lys Asn Ile Lys Glu Phe Leu Gln Ser Phe Val His
                340                 345                 350

Ile Val Gln Met Phe Ile Asn Thr Ser Gly Gly Pro Leu Gly Met Leu
            355                 360                 365

Ser Gln Ser Ile Thr Cys Pro Pro Met Ser Val Glu His Ala Asp
        370                 375                 380

Ile Trp Val Lys Ser Tyr Ser Leu Tyr Ser Arg Glu Arg Tyr Ile Cys
385                 390                 395                 400

Asn Ser Gly Phe Lys Arg Lys Ala Gly Thr Ser Ser Leu Thr Glu Cys
                405                 410                 415

Val Leu Asn Lys Ala Thr Asn Val Ala His Trp Thr Thr Pro Ser Leu
            420                 425                 430

Lys Cys Ile Arg Asp Pro Ala Leu Val His Gln Arg Pro Ala Pro Pro
        435                 440                 445

<210> SEQ ID NO 172
<211> LENGTH: 448
<212> TYPE: PRT
<213> ORGANISM: Artificial
<220> FEATURE:
<223> OTHER INFORMATION: P-0663 Hole Chain with extended half-life

<400> SEQUENCE: 172

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
                20                  25                  30
```

-continued

```
Ile Ser Arg Thr Pro Glu Val Thr Cys Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Cys Arg Glu Glu Met Thr Lys Asn Gln Val Ser
    130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Ala His Tyr Thr Gln Lys Ser Leu Ser Leu Ser
    210                 215                 220
Pro Gly Gly Gly Gly Ser Leu Gly Gly Gly Ser Arg Ser Ala Asn
225                 230                 235                 240
Ala Ile Leu Glu Gly Gly Ser Asn Trp Val Asn Val Ile Ser Asp Leu
                245                 250                 255
Lys Lys Ile Glu Asp Leu Ile Gln Ser Met His Ile Asp Ala Thr Leu
            260                 265                 270
Tyr Thr Glu Ser Asp Val His Pro Ser Cys Lys Val Thr Ala Met Lys
        275                 280                 285
Cys Phe Leu Leu Glu Leu Gln Val Ile Ser Leu Glu Ser Gly Asp Ala
    290                 295                 300
Asp Ile His Asp Thr Val Glu Asn Leu Ile Ile Leu Ala Asn Asn Ser
305                 310                 315                 320
Leu Ser Ser Asn Gly Asn Val Thr Glu Ser Gly Cys Lys Glu Cys Glu
                325                 330                 335
Glu Leu Glu Glu Lys Asn Ile Lys Glu Phe Leu Gln Ser Phe Val His
            340                 345                 350
Ile Val Gln Met Phe Ile Asn Thr Ser Gly Gly Pro Leu Gly Met Leu
        355                 360                 365
Ser Gln Ser Ile Thr Cys Pro Pro Met Ser Val Glu His Ala Asp
    370                 375                 380
Ile Trp Val Lys Ser Tyr Ser Leu Tyr Ser Arg Glu Arg Tyr Ile Cys
385                 390                 395                 400
Asn Ser Gly Phe Lys Arg Lys Ala Gly Thr Ser Ser Leu Thr Glu Cys
                405                 410                 415
Val Leu Asn Lys Ala Thr Asn Val Ala His Trp Thr Thr Pro Ser Leu
            420                 425                 430
Lys Cys Ile Arg Asp Pro Ala Leu Val His Gln Arg Pro Ala Pro Pro
        435                 440                 445
```

<210> SEQ ID NO 173
<211> LENGTH: 442
<212> TYPE: PRT
<213> ORGANISM: Artificial
<220> FEATURE:
<223> OTHER INFORMATION: P-0664 Hole chain with extended half-life

<400> SEQUENCE: 173

```
Asp Lys Thr His Thr Cys Pro Pro Cys Pro Ala Pro Glu Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Ala His Tyr Thr Gln Lys Ser Leu Ser Leu Ser
    210                 215                 220

Pro Gly Gly Gly Gly Ser Gly Gly Gly Gly Ser Gly Gly Gly Gly
225                 230                 235                 240

Ser Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
            260                 265                 270

His Pro Ser Cys Lys Val Thr Ala Met Lys Cys Phe Leu Leu Glu Leu
        275                 280                 285

Gln Val Ile Ser Leu Glu Ser Gly Asp Ala Asp Ile His Asp Thr Val
    290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
                325                 330                 335

Ile Lys Glu Phe Leu Gln Ser Phe Val His Ile Val Gln Met Phe Ile
            340                 345                 350

Asn Thr Ser Gly Gly Pro Leu Gly Met Leu Ser Gln Ser Ile Thr Cys
        355                 360                 365
```

```
Pro Pro Pro Met Ser Val Glu His Ala Asp Ile Trp Val Lys Ser Tyr
    370             375                 380

Ser Leu Tyr Ser Arg Glu Arg Tyr Ile Cys Asn Ser Gly Phe Lys Arg
385             390                 395                 400

Lys Ala Gly Thr Ser Ser Leu Thr Glu Cys Val Leu Asn Lys Ala Thr
                405                 410                 415

Asn Val Ala His Trp Thr Thr Pro Ser Leu Lys Cys Ile Arg Asp Pro
                420                 425                 430

Ala Leu Val His Gln Arg Pro Ala Pro Pro
                435                 440

<210> SEQ ID NO 174
<211> LENGTH: 442
<212> TYPE: PRT
<213> ORGANISM: Artificial
<220> FEATURE:
<223> OTHER INFORMATION: P-0665 Hole chain with extended half-life

<400> SEQUENCE: 174

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Ala His Tyr Thr Gln Lys Ser Leu Ser Leu Ser
        210                 215                 220

Pro Gly Gly Ser Ser Ser Gly Arg Ser Glu Asn Ile Arg Thr Ala Gly
225                 230                 235                 240

Thr Asn Trp Val Asn Val Ile Ser Asp Leu Lys Lys Ile Glu Asp Leu
                245                 250                 255

Ile Gln Ser Met His Ile Asp Ala Thr Leu Tyr Thr Glu Ser Asp Val
                260                 265                 270

His Pro Ser Cys Lys Val Thr Ala Met Lys Cys Phe Leu Leu Glu Leu
            275                 280                 285
```

```
Gln Val Ile Ser Leu Glu Ser Gly Asp Ala Asp Ile His Asp Thr Val
    290                 295                 300
Glu Asn Leu Ile Ile Leu Ala Asn Asn Ser Leu Ser Ser Asn Gly Asn
305                 310                 315                 320
Val Thr Glu Ser Gly Cys Lys Glu Cys Glu Glu Leu Glu Glu Lys Asn
                325                 330                 335
Ile Lys Glu Phe Leu Gln Ser Phe Val His Ile Val Gln Met Phe Ile
                340                 345                 350
Asn Thr Ser Gly Gly Pro Leu Gly Met Leu Ser Gln Ser Ile Thr Cys
                355                 360                 365
Pro Pro Pro Met Ser Val Glu His Ala Asp Ile Trp Val Lys Ser Tyr
370                 375                 380
Ser Leu Tyr Ser Arg Glu Arg Tyr Ile Cys Asn Ser Gly Phe Lys Arg
385                 390                 395                 400
Lys Ala Gly Thr Ser Ser Leu Thr Glu Cys Val Leu Asn Lys Ala Thr
                405                 410                 415
Asn Val Ala His Trp Thr Thr Pro Ser Leu Lys Cys Ile Arg Asp Pro
                420                 425                 430
Ala Leu Val His Gln Arg Pro Ala Pro Pro
                435                 440

<210> SEQ ID NO 175
<211> LENGTH: 299
<212> TYPE: PRT
<213> ORGANISM: Artificial
<220> FEATURE:
<223> OTHER INFORMATION: P-0156 Knob-chain

<400> SEQUENCE: 175

Ile Thr Cys Pro Pro Pro Met Ser Val Glu His Ala Asp Ile Trp Val
1               5                   10                  15
Lys Ser Tyr Ser Leu Tyr Ser Arg Glu Arg Tyr Ile Cys Asn Ser Gly
                20                  25                  30
Phe Lys Arg Lys Ala Gly Thr Ser Ser Leu Thr Glu Cys Val Leu Asn
            35                  40                  45
Lys Ala Thr Asn Val Ala His Trp Thr Thr Pro Ser Leu Lys Cys Ile
50                  55                  60
Arg Asp Pro Ala Leu Val His Gln Arg Pro Ala Pro Pro Gly Cys Pro
65                  70                  75                  80
Pro Cys Pro Ala Pro Glu Ala Ala Gly Ala Pro Ser Val Phe Leu Phe
                85                  90                  95
Pro Pro Lys Pro Lys Asp Thr Leu Met Ile Ser Arg Thr Pro Glu Val
                100                 105                 110
Thr Cys Val Val Val Asp Val Ser His Glu Asp Pro Glu Val Lys Phe
            115                 120                 125
Asn Trp Tyr Val Asp Gly Val Glu Val His Asn Ala Lys Thr Lys Pro
130                 135                 140
Arg Glu Glu Gln Tyr Asn Ser Thr Tyr Arg Val Val Ser Val Leu Thr
145                 150                 155                 160
Val Leu His Gln Asp Trp Leu Asn Gly Lys Glu Tyr Lys Cys Lys Val
                165                 170                 175
Ser Asn Lys Ala Leu Pro Ala Pro Ile Glu Lys Thr Ile Ser Lys Ala
                180                 185                 190
Lys Gly Gln Pro Arg Glu Pro Gln Val Cys Thr Leu Pro Pro Ser Arg
            195                 200                 205
```

Glu Glu Met Thr Lys Asn Gln Val Ser Leu Trp Cys Leu Val Lys Gly
210                 215                 220
Phe Tyr Pro Ser Asp Ile Ala Val Glu Trp Glu Ser Asn Gly Gln Pro
225                 230                 235                 240
Glu Asn Asn Tyr Lys Thr Thr Pro Pro Val Leu Asp Ser Asp Gly Ser
            245                 250                 255
Phe Phe Leu Tyr Ser Lys Leu Thr Val Asp Lys Ser Arg Trp Gln Gln
            260                 265                 270
Gly Asn Val Phe Ser Cys Ser Val Met His Glu Ala Leu His Asn His
            275                 280                 285
Tyr Thr Gln Lys Ser Leu Ser Leu Ser Pro Gly
290                 295

<210> SEQ ID NO 176
<211> LENGTH: 336
<212> TYPE: PRT
<213> ORGANISM: Artificial
<220> FEATURE:
<223> OTHER INFORMATION: P-0156 hole-chain

<400> SEQUENCE: 176

Asn Trp Val Asn Val Ile Ser Asp Leu Lys Lys Ile Glu Asp Leu Ile
1               5                   10                  15
Gln Ser Met His Ile Asp Ala Thr Leu Tyr Thr Glu Ser Asp Val His
            20                  25                  30
Pro Ser Cys Lys Val Thr Ala Met Lys Cys Phe Leu Leu Glu Leu Gln
        35                  40                  45
Val Ile Ser Leu Glu Ser Gly Asp Ala Ser Ile His Asp Thr Val Glu
50                  55                  60
Asn Leu Ile Ile Leu Ala Asn Asn Ser Leu Ser Ser Asn Gly Asn Val
65                  70                  75                  80
Thr Glu Ser Gly Cys Lys Glu Cys Glu Glu Leu Glu Glu Lys Asn Ile
                85                  90                  95
Lys Glu Phe Leu Gln Ser Phe Val His Ile Val Gln Met Phe Ile Asn
            100                 105                 110
Thr Ser Gly Cys Pro Pro Cys Pro Ala Pro Glu Ala Ala Gly Ala Pro
        115                 120                 125
Ser Val Phe Leu Phe Pro Pro Lys Pro Lys Asp Thr Leu Met Ile Ser
130                 135                 140
Arg Thr Pro Glu Val Thr Cys Val Val Val Asp Val Ser His Glu Asp
145                 150                 155                 160
Pro Glu Val Lys Phe Asn Trp Tyr Val Asp Gly Val Glu Val His Asn
                165                 170                 175
Ala Lys Thr Lys Pro Arg Glu Glu Gln Tyr Asn Ser Thr Tyr Arg Val
            180                 185                 190
Val Ser Val Leu Thr Val Leu His Gln Asp Trp Leu Asn Gly Lys Glu
        195                 200                 205
Tyr Lys Cys Lys Val Ser Asn Lys Ala Leu Pro Ala Pro Ile Glu Lys
210                 215                 220
Thr Ile Ser Lys Ala Lys Gly Gln Pro Arg Glu Pro Gln Val Tyr Thr
225                 230                 235                 240
Leu Pro Pro Cys Arg Glu Glu Met Thr Lys Asn Gln Val Ser Leu Ser
                245                 250                 255
Cys Ala Val Lys Gly Phe Tyr Pro Ser Asp Ile Ala Val Glu Trp Glu
            260                 265                 270

```
Ser Asn Gly Gln Pro Glu Asn Tyr Lys Thr Thr Pro Val Leu
            275                 280                 285

Asp Ser Asp Gly Ser Phe Phe Leu Val Ser Lys Leu Thr Val Asp Lys
290                 295                 300

Ser Arg Trp Gln Gln Gly Asn Val Phe Ser Cys Ser Val Met His Glu
305                 310                 315                 320

Ala Leu His Asn His Tyr Thr Gln Lys Ser Leu Ser Leu Ser Pro Gly
                325                 330                 335

<210> SEQ ID NO 177
<211> LENGTH: 350
<212> TYPE: PRT
<213> ORGANISM: Artificial
<220> FEATURE:
<223> OTHER INFORMATION: Benchmark chain 1

<400> SEQUENCE: 177

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asn Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Gln
50                  55                  60

Asp Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Gly Ser Glu Pro Lys Ser Ser Asp Lys Thr His
        115                 120                 125

Thr Cys Pro Pro Cys Pro Ala Pro Pro Val Ala Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Lys His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Glu Tyr Asn Ser Thr Tyr Arg Val Val Ser Val
        195                 200                 205

Leu Thr Val Leu His Gln Asp Trp Leu Asn Gly Lys Glu Tyr Lys Cys
210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Asp Val
            260                 265                 270

Ser Gly Phe Tyr Pro Ser Asp Ile Ala Val Glu Trp Glu Ser Asp Gly
        275                 280                 285

Gln Pro Glu Asn Asn Tyr Lys Thr Thr Pro Pro Val Leu Asp Ser Asp
290                 295                 300
```

```
Gly Ser Phe Phe Leu Tyr Ser Lys Leu Thr Val Asp Lys Ser Arg Trp
305                 310                 315                 320

Glu Gln Gly Asp Val Phe Ser Cys Ser Val Leu His Glu Ala Leu His
                325                 330                 335

Ser His Tyr Thr Gln Lys Ser Leu Ser Leu Ser Pro Gly Lys
            340                 345                 350

<210> SEQ ID NO 178
<211> LENGTH: 301
<212> TYPE: PRT
<213> ORGANISM: Artificial
<220> FEATURE:
<223> OTHER INFORMATION: Benchmark chain 2

<400> SEQUENCE: 178

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
50                  55                  60

Arg Gly Gly Gly Gly Ser Glu Pro Lys Ser Ser Asp Lys Thr His Thr
65                  70                  75                  80

Cys Pro Pro Cys Pro Ala Pro Val Ala Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Lys His Glu Asp Pro Glu Val Lys
            115                 120                 125

Phe Asn Trp Tyr Val Asp Gly Val Glu Val His Asn Ala Lys Thr Lys
130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Glu Gln Met Thr Lys Asn Gln Val Lys Leu Thr Cys Leu Val Lys
210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Leu His Glu Ala Leu His Ser
        275                 280                 285

His Tyr Thr Gln Lys Ser Leu Ser Leu Ser Pro Gly Lys
290                 295                 300

<210> SEQ ID NO 179
<211> LENGTH: 465
```

```
<212> TYPE: PRT
<213> ORGANISM: Artificial
<220> FEATURE:
<223> OTHER INFORMATION: P-0321

<400> SEQUENCE: 179
```

| | | | | | | | | | | | | | | |
|---|---|---|---|---|---|---|---|---|---|---|---|---|---|---|
| Asp | Lys | Thr | His | Thr | Cys | Pro | Pro | Cys | Pro | Ala | Pro | Glu | Ala | Ala | Gly |
| 1 | | | | 5 | | | | | 10 | | | | | 15 | |
| Ala | Pro | Ser | Val | Phe | Leu | Phe | Pro | Pro | Lys | Pro | Lys | Asp | Thr | Leu | Met |
| | | | 20 | | | | | 25 | | | | | 30 | | |
| Ile | Ser | Arg | Thr | Pro | Glu | Val | Thr | Cys | Val | Val | Val | Asp | Val | Ser | His |
| | | | 35 | | | | | 40 | | | | | 45 | | |
| Glu | Asp | Pro | Glu | Val | Lys | Phe | Asn | Trp | Tyr | Val | Asp | Gly | Val | Glu | Val |
| | 50 | | | | | 55 | | | | | 60 | | | | |
| His | Asn | Ala | Lys | Thr | Lys | Pro | Arg | Glu | Glu | Gln | Tyr | Asn | Ser | Thr | Tyr |
| 65 | | | | | 70 | | | | | 75 | | | | | 80 |
| Arg | Val | Val | Ser | Val | Leu | Thr | Val | Leu | His | Gln | Asp | Trp | Leu | Asn | Gly |
| | | | | 85 | | | | | 90 | | | | | 95 | |
| Lys | Glu | Tyr | Lys | Cys | Lys | Val | Ser | Asn | Lys | Ala | Leu | Pro | Ala | Pro | Ile |
| | | | 100 | | | | | 105 | | | | | 110 | | |
| Glu | Lys | Thr | Ile | Ser | Lys | Ala | Lys | Gly | Gln | Pro | Arg | Glu | Pro | Gln | Val |
| | | | 115 | | | | | 120 | | | | | 125 | | |
| Tyr | Thr | Leu | Pro | Pro | Ser | Arg | Asp | Glu | Leu | Thr | Lys | Asn | Gln | Val | Ser |
| | 130 | | | | | 135 | | | | | 140 | | | | |
| Leu | Thr | Cys | Leu | Val | Lys | Gly | Phe | Tyr | Pro | Ser | Asp | Ile | Ala | Val | Glu |
| 145 | | | | | 150 | | | | | 155 | | | | | 160 |
| Trp | Glu | Ser | Asn | Gly | Gln | Pro | Glu | Asn | Asn | Tyr | Lys | Thr | Thr | Pro | Pro |
| | | | | 165 | | | | | 170 | | | | | 175 | |
| Val | Leu | Asp | Ser | Asp | Gly | Ser | Phe | Phe | Leu | Tyr | Ser | Lys | Leu | Thr | Val |
| | | | 180 | | | | | 185 | | | | | 190 | | |
| Asp | Lys | Ser | Arg | Trp | Gln | Gln | Gly | Asn | Val | Phe | Ser | Cys | Ser | Val | Met |
| | | | 195 | | | | | 200 | | | | | 205 | | |
| His | Glu | Ala | Leu | His | Asn | His | Tyr | Thr | Gln | Lys | Ser | Leu | Ser | Leu | Ser |
| | 210 | | | | | 215 | | | | | 220 | | | | |
| Pro | Gly | Gly | Gly | Gly | Ser | Leu | Gly | Gly | Ser | Gly | Arg | Ser | Ala | Asn |
| 225 | | | | | 230 | | | | | 235 | | | | | 240 |
| Ala | Ile | Leu | Glu | Gly | Gly | Ser | Ala | Pro | Thr | Ser | Ser | Thr | Lys | Lys |
| | | | | 245 | | | | | 250 | | | | | 255 | |
| Thr | Gln | Leu | Gln | Leu | Glu | His | Leu | Leu | Leu | Asp | Leu | Gln | Met | Ile | Leu |
| | | | 260 | | | | | 265 | | | | | 270 | | |
| Asn | Gly | Ile | Asn | Asn | Tyr | Lys | Asn | Pro | Lys | Leu | Thr | Arg | Met | Leu | Thr |
| | | | 275 | | | | | 280 | | | | | 285 | | |
| Phe | Lys | Phe | Tyr | Met | Pro | Lys | Lys | Ala | Thr | Glu | Leu | Lys | His | Leu | Gln |
| | 290 | | | | | 295 | | | | | 300 | | | | |
| Cys | Leu | Glu | Glu | Glu | Leu | Lys | Pro | Leu | Glu | Glu | Val | Leu | Asn | Leu | Ala |
| 305 | | | | | 310 | | | | | 315 | | | | | 320 |
| Gln | Ser | Lys | Asn | Phe | His | Leu | Arg | Pro | Arg | Asp | Leu | Ile | Ser | Asn | Ile |
| | | | | 325 | | | | | 330 | | | | | 335 | |
| Asn | Val | Ile | Val | Leu | Glu | Leu | Lys | Gly | Ser | Glu | Thr | Thr | Phe | Met | Cys |
| | | | 340 | | | | | 345 | | | | | 350 | | |
| Glu | Tyr | Ala | Asp | Glu | Thr | Ala | Thr | Ile | Val | Glu | Phe | Leu | Asn | Arg | Trp |
| | | | 355 | | | | | 360 | | | | | 365 | | |
| Ile | Thr | Phe | Ser | Gln | Ser | Ile | Ile | Ser | Thr | Leu | Thr | Gly | Gly | Gly | Gly |
| | 370 | | | | | 375 | | | | | 380 | | | | |

```
Ser Gly Gly Gly Gly Ser Gly Gly Gly Ser Gly His Cys Arg Glu
385                 390                 395                 400

Pro Pro Pro Trp Glu Asn Glu Ala Thr Glu Arg Ile Tyr His Phe Val
                405                 410                 415

Tyr Lys Glu Gly Thr Met Leu Asn Cys Glu Cys Lys Arg Gly Phe Arg
            420                 425                 430

Arg Ile Lys Ser Gly Ser Leu Tyr Met Leu Cys Thr Gly Asn Ser Ser
        435                 440                 445

His Ser Ser Trp Asp Asn Gln Cys Gln Cys Thr Ser Ser Ala Thr Arg
    450                 455                 460

Asn
465

<210> SEQ ID NO 180
<211> LENGTH: 669
<212> TYPE: PRT
<213> ORGANISM: Artificial
<220> FEATURE:
<223> OTHER INFORMATION: Tecentriq-IL-15-VitoKineHC

<400> SEQUENCE: 180

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

```
Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Gly
        435                 440                 445

Gly Gly Gly Ser Leu Gly Gly Ser Gly Arg Ser Ala Asn Ala Ile Leu
450                 455                 460

Glu Gly Gly Ser Asn Trp Val Asn Val Ile Ser Asp Leu Lys Lys Ile
465                 470                 475                 480

Glu Asp Leu Ile Gln Ser Met His Ile Asp Ala Thr Leu Tyr Thr Glu
                485                 490                 495

Ser Asp Val His Pro Ser Cys Lys Val Thr Ala Met Lys Cys Phe Leu
            500                 505                 510

Leu Glu Leu Gln Val Ile Ser Leu Glu Ser Gly Asp Ala Asp Ile His
        515                 520                 525

Asp Thr Val Glu Asn Leu Ile Ile Leu Ala Asn Asn Ser Leu Ser Ser
530                 535                 540

Asn Gly Asn Val Thr Glu Ser Gly Cys Lys Glu Cys Glu Glu Leu Glu
545                 550                 555                 560

Glu Lys Asn Ile Lys Glu Phe Leu Gln Ser Phe Val His Ile Val Gln
                565                 570                 575

Met Phe Ile Asn Thr Ser Gly Gly Pro Leu Gly Met Leu Ser Gln Ser
            580                 585                 590

Ile Thr Cys Pro Pro Met Ser Val Glu His Ala Asp Ile Trp Val
        595                 600                 605

Lys Ser Tyr Ser Leu Tyr Ser Arg Glu Arg Tyr Ile Cys Asn Ser Gly
610                 615                 620

Phe Lys Arg Lys Ala Gly Thr Ser Ser Leu Thr Glu Cys Val Leu Asn
625                 630                 635                 640

Lys Ala Thr Asn Val Ala His Trp Thr Thr Pro Ser Leu Lys Cys Ile
                645                 650                 655

Arg Asp Pro Ala Leu Val His Gln Arg Pro Ala Pro
            660                 665

<210> SEQ ID NO 181
<211> LENGTH: 214
<212> TYPE: PRT
```

```
<213> ORGANISM: Artificial
<220> FEATURE:
<223> OTHER INFORMATION: Tecentriq-L

<400> SEQUENCE: 181
```

| | | | | | | | | | | | | | | | |
|---|---|---|---|---|---|---|---|---|---|---|---|---|---|---|---|
| Asp | Ile | Gln | Met | Thr | Gln | Ser | Pro | Ser | Ser | Leu | Ser | Ala | Ser | Val | Gly |
| 1 | | | | 5 | | | | | 10 | | | | | 15 | |
| Asp | Arg | Val | Thr | Ile | Thr | Cys | Arg | Ala | Ser | Gln | Asp | Val | Ser | Thr | Ala |
| | | | 20 | | | | | 25 | | | | | 30 | | |
| Val | Ala | Trp | Tyr | Gln | Gln | Lys | Pro | Gly | Lys | Ala | Pro | Lys | Leu | Leu | Ile |
| | | 35 | | | | | 40 | | | | | 45 | | | |
| Tyr | Ser | Ala | Ser | Phe | Leu | Tyr | Ser | Gly | Val | Pro | Ser | Arg | Phe | Ser | Gly |
| 50 | | | | | 55 | | | | | 60 | | | | | |
| Ser | Gly | Ser | Gly | Thr | Asp | Phe | Thr | Leu | Thr | Ile | Ser | Ser | Leu | Gln | Pro |
| 65 | | | | | 70 | | | | | 75 | | | | | 80 |
| Glu | Asp | Phe | Ala | Thr | Tyr | Tyr | Cys | Gln | Gln | Tyr | Leu | Tyr | His | Pro | Ala |
| | | | | 85 | | | | | 90 | | | | | 95 | |
| Thr | Phe | Gly | Gln | Gly | Thr | Lys | Val | Glu | Ile | Lys | Arg | Thr | Val | Ala | Ala |
| | | | 100 | | | | | 105 | | | | | 110 | | |
| Pro | Ser | Val | Phe | Ile | Phe | Pro | Pro | Ser | Asp | Glu | Gln | Leu | Lys | Ser | Gly |
| | | 115 | | | | | 120 | | | | | 125 | | | |
| Thr | Ala | Ser | Val | Val | Cys | Leu | Leu | Asn | Asn | Phe | Tyr | Pro | Arg | Glu | Ala |
| 130 | | | | | 135 | | | | | 140 | | | | | |
| Lys | Val | Gln | Trp | Lys | Val | Asp | Asn | Ala | Leu | Gln | Ser | Gly | Asn | Ser | Gln |
| 145 | | | | | 150 | | | | | 155 | | | | | 160 |
| Glu | Ser | Val | Thr | Glu | Gln | Asp | Ser | Lys | Asp | Ser | Thr | Tyr | Ser | Leu | Ser |
| | | | | 165 | | | | | 170 | | | | | 175 | |
| Ser | Thr | Leu | Thr | Leu | Ser | Lys | Ala | Asp | Tyr | Glu | Lys | His | Lys | Val | Tyr |
| | | | 180 | | | | | 185 | | | | | 190 | | |
| Ala | Cys | Glu | Val | Thr | His | Gln | Gly | Leu | Ser | Ser | Pro | Val | Thr | Lys | Ser |
| | | 195 | | | | | 200 | | | | | 205 | | | |
| Phe | Asn | Arg | Gly | Glu | Cys | | | | | | | | | | |
| | | | 210 | | | | | | | | | | | | |

```
<210> SEQ ID NO 182
<211> LENGTH: 1410
<212> TYPE: DNA
<213> ORGANISM: Artificial
<220> FEATURE:
<223> OTHER INFORMATION: P-0315

<400> SEQUENCE: 182
atggatatgc gggtgcctgc tcagctgctg ggcctgctgc tgctgtggct gcgagggct       60 agatgtgata aaactcatac ttgtcctcca tgcccagcac ctgaggcagc aggcgcccca     120
tccgtgttcc tgtttccccc taagcccaag gacacactga tgatctcccg tacgccagag     180
gtgacatgcg tggtggtgga cgtgagccac gaggacccg aggtgaagtt taactgggtac     240 gtggacggcg tggaggtgca caatgccaag acaaagccta gggaggagca gtacaattct    300
acctatcgcg tggtgagcgt gctgacagtg ctgcaccagg attggctgaa cggcaaggag     360
tataagtgca aggtgtccaa taaggccctg cctgccccaa tcgagaagac catctctaag     420
gccaagggcc agcccagaga gcctcaggtg tacacactgc ctccaagcag agacgagctg    480
accaagaacc aggtgtccct gacatgtctg gtgaagggct ctatccctc tgatatcgcc      540 gtggagtggg agagcaatgg ccagcctgag acaattaca agaccacacc ccctgtgctg     600
gacagcgatg gctccttctt tctgtattcc aagctgaccg tggataagtc tcggtggcag    660
```

```
cagggcaacg tgttttcctg ctctgtgatg cacgaagcac tgcataacca ctacacccag    720
aagagcctga gcctgtcccc cggggcggc ggaggaagtc tgggagggag tgggcgaagt     780
gccaacgcta ttctggaggg cggaagtaac tgggtcaatg tgattagtga tctgaagaag    840
atcgaggacc tgatccagag catgcacatc gatgccaccc tgtacacaga gtccgacgtg    900 caccccctctt gcaaggtgac cgccatgaag tgtttcctgc tggagctgca ggtcatcagc   960
ctggagagcg gcgacgccga tatccacgat accgtggaga acctgatcat cctgccaaac   1020
aattctctga gctccaacgg caatgtgaca gagagcggct gcaaggagtg tgaggagctg    1080
gaggagaaga acatcaagga gttcctgcag tcctttgtgc acatcgtgca gatgttcatc    1140
aatacctctg gaggaccact gggaatgctg tcccagtcta tcacatgccc acctccaatg    1200
tccgtggagc acgcagacat ctgggtgaag agctactccc tgtatagccg ggagagatat    1260
atctgcaatt ccggctttaa gcggaaggcc ggcacctcta gcctgacaga gtgcgtgctg    1320
aacaaggcca ccaatgtggc ccactggaca accccaagcc tgaaatgtat tcgcgaccct    1380
gccctggtcc accagcgccc tgcccccccc                                    1410

<210> SEQ ID NO 183
<211> LENGTH: 1392
<212> TYPE: DNA
<213> ORGANISM: Artificial
<220> FEATURE:
<223> OTHER INFORMATION: P-0350

<400> SEQUENCE: 183
atggatatgc gggtgcctgc tcagctgctg ggcctgctgc tgctgtggct gcgagggct     60 agatgtgata aaactcatac ttgtcctcca tgcccagcac ctgaggcagc aggcgcccca    120
tccgtgttcc tgtttccccc taagcccaag gacacactga tgatctcccg tacgccagag    180
gtgacatgcg tggtggtgga cgtgagccac gaggacccg aggtgaagtt taactggtac     240
gtggacggcg tggaggtgca caatgccaag acaaagccta gggaggagca gtacaattct    300
acctatcgcg tggtgagcgt gctgacagtg ctgcaccagg attggctgaa cggcaaggag    360
tataagtgca aggtgtccaa taaggccctg cctgccccaa tcgagaagac catctctaag    420
gccaagggcc agcccagaga gcctcaggtg tacacactgc ctccaagcag agacgagctg    480
accaagaacc aggtgtccct gacatgtctg gtgaagggct ctatccctc tgatatcgcc     540 gtggagtggg agagcaatgg ccagcctgag aacaattaca agaccacacc ccctgtgctg    600
gacagcgatg gctccttctt tctgtattcc aagctgaccg tggataagtc tcggtggcag    660
cagggcaacg tgttttcctg ctctgtgatg cacgaagcac tgcataacca ctacacccag    720
aagagcctga gcctgtcccc cggggcggc ggaggaagtg gcgaggagg ctctggcgga    780 ggcggaagta actgggtcaa tgtgattagt gatctgaaga gatcgagga cctgatccag    840 agcatgcaca tcgatgccac cctgtacaca gagtccgacg tgcacccctc ttgcaaggtg    900
accgccatga agtgtttcct gctggagctg caggtcatca gcctggagag cggcgacgcc    960
gatatccacg ataccgtgga gaacctgatc atcctggcca acaattctct gagctccaac    1020
ggcaatgtga cagagagcgg ctgcaaggag tgtgaggagc tggaggagaa gaacatcaag    1080
gagttcctgc agtcctttgt gcacatcgtg cagatgttca tcaatacctc tggaggacca    1140 ctggaatgc tgtcccagtc tatcacatgc ccacctccaa tgtccgtgga gcacgcagac    1200
atctgggtga agagctactc cctgtatagc cgggagagat atatctgcaa ttccggcttt    1260
```

| aagcggaagg ccggcaccte tagcetgaca gagtgegtge tgaacaagge caccaatgtg | 1320 |
| gcccactgga caaccccaag cctgaaatgt attcgcgacc ctgccctggt ccaccagcgc | 1380 |
| cctgcccccc cc | 1392 |

<210> SEQ ID NO 184
<211> LENGTH: 1392
<212> TYPE: DNA
<213> ORGANISM: Artificial
<220> FEATURE:
<223> OTHER INFORMATION: P-0351

<400> SEQUENCE: 184

| atggatatgc gggtgcctgc tcagctgctg ggcctgctgc tgctgtggct gcgaggggct | 60 |
| agatgtgata aaactcatac ttgtcctcca tgcccagcac ctgaggcagc aggcgcccca | 120 |
| tccgtgttcc tgtttccccc taagcccaag gacacactga tgatctcccg tacgccagag | 180 |
| gtgacatgcg tggtggtgga cgtgagccac gaggaccccg aggtgaagtt taactgGtac | 240 |
| gtggacggcg tggaggtgca caatgccaag acaaagccta gggaggagca gtacaattct | 300 |
| acctatcgcg tggtgagcgt gctgacagtg ctgcaccagg attggctgaa cggcaaggag | 360 |
| tataagtgca aggtgtccaa taaggccctg cctgccccaa tcgagaagac catctctaag | 420 |
| gccaagggcc agcccagaga gcctcaggtg tacacactgc ctccaagcag agacgagctg | 480 |
| accaagaacc aggtgtccct gacatgtctg gtgaagggct ctatccctc tgatatcgcc | 540 |
| gtggagtggg agagcaatgg ccagcctgag aacaattaca agaccacacc cctgtgctg | 600 |
| gacagcgatg gctccttctt tctgtattcc aagctgaccg tggataagtc tcggtggcag | 660 |
| cagggcaacg tgttttcctg ctctgtgatg cacgaagcac tgcataacca ctacacccag | 720 |
| aagagcctga gctgtccccc gggggcggc ggcggctctg gaggaggagg cagcggcgga | 780 |
| ggaggctcca actgggtgaa tgtgatctct gacctgaaga gatcgagga tctgatccag | 840 |
| agcatgcaca tcgacgccac cctgtacaca gagtctgatg tgcaccctag ctgcaaggtg | 900 |
| accgccatga agtgtttcct gctggagctg caggtcatca gcctggagtc cggcgacgcc | 960 |
| gatatccacg acaccgtgga gaacctgatc atcctggcca caatagcct gagctccaac | 1020 |
| ggcaatgtga cagagtccgg ctgcaaggag tgtgaggagc tggaggagaa gaacatcaag | 1080 |
| gagttcctgc agtcctttgt gcacatcgtg cagatgttca tcaataccct cggaggagga | 1140 |
| ggctctggcg gcggaggcag catcacatgc ccccctccaa tgtctgtgga gcacgccgac | 1200 |
| atctgggtga gtcctactc tctgtacagc cgggagcggt acatctgcaa ttctggcttt | 1260 |
| aagcggaagg ccggcaccte tagcctgaca gagtgcgtgc tgaacaagge cacaaatgtg | 1320 |
| gcccactgga ccacacccag cctgaagtgt atccgggacc ccgccctggt gcaccagcgc | 1380 |
| cccgcccccc ct | 1392 |

<210> SEQ ID NO 185
<211> LENGTH: 1392
<212> TYPE: DNA
<213> ORGANISM: Artificial
<220> FEATURE:
<223> OTHER INFORMATION: P-0650

<400> SEQUENCE: 185

| atggatatgc gggtgcctgc tcagctgctg ggcctgctgc tgctgtggct gcgaggggct | 60 |
| agatgtgata aaactcatac ttgtcctcca tgcccagcac ctgaggcagc aggcgcccca | 120 |
| tccgtgttcc tgtttccccc taagcccaag gacacactga tgatctcccg tacgccagag | 180 |

```
gtgacatgcg tggtggtgga cgtgagccac gaggacccog aggtgaagtt aactggtac    240 gtggacggcg tggaggtgca caatgccaag acaaagccta gggaggagca gtacaattct    300
acctatcgcg tggtgagcgt gctgacagtg ctgcaccagg attggctgaa cggcaaggag    360
tataagtgca aggtgtccaa taaggccctg cctgccccaa tcgagaagac catctctaag    420
gccaagggcc agcccagaga gcctcaggtg tacacactgc ctccaagcag agacgagctg    480
accaagaacc aggtgtccct gacatgtctg gtgaagggct tctatccctc tgatatcgcc    540
gtggagtggg agagcaatgg ccagcctgag aacaattaca agaccacacc cctgtgctg    600 gacagcgatg gctccttctt tctgtattcc aagctgaccg tggataagtc tcggtggcag    660
cagggcaacg tgttttcctg ctctgtgatg cacgaagcac tgcatgctca ctacacccag    720
aagagcctga gcctgtcccc cgggggcggc ggaggaagtg gcggaggagg ctctggcgga    780
ggcggaagta actgggtcaa tgtgattagt gatctgaaga agatcgagga cctgatccag    840
agcatgcaca tcgatgccac cctgtacaca gagtccgacg tgcacccctc ttgcaaggtg    900
accgccatga agtgtttcct gctggagctg caggtcatca gcctggagag cggcgacgcc    960
gatatccacg ataccgtgga gaacctgatc atcctggcca acaattctct gagctccaac   1020
ggcaatgtga cagagagcgg ctgcaaggag tgtgaggagc tggaggagaa gaacatcaag   1080
gagttcctgc agtcctttgt gcacatcgtg cagatgttca tcaataccgtc tggaggacca   1140 ctgggaatgc tgtcccagtc tatcacatgc ccacctccaa tgtccgtgga gcacgcagac   1200
atctgggtga agagctactc cctgtatagc cgggagagat atatctgcaa ttccggcttt   1260
aagcggaagg ccggcaccctc tagcctgaca gagtgcgtgc tgaacaaggc caccaatgtg   1320
gcccactgga caaccccaag cctgaaatgt attcgcgacc ctgccctggt ccaccagcgc   1380 cctgccccc cc                                                          1392

<210> SEQ ID NO 186
<211> LENGTH: 1392
<212> TYPE: DNA
<213> ORGANISM: Artificial
<220> FEATURE:
<223> OTHER INFORMATION: P-0651

<400> SEQUENCE: 186
atggatatgc gggtgcctgc tcagctgctg ggcctgctgc tgctgtggct gcgagggct      60 agatgtgata aaactcatac ttgtcctcca tgcccagcac ctgaggcagc aggcgcccca    120
tccgtgttcc tgtttccccc taagcccaag gacacactga tgatctcccg tacgccagag    180
gtgacatgcg tggtggtgga cgtgagccac gaggacccog aggtgaagtt aactggtac    240 gtggacggcg tggaggtgca caatgccaag acaaagccta gggaggagca gtacaattct    300
acctatcgcg tggtgagcgt gctgacagtg ctgcaccagg attggctgaa cggcaaggag    360
tataagtgca aggtgtccaa taaggccctg cctgccccaa tcgagaagac catctctaag    420
gccaagggcc agcccagaga gcctcaggtg tacacactgc ctccaagcag agacgagctg    480
accaagaacc aggtgtccct gacatgtctg gtgaagggct tctatccctc tgatatcgcc    540
gtggagtggg agagcaatgg ccagcctgag aacaattaca agaccacacc cctgtgctg    600 gacagcgatg gctccttctt tctgtattcc aagctgaccg tggataagtc tcggtggcag    660
cagggcaacg tgttttcctg ctctgtgatg cacgaagcac tgcatgctca ctacacccag    720
aagagcctga gcctgtcccc cgggggcggc ggcggctctg gaggaggagg cagcggcgga    780
```

| | |
|---|---:|
| ggaggctcca actgggtgaa tgtgatctct gacctgaaga agatcgagga tctgatccag | 840 |
| agcatgcaca tcgacgccac cctgtacaca gagtctgatg tgcaccctag ctgcaaggtg | 900 |
| accgccatga agtgtttcct gctggagctg caggtcatca gcctggagtc cggcgacgcc | 960 |
| gatatccacg acaccgtgga gaacctgatc atcctggcca acaatagcct gagctccaac | 1020 |
| ggcaatgtga cagagtccgg ctgcaaggag tgtgaggagc tggaggagaa gaacatcaag | 1080 |
| gagttcctgc agtcctttgt gcacatcgtg cagatgttca tcaataccct cggaggagga | 1140 |
| ggctctggcg gcggaggcag catcacatgc ccccctccaa tgtctgtgga gcacgccgac | 1200 |
| atctgggtga gtcctactc tctgtacagc cgggagcggt acatctgcaa ttctggctttt | 1260 |
| aagcggaagg ccggcacctc tagcctgaca gagtgcgtgc tgaacaaggc cacaaatgtg | 1320 |
| gcccactgga ccacacccag cctgaagtgt atccgggacc ccgccctggt gcaccagcgc | 1380 |
| cccgcccccc ct | 1392 |

<210> SEQ ID NO 187
<211> LENGTH: 1410
<212> TYPE: DNA
<213> ORGANISM: Artificial
<220> FEATURE:
<223> OTHER INFORMATION: P-0662 Chain 1

<400> SEQUENCE: 187

| | |
|---|---:|
| atggatatgc gggtgcctgc tcagctgctg ggcctgctgc tgctgtggct gcgaggggct | 60 |
| agatgtgata aaactcatac ctgtcctcca tgcccagcac ctgaggcagc aggcgcccca | 120 |
| tccgtgttcc tgtttccccc taagcccaag gacacctga tgatctctcg tacgcccgag | 180 |
| gtgacatgcg tggtggtgga cgtgagccac gaggacccg aggtgaagtt caactggtac | 240 |
| gtggatggcg tggaggtgca caatgccaag acaaagcctc gggaggagca gtacaactcc | 300 |
| acctatagag tggtgtctgt gctgacagtg ctgcaccagg actggctgaa cggcaaggag | 360 |
| tacaagtgca aggtgtccaa taaggccctg ccagccccca tcgagaagac catcagcaag | 420 |
| gccaagggcc agcctaggga gccacaggtg tataccctgc caccctgccg cgaggagatg | 480 |
| acaaagaacc aggtgtccct gtcttgtgcc gtgaagggct ctacccttc tgacatcgcc | 540 |
| gtggagtggg agagcaatgg ccagccagag aacaattata agaccacacc tccagtgctg | 600 |
| gactctgatg gcagcttctt tctggtgagc aagctgaccg tggataagtc caggtggcag | 660 |
| cagggcaacg tgtttagctg ttccgtgatg cacgaggccc tgcacaatca ctacacacag | 720 |
| aagtctctga gcctgtcccc cggggcgg ggaggaagtc tggagggag tgggcgaagt | 780 |
| gccaacgcta ttctggaggg cggaagtaac tgggtcaatg tgattagtga tctgaagaag | 840 |
| atcgaggacc tgatccagag catgcacatc gatgccaccc tgtacacaga gtccgacgtg | 900 |
| caccctcttt gcaaggtgac cgccatgaag tgtttcctgc tggagctgca ggtcatcagc | 960 |
| ctggagagcg gcgacgccga tatccacgat accgtggaga acctgatcat cctggccaac | 1020 |
| aattctctga gctccaacgg caatgtgaca gagagcggct gcaaggagtg tgaggagctg | 1080 |
| gaggagaaga acatcaagga gttcctgcag tcctttgtgc acatcgtgca gatgttcatc | 1140 |
| aatacctctg gaggaccact gggaatgctg tcccagtcta tcacatgccc acctccaatg | 1200 |
| tccgtggagc acgcagacat ctgggtgaag agctactccc tgtatagccg ggagagatat | 1260 |
| atctgcaatt ccggctttaa gcggaaggcc ggcacctcta gcctgacaga gtgcgtgctg | 1320 |
| aacaaggcca caatgtggc ccactggaca accccaagcc tgaaatgtat tcgcgaccct | 1380 |
| gccctggtcc accagcgccc tgcccccccc | 1410 |

<210> SEQ ID NO 188
<211> LENGTH: 744
<212> TYPE: DNA
<213> ORGANISM: Artificial
<220> FEATURE:
<223> OTHER INFORMATION: P-0662 Chain 2

<400> SEQUENCE: 188

| | |
|---|---|
| atggatatgc gggtgcctgc tcagctgctg ggcctgctgc tgctgtggct gcgagggget | 60 |
| agatgtgata aaactcatac ttgtcctcca tgcccagcac ctgaggcagc aggcgcccca | 120 |
| tccgtgttcc tgtttccccc taagcccaag gacacactga tgatctcccg tacgccagag | 180 |
| gtgacatgcg tggtggtgga cgtgtctcac gaggaccccg aggtgaagtt caactggtac | 240 |
| gtggatggcg tggaggtgca caatgccaag accaagccca gggaggagca gtacaacagc | 300 |
| acctatcgcg tggtgtccgt gctgacagtg ctgcaccagg actggctgaa cggcaaggag | 360 |
| tataagtgca aggtgtccaa taaggccctg ccagccccca tcgagaagac catcagcaag | 420 |
| gcaaagggac agcctcggga gccacaggtg tgcaccctgc caccctctag agaggagatg | 480 |
| acaaagaacc aggtgagcct gtggtgtctg gtgaagggct ctacccttc cgacatcgcc | 540 |
| gtggagtggg agtctaatgg ccagccagag aacaattaca agaccacacc tccagtgctg | 600 |
| gactctgatg gcagcttctt tctgtattct aagctgaccg tggataagag caggtggcag | 660 |
| cagggcaacg tgttttcctg ctctgtgatg cacgaggccc tgcacaatca ctacacacag | 720 |
| aagagcctgt ccctgtctcc cggg | 744 |

<210> SEQ ID NO 189
<211> LENGTH: 1410
<212> TYPE: DNA
<213> ORGANISM: Artificial
<220> FEATURE:
<223> OTHER INFORMATION: P-0663 Chain 1

<400> SEQUENCE: 189

| | |
|---|---|
| atggatatgc gggtgcctgc tcagctgctg ggcctgctgc tgctgtggct gcgagggget | 60 |
| agatgtgata aaactcatac ctgtcctcca tgcccagcac ctgaggcagc aggcgcccca | 120 |
| tccgtgttcc tgtttccccc taagcccaag gacaccctga tgatctctcg tacgcccgag | 180 |
| gtgacatgcg tggtggtgga cgtgagccac gaggaccccg aggtgaagtt caactggtac | 240 |
| gtggatggcg tggaggtgca caatgccaag acaaagcctc gggaggagca gtacaactcc | 300 |
| acctatagag tggtgtctgt gctgacagtg ctgcaccagg actggctgaa cggcaaggag | 360 |
| tacaagtgca aggtgtccaa taaggccctg ccagccccca tcgagaagac catcagcaag | 420 |
| gccagggcc agcctaggga gccacaggtg tataccctgc caccctgccg cgaggagatg | 480 |
| acaaagaacc aggtgtccct gtcttgtgcc gtgaagggct ctacccttc tgacatcgcc | 540 |
| gtggagtggg agagcaatgg ccagccagag aacaattata agaccacacc tccagtgctg | 600 |
| gactctgatg gcagcttctt tctggtgagc aagctgaccg tggataagtc caggtggcag | 660 |
| cagggcaacg tgtttagctg ttccgtgatg cacgaggccc tgcacgctca ctacacacag | 720 |
| aagtctctga gcctgtcccc cggggggcggc ggaggaagtc tgggagggag tgggcgaagt | 780 |
| gccaacgcta ttctggaggg cggaagtaac tgggtcaatg tgattagtga tctgaagaag | 840 |
| atcgaggacc tgatccagag catgcacatc gatgccaccc tgtacacaga gtccgacgtg | 900 |
| cacccctctt gcaaggtgac cgccatgaag tgtttcctgc tggagctgca ggtcatcagc | 960 |

```
ctggagagcg gcgacgccga tatccacgat accgtggaga acctgatcat cctggccaac    1020
aattctctga gctccaacgg caatgtgaca gagagcggct gcaaggagtg tgaggagctg    1080
gaggagaaga acatcaagga gttcctgcag tcctttgtgc acatcgtgca gatgttcatc    1140
aatacctctg gaggaccact gggaatgctg tcccagtcta tcacatgccc acctccaatg    1200
tccgtggagc acgcagacat ctgggtgaag agctactccc tgtatagccg ggagagatat    1260
atctgcaatt ccggctttaa gcggaaggcc ggcacctcta gcctgacaga gtgcgtgctg    1320
aacaaggcca ccaatgtggc ccactggaca accccaagcc tgaaatgtat tcgcgaccct    1380
gccctggtcc accagcgccc tgcccccccc                                    1410

<210> SEQ ID NO 190
<211> LENGTH: 1392
<212> TYPE: DNA
<213> ORGANISM: Artificial
<220> FEATURE:
<223> OTHER INFORMATION: P-0664 Chain 1

<400> SEQUENCE: 190
atggatatgc gggtgcctgc tcagctgctg ggcctgctgc tgctgtggct gcgaggggct      60
agatgtgata aaactcatac ctgtcctcca tgcccagcac ctgaggcagc aggcgcccca    120
tccgtgttcc tgtttccccc taagcccaag acaccctga tgatctctcg tacgcccgag     180
gtgacatgcg tggtggtgga cgtgagccac gaggaccccg aggtgaagtt caactggtac    240
gtggatggcg tggaggtgca caatgccaag acaaagcctc gggaggagca gtacaactcc    300
acctatagag tggtgtctgt gctgacagtg ctgcaccagg actggctgaa cggcaaggag    360
tacaagtgca aggtgtccaa taaggccctg ccagccccca tcgagaagac catcagcaag    420
gccaagggcc agcctaggga gccacaggtg tatccctgc cacccctgccg cgaggagatg     480 acaaagaacc aggtgtccct gtcttgtgcc gtgaagggct ctacccttc tgacatcgcc    540 gtggagtggg agagcaatgg ccagccagag aacaattata agaccacacc tccagtgctg    600
gactctgatg gcagcttctt tctggtgagc aagctgaccg tggataagtc caggtggcag    660
cagggcaacg tgtttagctg ttccgtgatg cacgaggccc tgcacgctca ctacacacag    720
aagtctctga gcctgtcccc cggggggcggc ggaggaagtg gcggaggagg ctctggcgga    780 ggcgaagta actgggtcaa tgtgattagt gatctgaaga gatcgagga cctgatccag    840 agcatgcaca tcgatgccac cctgtacaca gagtccgacg tgcaccctc ttgcaaggtg     900 accgccatga gtgtttcct gctggagctg caggtcatca gcctggagag cggcgacgcc    960
gatatccacg ataccgtgga gaacctgatc atcctggcca caattctct gagctccaac    1020 ggcaatgtga cagagagcgg ctgcaaggag tgtgaggagc tggaggagaa gaacatcaag    1080
gagttcctgc agtcctttgt gcacatcgtg cagatgttca tcaatacctc tggaggacca    1140
ctgggaatgc tgtcccagtc tatcacatgc ccacctccaa tgtccgtgga gcacgcagac    1200
atctgggtga agagctactc cctgtatagc cgggagagat atatctgcaa ttccggcttt    1260
aagcggaagg ccggcaccct cagcctgaca gagtgcgtgc tgaacaaggc caccaatgtg    1320
gcccactgga caaccccaag cctgaaatgt attcgcgacc ctgccctggt ccaccagcgc    1380
cctgcccccc cc                                                        1392

<210> SEQ ID NO 191
<211> LENGTH: 1395
<212> TYPE: DNA
<213> ORGANISM: Artificial
```

<220> FEATURE:
<223> OTHER INFORMATION: P-0665 Chain 1

<400> SEQUENCE: 191

| | |
|---|---|
| atggatatgc gggtgcctgc tcagctgctg ggcctgctgc tgctgtggct gcgaggggct | 60 |
| agatgtgata aaactcatac ctgtcctcca tgcccagcac ctgaggcagc aggcgcccca | 120 |
| tccgtgttcc tgtttccccc taagcccaag acaccctga tgatctctcg tacgcccgag | 180 |
| gtgacatgcg tggtggtgga cgtgagccac gaggaccccg aggtgaagtt caactggtac | 240 |
| gtggatggcg tggaggtgca caatgccaag acaaagcctc gggaggagca gtacaactcc | 300 |
| acctatagag tggtgtctgt gctgacagtg ctgcaccagg actggctgaa cggcaaggag | 360 |
| tacaagtgca aggtgtccaa taaggccctg ccagccccca tcgagaagac catcagcaag | 420 |
| gccaagggcc agcctaggga gccacaggtg tataccctgc caccctgccg cgaggagatg | 480 |
| acaaagaacc aggtgtccct gtcttgtgcc gtgaagggct tctacccttc tgacatcgcc | 540 |
| gtggagtggg agagcaatgg ccagccagag aacaattata agaccacacc tccagtgctg | 600 |
| gactctgatg gcagcttctt tctggtgagc aagctgaccg tggataagtc caggtggcag | 660 |
| cagggcaacg tgtttagctg ttccgtgatg cacgaggccc tgcacgctca ctacacacag | 720 |
| aagtctctga gcctgtcccc cgggggcagc tccggaagcg gcaggtccga gaatatccgc | 780 |
| accgccggaa caaactgggt caatgtgatt agtgatctga agaagatcga ggacctgatc | 840 |
| cagagcatgc acatcgatgc caccctgtac acagagtccg acgtgcaccc ctcttgcaag | 900 |
| gtgaccgcca tgaagtgttt cctgctggag ctgcaggtca tcagcctgga gagcggcgac | 960 |
| gccgatatcc acgataccgt ggagaacctg atcatcctgg ccaacaattc tctgagctcc | 1020 |
| aacggcaatg tgacagagag cggctgcaag gagtgtgagg agctggagga agaacatc | 1080 |
| aaggagttcc tgcagtcctt tgtgcacatc gtgcagatgt tcatcaatac ctctggagga | 1140 |
| ccactgggaa tgctgtccca gtctatcaca tgcccacctc aatgtccgt ggagcacgca | 1200 |
| gacatctggg tgaagagcta ctccctgtat agccgggaga gatatatctg caattccggc | 1260 |
| tttaagcgga aggccggcac ctctagcctg acagagtgcg tgctgaacaa ggccaccaat | 1320 |
| gtggcccact ggacaacccc aagcctgaaa tgtattcgcg accctgccct ggtccaccag | 1380 |
| cgccctgccc ccccc | 1395 |

<210> SEQ ID NO 192
<211> LENGTH: 744
<212> TYPE: DNA
<213> ORGANISM: Artificial
<220> FEATURE:
<223> OTHER INFORMATION: P-0663/P-0664/P-0665 Chain 2

<400> SEQUENCE: 192

| | |
|---|---|
| atggatatgc gggtgcctgc tcagctgctg ggcctgctgc tgctgtggct gcgaggggct | 60 |
| agatgtgata aaactcatac ttgtcctcca tgcccagcac ctgaggcagc aggcgcccca | 120 |
| tccgtgttcc tgtttccccc taagcccaag acacactga tgatctcccg tacgccagag | 180 |
| gtgacatgcg tggtggtgga cgtgtctcac gaggaccccg aggtgaagtt caactggtac | 240 |
| gtggatggcg tggaggtgca caatgccaag accaagccca gggaggagca gtacaacagc | 300 |
| acctatcgcg tggtgtccgt gctgacagtg ctgcaccagg actggctgaa cggcaaggag | 360 |
| tataagtgca aggtgtccaa taaggccctg ccagccccca tcgagaagac catcagcaag | 420 |
| gcaaagggac agcctcggga gccacaggtg tgcaccctgc caccctctag agaggagatg | 480 |

-continued

```
acaaagaacc aggtgagcct gtggtgtctg gtgaagggct tctacccttc cgacatcgcc      540
gtggagtggg agtctaatgg ccagccagag aacaattaca agaccacacc tccagtgctg      600
gactctgatg gcagcttctt tctgtattct aagctgaccg tggataagag caggtggcag      660
cagggcaacg tgttttcctg ctctgtgatg cacgaggccc tgcacgctca ctacacacag      720
aagagcctgt ccctgtctcc cggg                                              744
```